United States Patent
Voskoboynikov et al.

(10) Patent No.: US 8,058,461 B2
(45) Date of Patent: Nov. 15, 2011

(54) MONO-INDENYL TRANSITION METAL COMPOUNDS AND POLYMERIZATION THEREWITH

(75) Inventors: Alexander Z. Voskoboynikov, Moscow (RU); Mikhail V. Nikulin, Podolsk (RU); Aleksey A. Tsarev, Tula (RU); Andrey F. Asachenko, Chelyabinsk (RU); Alexander V. Babkin, Kolomna (RU); Garth R. Giesbrecht, The Woodlands, TX (US); Jo Ann M. Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 96 days.

(21) Appl. No.: 12/715,068

(22) Filed: Mar. 1, 2010

(65) Prior Publication Data

US 2011/0213109 A1    Sep. 1, 2011

(51) Int. Cl.
C08F 4/6592 (2006.01)
B01J 31/22 (2006.01)
C07F 17/00 (2006.01)

(52) U.S. Cl. ............. 556/53; 556/1; 502/103; 502/155; 526/161; 526/165; 526/943

(58) Field of Classification Search ............... 556/1, 53; 502/103, 155; 526/161, 165
See application file for complete search history.

(56) References Cited

U.S. PATENT DOCUMENTS

| | | |
|---|---|---|
| 5,055,438 A | 10/1991 | Canich |
| 6,420,301 B1 | 7/2002 | Kristen et al. |
| 7,074,863 B2 | 7/2006 | Ekholm et al. |
| 7,163,907 B1 | 1/2007 | Canich et al. |
| 2006/0160967 A1 | 7/2006 | Voskoboynikov et al. |
| 2006/0160968 A1 | 7/2006 | Voskoboynikov et al. |
| 2007/0135594 A1 | 6/2007 | Voskoboynikov et al. |
| 2007/0135597 A1 | 6/2007 | Voskoboynikov et al. |

FOREIGN PATENT DOCUMENTS

| | | |
|---|---|---|
| JP | 3497920 | 2/2004 |
| JP | 2009-019035 | 1/2009 |
| JP | 2009-119681 | 6/2009 |
| WO | WO 2003/000744 | 1/2003 |

Primary Examiner — Caixia Lu

(57) ABSTRACT

This invention relates to transition metal compounds, catalyst systems comprising said compounds and polymerization processes using such catalyst systems, where the transition metal compound is represented by the formula:

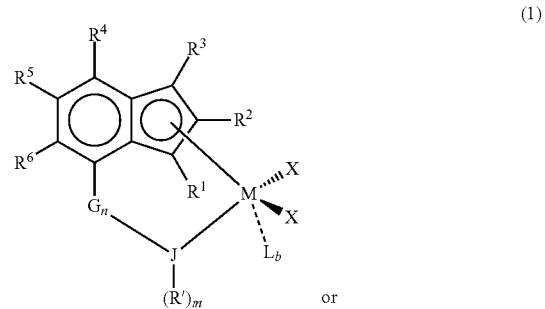

(1)

or

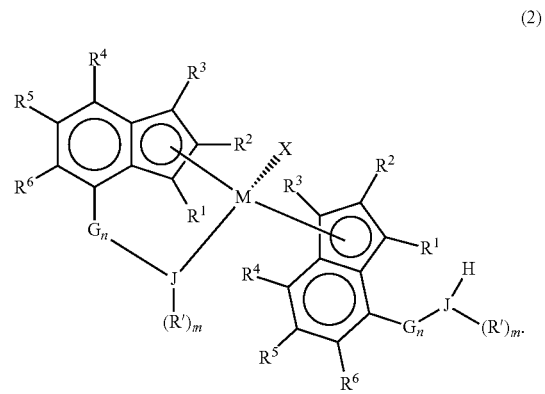

(2)

This invention also relates to process to produce such compounds.

20 Claims, No Drawings

MONO-INDENYL TRANSITION METAL COMPOUNDS AND POLYMERIZATION THEREWITH

FIELD OF THE INVENTION

This invention relates to a series of novel mono-indenyl transition metal compounds that, when activated, have been shown to be useful as olefin polymerization catalysts.

BACKGROUND OF THE INVENTION

There is a need in industry for new transition metal compounds useful as polymerization catalysts.

Bridged monocyclopentadienyl transition metal compounds have been disclosed in U.S. Pat. Nos. 5,055,438 and 7,163,907 (and other patents by the instant inventor J. M. Canich), that when activated with methyl alumoxane or a non-coordinating anion produce polyolefins.

U.S. 2006/0160968 discloses a process to make substituted metallocenes where the ligand has been halogenated prior to reactions with the metal complex.

U.S. 2007/0135594 discloses halogenated mono-cyclopentadienyl-amido transition metal compounds.

U.S. 2007/0135597 discloses bridged bis cyclopentadienyl transition metal compounds where on ligand is an indene and the other ligand is a cyclopentadiene, indene or fluorene and the bridge is located at the 4, 5, 6, or 7 position of the indene or the 1, 2, 3, 4, 5, or 6 position of the fluorene.

U.S. 2006-0160967 disclose bridged indenyl compounds where the bridged is at the 4, 5, 6, or 7 position of the indene and at least one of the two ligands is substituted with a halogen.

U.S. Pat. No. 7,074,863 and WO 2003/000744 disclose bridged and unbridged bis indenyl compounds substituted at the 4, 5, 6, or 7 positions by a siloxy or germyloxy group. Also disclosed is one mono-indenyl amido titanium complex where the indenyl ligand is bridged to the amido ligand via an O—SiMe$_2$ bridge.

U.S. Pat. No. 6,420,301 discloses bridged monocyclopentadienyl compounds where the bridging group —ZAA$^1$- is bonded to the "cyclopentadienyl" ligand by both Z and A$^1$ forming a multicyclic structure. The compounds exemplified are mono-fluorenyl species that are bridged via the 1 and 9 position of the fluorenyl ligand.

JP 3497920(B2) discloses bridged mono-indenyl transition metal compounds, where the indenyl ligand is connected to the metal via an ortho phenyl heteroatom linkage where the heteroatom appears to be —O—, —S—, —NR— or —PR—.

JP 2009-119681A and JP 2009-019035A discloses bridged monocyclopentadienyl compounds were the bridging group R$_2$Si(PhR$_4$) links the indenyl ligand to an oxygen atom bound to the metal.

Thus there is a need in the art for new transition metal compounds that can be used as pre-catalysts to produce very high to ultra high molecular weight polymers with narrow or broad polydispersities. Also needed is a general synthetic pathway to make bridged mono-indenyl amido group 4 transition metal complexes where the bridge is to the 6-membered ring of the indenyl ligand, and where the synthetic pathway is applicable to many substituted indenyls, substituted amides, and types of bridging groups.

SUMMARY OF THE INVENTION

This invention relates to a transition metal compound represented by the formula:

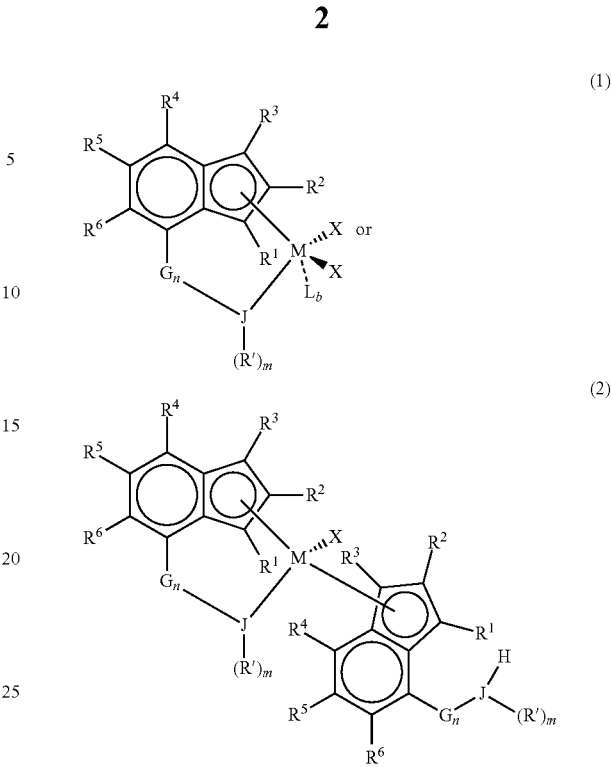

where M is a group 3, 4, 5, or 6 metal, particularly a group 4 metal, more particularly Ti, Zr, or Hf; J is a group 15 or 16 atom, particularly N, P, O, or S, and when J is a group 15 metal, m is 1, indicating the presence of R', and when J is a group 16 metal, m is zero, indicating the absence of R'; G is a bridging group and n is 1, 2, or 3 indicating the number of atoms in the direct chain between the indenyl ring and the ligand J; R$^1$, R$^2$, R$^3$, R$^4$, R$^5$, and R$^6$ are independently selected from a hydrogen, fluoro, or hydrocarbyl, substituted hydrocarbyl, halocarbyl, substituted halocarbyl, silylcarbyl, substituted silylcarbyl, germylcarbyl, or substituted germylcarbyl radical, and two or more adjacent of R$^1$, R$^2$, R$^3$, R$^4$, R$^5$, and R$^6$ can join together to form a cyclic group fused to the indenyl ring; R' is selected from a hydrocarbyl, halohydrocarbyl, or substituted hydrocarbyl radical; X is a univalent ionic ligand, L is a Lewis base ligand and b is 0 or 1 or 2 representing the presence (b=1 or 2) or absence (b=0) of L, provided that when n is 2, G is not O—SiR$_2$, or R$_4$Ph, and when n is 3, G is not SiR$_2$(R$_4$Ph), where Ph is phenyl and each R is as defined for R$^1$.

DEFINITIONS

As used herein, the "new" numbering scheme for the Periodic Table Groups is used as published in CHEMICAL AND ENGINEERING NEWS, 63(5), 27 (1985).

The terms "hydrocarbyl radical," "hydrocarbyl," and hydrocarbyl group" are used interchangeably throughout this document. Likewise the terms "group" and "substituent" are also used interchangeably in this document. For purposes of this disclosure, "hydrocarbyl radical" is defined to be C$_1$-C$_{100}$ radicals, that may be linear, branched, or cyclic, and when cyclic, aromatic, or non-aromatic, and include substituted hydrocarbyl radicals, halocarbyl radicals, and substituted halocarbyl radicals, silylcarbyl radicals, and germylcarbyl radicals as these terms are defined below.

Substituted hydrocarbyl radicals are radicals in which at least one hydrogen atom has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like; or where at least one non-hydrocarbon atom or group has been inserted within the hydrocarbyl radical, such as O, S, Se, Te, NR*, PR*, AsR*, SbR*, BR*, SiR*$_2$, GeR*$_2$, SnR*$_2$, PbR*$_2$, and the like; where R* is, independently, a hydrocarbyl or halocarbyl radical.

Halocarbyl radicals are radicals in which one or more hydrocarbyl hydrogen atoms have been substituted with at least one halogen (e.g., F, Cl, Br, I) or halogen-containing group (e.g., CF$_3$).

Substituted halocarbyl radicals are radicals in which at least one halocarbyl hydrogen or halogen atom has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like; or where at least one non-carbon atom or group has been inserted within the halocarbyl radical such as O, S, Se, Te, NR*, PR*, AsR*, SbR*, BR*, SiR*$_2$, GeR*$_2$, SnR*$_2$, PbR*$_2$, and the like; where R* is, independently, a hydrocarbyl or halocarbyl radical provided that at least one halogen atom remains on the original halocarbyl radical.

Silylcarbyl radicals (also called silylcarbyls) are groups in which the silyl functionality is bonded directly to the indicated atom or atoms. Examples include SiH$_3$, SiH$_2$R*, SiHR*$_2$, SiR*$_3$, SiH$_2$(OR*), SiH(OR*)$_2$, Si(OR*)$_3$, SiH$_2$(NR*$_2$), SiH(NR*$_2$)$_2$, Si(NR*$_2$)$_3$, and the like; where R* is, independently, a hydrocarbyl or halocarbyl radical as defined above and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include GeH$_3$, GeH$_2$R*, GeHR*$_2$, GeR$^5_3$, GeH$_2$(OR*), GeH(OR*)$_2$, Ge(OR*)$_3$, GeH$_2$(NR*$_2$), GeH(NR*$_2$)$_2$, Ge(NR*$_2$)$_3$, and the like; where R* is, independently, a hydrocarbyl or halocarbyl radical as defined above and two or more R* may join together to form a substituted or unsubstituted saturated, partially unsaturated or aromatic cyclic or polycyclic ring structure.

Polar radicals or polar groups are groups in which the heteroatom functionality is bonded directly to the indicated atom or atoms. They include heteroatoms of groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde, and their chalcogen (Group 14) analogues, alcohol, phenol, ether, peroxide, hydroperoxide, carboxylic amide, hydrazide, imide, amidine, and other nitrogen analogues of amides, nitrile, amine, imine, azo, nitro, other nitrogen compounds, sulfur acids, selenium acids, thiols, sulfides, sulfoxides, sulfones, phosphines, phosphates, other phosphorus compounds, silanes, boranes, borates, alanes, and aluminates. Functional groups may also be taken broadly to include organic polymer supports or inorganic support material such as alumina and silica. Preferred examples of polar groups include NR*$_2$, OR*, SeR*, TeR*, PR*$_2$, AsR*$_2$, SbR*$_2$, SR*, BR*$_2$, SnR*$_3$, PbR*$_3$, and the like; where R* is, independently, a hydrocarbyl, substituted hydrocarbyl, halocarbyl or substituted halocarbyl radical as defined above and two R* may join together to form a substituted or unsubstituted saturated, partially unsaturated, or aromatic cyclic, or polycyclic ring structure.

In some embodiments, the hydrocarbyl radical is, independently, selected from methyl, ethyl, ethenyl, isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated, and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this disclosure, when a radical is listed, it indicates that radical type and all other radicals formed when that radical type is subjected to the substitutions defined above. Alkyl, alkenyl, and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl, and 2-methyl-2-propenyl (cyclobutenyls and cyclopropenyls). Cyclic compound having substitutions include all isomer forms, for example, methylphenyl would include ortho-methylphenyl, meta-methylphenyl, and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For nomenclature purposes, the following numbering schemes are used for cyclopentadienyl, indenyl, and fluorenyl rings. For cyclopentadienyl drawn below as an anionic ligand, all five numbered positions are equivalent. For indenyl also drawn below as an anionic ligand, positions 1 and 3 are equivalent, 4 and 7 are equivalent, and 5 and 6 are equivalent. For fluorenyl drawn below as an anionic ligand, positions 1 and 8 are equivalent, 2 and 7 are equivalent, 3 and 6 are equivalent, and 4 and 5 are equivalent.

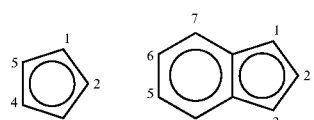

Cyclopentadienyl    Indenyl

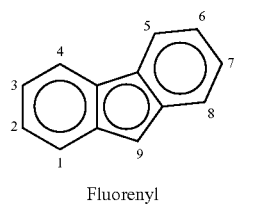

Fluorenyl

When a polymer or oligomer is referred to as comprising an olefin, the olefin present in the polymer or oligomer is the polymerized or oligomerized form of the olefin, respectively. The term polymer is meant to encompass homopolymers and copolymers. The term copolymer includes any polymer having two or more different monomers in the same chain and encompasses random copolymers, statistical copolymers, interpolymers, and (true) block copolymers. In the context of this document, "homopolymerization" would produce a polymer made from one monomer and "copolymerization" would produce polymers with more than one monomer type. Copolymerization can also incorporate α-olefinic macromonomers of up to 2000 mer units. Also an ethylene polymer (also referred to as polyethylene) is a homopolymer of ethylene or a copolymer having at least 50 wt % ethylene (preferably at least 60 wt %, preferably at least 70 wt %, preferably at least 80 wt %), based upon the weight of the polymer. Also a propylene polymer (also referred to as polypropylene) is a homopolymer of propylene or a copolymer having at least 50 wt % propylene (preferably at least 60 wt %, preferably at least 70 wt %, preferably at least 80 wt %), based upon the weight of the polymer.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

The term "catalyst system" means a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety. The transition metal compound or complex may be neutral as in a precatalyst, or a charged species with a counter ion as in an activated catalyst system. The term "catalyst-system" can also include more than one catalyst precursor and/or more than one activator and optionally a co-activator. Likewise, the term "catalyst-system" can also include more that one activated catalyst and one or more activator or other charge-balancing moiety, and optionally a co-activator.

Catalyst precursor is also often referred to as precatalyst, catalyst, catalyst compound, transition metal compound, or transition metal complex. These words are used interchangeably. Activator and cocatalyst (or co-catalyst) are also used interchangeably. A scavenger is a compound that is typically added to facilitate polymerization by scavenging impurities. Some scavengers may also act as activators and may be referred to as co-activators. A co-activator that is not a scavenger may also be used in conjunction with an activator in order to form an active catalyst. In some embodiments a co-activator can be pre-mixed with the transition metal compound to form an alkylated transition metal compound.

An activator or cocatalyst is a compound or mixture of compounds capable of activating a precatalyst to form an activated catalyst. The activator can be a neutral compound (Lewis acid activator) such as tris-perfluorophenyl boron or tris-perfluorophenyl aluminum, or an ionic compound (Ionic activator) such as, dimethylanilinium tetrakis-perfluorophenyl borate or dimethylanilinium tetrakis-perfluoronaphthyl borate. Activators are also commonly referred to as non-coordinating anion activators or ionic activators owing to the commonly held belief by those skilled in the art, that the reaction of the activator with the precatalyst forms a cationic metal complex and an anionic non-coordinating or weekly coordinating anion (NCA).

Noncoordinating anion (NCA) is further defined to mean an anion that either does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator and stoichiometric ionic activator can be used interchangeably. Likewise, the terms neutral stoichiometric activator and Lewis acid activator can be used interchangeably.

The following abbreviations are used: Me is methyl, Ph is phenyl, Et is ethyl, Pr is propyl, Bz is benzyl, iPr is isopropyl, n-Pr is normal propyl, Bu is butyl, iBu is isobutyl, tBu is tertiary butyl, p-tBu is para-tertiary butyl, Ts is tosyl, DMF is dimethylformamide, NBS is N-bromosuccinimide, TMS is trimethylsilyl, TIBA is triisobutylaluminum, MAO is methylalumoxane, pMe is para-methyl, flu is fluorenyl, Cp is cyclopentadienyl, and Ind is indenyl. The term "continuous" is defined to mean a system that operates without interruption or cessation. For example, a continuous process to produce a polymer would be one where the reactants are continually introduced into one or more reactors and polymer product is continually withdrawn.

Unless otherwise noted, all molecular weights units (e.g., Mw, Mn, Mz) are g/mol and all ppm's are wt ppm.

DETAILED DESCRIPTION OF THE INVENTION

In another embodiment, the invention further relates to a transition metal compound represented by the formula:

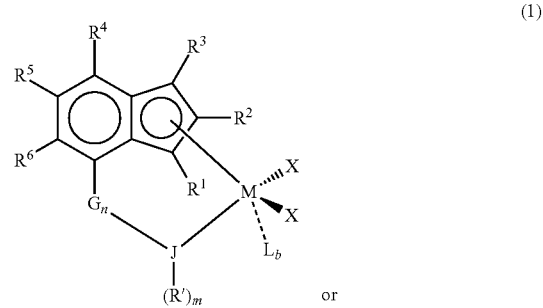

(1)

or

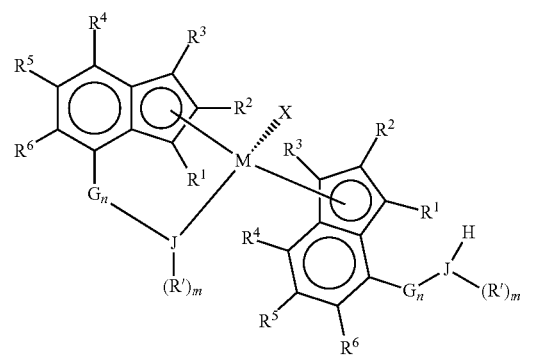

(2)

wherein

M is a group 3, 4, 5, or 6 transition metal atom, preferably a Group 4 transition metal atom, preferably a metal selected from Ti, Zr, and Hf;

$R^1$, $R^2$, $R^3$, $R^4$, $R^5$, and $R^6$ are, independently, hydrogen, fluoro, or a hydrocarbyl, substituted hydrocarbyl, halocarbyl, substituted halocarbyl, silylcarbyl, substituted silylcarbyl, germylcarbyl, or substituted germylcarbyl radical, and optionally, adjacent R groups may join together to form a substituted or unsubstituted, saturated, partially unsaturated, or aromatic cyclic or polycyclic substituent which are fused to the indenyl group;

J is a group 15 or 16 atom (preferably N, O, P, or S, preferably N), and when J is a group 15 metal, m is 1, indicating the presence of R', and when J is a group 16 atom, m is zero, indicating the absence of R;

R' is, independently, a hydrocarbyl, substituted hydrocarbyl, halocarbyl, substituted halocarbyl, silylcarbyl, substituted silylcarbyl, germylcarbyl, or substituted germylcarbyl radical;

G is a bridging group and n is 1, 2, or 3 indicating the number of atoms in the direct chain between the indenyl ring and the ligand J, when n is 2, then G is not O—$SiR_2$ or $R_4Ph$, and when n is 3, G is not $SiR_2(R_4Ph)$, where Ph is phenyl and each R is as defined for $R^1$;

L is a Lewis base;

b is 0, 1, or 2 representing the presence (b=1 or 2) or absence (b=0) of L; and each X is, independently, a univalent anionic ligand, preferably each X is selected from the group consisting of hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or when Lewis-acid activators, such as methylalumoxane, which are capable of donating an X ligand as described above to the transition metal component are used, both X may, independently, be a halogen, alkoxide, aryloxide, amide, phosphide or other univalent anionic ligand or both X can also be joined to form a anionic chelating ligand. Preferred X groups include halogen or a hydrocarbyl group, preferably Cl, Br, F, I, methyl, ethyl, propyl, butyl, phenyl, and benzyl.

Preferably, G is selected from $R''_2C$, $R''_2Si$, $R''_2Ge$, $R''_2CCR''_2$, $R''_2CCR''_2CR''_2$, $R''C=CR''$, $R''C=CR''CR''_2$, $R''_2CSiR''_2$, $R''_2SiSiR''_2$, $R''_2CSiR''_2CR''_2$, $R''_2SiCR''_2SiR''_2$, $R''_2SiCR''_2CR''_2$, $R''_2SiSiR''_2SiR''_2$, $R''C=CR''SiR''_2$, $R''_2CGeR''_2$, $R''_2GeGeR''_2$, $R''_2CGeR''_2CR''_2$, $R''_2GeCR''_2GeR''_2$, $R''_2SiGeR''_2$, $R''C=CR''GeR_{12}$, $R''B$, $R''_2C—BR''$, $R''_2C—BR''—CR''_2$, $R''_2C—NR''—CR''_2$, $R''_2C—PR''—CR''_2$, $R''_2C—O—CR''_2$, $R''_2C—S—CR''_2$, $R''_2Si—O—SiR''_2$, and $R''_2Ge—O—GeR_{12}$, where R" is, independently, hydrogen, hydrocarbyl, substituted hydrocarbyl, halocarbyl, substituted halocarbyl, silylcarbyl, or germylcarbyl, and two or more R" on the same atom or on adjacent atoms may join together to form a substituted or unsubstituted, saturated, partially unsaturated, or aromatic cyclic or polycyclic substituent provided that when G is $R''_2CCR''_2$, or $R''_2SiCR''_2CR''_2$ two or more R" on adjacent atoms may not join together to form a substituted or unsubstituted, aromatic cyclic or polycyclic group.

More preferably, G is selected from $R''_2C$, $R''_2Si$, $R''_2Ge$, $R''_2CCR''_2$, $R''_2CCR''_2CR''_2$, $R''C=CR''$, $R''C=CR''CR''_2$, $R''_2CSiR''_2$, $R''_2SiSiR''_2$, $R''_2CSiR''_2CR''_2$, $R''_2SiCR''_2SiR''_2$, $R''_2SiCR''_2CR''_2$, $R''_2SiSiR''_2SiR''_2$, $R''C=CR''SiR''_2$, $R''_2CGeR''_2$, $R''_2GeGeR''_2$, $R''_2CGeR''_2CR''_2$, $R''_2GeCR''_2GeR''_2$, $R''_2SiGeR''_2$, $R''C=CR''GeR_{12}$, $R''B$, $R''_2C—BR''$, $R''_2C—BR''—CR''_2$, $R''_2C—NR''—CR''_2$, $R''_2C—PR''—CR''_2$, $R''_2C—O—CR''_2$, $R''_2C—S—CR''_2$, $R''_2Si—O—SiR''_2$, and $R''_2Ge—O—GeR_{12}$, where R" is, independently, hydrogen, hydrocarbyl, substituted hydrocarbyl, halocarbyl, substituted halocarbyl, silylcarbyl, or germylcarbyl.

Even more preferably, G is selected from $R''_2Si$, $R''_2CCR''_2$, $R''_2CCR''_2CR''_2$, $R''_2CSiR''_2$, $R''_2SiSiR''_2$, $R''_2CSiR''_2CR''_2$, $R''_2SiCR''_2SiR''_2$, $R''_2SiCR''_2CR''_2$, $R''_2SiSiR''_2SiR''_2$, and $R''_2Si—O—SiR''_2$, where R" is, independently, hydrogen, hydrocarbyl, substituted hydrocarbyl, halocarbyl, substituted halocarbyl, silylcarbyl, or germylcarbyl.

Suitable examples for the bridging group G include dihydrocarbylsilylenes including dimethylsilylene, diethylsilylene, dipropylsilylene, dibutylsilylene, dipentylsilylene, dihexylsilylene, methylphenylsilylene, diphenylsilylene, dicyclohexylsilylene, methylcyclohexylsilylene, dibenzylsilylene, tetramethyldisilylene, cyclotrimethylenesilylene, cyclotetramethylenesilylene, cyclopentamethylenesilylene, divinylsilylene, and tetramethyldisiloxylene; dihydrocarbylgermylenes including dimethylgermylene, diethylgermylene, dipropylgermylene, dibutylgermylene, methylphenylgermylene, diphenylgermylene, dicyclohexylgermylene, methylcyclohexylgermylene, cyclotrimethylenegermylene, cyclotetramethylenegermylene, and cyclopentamethylenegermylene; carbylenes, and carbdiyls including methylene, dimethylmethylene, diethylmethylene, dibutylmethylene, dipropylmethylene, diphenylmethylene, ditolylmethylene, di(butylphenyl)methylene, di(trimethylsilylphenyl)methylene, dibenzylmethylene, cyclotetramethylenemethylene, cyclopentamethylenemethylene, ethylene, methylethylene, dimethylethylene, trimethylethylene, tetramethylethylene, cyclopropylene, cyclobutylene, cyclopentylene, cyclohexylene, propanediyl, methylpropanediyl, dimethylpropanediyl, trimethylpropanediyl, tetramethylpropanediyl, pentamethylpropanediyl, hexamethylpropanediyl, vinylene, and ethene-1,1-diyl; boranediyls including methylboranediyl, ethylboranediyl, propylboranediyl, butylboranediyl, pentylboranediyl, hexylboranediyl, cyclohexylboranediyl, and phenylboranediyl, and combinations thereof including dimethylsilylmethylene, diphenylsilylmethylene, dimethylsilylethylene, and methylphenylsilylmethylene.

Preferred examples for the bridging group G include $CH_2$, $CH_2CH_2$, $CH_2CH_2CH_2$, $CMe_2$, $SiMe_2$, $SiPh_2$, $SiMePh$, $Me_2SiSiMe_2$, $Me_2SiOSiMe_2$, $PhMeSiSiMePh$, $PhMeSiOSiMePh$, $Si(CH_2)_3$, and $Si(CH_2)_4$.

In some embodiments of the invention n is 1 or 2.

In some embodiments of the invention, the bridging group is preferably $CH_2CH_2$, $CH_2CH_2CH_2$, $SiMe_2$, $SiPh_2$, $SiMePh$, $Me_2SiSiMe_2$, $Me_2SiOSiMe_2$, $PhMeSiSiMePh$, $PhMeSiOSiMePh$, $Si(CH_2)_3$, and $Si(CH_2)_4$.

Suitable examples for X include chloride, bromide, fluoride, iodide, hydride, and $C_1$ to $C_{20}$ hydrocarbyls; preferably methyl, ethyl, propyl, butyl, pentyl, hexyl, phenyl, benzyl, and all isomers thereof, or two X together are selected from $C_4$ to $C_{10}$ dienes; preferably butadiene, methylbutadiene, pentadiene, methylpentadiene, dimethylpentadiene, hexadiene, methylhexadiene, dimethylhexadiene, or from $C_1$ to $C_{10}$ alkylidenes; preferably methylidene, ethylidene, propylidene, or from $C_3$ to $C_{10}$ alkyldiyls; preferably propandiyl, butandiyl, pentandiyl, and hexandiyl.

Preferred examples for X are chloride, methyl, and benzyl. Preferred examples of two X together are methylbutadiene, pentadiene, and methylpentadiene.

In some embodiments of the invention when b is 1, suitable examples for L include ethylene, propylene, butene, diethylether, tetrahydrofuran, furan, dimethylaniline, aniline, trimethylphosphine, trimethylamine, butylamine, lithium chloride, and the like.

In some embodiments of the invention b is 0 and L is absent.

Some invention embodiments select each $R^1$, $R^2$, $R^3$, $R^4$, $R^5$, and $R^6$ from hydrogen, a fluorine radical or hydrocarbyl radicals including methyl, ethyl, ethenyl, and all isomers (including cyclics such as cyclohexyl) of propyl, butyl, pentyl, hexyl, heptyl, octyl, nonyl, decyl, undecyl, dodecyl, propenyl, butenyl, and the like; and multiringed hydrocarbyls including norbornyl, adamantyl, and the like; and phenyl, and all isomers of hydrocarbyl-substituted phenyl including methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyl, and the like; and all isomers of benzyl, and all isomers of hydrocarbyl-substituted benzyl including methylbenzyl, dimethylbenzyl, and the like; and from halocarbyls and all isomers of halocarbyls, including perfluoropropyl, perfluorobutyl, perfluoroethyl, perfluoromethyl, and the like; and all isomers of halo-substituted phenyl (where halo is, independently, fluoro, chloro, bromo and iodo) including halophenyl, dihalophenyl, trihalophenyl, tetrahalophenyl, and pentahalophenyl, and the like; and all isomers of halo-substituted hydrocarbyl-substituted phenyl (where halo is, independently, fluoro, chloro, bromo and iodo) including halomethylphenyl, dihalomethylphenyl, (trifluoromethyl)phenyl, bis(trifluoromethyl)phenyl, and the like; and from substituted hydrocarbyl radicals and all isomers of substituted hydrocarbyl radicals including trimethylsilylpropyl, trimethylsilylmethyl, trimethylsilylethyl, methoxyphenyl, and the like.

In some embodiments of the invention, it is preferred that each $R^1$, $R^2$, $R^3$, $R^4$, $R^5$, or $R^6$ is selected from, hydrogen, fluoro, methyl, ethyl, n-propyl, iso-propyl, n-butyl, sec-butyl, iso-butyl, tert-butyl, pentyl, hexyl, cyclohexyl, phenyl, or trifluoromethyl.

In some embodiments $R^1$, $R^2$, $R^3$, $R^4$, $R^5$, or $R^6$ on adjacent atoms may join together to form a substituted or unsubstituted saturated, partially unsaturated or aromatic cyclic or polycyclic ring structure.

Some invention embodiments select each R' from hydrocarbyl radicals including methyl, ethyl, ethenyl, and all isomers (including cyclics such as cyclohexyl) of propyl, butyl, pentyl, hexyl, heptyl, octyl, nonyl, decyl, undecyl, dodecyl, propenyl, butenyl, and the like; and multiringed hydrocarbyls including norbornyl, adamantyl, and the like; and phenyl, and all isomers of hydrocarbyl substituted phenyl including methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyl, and the like; and all isomers of benzyl, and all isomers of hydrocarbyl substituted benzyl including methylbenzyl, dimethylbenzyl, and the like; and from halocarbyls and all isomers of halocarbyls including perfluoropropyl, perfluorobutyl, perfluoroethyl, perfluoromethyl, and the like; and all isomers of halo substituted phenyl (where halo is, independently, fluoro, chloro, bromo, and iodo) including halophenyl, dihalophenyl, trihalophenyl, tetrahalophenyl, and pentahalophenyl, and the like; and all isomers of halo substituted hydrocarbyl substituted phenyl (where halo is, independently, fluoro, chloro, bromo, and iodo) including halomethylphenyl, dihalomethylphenyl, (trifluoromethyl)phenyl, bis(trifluoromethyl)phenyl, and the like; and from substituted hydrocarbyl radicals and all isomers of substituted hydrocarbyl radicals including trimethylsilylpropyl, trimethylsilylmethyl, trimethylsilylethyl, methoxyphenyl, and the like.

In some embodiments, $R^2$ is preferably methyl and $R^1$, $R^3$, $R^4$, $R^5$, and $R^6$ are preferably hydrogen radicals, or $R^2$ is preferably methyl, $R^4$ is preferably fluoro and $R^1$, $R^3$, $R^5$, and $R^6$ are preferably hydrogen radicals.

In some embodiments of the invention, it is preferred that R' is selected from methyl, ethyl, n-propyl, iso-propyl, n-butyl, sec-butyl, iso-butyl, tert-butyl, pentyl, hexyl, cyclopentyl, cyclohexyl, cycloheptyl, cyclooctyl, cyclononyl, cyclodecyl, cycloundecyl, cyclododecyl, 2-norbornyl, 1-adamantyl, benzyl, phenyl, 2-methylphenyl, 3-methylphenyl, 4-methylphenyl, 3,5-dimethylphenyl, 3,5-diisopropylphenyl, 4-bromophenyl, 4-methoxyphenyl, or trifluoromethyl.

In some embodiments of the invention, it is preferred that R' is selected from tert-butyl, cyclopentyl, cyclohexyl, cyclododecyl, 2-norbornyl, 1-adamantyl, benzyl, phenyl, 2-methylphenyl, 3-methylphenyl, 4-methylphenyl, 3,5-dimethylphenyl, 3,5-diisopropylphenyl, 4-bromophenyl, or 4-methoxyphenyl.

A set of exemplary catalyst precursors is set out below. These are by way of example only and are not intended to list every catalyst precursor that is within the scope of the invention. In the following list, "metal" is titanium, zirconium, or hafnium, and while the dichloride species are listed, equally useful are the dimethyl analogs, for example, [ethylene(2-methylinden-4-yl)(methylamido)]titanium dimethyl.

Examples of useful pre-catalysts include:

[ethylene(2-methylinden-4-yl)(methylamido)]metal dichloride,
[ethylene(2-methylinden-4-yl)(isopropylamido)]metal dichloride,
[ethylene(2-methylinden-4-yl)(tert-butylamido)]metal dichloride,
[ethylene(2-methylinden-4-yl)(cyclopentylamido)]metal dichloride,
[ethylene(2-methylinden-4-yl)(norbornylamido)]metal dichloride,
[ethylene(2-methylinden-4-yl)(adamantyl)]metal dichloride,
[ethylene(2-methylinden-4-yl)(benzylamido)]metal dichloride,
[ethylene(2-methylinden-4-yl)(4-methylphenylamido)] metal dichloride,
[ethylene(2-methylinden-4-yl)(2-methylphenylamido)] metal dichloride,
[ethylene(2-methylinden-4-yl)(3,5-dimethylphenylamido)] metal dichloride,
[ethylene(2-methylinden-4-yl)(4-methoxyphenylamido)] metal dichloride,
[ethylene(2-methylinden-4-yl)(4-bromophenylamido)] metal dichloride,
[methylene(2-methylinden-4-yl)(methylamido)]metal dichloride,
[methylene(2-methylinden-4-yl)(isopropylamido)]metal dichloride,
[methylene(2-methylinden-4-yl)(tert-butylamido)]metal dichloride,
[methylene(2-methylinden-4-yl)(cyclopentylamido)]metal dichloride,
[methylene(2-methylinden-4-yl)(norbornylamido)]metal dichloride,
[methylene(2-methylinden-4-yl)(adamantyl)]metal dichloride,

[methylene(2-methylinden-4-yl)(benzylamido)]metal dichloride,
[methylene(2-methylinden-4-yl)(4-methylphenylamido)]metal dichloride,
[methylene(2-methylinden-4-yl)(2-methylphenylamido)]metal dichloride,
[methylene(2-methylinden-4-yl)(3,5-dimethylphenylamido)]metal dichloride,
[methylene(2-methylinden-4-yl)(4-methoxyphenylamido)]metal dichloride,
[methylene(2-methylinden-4-yl)(4-bromophenylamido)]metal dichloride,
[dimethylsilylene(2-methylinden-4-yl)(methylamido)]metal dichloride,
[dimethylsilylene(2-methylinden-4-yl)(isopropylamido)]metal dichloride,
[dimethylsilylene(2-methylinden-4-yl)(tert-butylamido)]metal dichloride,
[dimethylsilylene(2-methylinden-4-yl)(cyclopentylamido)]metal dichloride,
[dimethylsilylene(2-methylinden-4-yl)(norbornylamido)]metal dichloride,
[dimethylsilylene(2-methylinden-4-yl)(adamantyl)]metal dichloride,
[dimethylsilylene(2-methylinden-4-yl)(benzylamido)]metal dichloride,
[dimethylsilylene(2-methylinden-4-yl)(4-methylphenylamido)]metal dichloride,
[dimethylsilylene(2-methylinden-4-yl)(2-methylphenylamido)]metal dichloride,
[dimethylsilylene(2-methylinden-4-yl)(3,5-dimethylphenylamido)]metal dichloride,
[dimethylsilylene(2-methylinden-4-yl)(4-methoxyphenylamido)]metal dichloride,
[dimethylsilylene(2-methylinden-4-yl)(4-bromophenylamido)]metal dichloride,
[dimethylsilylene(2-methylinden-4-yl)(4-methylphenylamido)]metal dichloride,
[tetramethyldisilylene(2-methylinden-4-yl)(methylamido)]metal dichloride,
[tetramethyldisilylene(2-methylinden-4-yl)(isopropylamido)]metal dichloride,
[tetramethyldisilylene(2-methylinden-4-yl)(tert-butylamido)]metal dichloride,
[tetramethyldisilylene(2-methylinden-4-yl)(cyclopentylamido)]metal dichloride,
[tetramethyldisilylene(2-methylinden-4-yl)(norbornylamido)]metal dichloride,
[tetramethyldisilylene(2-methylinden-4-yl)(adamantyl)]metal dichloride,
[tetramethyldisilylene(2-methylinden-4-yl)(benzylamido)]metal dichloride,
[tetramethyldisilylene(2-methylinden-4-yl)(4-methylphenylamido)]metal dichloride,
[tetramethyldisilylene(2-methylinden-4-yl)(2-methylphenylamido)]metal dichloride,
[tetramethyldisilylene(2-methylinden-4-yl)(3,5-dimethylphenylamido)]metal dichloride,
[tetramethyldisilylene(2-methylinden-4-yl)(4-methoxyphenylamido)]metal dichloride,
[tetramethyldisilylene(2-methylinden-4-yl)(4-bromophenylamido)]metal dichloride,
[tetramethyldisilylene(2-methylinden-4-yl)(4-methylphenylamido)]metal dichloride,
[hexamethyltrisilylene(2-methylinden-4-yl)(methylamido)]metal dichloride,
[hexamethyltrisilylene(2-methylinden-4-yl)(isopropylamido)]metal dichloride,
[hexamethyltrisilylene(2-methylinden-4-yl)(tert-butylamido)]metal dichloride,
[hexamethyltrisilylene(2-methylinden-4-yl)(cyclopentylamido)]metal dichloride,
[hexamethyltrisilylene(2-methylinden-4-yl)(norbornylamido)]metal dichloride,
[hexamethyltrisilylene(2-methylinden-4-yl)(adamantyl)]metal dichloride,
[hexamethyltrisilylene(2-methylinden-4-yl)(benzylamido)]metal dichloride,
[hexamethyltrisilylene(2-methylinden-4-yl)(4-methylphenylamido)]metal dichloride,
[hexamethyltrisilylene(2-methylinden-4-yl)(2-methylphenylamido)]metal dichloride,
[hexamethyltrisilylene(2-methylinden-4-yl)(3,5-dimethylphenylamido)]metal dichloride,
[hexamethyltrisilylene(2-methylinden-4-yl)(4-methoxyphenylamido)]metal dichloride,
[hexamethyltrisilylene(2-methylinden-4-yl)(4-bromophenylamido)]metal dichloride,
[hexamethyltrisilylene(2-methylinden-4-yl)(4-methylphenylamido)]metal dichloride,
[tetramethyldisiloxylene(2-methylinden-4-yl)(methylamido)]metal dichloride,
[tetramethyldisiloxylene(2-methylinden-4-yl)(isopropylamido)]metal dichloride,
[tetramethyldisiloxylene(2-methylinden-4-yl)(tert-butylamido)]metal dichloride,
[tetramethyldisiloxylene(2-methylinden-4-yl)(cyclopentylamido)]metal dichloride,
[tetramethyldisiloxylene(2-methylinden-4-yl)(norbornylamido)]metal dichloride,
[tetramethyldisiloxylene(2-methylinden-4-yl)(adamantyl)]metal dichloride,
[tetramethyldisiloxylene(2-methylinden-4-yl)(benzylamido)]metal dichloride,
[tetramethyldisiloxylene(2-methylinden-4-yl)(4-methylphenylamido)]metal dichloride,
[tetramethyldisiloxylene(2-methylinden-4-yl)(2-methylphenylamido)]metal dichloride,
[tetramethyldisiloxylene(2-methylinden-4-yl)(3,5-dimethylphenylamido)]metal dichloride,
[tetramethyldisiloxylene(2-methylinden-4-yl)(4-methoxyphenylamido)]metal dichloride,
[tetramethyldisiloxylene(2-methylinden-4-yl)(4-bromophenylamido)]metal dichloride,
[tetramethyldisiloxylene(2-methylinden-4-yl)(4-methylphenylamido)]metal dichloride,
[ethylene(inden-4-yl)(methylamido)]metal dichloride,
[ethylene(inden-4-yl)(isopropylamido)]metal dichloride,
[ethylene(inden-4-yl)(tert-butylamido)]metal dichloride,
[ethylene(inden-4-yl)(cyclopentylamido)]metal dichloride,
[ethylene(inden-4-yl)(norbornylamido)]metal dichloride,
[ethylene(inden-4-yl)(adamantyl)]metal dichloride,
[ethylene(inden-4-yl)(benzylamido)]metal dichloride,
[ethylene(inden-4-yl)(4-methylphenylamido)]metal dichloride,
[ethylene(inden-4-yl)(2-methylphenylamido)]metal dichloride,
[ethylene(inden-4-yl)(3,5-dimethylphenylamido)]metal dichloride,
[ethylene(inden-4-yl)(4-methoxyphenylamido)]metal dichloride,
[ethylene(inden-4-yl)(4-bromophenylamido)]metal dichloride,

[methylene(inden-4-yl)(methylamido)]metal dichloride,
[methylene(inden-4-yl)(isopropylamido)]metal dichloride,
[methylene(inden-4-yl)(tert-butylamido)]metal dichloride,
[methylene(inden-4-yl)(cyclopentylamido)]metal dichloride,
[methylene(inden-4-yl)(norbornylamido)]metal dichloride,
[methylene(inden-4-yl)(adamantyl)]metal dichloride,
[methylene(inden-4-yl)(benzylamido)]metal dichloride,
[methylene(inden-4-yl)(4-methylphenylamido)]metal dichloride,
[methylene(inden-4-yl)(2-methylphenylamido)]metal dichloride,
[methylene(inden-4-yl)(3,5-dimethylphenylamido)]metal dichloride,
[methylene(inden-4-yl)(4-methoxyphenylamido)]metal dichloride,
[methylene(inden-4-yl)(4-bromophenylamido)]metal dichloride,
[dimethylsilylene(inden-4-yl)(methylamido)]metal dichloride,
[dimethylsilylene(inden-4-yl)(isopropylamido)]metal dichloride,
[dimethylsilylene(inden-4-yl)(tert-butylamido)]metal dichloride,
[dimethylsilylene(inden-4-yl)(cyclopentylamido)]metal dichloride,
[dimethylsilylene(inden-4-yl)(norbornylamido)]metal dichloride,
[dimethylsilylene(inden-4-yl)(adamantyl)]metal dichloride,
[dimethylsilylene(inden-4-yl)(benzylamido)]metal dichloride,
[dimethylsilylene(inden-4-yl)(4-methylphenylamido)]metal dichloride,
[dimethylsilylene(inden-4-yl)(2-methylphenylamido)]metal dichloride,
[dimethylsilylene(inden-4-yl)(3,5-dimethylphenylamido)]metal dichloride,
[dimethylsilylene(inden-4-yl)(4-methoxyphenylamido)]metal dichloride,
[dimethylsilylene(inden-4-yl)(4-bromophenylamido)]metal dichloride,
[dimethylsilylene(inden-4-yl)(4-methylphenylamido)]metal dichloride,
[tetramethyldisilylene(inden-4-yl)(methylamido)]metal dichloride,
[tetramethyldisilylene(inden-4-yl)(isopropylamido)]metal dichloride,
[tetramethyldisilylene(inden-4-yl)(tert-butylamido)]metal dichloride,
[tetramethyldisilylene(inden-4-yl)(cyclopentylamido)]metal dichloride,
[tetramethyldisilylene(inden-4-yl)(norbornylamido)]metal dichloride,
[tetramethyldisilylene(inden-4-yl)(adamantyl)]metal dichloride,
[tetramethyldisilylene(inden-4-yl)(benzylamido)]metal dichloride,
[tetramethyldisilylene(inden-4-yl)(4-methylphenylamido)]metal dichloride,
[tetramethyldisilylene(inden-4-yl)(2-methylphenylamido)]metal dichloride,
[tetramethyldisilylene(inden-4-yl)(3,5-dimethylphenylamido)]metal dichloride,
[tetramethyldisilylene(inden-4-yl)(4-methoxyphenylamido)]metal dichloride,
[tetramethyldisilylene(inden-4-yl)(4-bromophenylamido)]metal dichloride,
[tetramethyldisilylene(inden-4-yl)(4-methylphenylamido)]metal dichloride,
[hexamethyltrisilylene(inden-4-yl)(methylamido)]metal dichloride,
[hexamethyltrisilylene(inden-4-yl)(isopropylamido)]metal dichloride,
[hexamethyltrisilylene(inden-4-yl)(tert-butylamido)]metal dichloride,
[hexamethyltrisilylene(inden-4-yl)(cyclopentylamido)]metal dichloride,
[hexamethyltrisilylene(inden-4-yl)(norbornylamido)]metal dichloride,
[hexamethyltrisilylene(inden-4-yl)(adamantyl)]metal dichloride,
[hexamethyltrisilylene(inden-4-yl)(benzylamido)]metal dichloride,
[hexamethyltrisilylene(inden-4-yl)(4-methylphenylamido)]metal dichloride,
[hexamethyltrisilylene(inden-4-yl)(2-methylphenylamido)]metal dichloride,
[hexamethyltrisilylene(inden-4-yl)(3,5-dimethylphenylamido)]metal dichloride,
[hexamethyltrisilylene(inden-4-yl)(4-methoxyphenylamido)]metal dichloride,
[hexamethyltrisilylene(inden-4-yl)(4-bromophenylamido)]metal dichloride,
[hexamethyltrisilylene(inden-4-yl)(4-methylphenylamido)]metal dichloride,
[tetramethyldisiloxylene(inden-4-yl)(methylamido)]metal dichloride,
[tetramethyldisiloxylene(inden-4-yl)(isopropylamido)]metal dichloride,
[tetramethyldisiloxylene(inden-4-yl)(tert-butylamido)]metal dichloride,
[tetramethyldisiloxylene(inden-4-yl)(cyclopentylamido)]metal dichloride,
[tetramethyldisiloxylene(inden-4-yl)(norbornylamido)]metal dichloride,
[tetramethyldisiloxylene(inden-4-yl)(adamantyl)]metal dichloride,
[tetramethyldisiloxylene(inden-4-yl)(benzylamido)]metal dichloride,
[tetramethyldisiloxylene(inden-4-yl)(4-methylphenylamido)]metal dichloride,
[tetramethyldisiloxylene(inden-4-yl)(2-methylphenylamido)]metal dichloride,
[tetramethyldisiloxylene(inden-4-yl)(3,5-dimethylphenylamido)]metal dichloride,
[tetramethyldisiloxylene(inden-4-yl)(4-methoxyphenylamido)]metal dichloride,
[tetramethyldisiloxylene(inden-4-yl)(4-bromophenylamido)]metal dichloride,
[tetramethyldisiloxylene(inden-4-yl)(4-methylphenylamido)]metal dichloride,
[ethylene(7-fluoro-2-methylinden-4-yl)(methylamido)]metal dichloride,
[ethylene(7-fluoro-2-methylinden-4-yl)(isopropylamido)]metal dichloride,
[ethylene(7-fluoro-2-methylinden-4-yl)(tert-butylamido)]metal dichloride,
[ethylene(7-fluoro-2-methylinden-4-yl)(cyclopentylamido)]metal dichloride,
[ethylene(7-fluoro-2-methylinden-4-yl)(norbornylamido)]metal dichloride,
[ethylene(7-fluoro-2-methylinden-4-yl)(adamantyl)]metal dichloride,

[ethylene(7-fluoro-2-methylinden-4-yl)(benzylamido)]
metal dichloride,
[ethylene(7-fluoro-2-methylinden-4-yl)(4-methylphenylamido)]metal dichloride,
[ethylene(7-fluoro-2-methylinden-4-yl)(2-methylphenylamido)]metal dichloride,
[ethylene(7-fluoro-2-methylinden-4-yl)(3,5-dimethylphenylamido)]metal dichloride,
[ethylene(7-fluoro-2-methylinden-4-yl)(4-methoxyphenylamido)]metal dichloride,
[ethylene(7-fluoro-2-methylinden-4-yl)(4-bromophenylamido)]metal dichloride,
[methylene(7-fluoro-2-methylinden-4-yl)(methylamido)]
metal dichloride,
[methylene(7-fluoro-2-methylinden-4-yl)(isopropylamido)]
metal dichloride,
[methylene(7-fluoro-2-methylinden-4-yl)(tert-butylamido)]
metal dichloride,
[methylene(7-fluoro-2-methylinden-4-yl)(cyclopentylamido)]metal dichloride,
[methylene(7-fluoro-2-methylinden-4-yl)(norbornylamido)]
metal dichloride,
[methylene(7-fluoro-2-methylinden-4-yl)(adamantyl)]metal
dichloride,
[methylene(7-fluoro-2-methylinden-4-yl)(benzylamido)]
metal dichloride,
[methylene(7-fluoro-2-methylinden-4-yl)(4-methylphenylamido)]metal dichloride,
[methylene(7-fluoro-2-methylinden-4-yl)(2-methylphenylamido)]metal dichloride,
[methylene(7-fluoro-2-methylinden-4-yl)(3,5-dimethylphenylamido)]metal dichloride,
[methylene(7-fluoro-2-methylinden-4-yl)(4-methoxyphenylamido)]metal dichloride,
[methylene(7-fluoro-2-methylinden-4-yl)(4-bromophenylamido)]metal dichloride,
[dimethylsilylene(7-fluoro-2-methylinden-4-yl)(methylamido)]metal dichloride,
[dimethylsilylene(7-fluoro-2-methylinden-4-yl)(isopropylamido)]metal dichloride,
[dimethylsilylene(7-fluoro-2-methylinden-4-yl)(tert-butylamido)]metal dichloride,
[dimethylsilylene(7-fluoro-2-methylinden-4-yl)(cyclopentylamido)]metal dichloride,
[dimethylsilylene(7-fluoro-2-methylinden-4-yl)(norbornylamido)]metal dichloride,
[dimethylsilylene(7-fluoro-2-methylinden-4-yl)(adamantyl)]metal dichloride,
[dimethylsilylene(7-fluoro-2-methylinden-4-yl)(benzylamido)]metal dichloride,
[dimethylsilylene(7-fluoro-2-methylinden-4-yl)(4-methylphenylamido)]metal dichloride,
[dimethylsilylene(7-fluoro-2-methylinden-4-yl)(2-methylphenylamido)]metal dichloride,
[dimethylsilylene(7-fluoro-2-methylinden-4-yl)(3,5-dimethylphenylamido)]metal dichloride,
[dimethylsilylene(7-fluoro-2-methylinden-4-yl)(4-methoxyphenylamido)]metal dichloride,
[dimethylsilylene(7-fluoro-2-methylinden-4-yl)(4-bromophenylamido)]metal dichloride,
[dimethylsilylene(7-fluoro-2-methylinden-4-yl)(4-methylphenylamido)]metal dichloride,
[tetramethyldisilylene(7-fluoro-2-methylinden-4-yl)(methylamido)]metal dichloride,
[tetramethyldisilylene(7-fluoro-2-methylinden-4-yl)(isopropylamido)]metal dichloride,
[tetramethyldisilylene(7-fluoro-2-methylinden-4-yl)(tert-butylamido)]metal dichloride,
[tetramethyldisilylene(7-fluoro-2-methylinden-4-yl)(cyclopentylamido)]metal dichloride,
[tetramethyldisilylene(7-fluoro-2-methylinden-4-yl)(norbornylamido)]metal dichloride,
[tetramethyldisilylene(7-fluoro-2-methylinden-4-yl)(adamantyl)]metal dichloride,
[tetramethyldisilylene(7-fluoro-2-methylinden-4-yl)(benzylamido)]metal dichloride,
[tetramethyldisilylene(7-fluoro-2-methylinden-4-yl)(4-methylphenylamido)]metal dichloride,
[tetramethyldisilylene(7-fluoro-2-methylinden-4-yl)(2-methylphenylamido)]metal dichloride,
[tetramethyldisilylene(7-fluoro-2-methylinden-4-yl)(3,5-dimethylphenylamido)]metal dichloride,
[tetramethyldisilylene(7-fluoro-2-methylinden-4-yl)(4-methoxyphenylamido)]metal dichloride,
[tetramethyldisilylene(7-fluoro-2-methylinden-4-yl)(4-bromophenylamido)]metal dichloride,
[tetramethyldisilylene(7-fluoro-2-methylinden-4-yl)(4-methylphenylamido)]metal dichloride,
[hexamethyltrisilylene(7-fluoro-2-methylinden-4-yl)(methylamido)]metal dichloride,
[hexamethyltrisilylene(7-fluoro-2-methylinden-4-yl)(isopropylamido)]metal dichloride,
[hexamethyltrisilylene(7-fluoro-2-methylinden-4-yl)(tert-butylamido)]metal dichloride,
[hexamethyltrisilylene(7-fluoro-2-methylinden-4-yl)(cyclopentylamido)]metal dichloride,
[hexamethyltrisilylene(7-fluoro-2-methylinden-4-yl)(norbornylamido)]metal dichloride,
[hexamethyltrisilylene(7-fluoro-2-methylinden-4-yl)(adamantyl)]metal dichloride,
[hexamethyltrisilylene(7-fluoro-2-methylinden-4-yl)(benzylamido)]metal dichloride,
[hexamethyltrisilylene(7-fluoro-2-methylinden-4-yl)(4-methylphenylamido)]metal dichloride,
[hexamethyltrisilylene(7-fluoro-2-methylinden-4-yl)(2-methylphenylamido)]metal dichloride,
[hexamethyltrisilylene(7-fluoro-2-methylinden-4-yl)(3,5-dimethylphenylamido)]metal dichloride,
[hexamethyltrisilylene(7-fluoro-2-methylinden-4-yl)(4-methoxyphenylamido)]metal dichloride,
[hexamethyltrisilylene(7-fluoro-2-methylinden-4-yl)(4-bromophenylamido)]metal dichloride,
[hexamethyltrisilylene(7-fluoro-2-methylinden-4-yl)(4-methylphenylamido)]metal dichloride,
[tetramethyldisiloxylene(7-fluoro-2-methylinden-4-yl)(methylamido)]metal dichloride,
[tetramethyldisiloxylene(7-fluoro-2-methylinden-4-yl)(isopropylamido)]metal dichloride,
[tetramethyldisiloxylene(7-fluoro-2-methylinden-4-yl)(tert-butylamido)]metal dichloride,
[tetramethyldisiloxylene(7-fluoro-2-methylinden-4-yl)(cyclopentylamido)]metal dichloride,
[tetramethyldisiloxylene(7-fluoro-2-methylinden-4-yl)(norbornylamido)]metal dichloride,
[tetramethyldisiloxylene(7-fluoro-2-methylinden-4-yl)(adamantyl)]metal dichloride,
[tetramethyldisiloxylene(7-fluoro-2-methylinden-4-yl)(benzylamido)]metal dichloride,
[tetramethyldisiloxylene(7-fluoro-2-methylinden-4-yl)(4-methylphenylamido)]metal dichloride,
[tetramethyldisiloxylene(7-fluoro-2-methylinden-4-yl)(2-methylphenylamido)]metal dichloride,

[tetramethyldisiloxylene(7-fluoro-2-methylinden-4-yl)(3,5-dimethylphenylamido)]metal dichloride,
[tetramethyldisiloxylene(7-fluoro-2-methylinden-4-yl)(4-methoxyphenylamido)]metal dichloride,
[tetramethyldisiloxylene(7-fluoro-2-methylinden-4-yl)(4-bromophenylamido)]metal dichloride,
[tetramethyldisiloxylene(7-fluoro-2-methylinden-4-yl)(4-methylphenylamido)]metal dichloride,
[ethylene(5-tert-butyl-2-methylinden-7-yl)(methylamido)]metal dichloride,
[ethylene(5-tert-butyl-2-methylinden-7-yl)(isopropylamido)]metal dichloride,
[ethylene(5-tert-butyl-2-methylinden-7-yl)(tert-butylamido)]metal dichloride,
[ethylene(5-tert-butyl-2-methylinden-7-yl)(cyclopentylamido)]metal dichloride,
[ethylene(5-tert-butyl-2-methylinden-7-yl)(norbornylamido)]metal dichloride,
[ethylene(5-tert-butyl-2-methylinden-7-yl)(adamantyl)]metal dichloride,
[ethylene(5-tert-butyl-2-methylinden-7-yl)(benzylamido)]metal dichloride,
[ethylene(5-tert-butyl-2-methylinden-7-yl)(4-methylphenylamido)]metal dichloride,
[ethylene(5-tert-butyl-2-methylinden-7-yl)(2-methylphenylamido)]metal dichloride,
[ethylene(5-tert-butyl-2-methylinden-7-yl)(3,5-dimethylphenylamido)]metal dichloride,
[ethylene(5-tert-butyl-2-methylinden-7-yl)(4-methoxyphenylamido)]metal dichloride,
[ethylene(5-tert-butyl-2-methylinden-7-yl)(4-bromophenylamido)]metal dichloride,
[methylene(5-tert-butyl-2-methylinden-7-yl)(methylamido)]metal dichloride,
[methylene(5-tert-butyl-2-methylinden-7-yl)(isopropylamido)]metal dichloride,
[methylene(5-tert-butyl-2-methylinden-7-yl)(tert-butylamido)]metal dichloride,
[methylene(5-tert-butyl-2-methylinden-7-yl)(cyclopentylamido)]metal dichloride,
[methylene(5-tert-butyl-2-methylinden-7-yl)(norbornylamido)]metal dichloride,
[methylene(5-tert-butyl-2-methylinden-7-yl)(adamantyl)]metal dichloride,
[methylene(5-tert-butyl-2-methylinden-7-yl)(benzylamido)]metal dichloride,
[methylene(5-tert-butyl-2-methylinden-7-yl)(4-methylphenylamido)]metal dichloride,
[methylene(5-tert-butyl-2-methylinden-7-yl)(2-methylphenylamido)]metal dichloride,
[methylene(5-tert-butyl-2-methylinden-7-yl)(3,5-dimethylphenylamido)]metal dichloride,
[methylene(5-tert-butyl-2-methylinden-7-yl)(4-methoxyphenylamido)]metal dichloride,
[methylene(5-tert-butyl-2-methylinden-7-yl)(4-bromophenylamido)]metal dichloride,
[dimethylsilylene(5-tert-butyl-2-methylinden-7-yl)(methylamido)]metal dichloride,
[dimethylsilylene(5-tert-butyl-2-methylinden-7-yl)(isopropylamido)]metal dichloride,
[dimethylsilylene(5-tert-butyl-2-methylinden-7-yl)(tert-butylamido)]metal dichloride,
[dimethylsilylene(5-tert-butyl-2-methylinden-7-yl)(cyclopentylamido)]metal dichloride,
[dimethylsilylene(5-tert-butyl-2-methylinden-7-yl)(norbornylamido)]metal dichloride,
[dimethylsilylene(5-tert-butyl-2-methylinden-7-yl)(adamantyl)]metal dichloride,
[dimethylsilylene(5-tert-butyl-2-methylinden-7-yl)(benzylamido)]metal dichloride,
[dimethylsilylene(5-tert-butyl-2-methylinden-7-yl)(4-methylphenylamido)]metal dichloride,
[dimethylsilylene(5-tert-butyl-2-methylinden-7-yl)(2-methylphenylamido)]metal dichloride,
[dimethylsilylene(5-tert-butyl-2-methylinden-7-yl)(3,5-dimethylphenylamido)]metal dichloride,
[dimethylsilylene(5-tert-butyl-2-methylinden-7-yl)(4-methoxyphenylamido)]metal dichloride,
[dimethylsilylene(5-tert-butyl-2-methylinden-7-yl)(4-bromophenylamido)]metal dichloride,
[dimethylsilylene(5-tert-butyl-2-methylinden-7-yl)(4-methylphenylamido)]metal dichloride,
[tetramethyldisilylene(5-tert-butyl-2-methylinden-7-yl)(methylamido)]metal dichloride,
[tetramethyldisilylene(5-tert-butyl-2-methylinden-7-yl)(isopropylamido)]metal dichloride,
[tetramethyldisilylene(5-tert-butyl-2-methylinden-7-yl)(tert-butylamido)]metal dichloride,
[tetramethyldisilylene(5-tert-butyl-2-methylinden-7-yl)(cyclopentylamido)]metal dichloride,
[tetramethyldisilylene(5-tert-butyl-2-methylinden-7-yl)(norbornylamido)]metal dichloride,
[tetramethyldisilylene(5-tert-butyl-2-methylinden-7-yl)(adamantyl)]metal dichloride,
[tetramethyldisilylene(5-tert-butyl-2-methylinden-7-yl)(benzylamido)]metal dichloride,
[tetramethyldisilylene(5-tert-butyl-2-methylinden-7-yl)(4-methylphenylamido)]metal dichloride,
[tetramethyldisilylene(5-tert-butyl-2-methylinden-7-yl)(2-methylphenylamido)]metal dichloride,
[tetramethyldisilylene(5-tert-butyl-2-methylinden-7-yl)(3,5-dimethylphenylamido)]metal dichloride,
[tetramethyldisilylene(5-tert-butyl-2-methylinden-7-yl)(4-methoxyphenylamido)]metal dichloride,
[tetramethyldisilylene(5-tert-butyl-2-methylinden-7-yl)(4-bromophenylamido)]metal dichloride,
[tetramethyldisilylene(5-tert-butyl-2-methylinden-7-yl)(4-methylphenylamido)]metal dichloride,
[hexamethyltrisilylene(5-tert-butyl-2-methylinden-7-yl)(methylamido)]metal dichloride,
[hexamethyltrisilylene(5-tert-butyl-2-methylinden-7-yl)(isopropylamido)]metal dichloride,
[hexamethyltrisilylene(5-tert-butyl-2-methylinden-7-yl)(tert-butylamido)]metal dichloride,
[hexamethyltrisilylene(5-tert-butyl-2-methylinden-7-yl)(cyclopentylamido)]metal dichloride,
[hexamethyltrisilylene(5-tert-butyl-2-methylinden-7-yl)(norbornylamido)]metal dichloride,
[hexamethyltrisilylene(5-tert-butyl-2-methylinden-7-yl)(adamantyl)]metal dichloride,
[hexamethyltrisilylene(5-tert-butyl-2-methylinden-7-yl)(benzylamido)]metal dichloride,
[hexamethyltrisilylene(5-tert-butyl-2-methylinden-7-yl)(4-methylphenylamido)]metal dichloride,
[hexamethyltrisilylene(5-tert-butyl-2-methylinden-7-yl)(2-methylphenylamido)]metal dichloride,
[hexamethyltrisilylene(5-tert-butyl-2-methylinden-7-yl)(3,5-dimethylphenylamido)]metal dichloride,
[hexamethyltrisilylene(5-tert-butyl-2-methylinden-7-yl)(4-methoxyphenylamido)]metal dichloride,
[hexamethyltrisilylene(5-tert-butyl-2-methylinden-7-yl)(4-bromophenylamido)]metal dichloride,

[hexamethyltrisilylene(5-tert-butyl-2-methylinden-7-yl)(4-methylphenylamido)]metal dichloride,
[tetramethyldisiloxylene(5-tert-butyl-2-methylinden-7-yl)(methylamido)]metal dichloride,
[tetramethyldisiloxylene(5-tert-butyl-2-methylinden-7-yl)(isopropylamido)]metal dichloride,
[tetramethyldisiloxylene(5-tert-butyl-2-methylinden-7-yl)(tert-butylamido)]metal dichloride,
[tetramethyldisiloxylene(5-tert-butyl-2-methylinden-7-yl)(cyclopentylamido)]metal dichloride,
[tetramethyldisiloxylene(5-tert-butyl-2-methylinden-7-yl)(norbornylamido)]metal dichloride,
[tetramethyldisiloxylene(5-tert-butyl-2-methylinden-7-yl)(adamantyl)]metal dichloride,
[tetramethyldisiloxylene(5-tert-butyl-2-methylinden-7-yl)(benzylamido)]metal dichloride,
[tetramethyldisiloxylene(5-tert-butyl-2-methylinden-7-yl)(4-methylphenylamido)]metal dichloride,
[tetramethyldisiloxylene(5-tert-butyl-2-methylinden-7-yl)(2-methylphenylamido)]metal dichloride,
[tetramethyldisiloxylene(5-tert-butyl-2-methylinden-7-yl)(3,5-dimethylphenylamido)]metal dichloride,
[tetramethyldisiloxylene(5-tert-butyl-2-methylinden-7-yl)(4-methoxyphenylamido)]metal dichloride,
[tetramethyldisiloxylene(5-tert-butyl-2-methylinden-7-yl)(4-bromophenylamido)]metal dichloride,
[tetramethyldisiloxylene(5-tert-butyl-2-methylinden-7-yl)(4-methylphenylamido)]metal dichloride,
[ethylene(5-tert-butyl-2-ethylinden-7-yl)(methylamido)]metal dichloride,
[ethylene(5-tert-butyl-2-ethylinden-7-yl)(isopropylamido)]metal dichloride,
[ethylene(5-tert-butyl-2-ethylinden-7-yl)(tert-butylamido)]metal dichloride,
[ethylene(5-tert-butyl-2-ethylinden-7-yl)(cyclopentylamido)]metal dichloride,
[ethylene(5-tert-butyl-2-ethylinden-7-yl)(norbornylamido)]metal dichloride,
[ethylene(5-tert-butyl-2-ethylinden-7-yl)(adamantyl)]metal dichloride,
[ethylene(5-tert-butyl-2-ethylinden-7-yl)(benzylamido)]metal dichloride,
[ethylene(5-tert-butyl-2-ethylinden-7-yl)(4-methylphenylamido)]metal dichloride,
[ethylene(5-tert-butyl-2-ethylinden-7-yl)(2-methylphenylamido)]metal dichloride,
[ethylene(5-tert-butyl-2-ethylinden-7-yl)(3,5-dimethylphenylamido)]metal dichloride,
[ethylene(5-tert-butyl-2-ethylinden-7-yl)(4-methoxyphenylamido)]metal dichloride,
[ethylene(5-tert-butyl-2-ethylinden-7-yl)(4-bromophenylamido)]metal dichloride,
[methylene(5-tert-butyl-2-ethylinden-7-yl)(methylamido)]metal dichloride,
[methylene(5-tert-butyl-2-ethylinden-7-yl)(isopropylamido)]metal dichloride,
[methylene(5-tert-butyl-2-ethylinden-7-yl)(tert-butylamido)]metal dichloride,
[methylene(5-tert-butyl-2-ethylinden-7-yl)(cyclopentylamido)]metal dichloride,
[methylene(5-tert-butyl-2-ethylinden-7-yl)(norbornylamido)]metal dichloride,
[methylene(5-tert-butyl-2-ethylinden-7-yl)(adamantyl)]metal dichloride,
[methylene(5-tert-butyl-2-ethylinden-7-yl)(benzylamido)]metal dichloride,
[methylene(5-tert-butyl-2-ethylinden-7-yl)(4-methylphenylamido)]metal dichloride,
[methylene(5-tert-butyl-2-ethylinden-7-yl)(2-methylphenylamido)]metal dichloride,
[methylene(5-tert-butyl-2-ethylinden-7-yl)(3,5-dimethylphenylamido)]metal dichloride,
[methylene(5-tert-butyl-2-ethylinden-7-yl)(4-methoxyphenylamido)]metal dichloride,
[methylene(5-tert-butyl-2-ethylinden-7-yl)(4-bromophenylamido)]metal dichloride,
[dimethylsilylene(5-tert-butyl-2-ethylinden-7-yl)(methylamido)]metal dichloride,
[dimethylsilylene(5-tert-butyl-2-ethylinden-7-yl)(isopropylamido)]metal dichloride,
[dimethylsilylene(5-tert-butyl-2-ethylinden-7-yl)(tert-butylamido)]metal dichloride,
[dimethylsilylene(5-tert-butyl-2-ethylinden-7-yl)(cyclopentylamido)]metal dichloride,
[dimethylsilylene(5-tert-butyl-2-ethylinden-7-yl)(norbornylamido)]metal dichloride,
[dimethylsilylene(5-tert-butyl-2-ethylinden-7-yl)(adamantyl)]metal dichloride,
[dimethylsilylene(5-tert-butyl-2-ethylinden-7-yl)(benzylamido)]metal dichloride,
[dimethylsilylene(5-tert-butyl-2-ethylinden-7-yl)(4-methylphenylamido)]metal dichloride,
[dimethylsilylene(5-tert-butyl-2-ethylinden-7-yl)(2-methylphenylamido)]metal dichloride,
[dimethylsilylene(5-tert-butyl-2-ethylinden-7-yl)(3,5-dimethylphenylamido)]metal dichloride,
[dimethylsilylene(5-tert-butyl-2-ethylinden-7-yl)(4-methoxyphenylamido)]metal dichloride,
[dimethylsilylene(5-tert-butyl-2-ethylinden-7-yl)(4-bromophenylamido)]metal dichloride,
[dimethylsilylene(5-tert-butyl-2-ethylinden-7-yl)(4-methylphenylamido)]metal dichloride,
[tetramethyldisilylene(5-tert-butyl-2-ethylinden-7-yl)(methylamido)]metal dichloride,
[tetramethyldisilylene(5-tert-butyl-2-ethylinden-7-yl)(isopropylamido)]metal dichloride,
[tetramethyldisilylene(5-tert-butyl-2-ethylinden-7-yl)(tert-butylamido)]metal dichloride,
[tetramethyldisilylene(5-tert-butyl-2-ethylinden-7-yl)(cyclopentylamido)]metal dichloride,
[tetramethyldisilylene(5-tert-butyl-2-ethylinden-7-yl)(norbornylamido)]metal dichloride,
[tetramethyldisilylene(5-tert-butyl-2-ethylinden-7-yl)(adamantyl)]metal dichloride,
[tetramethyldisilylene(5-tert-butyl-2-ethylinden-7-yl)(benzylamido)]metal dichloride,
[tetramethyldisilylene(5-tert-butyl-2-ethylinden-7-yl)(4-methylphenylamido)]metal dichloride,
[tetramethyldisilylene(5-tert-butyl-2-ethylinden-7-yl)(2-methylphenylamido)]metal dichloride,
[tetramethyldisilylene(5-tert-butyl-2-ethylinden-7-yl)(3,5-dimethylphenylamido)]metal dichloride,
[tetramethyldisilylene(5-tert-butyl-2-ethylinden-7-yl)(4-methoxyphenylamido)]metal dichloride,
[tetramethyldisilylene(5-tert-butyl-2-ethylinden-7-yl)(4-bromophenylamido)]metal dichloride,
[tetramethyldisilylene(5-tert-butyl-2-ethylinden-7-yl)(4-methylphenylamido)]metal dichloride,
[hexamethyltrisilylene(5-tert-butyl-2-ethylinden-7-yl)(methylamido)]metal dichloride,
[hexamethyltrisilylene(5-tert-butyl-2-ethylinden-7-yl)(isopropylamido)]metal dichloride,

[hexamethyltrisilylene(5-tert-butyl-2-ethylinden-7-yl)(tert-butylamido)]metal dichloride,
[hexamethyltrisilylene(5-tert-butyl-2-ethylinden-7-yl)(cyclopentylamido)]metal dichloride,
[hexamethyltrisilylene(5-tert-butyl-2-ethylinden-7-yl)(norbornylamido)]metal dichloride,
[hexamethyltrisilylene(5-tert-butyl-2-ethylinden-7-yl)(adamantyl)]metal dichloride,
[hexamethyltrisilylene(5-tert-butyl-2-ethylinden-7-yl)(benzylamido)]metal dichloride,
[hexamethyltrisilylene(5-tert-butyl-2-ethylinden-7-yl)(4-methylphenylamido)]metal dichloride,
[hexamethyltrisilylene(5-tert-butyl-2-ethylinden-7-yl)(2-methylphenylamido)]metal dichloride,
[hexamethyltrisilylene(5-tert-butyl-2-ethylinden-7-yl)(3,5-dimethylphenylamido)]metal dichloride,
[hexamethyltrisilylene(5-tert-butyl-2-ethylinden-7-yl)(4-methoxyphenylamido)]metal dichloride,
[hexamethyltrisilylene(5-tert-butyl-2-ethylinden-7-yl)(4-bromophenylamido)]metal dichloride,
[hexamethyltrisilylene(5-tert-butyl-2-ethylinden-7-yl)(4-methylphenylamido)]metal dichloride,
[tetramethyldisiloxylene(5-tert-butyl-2-ethylinden-7-yl)(methylamido)]metal dichloride,
[tetramethyldisiloxylene(5-tert-butyl-2-ethylinden-7-yl)(isopropylamido)]metal dichloride,
[tetramethyldisiloxylene(5-tert-butyl-2-ethylinden-7-yl)(tert-butylamido)]metal dichloride,
[tetramethyldisiloxylene(5-tert-butyl-2-ethylinden-7-yl)(cyclopentylamido)]metal dichloride,
[tetramethyldisiloxylene(5-tert-butyl-2-ethylinden-7-yl)(norbornylamido)]metal dichloride,
[tetramethyldisiloxylene(5-tert-butyl-2-ethylinden-7-yl)(adamantyl)]metal dichloride,
[tetramethyldisiloxylene(5-tert-butyl-2-ethylinden-7-yl)(benzylamido)]metal dichloride,
[tetramethyldisiloxylene(5-tert-butyl-2-ethylinden-7-yl)(4-methylphenylamido)]metal dichloride,
[tetramethyldisiloxylene(5-tert-butyl-2-ethylinden-7-yl)(2-methylphenylamido)]metal dichloride,
[tetramethyldisiloxylene(5-tert-butyl-2-ethylinden-7-yl)(3,5-dimethylphenylamido)]metal dichloride,
[tetramethyldisiloxylene(5-tert-butyl-2-ethylinden-7-yl)(4-methoxyphenylamido)]metal dichloride,
[tetramethyldisiloxylene(5-tert-butyl-2-ethylinden-7-yl)(4-bromophenylamido)]metal dichloride, and
[tetramethyldisiloxylene(5-tert-butyl-2-ethylinden-7-yl)(4-methylphenylamido)]metal dichloride.

The following useful compounds are exemplified in the experimental section:

[ethylene(2-methylinden-4-yl)(methylamido)]titanium dichloride (aka [$\eta^5$:$\eta^1$-N-methyl-2-(2-methylinden-4-yl)ethanamido]titanium dichloride, compound A),

[ethylene(2-methylinden-4-yl)(isopropylamido)]titanium dichloride (aka [$\eta^5$:$\eta^1$-N-isopropyl-2-(2-methylinden-4-yl)ethanamido]titanium dichloride, compound B),

[ethylene(2-methylinden-4-yl)(benzylamido)]titanium dichloride (aka [$\eta^5$:$\eta^1$-N-benzyl-2-(2-methylinden-4-yl)ethanamido]titanium dichloride, compound C),

[ethylene(2-methylinden-4-yl)(tert-butylamido)]titanium dichloride (aka [$\eta^5$:$\eta^1$-N-tert-butyl-2-(2-methylinden-4-yl)ethanamido]titanium dichloride, compound D),

[methylene(2-methylinden-4-yl)(4-methylphenylamido)]titanium dichloride (aka {$\eta^5$:$\eta^1$-[(2-methylinden-4-yl)methyl](4-methylphenyl)amido}titaniumdichloride, compound E)

[methylene(inden-4-yl)(4-methylphenylamido)]titanium dichloride (aka {$\eta^5$:$\eta^1$-[(inden-4-yl)methyl](4-methylphenyl)amido}titanium dichloride, compound F),

[dimethylsilylene(2-methylinden-4-yl)(cyclopentylamido)]titanium dichloride (aka {$\eta^5$:$\eta^1$-N-cyclopentyl-1,1-dimethyl-1-(2-methylinden-4-yl)silanamido}titanium dichloride, compound G),

[dimethylsilylene(2-methylinden-4-yl)(tert-butylamido)]titanium dichloride (aka {$\eta^5$:$\eta^1$-N-tert-butyl-1,1-dimethyl-1-(2-methylinden-4-yl)silanamido}titanium dichloride, compound H),

[dimethylsilylene(2-methylinden-4-yl)(tert-butylamido)](tetrahydrofurano)zirconium dichloride (aka {$\eta^5$:$\eta^1$-N-tert-butyl-1,1-dimethyl-1-(2-methylinden-4-yl)silanamido}(tetrahydrofurano)zirconiumdichloride, compound I),

[dimethylsilylene(2-methylinden-4-yl)(4-methoxyphenylamido)]titanium dichloride (aka {$\eta^5$:$\eta^1$-N-(4-methoxyphenyl)-1,1-dimethyl-1-(2-methylinden-4-yl)silanamido}titanium dichloride, compound J),

[dimethylsilylene(2-methylinden-4-yl)(3,5-dimethylphenylamido)]titanium dichloride (aka {$\eta^5$:$\eta^1$-N-(3,5-dimethylphenyl)-1,1-dimethyl-1-(2-methylinden-4-yl)silanamido}titanium dichloride, compound K),

[dimethylsilylene(2-methylinden-4-yl)(4-methylphenylamido)]titanium dichloride (aka {$\eta^5$:$\eta^1$-N-(4-methylphenyl)-1,1-dimethyl-1-(2-methylinden-4-yl)silanamido}titanium dichloride, compound L),

[dimethylsilylene(2-methylinden-4-yl)(4-methylphenylamido)]{(2-methylinden-4-yl)dimethylsilylene(4-methylphenylamine)}zirconium dichloride (aka {$\eta^5$:$\eta^1$-N-(4-methylphenyl)-1,1-dimethyl-1-(2-methylinden-4-yl)silanamido}{$\eta^5$-N-(4-methylphenyl)-1,1-dimethyl-1-(2-methylinden-4-yl)silanamine}(chlorido)zirconium, compound M),

[dimethylsilylene(2-methylinden-4-yl)(4-bromophenylamido)]titanium dichloride (aka {$\eta^5$:$\eta^1$-N-(4-bromophenyl)-1,1-dimethyl-1-(2-methylinden-4-yl)silanamido}titanium dichloride, compound N),

[dimethylsilylene(5-tert-butyl-2-methylinden-7-yl)(4-methylphenylamido)]titanium dichloride (aka ({$\eta^5$:$\eta^1$-1-(5-tert-butyl-2-methylinden-7-yl)-1,1-dimethyl-N-(4-methylphenyl)silanamido}titaniumdichloride, compound O),

[tetramethyldisilylene(2-methylinden-7-yl)(4-methylphenylamido)]titanium dichloride (aka {$\eta^5$:$\eta^1$-(4-methylphenyl)[1,1,2,2-tetramethyl-2-(2-methylinden-7-yl)disilanyl]-amido}titaniumdichloride, compound P),

[tetramethyldisilylene(2-methylinden-7-yl)(2-methylphenylamido)]titanium dichloride (aka {$\eta^5$:$\eta^1$-(2-methylphenyl) [1,1,2,2-tetramethyl-2-(2-methylinden-7-yl)disilanyl]-amido}-titaniumdichloride, compound Q),

[tetramethyldisilylene(7-fluoro-2-methylinden-4-yl)(tert-butylamido)]titanium dichloride (aka {$\eta^5$:$\eta^1$-N-(tert-butyl)-2-(7-fluoro-2-methylinden-4-yl)-1,1,2,2-tetramethyldisilamido}titaniumdichloride, compound R),

[tetramethyldisilylene(7-fluoro-2-methylinden-4-yl)(4-methylphenylamido)]titanium dichloride (aka {$\eta^5$:$\eta^1$-2-(7-fluoro-2-methylinden-4-yl)-1,1,2,2-tetramethyl-N-(4-methylphenyl)disilanamido}titanium dichloride, compound S),

[tetramethyldisilylene(7-fluoro-2-methylinden-4-yl)(3,5-dimethylphenylamido)]titanium dichloride (aka {$\eta^5$:$\eta^1$-2-(7-fluoro-2-methylinden-4-yl)-1,1,2,2-tetramethyl-N-(3,5-dimethylphenyl)disilanamido}titaniumdichloride, compound T),

[tetramethyldisilylene(7-fluoro-2-methylinden-4-yl)(cyclopentylamido)]titanium dichloride (aka {$\eta^5$:$\eta^1$-N-cyclopentyl-2-(7-fluoro-2-methylinden-4-yl)-1,1,2,2-tetramethyldisilanamido}titanium dichloride, compound U), and

[tetramethyldisilylene(5-tert-butyl-2-ethylinden-7-yl)(2-methylphenylamido)]titanium dichloride (aka {$\eta^5$:$\eta^1$-2-

(5-tert-butyl-2-ethylinden-7-yl)-1,1,2,2-tetramethyl-N-(2-methylphenyl)disilanamido}titanium dichloride, compound V).

Transition Metal Compound Synthesis

Metallocene precursor ligands wherein the bridging group (G, which is denoted as Y in Generic Reaction Scheme 1, below) contains one or more silicon, germanium and/or boron atom(s) directly bonded to the indenyl ligand and to the heteroatom (J, which is denoted as E in Generic Reaction Scheme 1) can be prepared by reacting a 4-bromo substituted indene with magnesium followed by a silicon, germanium and/or boron containing dihalide. The subsequent reaction to add on the heteroatom involves reacting the above reaction product with a lithiated amine or phosphine or alternatively two equivalents of a primary amine or phosphine. Examples of such reactions are illustrated below in Generic Reaction Scheme 1.

Generic Reaction Scheme 1: Formation of a metallocene precursor ligand wherein the atom(s) in the direct chain and bonded to the indenyl ligand and to the heteroatom (J) are chosen from silicon, germanium, and/or boron:

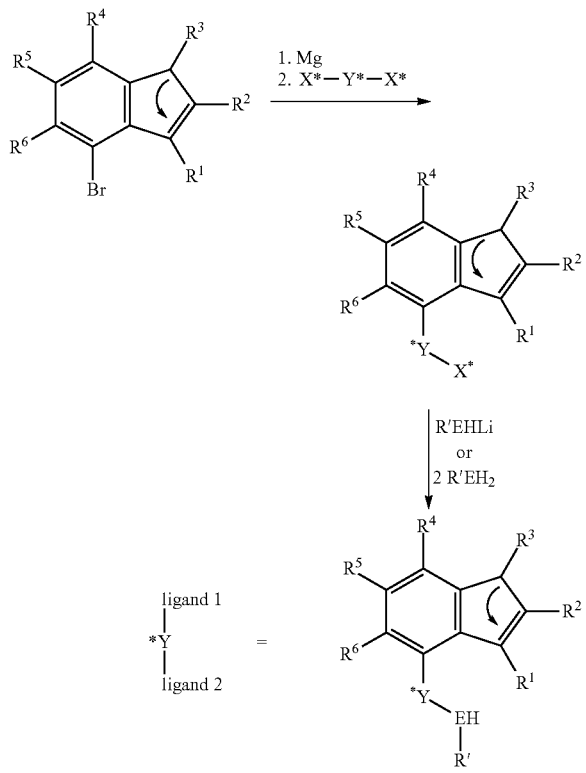

and wherein $R^1$, $R^2$, $R^3$, $R^4$, $R^5$, $R^6$, and R' are as previously defined for Formula (1) and (2) above, E is nitrogen or phosphorus, Y* is the bridging group G (as defined above for Formula (1) and (2)), preferably Y* is $R''_2Si$, $R''_2Ge$, $R''_2SiSiR''_2$, $R''_2SiCR''_2SiR''_2$, $R''_2SiSiR''_2SiR''_2$, $R''_2GeGeR''_2$, $R''_2GeCR''_2GeR''_2$, $R''_2SiGeR''_2$, $R''B$, $R''_2Si$—O—$SiR''_2$, and $R''_2Ge$—O—$GeR_{12}$, where R'' is as previously defined for Formula (1) and (2), and X* is halide, preferably chloro or bromo.

In the discussion herein in the term "ligand 1-Y*-ligand 2", such as used above in general Reaction Scheme 1, ligand 1 means the indenyl portion of formula (1) and (2) bonded to G and M, e.g.,

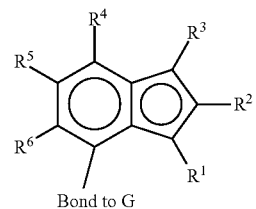

Bond to G where $R^1$, $R^2$, $R^3$, $R^4$, $R^5$, and $R^6$ are as previously defined for Formula (1) and (2) above, and ligand 2 means the heteroatom portion of Formula (1) and (2) bonded to G and M, e.g., $-J(R)_m$.

Metallocene precursor ligands wherein the bridging group (G in Formula (1) and (2) above or Y* in the generic reaction schemes), contains two carbon atom(s) directly bonded to the indenyl ligand and to the heteroatom (J) can be prepared by reacting a 4-bromo substituted indene with magnesium followed by a substituted or unsubstituted N-(p-tosyl)aziridine. The subsequent reaction to add on the substituent on the heteroatom involves reacting the above reaction product with $Cs_2CO_3$ followed by a hydrocarbyl halide. Examples of such reactions are illustrated below in Generic Reaction Scheme 2

Generic Reaction Scheme 2: Formation of a metallocene precursor ligand wherein two carbon atom(s) are in the direct chain and bonded to both the indenyl ligand and to the heteroatom (J):

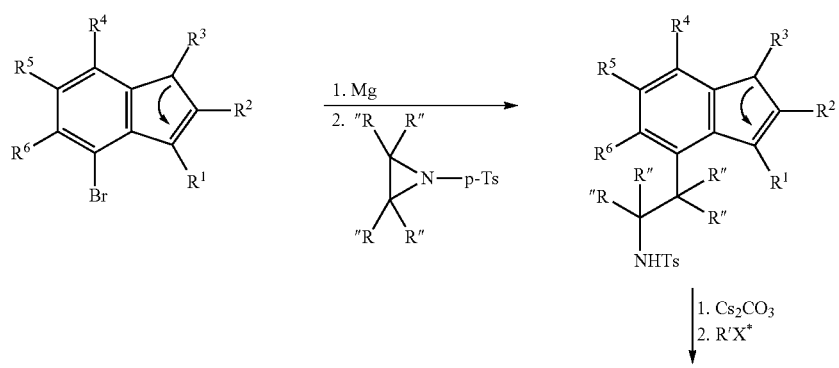

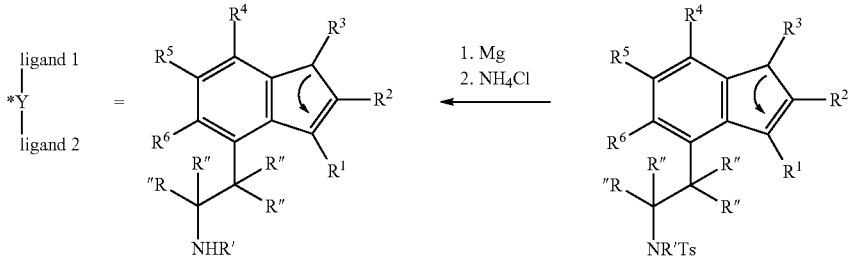

and wherein $R^1$, $R^2$, $R^3$, $R^4$, $R^5$, $R^6$, $R'$ and $R''$ are as previously defined for Formula (1) and (2) above, $X^*$ is halide, preferably chloro or iodo, Ts is tosyl, and the bridging group, $Y^*$, is $R''_2CCR''_2$ as illustrated in Generic Reaction Scheme 2.

An alternate preparation of metallocene precursor ligands wherein the bridging group contains two carbon atom(s) directly bonded to the indenyl ligand and to the heteroatom (J) is illustrated in Generic Reaction Scheme 3.

Generic Reaction Scheme 3: Formation of a metallocene precursor ligand wherein two carbon atom(s) are in the direct chain and bonded to both the indenyl ligand and to the heteroatom (J):

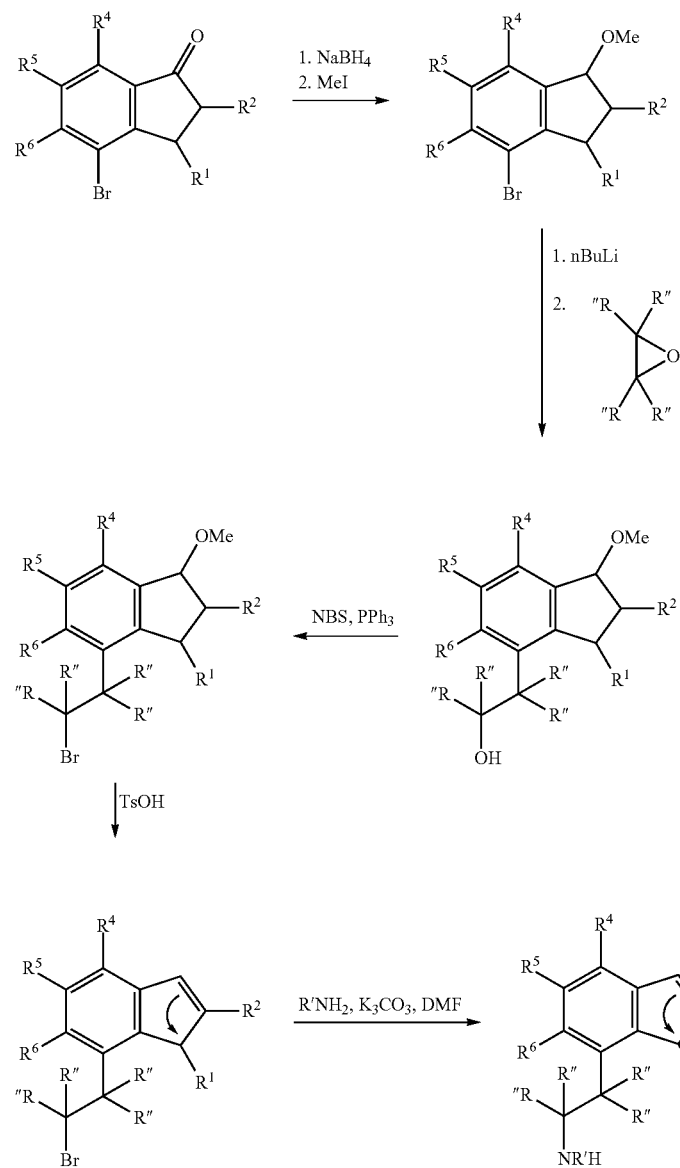

and wherein $R^1$, $R^2$, $R^4$, $R^5$, $R^6$, R' and R" are as previously defined for Formula (1) and (2) above. Y* is $R''_2CCR''_2$ as illustrated in Generic Reaction Scheme 3.

Metallocene precursor ligands wherein the bridging group contains one carbon atom directly bonded to the indenyl ligand and to the heteroatom (J) can be prepared as illustrated in Generic Reaction Scheme 4.

Generic Reaction Scheme 4: Formation of a ligand wherein one carbon atom is in the direct chain and bonded to both the indenyl ligand and to the heteroatom (J):

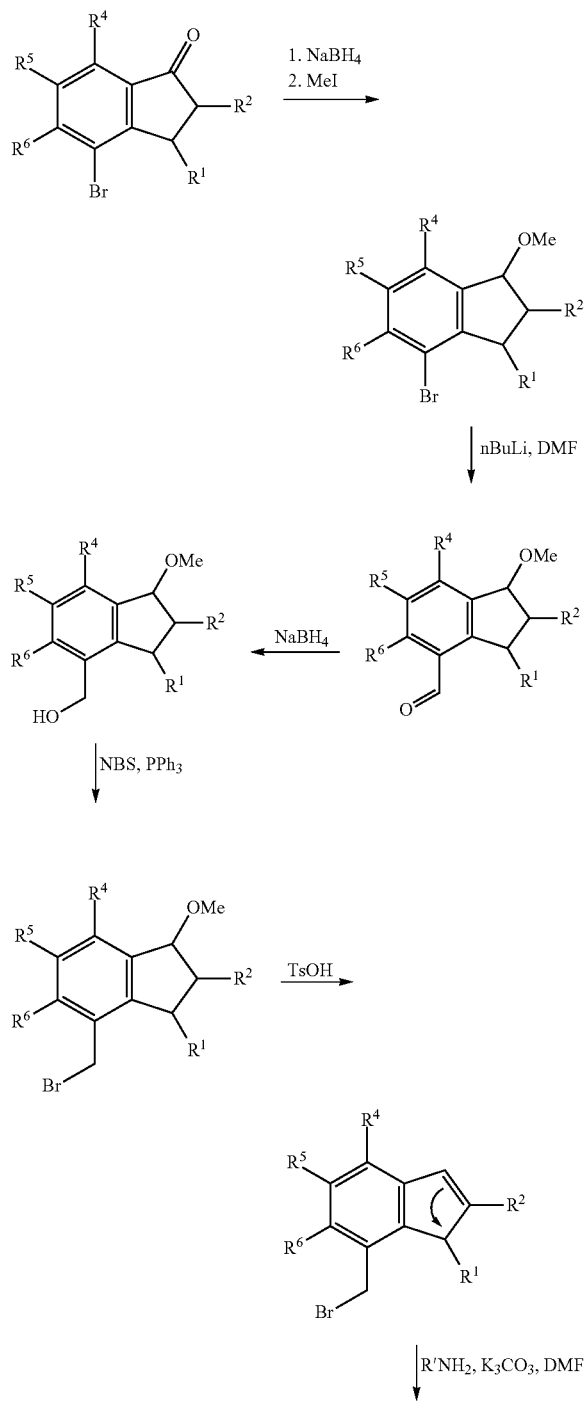

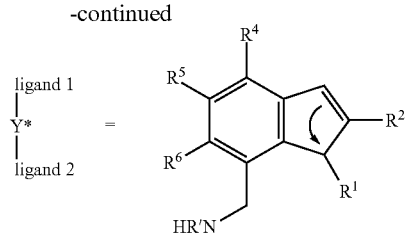

and wherein $R^1$, $R^2$, $R^4$, $R^5$, $R^6$, and R' are as previously defined for Formula (1) and (2) above. Y* is $CH_2$ as illustrated in Generic Reaction Scheme 4.

The metallocene precursor ligands (ligand 1-Y*-ligand 2 as defined above), typically are converted to a dianionic metallocene precursor ligands or a reactive metallocene precursor ligands prior to reaction with a transition metal compound to form an invention catalyst precursor compound. Non-limiting examples of these reactions are illustrated in Generic Reaction Schemes A through E where ligand 1 and ligand 2 have the same definition as defined in Generic Reaction Schemes 1 through 4 above, Y* is as previously defined above in Generic Reaction Schemes 1 through 4, R* is hydrocarbyl, preferably alkyl, more preferably methyl or butyl; R** is, independently, substituted or unsubstituted hydrocarbyl, X* is halide, preferably chloro or bromo, $M^1$ is a Group 1 atom and is preferably lithium, $M^2$ is a Group 2 atom and is preferably magnesium, M is a Group 3, 4, 5, or 6 transition metal atom, preferably a Group 4 transition metal atom selected from titanium, zirconium, or hafnium and most preferably titanium, $R^\#$ is a hydrocarbyl and is preferably methyl, ethyl, propyl, or butyl, Sn is tin, and Si is silicon.

Metallation reactions between a dianionic metallocene precursor ligand and a transition metal compound, preferably a transition metal halide, are illustrated in Generic Reaction Schemes F through H.

Metallation reactions between a reactive metallocene precursor ligand and a transition metal compound, preferably a transition metal halide, are illustrated in Generic Reaction Schemes I through J.

Metallation reactions between a metallocene precursor ligand and a transition metal amide are illustrated in Generic Reaction Scheme K. The resulting metallocene diamide can be used as a catalyst precursor or can be converted to a metallocene dihalide by reaction with HX* where H is hydrogen and X* is halide.

Generic Reaction Scheme A: Reaction of a metallocene precursor ligand with a Group 1 metal hydrocarbyl compound to form a dianionic metallocene precursor ligand. For this reaction, $M^1$ is preferably lithium and R* is preferably n-butyl or methyl.

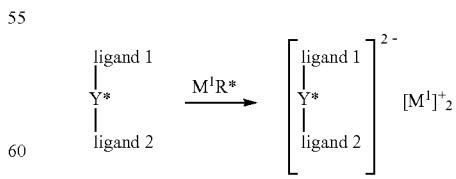

Generic Reaction Scheme B: Reaction of a metallocene precursor ligand with a Group 2 metal hydrocarbyl compound to form a dianionic metallocene precursor ligand. In this reaction $M^2$ is preferably magnesium, and R* is preferably methyl, ethyl, propyl, or butyl.

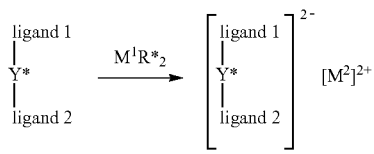

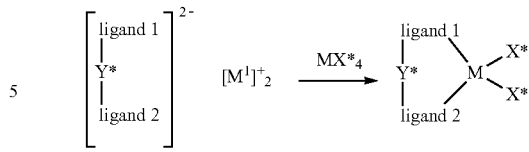

Generic Reaction Scheme C: Reaction of a metallocene precursor ligand with a Group 2 hydrocarbyl halide (a Grignard reagent) to form a dianionic metallocene precursor ligand. In this reaction $M^2$ is preferably magnesium, $R^*$ is preferably methyl, ethyl, propyl, or butyl, and $X^*$ is preferably chloride or bromide.

Generic Reaction Scheme G: Reaction of a cationic Group 2 metal stabilized dianionic metallocene precursor ligand with a transition metal halide to form a metallocene. In this reaction $M^2$ is preferably magnesium, M is preferably titanium, zirconium, or hafnium, and $X^*$ is preferably chloride.

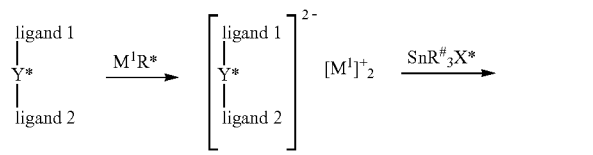

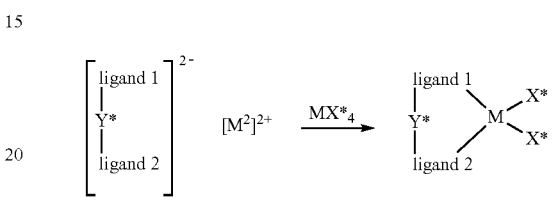

Generic Reaction Scheme H: Reaction of a cationic Group 2 halide stabilized dianionic metallocene precursor ligand with a metal halide to form a metallocene. In this reaction $M^2$ is preferably magnesium, M is preferably titanium, zirconium, or hafnium, and $X^*$ is preferably chloride or bromide.

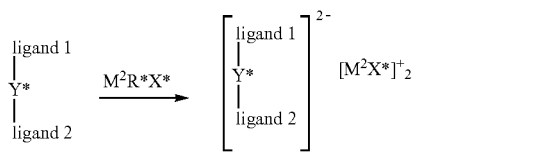

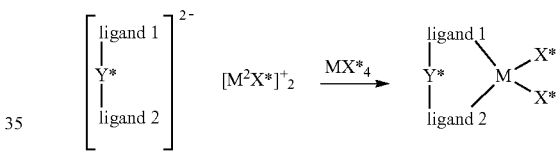

Generic Reaction Scheme D: Reaction of a metallocene precursor ligand with a Group 1 hydrocarbyl compound followed by reaction with a trihydrocarbyltin halide to form reactive metallocene precursor ligand. In this reaction $M^1$ is preferably lithium, $R^*$ is preferably n-butyl or methyl, $R^\#$ is preferably methyl, ethyl, propyl, or butyl with ethyl being most preferred, and $X^*$ is preferably chloride.

Generic Reaction Scheme E: Reaction of a metallocene precursor ligand with a Group 1 hydrocarbyl compound followed by reaction with a trihydrocarbylsilicon halide to form reactive metallocene precursor ligand. In this reaction $M^1$ is preferably lithium, $R^*$ is preferably n-butyl or methyl, $R^\#$ is preferably methyl, ethyl, propyl, or butyl with methyl being most preferred, and $X^*$ is preferably chloride.

Generic Reaction Scheme I: Reaction of a trihydrocarbyltin based reactive metallocene precursor ligand with a metal halide to form a metallocene In this reaction M is preferably titanium, zirconium, or hafnium, $R^\#$ is preferably methyl, ethyl, propyl, or butyl with ethyl being most preferred, and $X^*$ is preferably chloride.

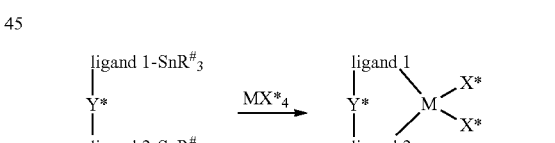

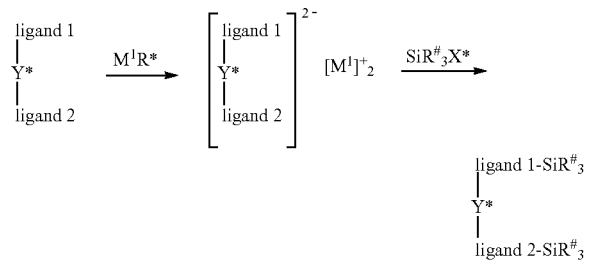

Generic Reaction Scheme J: Reaction of a trihydrocarbylsilicon based reactive metallocene precursor ligand with a metal halide to form a metallocene. In this reaction M is preferably titanium, zirconium, or hafnium, $R^\#$ is preferably methyl, ethyl, propyl, or butyl with methyl being most preferred, and $X^*$ is preferably chloride.

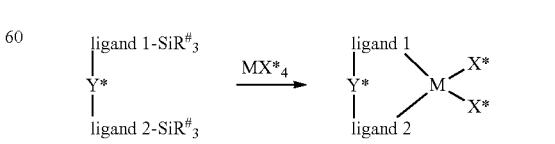

Generic Reaction Scheme F: Reaction of a cationic Group 1 metal stabilized dianionic metallocene precursor ligand with a metal halide to form a metallocene. In this reaction $M^1$ is preferably lithium, M is preferably titanium, zirconium, or hafnium, and $X^*$ is preferably chloride.

Generic Reaction Scheme K: Reaction of a metallocene precursor ligand with a metal amide to form a metallocene diamide which optionally can further be reacted with an acid halide to from a metallocene dihalide. In this reaction M is preferably titanium, zirconium, or hafnium, R** is preferably methyl, ethyl, propyl, or butyl, and X* is preferably chloride.

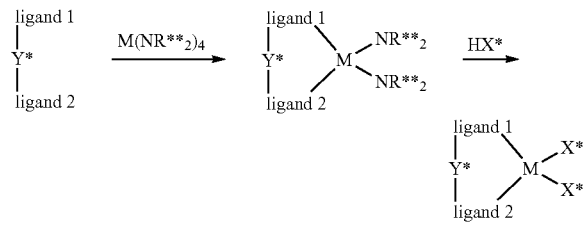

Metallocene halides formed in Generic Reaction Schemes F though K can readily be converted to metallocene dialkyls by one of several well known routes. For example, the metallocene dihalide can be reacted with two equivalents of methyl lithium, of methyl magnesium bromide to form the corresponding metallocene dimethyl complex. Other lithiated or Grinard reagents can be used to make other metallocene dihydrocarbyls, for example, two equivalents of benzyl magnesium bromide can be reacted with a metallocene dihalide to form a metallocene dibenzyl complex.

More specifically, the compounds described herein can be made by the following four general synthetic routes (A-D):

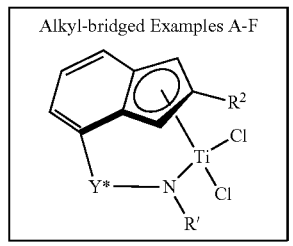

A.

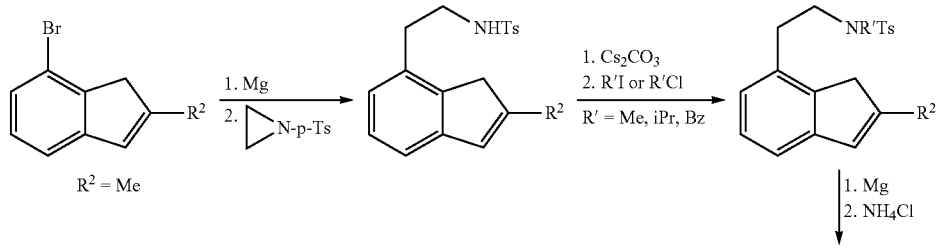

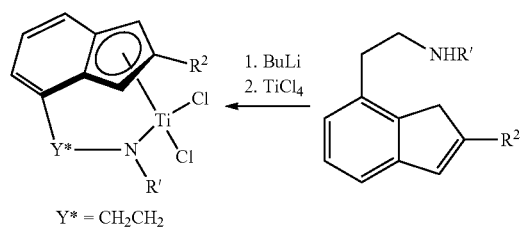

B.

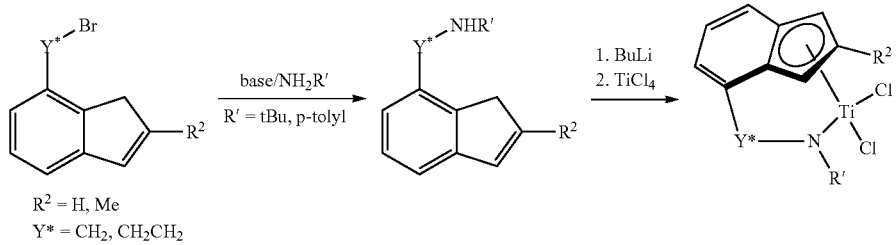

-continued
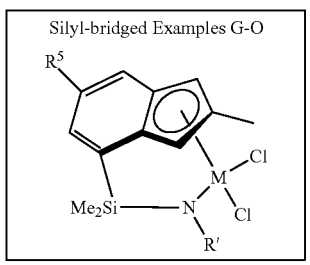
C.
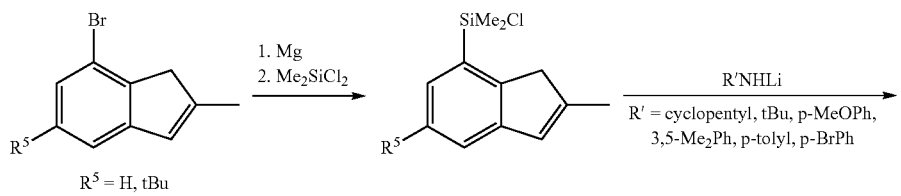
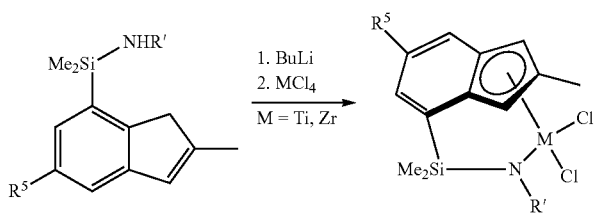
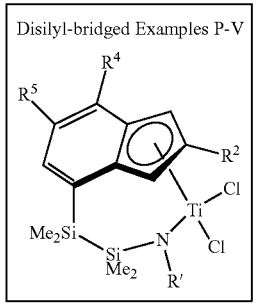
D.
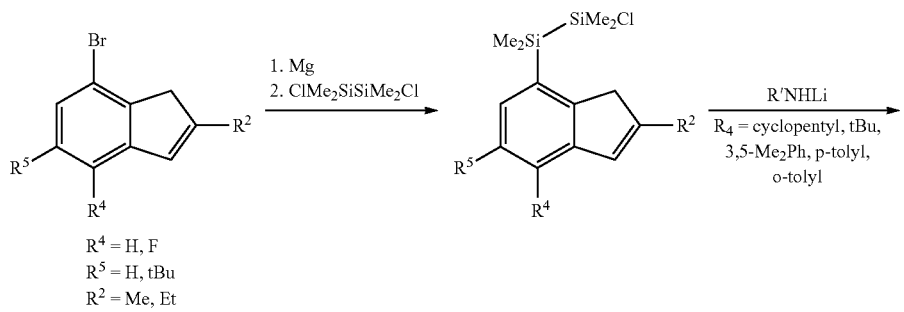
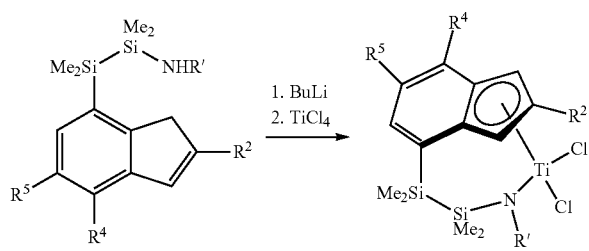
where R', Y*, and R² are as defined above for Formula (1) and (2), unless otherwise noted.

Mixed Catalysts

Mixed catalyst systems can also be used, for example, the invention catalyst can be used in conjunction with a "second catalyst" in the same reactor or in a series of reactors where the invention catalyst produces oligomers, macromers, or polymers with olefinic end-groups, and the "second catalyst" incorporates these oligomers, macromers, or polymers into a polymer backbone as a copolymer with other monomers, such as ethylene, propylene, butene, and other $C_2$ to $C_{20}$ olefins. Alternatively, the invention catalyst can be used in conjunction with a second catalyst in the same reactor or in a series of reactors where the second catalyst produces oligomers, macromers, or polymers with olefinic end-groups, and the invention catalyst incorporates these oligomers, macromers, or polymers into a polymer backbone as a copolymer with other monomers, such as ethylene, propylene, butene, and other $C_2$ to $C_{20}$ olefins. The "second catalyst" can be of the same family as the invention catalyst or can be from a completely different catalyst family. Likewise, the invention catalyst can be used in conjunction with a "second catalyst" in the same reactor or in a series of reactors where the invention catalyst and the "second catalyst" produces mixtures or blends of polymers.

Invention polymerization catalyst systems can comprise additional olefin polymerization catalysts, sometimes referred to as the "second catalyst." These additional olefin polymerization catalysts are any of those well known in the art to catalyze the olefin to polyolefin reaction. Some invention catalysts systems include Group-4-6 metallocenes as additional olefin polymerization catalysts. Metallocenes include (un)bridged compounds containing one (mono(cyclopentadienyl) metallocenes) or two (bis(cyclopentadienyl) metallocenes) (un)substituted cyclopentadienyl ligand(s). In bridged metallocenes, a single, cyclopentadienyl ligand connects to a heteroatom ligand with both coordinating to the metal center or two cyclopentadienyl ligands connect together with both cyclopentadienyl ligands coordinating to the metal center. Typical catalysts and their precursors are well known in the art. Suitable description appears in the patent literature, for example, U.S. Pat. Nos. 4,871,705; 4,937,299; 5,324,800; EP-A-0418044; EP-A-0591756; WO-A-92/00333; and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means comprising at least two different monomers) are essentially those disclosed in WO-A-92/00333; WO 97/44370; and U.S. Pat. Nos. 5,001,205; 5,057,475; 5,198,401; 5,304,614; 5,308,816; and 5,324,800. Selection of metallocene compounds for isotactic or syndiotactic polypropylene blend production, and their syntheses, are well-known in the patent and academic literature, e.g., *Journal of Organometallic Chemistry* 369, 359-370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: mono-cyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5-10 transition-metal centers are known and can serve as the additional olefin polymerization catalysts with invention catalyst systems.

Invention catalyst systems can use non-cyclopentadienyl, Group-4-5 precursor compounds as the additional olefin polymerization catalysts. Non-cyclopentadienyl, Group-4-5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (III) Alkyne Derivatives", D. H. McConville, et al, *Organometallics,* 1995, 14, 3154-3156. U.S. Pat. No. 5,318,935 describes bridged and unbridged, bis-amido catalyst compounds of Group-4 metals capable of α-olefins polymerization. Bridged bis(arylamido) Group-4 compounds for olefin polymerization are described by D. H. McConville, et al., in *Organometallics* 1995, 14, 5478-5480. Synthetic methods and compound characterization are presented. Further work appearing in D. H. McConville, et al, *Macromolecules* 1996, 29, 5241-5243, describes bridged bis (arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408,050, filed 29 Sep. 1999, and its equivalent PCT/US99/22690. A monoanionic bidentate ligand and two monoanionic ligands stabilize those catalyst precursors; they are activable with this invention's ionic cocatalysts. Other suitable Group-4-5 non-metallocene catalysts are bimetallocyclic catalyst compounds comprising two independently selected Group-4-5 metal atoms directly linked through two bridging groups to form cyclic compounds.

Invention catalyst systems can use transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, J. Am. Chem. Soc., 1995, 117, 6414-6415, WO 96/23010 and WO 97/02298. See additionally the related bis(imino) Group-8 and -9 organometallic compounds described by V. C. Gibson and others in "Novel olefin polymerization catalysts based on iron and cobalt," Chem. Commun., 849-850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

In another embodiment, diethyl zinc is used in combination with two or more catalyst compounds described herein. In another embodiment, any scavenger as described herein is used in combination with two or more catalyst compounds described herein.

Activators and Catalyst Activation

In addition to the catalyst precursor described above, the catalyst system employed in the present process employs an activator preferably selected from alumoxanes, such as methyl alumoxane, modified methyl alumoxane, ethyl alumoxane, iso-butyl alumoxane, and the like; neutral activators such as triphenyl boron, tris-perfluorophenyl boron, tris-perfluoronaphthylboron, tris-perfluorophenyl aluminum, and the like; and ionic activators such as N,N-dimethylanilinium tetrakis perfluorophenyl borate, triphenyl carbonium tetrakis perfluorophenyl borate, N,N-dimethylanilinium tetrakis perfluoronaphthyl borate, N,N-dimethylanilinium tetrakis perfluorophenyl aluminate, and the like.

A co-activator is a compound capable of alkylating the transition metal complex, such that when used in combination with an activator, an active catalyst is formed. Co-activators include alumoxanes, such as methyl alumoxane, modified alumoxanes, such as modified methyl alumoxane, and aluminum alkyls, such as trimethyl aluminum, tri-isobutyl aluminum, triethyl aluminum, and tri-isopropyl aluminum. Co-activators are typically only used in combination with neutral activators and ionic activators when the pre-catalyst is not a dihydrocarbyl or dihydride complex.

The alumoxane component useful as an activator typically is an oligomeric aluminum compound represented by the general formula $(R^x\text{—}Al\text{—}O)_n$, which is a cyclic compound, or $R^x(R^x\text{—}Al\text{—}O)_n AlR^x_2$, which is a linear compound. In the general alumoxane formula, $R^x$ is, independently, a $C_1\text{-}C_{20}$ alkyl radical, for example, methyl, ethyl, propyl, butyl, pentyl, isomers thereof, and the like; and "n" is an integer from 1-50. Most preferably, $R^x$ is methyl and "n" is at least 4. Methyl alumoxane and modified methyl alumoxanes are most preferred. For further descriptions see, EP 0 279 586; EP 0 594 218; EP 0 561 476; WO94/10180; and U.S. Pat. Nos. 4,665,208; 4,874,734; 4,908,463; 4,924,018; 4,952,540; 4,968,827; 5,041,584; 5,091,352; 5,103,031; 5,157,137; 5,204,419; 5,206,199; 5,235,081; 5,248,801; 5,329,032; 5,391,793; and 5,416,229.

When an alumoxane or modified alumoxane is used, the pre-catalyst (all pre-catalysts)-to-activator molar ratio is from about 1:3000-10:1; alternatively 1:2000-10:1; alternatively 1:1000-10:1; alternatively 1:500-1:1; alternatively 1:300-1:1; alternatively 1:200-1:1; alternatively 1:100-1:1; alternatively 1:50-1:1; alternatively 1:10-1:1. When the activator is an alumoxane (modified or unmodified), some embodiments select the maximum amount of activator at a 5000-fold molar excess over the pre-catalyst (per metal catalytic site). The preferred minimum activator-to-pre-catalyst-ratio is 1:1 molar ratio.

NCA activators (at times used in combination with a co-activator) may be used in the practice of this invention. Preferably, discrete ionic activators such as $[Me_2PhNH][B(C_6F_5)_4]$, $[Ph_3C][B(C_6F_5)_4]$, $[Me_2PhNH][B((C_6H_3\text{-}3,5\text{-}(CF_3)_2))_4]$, $[Ph_3C][B((C_6H_3\text{-}3,5\text{-}(CF_3)_2))_4]$, $[NH_4][B(C_6H_5)_4]$, $[Me_2PhNH][B(C_{10}F_7)_4]$, $[Ph_3C][B(C_{10}F_7)_4]$, or neutral activators such as $B(C_6F_5)_3$, $B(C_{10}F_7)_3$, or $B(C_6H_5)_3$ can be used (where $C_6F_5$ is perfluorophenyl, $C_{10}F_7$ is perfluoronaphthyl, $C_6H_3\text{-}3,5\text{-}(CF_3)_2$ is 3.5-bis(trifluoromethyl)phenyl). Preferred co-activators, when used, are alumoxanes, such as methyl alumoxane, modified alumoxanes, such as modified methyl alumoxane, and aluminum alkyls, such as tri-isobutyl aluminum, and trimethyl aluminum.

It is within the scope of this invention to use one or more type of NCA activators, which may be neutral or ionic, such as tri (n-butyl) ammonium tetrakis (pentafluorophenyl) borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459).

Activated ionic catalysts can be prepared by reacting a transition metal compound (pre-catalyst) with a neutral activator, such as $B(C_6F_6)_3$, which upon reaction with the hydrolyzable ligand (X) of the transition metal compound forms an anion, such as $([B(C_6F_5)_3(X)]^-)$, which stabilizes the cationic transition metal species generated by the reaction.

Examples of neutral NCA activators include tri-substituted boron, tellurium, aluminum, gallium, and indium, or mixtures thereof. The three substituent groups are each independently selected from alkyls, alkenyls, halogen, substituted alkyls, aryls, arylhalides, alkoxy, and halides. Preferably, the three groups are independently selected from halogen, mono, or multicyclic (including halosubstituted) aryls, alkyls, and alkenyl compounds, and mixtures thereof, preferred are alkenyl groups having 1-20 carbon atoms, alkyl groups having 1-20 carbon atoms, alkoxy groups having 1-20 carbon atoms, and aryl groups having 3-20 carbon atoms (including substituted aryls). More preferably, the three groups are alkyls having 1-4 carbon groups, phenyl, naphthyl, or mixtures thereof. Even more preferably, the three groups are halogenated, preferably fluorinated, aryl groups. Most preferably, the neutral NCA activator is trisperfluorophenyl boron or trisperfluoronaphthyl boron.

Ionic NCA activator compounds may contain an active proton or some other cation associated with, but not coordinated to, or only loosely coordinated to, the remaining ion of the ionizing compound. Such compounds and the like, are described in European publications EP-A-0 570 982; EP-A-0 520 732; EP-A-0 495 375; EP-B1-0 500 944; EP-A-0 277 003; EP-A-0 277 004; and U.S. Pat. Nos. 5,153,157; 5,198,401; 5,066,741; 5,206,197; 5,241,025; 5,384,299; 5,502,124; and U.S. Ser. No. 08/285,380, filed Aug. 3, 1994; all of which are herein fully incorporated by reference. In this case, the ionic activator reacts with the transition metal compound (pre-catalyst) to form a cationic transition metal species, an anion, and byproduct(s). The byproducts are defined by the cation associated with the ionic NCA activator used.

Compounds useful as an ionic NCA activator comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles, and the like. Two classes of compatible non-coordinating anions have been disclosed in EP-A-0 277 003 and EP-A-0 277 004 published 1988: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the ionic NCA activators include a cation and an anion component, and may be represented by the following formula:

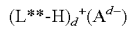

$$(L^{**}\text{-}H)_d^+(A^{d-})$$

wherein $L^{}$ is a neutral Lewis base; H is hydrogen; $(L^{}\text{-}H)^+$ is a Bronsted acid; $A^{d-}$ is a non-coordinating anion having the charge d−; d is an integer from 1-3.

The cation component, $(L^{**}\text{-}H)_d^+$ may include Bronsted acids such as protons or protonated Lewis bases or reducible Lewis acids capable of protonating or abstracting a moiety, such as an alkyl or aryl, from the pre-catalyst after alkylation.

The activating cation $(L^{}\text{-}H)_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether, diethyl ether, tetrahydrofuran, and dioxane, sulfoniums from thioethers, such as diethyl thioethers and tetrahydrothiophene, and mixtures thereof. The activating cation $(L^{}-H)_d^+$ may also be a moiety such as silver, tropylium, carbeniums, ferroceniums, and mixtures thereof, preferably carboniums and ferroceniums; most preferably triphenyl carbonium.

The anion component $A^{d-}$ include those having the formula $[M^{k+}Q_n]^{d-}$ wherein k is an integer from 1-3; n is an integer from 2-6; n−k=d; M is an element selected from group 13 of the Periodic Table of the Elements, preferably boron or aluminum; and Q is, independently, a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl having 1-20 carbon atoms, more preferably, each Q is a fluorinated aryl group, and most preferably, each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of ionic NCA activators which may be used as an activator in the preparation of the catalysts of this invention include tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl) ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(tert-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl) borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene (diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium) tetrakis(3,5-bis(trifluoromethyl)phenyl)borate.

Most preferably, the ionic NCA activator is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate, or triphenylcarbenium tetra(perfluorophenyl) borate.

The catalyst precursors employed in the present process can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst pre-cursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal complex cation in the sense of balancing its ionic charge at +1, and yet retain sufficient lability to permit displacement by an ethylenically or acetylenically unsaturated monomer during polymerization. These types of cocatalysts sometimes use scavengers, such as, but not limited to, tri-iso-butyl aluminum, tri-n-octyl aluminum, tri-n-hexyl aluminum, triethylaluminum, or trimethylaluminum.

The present process also can employ cocatalyst compounds or activator compounds that are initially neutral Lewis acids but form a cationic metal complex and a noncoordinating anion, or a zwitterionic complex upon reaction with the alkylated transition metal compounds. The alkylated transition metal compound is formed from the reaction of the catalyst pre-cursor and the co-activator. For example, tris(pentafluorophenyl)boron or aluminum act to abstract a hydrocarbyl ligand to yield an invention cationic transition metal complex and stabilizing noncoordinating anion, see EP-A-0 427 697 and EP-A-0 520 732 for illustrations of analogous group 4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See, in particular, the review article by E. Y.-X. Chen and T. J. Marks, "Cocatalysts for Metal-Catalyzed Olefin Polymerization: Activators, Activation Processes, and Structure-Activity Relationships", Chem. Rev., 100, 1391-1434 (2000).

When the cations of noncoordinating anion precursors are Bronsted acids such as protons or protonated Lewis bases (excluding water) or reducible Lewis acids, such as ferrocenium or silver cations or alkali or alkaline earth metal cations, such as those of sodium, magnesium, or lithium, the catalyst-precursor-to-activator molar ratio may be any ratio. Combinations of the described activator compounds may also be used for activation.

When an NCA activator is used, the pre-catalyst (all pre-catalysts)-to-activator molar ratio is from 1:10-1:1; 1:10-10:1; 1:10-2:1; 1:10-3:1; 1:10-5:1; 1:2-1.2:1; 1:2-10:1; 1:2-2:1; 1:2-3:1; 1:2-5:1; 1:3-1.2:1; 1:3-10:1; 1:3-2:1; 1:3-3:1; 1:3-5:1; 1:5-1:1; 1:5-10:1; 1:5-2:1; 1:5-3:1; 1:5-5:1; 1:1-1:1.2. The pre-catalyst-to-co-activator molar ratio is from 1:100-100:1; 1:75-75:1; 1:50-50:1; 1:25-25:1; 1:15-15:1; 1:10-10:1; 1:5-5:1, 1:2-2:1; 1:100-1:1; 1:75-1:1; 1:50-1:1; 1:25-1:1; 1:15-1:1; 1:10-1:1; 1:5-1:1; 1:2-1:1; 1:10-2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl)boron, and mixtures of trimethyl aluminum or triethyl aluminum or triisobutyl aluminum or tri-n-octylaluminum with dimethylanilinium tetrakis(pentafluorophenyl)borate or tris(pentafluorophenyl)boron or dimethylanilinium tetrakis(perfluoronaphthyl)borate. Particularly preferred, activator/co-activator combinations include tri-n-octylaluminum with dimethylanilinium tetrakis(pentafluorophenyl)borate, tri-n-octylaluminum with dimethylanilinium tetrakis(perfluoronaphthyl)borate, and methylalumoxane with dimethylanilinium tetrakis(pentafluorophenyl)borate.

In some embodiments, scavenging compounds are used with NCA activators. Typical aluminum or boron alkyl components useful as scavengers are represented by the general formula $R^xJZ_2$, where J is aluminum or boron, $R^x$ is a $C_1$-$C_{20}$ alkyl radical, for example, methyl, ethyl, propyl, butyl, pentyl, isomers thereof, and each Z is, independently, Rx or a different univalent anionic ligand such as halogen (Cl, Br, I), alkoxide (OW), and the like. Most preferred, aluminum alkyls include triethylaluminum, diethylaluminum chloride, tri-isobutylaluminum, tri-n-octylaluminum, tri-n-hexylaluminum, trimethylaluminum, and the like. Preferred boron alkyls include triethylboron. Scavenging compounds may also be alumoxanes and modified alumoxanes including methylalumoxane and modified methylalumoxane.

Monomers

In a preferred embodiment the catalyst compounds of this invention are used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methylpentene-1, 3-methylpentene-1, 3,5,5-trimethylhexene-1, and 5-ethylnonene-1.

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene, and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha-omega-diene monomers (i.e., di-vinyl monomers). More preferably, the diolefin monomers are linear di-vinyl monomers, most preferably, those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene; particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene, or higher ring containing diolefins with or without substituents at various ring positions.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and/or butene are prepared. A preferred feedstock for the oligomerization process is the alpha-olefin, ethylene. But other alpha-olefins, including, but not limited to, propylene and 1-butene, may also be used alone or combined with ethylene. Preferred alpha-olefins include any $C_2$ to $C_{40}$ alpha-olefin, preferably any $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha-omega-dienes are used alone or in combination with mono-alpha olefins.

In a preferred embodiment, the process described herein may be used to produce homopolymers or copolymers. Preferred polymers produced herein include homopolymers or copolymers of any of the above monomers. In a preferred embodiment, the polymer is a homopolymer of any $C_2$ to $C_{12}$ alpha-olefin. Preferably, the polymer is a homopolymer of ethylene or a homopolymer of propylene. In another embodiment, the polymer is a copolymer comprising ethylene and one or more of any of the monomers listed above. In another embodiment, the polymer is a copolymer comprising propylene and one or more of any of the monomers listed above. In another preferred embodiment, the homopolymers or copolymers described additionally comprise one or more diolefin comonomers, preferably one or more $C_4$ to $C_{40}$ diolefins.

In another preferred embodiment, the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably, the polymer produced herein is a copolymer of ethylene and one or more of propylene, butene, pentene, hexene, heptene, octene, nonene, decene, dodecene, 4-methylpentene-1, 3-methylpentene-1, 3,5,5-trimethylhexene-1, cyclopentene, 4-methylcyclopentene, cyclohexene, and 4-methylcyclohexene.

In another preferred embodiment, the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably, the polymer produced herein is a copolymer of propylene and one or more of ethylene, butene, pentene, hexene, heptene, octene, nonene, decene, dodecene, 4-methylpentene-1, 3-methylpentene-1, and 3,5,5-trimethylhexene-1.

In a preferred embodiment, the polymer produced herein is a homopolymer of norbornene or a copolymer of norbornene and a substituted norbornene, including polar functionalized norbornenes.

In a preferred embodiment, the copolymers described herein comprise at least 50 mole % of a first monomer and up to 50 mole % of other monomers.

In a preferred embodiment, the polymers described above further comprise one or more dienes at up to 10 wt %, preferably at 0.00001 wt % to 1.0 wt %, preferably 0.002 wt % to 0.5 wt %, even more preferably 0.003 wt % to 0.2 wt %, based upon the total weight of the composition. In some embodiments, 500 ppm or less of diene is added to the polymerization, preferably 400 ppm or less, preferably 300 ppm or less. In other embodiments, at least 50 ppm of diene is added to the polymerization, or 100 ppm or more, or 150 ppm or more.

Polymerization Processes

Invention catalyst complexes are useful in polymerizing unsaturated monomers conventionally known to undergo metallocene-catalyzed polymerization such as solution, slurry, gas-phase, and high-pressure polymerization. Typically, one or more transition metal compounds, one or more activators, and one or more monomers are contacted to produce polymer. These catalysts may be supported and, as such, will be particularly useful in the known, fixed-bed, moving-bed, fluid-bed, slurry, solution, or bulk operating modes conducted in single, series, or parallel reactors.

One or more reactors in series or in parallel may be used in the present invention. The transition metal compound, activator, and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin.

Ethylene polymers can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69-6895 kPa) and the polymerization diluent temperature will typically be between −10° C. and 160° C. The process can be carried out in a stirred tank reactor or a tubular reactor, or more than one reactor operated in series or in parallel. See the general disclosure of U.S. Pat. No. 5,001,205 for general process conditions. All documents are incorporated by reference for description of polymerization processes, ionic activators and useful scavenging compounds.

The invention catalyst compositions can be used individually or can be mixed with other known polymerization catalysts to prepare polymer blends. Monomer and catalyst selection allows polymer blend preparation under conditions analogous to those using individual catalysts. Polymers having increased Mw/Mn for improved processing and other traditional benefits available from polymers made with mixed catalyst systems can thus be achieved.

Generally, when using invention catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157; 5,241,025; and WO-A-91/09882; WO-A-94/03506; WO-A-93/14132; and WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, [Me$_2$HNPh]$^+$[B(pfp)$_4$]$^-$ or B(pfp)$_3$ (perfluorophenyl=pfp=$C_6F_5$).

In terms of polymer density, the polymers capable of production in accordance the invention, can range from about 0.85 g/cc to about 0.95 g/cc, preferably from 0.87 g/cc to 0.93 g/cc, more preferably 0.89 g/cc to 0.920 g/cc. Polymer molecular weights can range from about 3000 g/mol Mn to about 4,000,000 g/mol Mn or greater. Molecular weight distributions can range from about 1.1 to about 80.0, with molecular weight distributions from 1.2 to about 12.0 being more typical. Pigments, antioxidants, and other additives, as are known in the art, may be added to the polymer.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399; 4,588,790; 5,028,670; 5,317,036; 5,352, 749; 5,405,922; 5,436,304; 5,453,471; 5,462,999; 5,616,661; and 5,668,228; all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to 110° C., and most preferably in the range of from about 70° C. to about 95° C. In another embodiment, when high density polyethylene is desired then the reactor temperature is typically between 70° C. and 105° C.

The productivity of the catalyst or catalyst system in a gas phase system is influenced by the partial pressure of the main monomer. The preferred mole percent of the main monomer, ethylene, or propylene, preferably ethylene, is from about 25 mole % to 90 mole % and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11, 300 Kg/hr), still more preferably greater than 35,000 lbs/hr (15,900 Kg/hr), still even more preferably greater than 50,000 lbs/hr (22,700 Kg/hr), and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627, 242; 5,665,818; 5,677,375; European publications EP-A-0 794 200; EP-A-0 802 202; and EP-B-634 421; all of which are herein fully incorporated by reference.

In another preferred embodiment, the catalyst system is in liquid form and is introduced into the gas phase reactor into a resin particle lean zone. For information on how to introduce a liquid catalyst system into a fluidized bed polymerization into a particle lean zone, please see U.S. Pat. No. 5,693,727; which is incorporated by reference herein.

Slurry Phase Polymerization

A slurry polymerization process generally operates between about 1 to about 50 atmosphere pressure range (15 psig to 735 psig, 103 kPa to 5068 kPa) or even greater and temperatures in the range of about 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in, for instance, U.S. Pat. No. 3,248,179; which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484; which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and a temperature in the range of about 60° C. to about 104° C., depending on the desired polymer melting characteristics. Reaction heat is removed through the loop wall since much of the reactor is in the form of a double jacketed pipe. The slurry is allowed to exit the reactor at regular intervals or continuously to a heated low pressure flash vessel, rotary dryer, and a nitrogen purge column in sequence for removal of the isobutane diluent and all unreacted monomer and comonomers. The resulting hydrocarbon free powder is then compounded for use in various applications.

In another embodiment in the slurry process of the invention, the total reactor pressure is in the range of from about 400 psig (2758 kPa) to about 800 psig (5516 kPa), preferably about 450 psig (3103 kPa) to about 700 psig (4827 kPa), more preferably about 500 psig (3448 kPa) to about 650 psig (4482 kPa), most preferably from about 525 psig (3620 kPa) to about 625 psig (4309 kPa).

In yet another embodiment in the slurry process of the invention, the concentration of predominant monomer in the reactor liquid medium is in the range of from about 1 wt % to 10 wt %, preferably from about 2 wt % to about 7 wt %, more preferably from about 2.5 wt % to about 6 wt %, most preferably from about 3 wt % to about 6 wt %.

Another process of the invention is where the process, preferably a slurry or gas phase process, is operated in the absence of or essentially free of any scavengers, such as triethylaluminum, trimethylaluminum, tri-iso-butylaluminum, tri-n-hexylaluminum and diethyl aluminum chloride, dibutyl zinc, and the like. This process is described in PCT publication WO 96/08520 and U.S. Pat. No. 5,712,352; which are herein fully incorporated by reference.

In another embodiment, the process is run with scavengers. Typical scavengers include trimethyl aluminum, tri-iso-butyl aluminum, and an excess of alumoxane or modified alumoxane.

Homogeneous, Bulk or Solution Phase Polymerization

The catalysts described herein can be used advantageously in homogeneous solution processes. Generally, this involves polymerization in a continuous reactor in which the polymer formed and the starting monomer and catalyst materials supplied are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers, or solvent), or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel, or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,001,205 for general process conditions. See also, International Applications WO 96/33227 and WO 97/22639.

Medium and High Pressure Polymerizations

In the high pressure process for the polymerization of ethylene alone or in combination with $C_3$ to $C_{10}$ alpha-olefins and optionally other copolymerizable olefins, the temperature of the medium within which the polymerization reaction occurs is at least 120° C. and preferably above 140° C. and may range to 350° C., but below the decomposition temperature of said polymer product, typically from 310° C. to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

For medium pressure process, the temperature within which the polymerization reaction occurs is at least 80° C. and ranges from 80° C. to 250° C., preferably from 100° C. to 220° C., and should for a given polymer in the reactor, be above the melting point of said polymer so as to maintain the fluidity of the polymer-rich phase. The pressure can be varied between 100 and 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

More recently, polymerization conditions for high pressure and/or temperature polymerizations to prepare propylene homopolymers and copolymers of propylene with $C_3$ to $C_{10}$ olefins and optionally other copolymerizable olefins have been reported. See U.S. Patent Applications 60/431,185 filed Dec. 5, 2002; 60/431,077, filed Dec. 5, 2002; and 60/412,541, filed Sep. 20, 2002.

After polymerization and deactivation of the catalyst, the polymer product can be recovered by processes well known in the art. Any excess reactants may be flashed off from the polymer and the polymer obtained extruded into water and cut into pellets or other suitable comminuted shapes. For general process conditions, see the general disclosure of U.S. Pat. Nos. 5,084,534; 5,408,017; 6,127,497; and 6,255,410; which are incorporated herein by reference.

The catalyst system described herein may also be used in a supercritical process, preferably a supercritical process above the melting point of the polymers being produced, preferably a supercritical process above the cloud point of the polymerization system. For more information on the details of the supercritical process (including definitions of cloud point and polymerization system) please see WO 2004/026921.

Polymer Product

Polymers produced herein may have Mw's of 50,000 g/mol or more, alternately from 50,000 to 5,000,000 g/mol, alternately from 100,000 to 4,000,000 g/mol, alternately from 200,000 to 2,000,000 g/mol.

Preferred polymers include ethylene homopolymers and copolymers. Preferred copolymers include ethylene-hexene or ethylene-octene copolymers having 50 wt % or more ethylene, preferably 60 wt % to 95 wt %, preferably 70 wt % to 95 wt % ethylene, with the balance being hexene or octene. Additional preferred copolymers include ethylene-hexene or ethylene-octene copolymers having 60 wt % or more ethylene, preferably 70 wt % or more ethylene, preferably 85 wt % or more ethylene, with the balance being hexene or octene.

The polymers produced herein are useful in a wide variety of applications, including films, sheets molded articles and the like. In particular, the polymers described herein can be used for furniture, automotive components, toys, sportswear, medical devices, sterilizable medical devices, and sterilization containers, nonwoven fibers and fabrics, and articles therefrom, such as drapes, gowns, filters, hygiene products, diapers, films, oriented films, sheets, tubes, pipes, fibers, woven, and nonwoven fabrics, automotive components, furniture, sporting equipment, food storage containers, transparent, and semi-transparent articles, packaging, bags, sacks, coatings, caps, closures, crates, pallets, cups, non-food containers, pails, insulation, wire and cable jacketing, cast or blown packaging films. Ultra high molecular weight polyethylenes can additionally be used for rope, twine, fishing line, cord, cables, hawsers, and for fabrics and fibers. Preferably, the ultra high molecular weight polyethylenes prepared herein is used for fibers used, for example, in sails, parachutes, hang gliders, paragliders, and the like, and for fibers used in cut and/or puncture resistant garments including gloves and body armor.

Fabrication of these articles may be accomplished by injection molding, extrusion, thermoforming, blow molding, rotational molding (rotomolding), fiber spinning, gel spinning, spin bonding, or melt blown bonding, such as for non-woven fabrics, film blowing, stretching for oriented films, casting such as for films (including use of chill rolls), profile deformation, coating (film, wire, and cable), compression molding, calendering, foaming, laminating, transfer molding, cast molding, pultrusion, protrusion, draw reduction, and other common processing methods, or combinations thereof, such as is known in the art and described in, for example, PLASTICS PROCESSING (Radian Corporation, Noyes Data Corp. 1986). Use of at least thermoforming or film applications allows for the possibility of and derivation of benefits from uniaxial or biaxial orientation.

In another embodiment this invention relates to:
1. A transition metal compound represented by the formula:

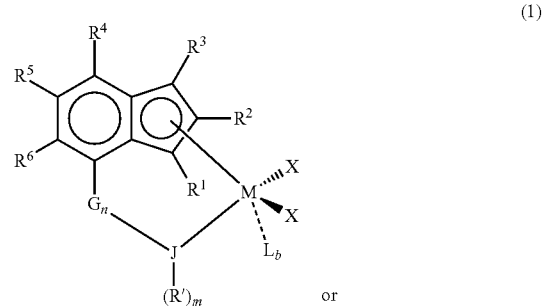

(1)

or

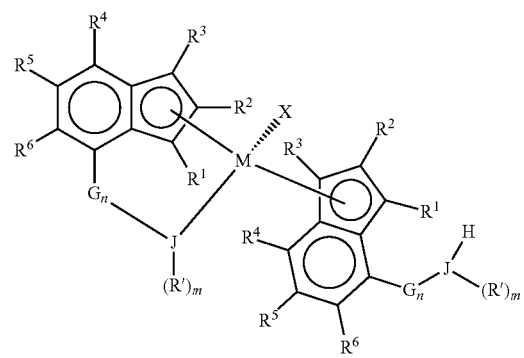

(2)

where M is a group 3, 4, 5, or 6 metal; J is a group 15 or 16 atom, and when J is a group 15 metal, m is 1, indicating the presence of R', and when J is a group 16 metal, m is zero, indicating the absence of R; G is a bridging group and n is 1, 2, or 3 indicating the number of atoms in the direct chain between the indenyl ring and the ligand J; $R^1$, $R^2$, $R^3$, $R^4$, $R^5$, and $R^6$ are independently selected from a hydrogen, fluoro, or hydrocarbyl, substituted hydrocarbyl, halocarbyl, substituted halocarbyl, silylcarbyl, substituted silylcarbyl, germylcarbyl, or substituted germylcarbyl radical, and two or more adjacent $R^1$, $R^2$, $R^3$, $R^4$, $R^5$, and $R^6$ can join together to form a cyclic group fused to the indenyl ring; R' is selected from a hydrocarbyl, halohydrocarbyl, or substituted hydrocarbyl radical; X is a univalent ionic ligand; L is a Lewis base ligand and b is 0, 1 or 2 representing the presence (b=1 or 2) or absence (b=0) of L, provided that when n is 2, G is not O—$SiR_2$, or $R_4Ph$, and when n is 3, G is not $SiR_2(R_4Ph)$, where Ph is phenyl, and each R is as defined for $R^1$.

2. The compound of paragraph 1, wherein M is a group 4 metal.

3. The compound of paragraph 1 or 2, wherein J is N, P, O or S, preferably N.

4. The compound of paragraph 1, 2, or 3, wherein $R^2$ is methyl and $R^1$, $R^3$, $R^4$, $R^5$, and $R^6$ are hydrogen radicals.

5. The compound of any of paragraphs 1 to 4, wherein $R^2$ is methyl, $R^4$ is fluoro, and $R^1$, $R^3$, $R^5$, and $R^6$ are hydrogen radicals.

6. The compound of any of paragraphs 1 to 5, wherein R' is selected from tert-butyl, cyclopentyl, cyclohexyl, cyclododecyl, 2-norbornyl, 1-adamantyl, benzyl, phenyl, 2-methylphenyl, 3-methylphenyl, 4-methylphenyl, 3,5-dimethylphenyl, 3,5-diisopropylphenyl, 4-bromophenyl, and 4-methoxyphenyl.

7. The compound of any of paragraphs 1 to 6, wherein n is 1 or 2.

8. The compound of any of paragraphs 1 to 7, wherein at least one of $R^1$, $R^2$, $R^3$, $R^4$, $R^5$, and $R^6$ is fluoro.

9. The compound of any of paragraphs 1 to 8, wherein $R^1$, $R^2$, $R^3$, $R^4$, $R^5$, and $R^6$ are selected from group consisting of hydrogen, hydrocarbyl and fluoro.

10. The compound of any of paragraphs 1 to 9, wherein J is nitrogen.

11. The compound of any of paragraphs 1 to 10, wherein each X is, independently, selected from the group consisting of hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, substituted germylcarbyl radicals, halogens, alkoxides, aryloxides, amides, phosphides; or both X are joined and bound to the metal atom to form a metallacycle ring containing from about 3 to about 20 carbon atoms; or both X together can be an olefin, diolefin or aryne ligand; or both X can also be joined to form an anionic chelating ligand.

12. The compound of any of paragraphs 1 to 11, wherein each X is, independently, a halogen or a hydrocarbyl group.

13. The compound of any of paragraphs 1 to 12, wherein each X is, independently, Cl, Br, F, I, methyl, ethyl, propyl, butyl, phenyl, or benzyl.

14. The compound of any of paragraphs 1 to 13, wherein G is selected from $R''_2C$, $R''_2Si$, $R''_2Ge$, $R''_2CCR''_2$, $R''_2CCR''_2CR''_2$, $R''C=CR''$, $R''C=CR''CR''_2$, $R''_2CSiR''_2$, $R''_2SiSiR''_2$, $R''_2CSiR''_2CR''_2$, $R''_2SiCR''_2SiR''_2$, $R''_2SiCR''_2CR''_2$, $R''_2SiSiR''_2SiR''_2$, $R''C=CR''SiR''_2$, $R''_2CGeR''_2$, $R''_2GeGeR''_2$, $R''_2CGeR''_2CR''_2$, $R''_2GeCR''_2GeR''_2$, $R''_2SiGeR''_2$, $R''C=CR''GeR_{12}$, $R''B$, $R''_2C—BR''$, $R''_2C—BR''—CR''_2$, $R''_2C—NR''—CR''_2$, $R''_2C—PR''—CR''_2$, $R''_2C—O—CR''_2$, $R''_2C—S—CR''_2$, $R''_2Si—O—SiR''_2$, and $R''_2Ge—O—GeR_{12}$, where R'' is, independently, hydrogen, hydrocarbyl, substituted hydrocarbyl, halocarbyl, substituted halocarbyl, silylcarbyl, or germylcarbyl, and two or more R'' on the same atom or on adjacent atoms may join together to form a substituted or unsubstituted, saturated, partially unsaturated, or aromatic cyclic or polycyclic substituent provided that when G is $R''_2CCR''_2$, or $R''_2SiCR''_2CR''_2$ two or more R'' on adjacent atoms may not join together to form a substituted or unsubstituted, aromatic cyclic or polycyclic group.

15. The compound of any of paragraphs 1 to 14, wherein G is selected from $R''_2C$, $R''_2Si$, $R''_2Ge$, $R''_2CCR''_2$, $R''_2CCR''_2CR''_2$, $R''C=CR''$, $R''C=CR''CR''_2$, $R''_2CSiR''_2$, $R''_2SiSiR''_2$, $R''_2CSiR''_2CR''_2$, $R''_2SiCR''_2SiR''_2$, $R''_2SiCR''_2CR''_2$, $R''_2SiSiR''_2SiR''_2$, $R''C=CR''SiR''_2$, $R''_2CGeR''_2$, $R''_2GeGeR''_2$, $R''_2CGeR''_2CR''_2$, $R''_2GeCR''_2GeR''_2$, $R''_2SiGeR''_2$, $R''C=CR''GeR_{12}$, $R''B$, $R''_2C—BR''$, $R''_2C—BR''—CR''_2$, $R''_2C—NR''—CR''_2$, $R''_2C—PR''—CR''_2$, $R''_2C—O—CR''_2$, $R''_2C—S—CR''_2$, $R''_2Si—O—SiR''_2$, and $R''_2Ge—O—GeR_{12}$, where R'' is, independently, hydrogen, hydrocarbyl, substituted hydrocarbyl, halocarbyl, substituted halocarbyl, silylcarbyl, or germylcarbyl.

16. The compound of any of paragraphs 1 to 15, wherein G is selected from $R''_2Si$, $R''_2CCR''_2$, $R''_2CCR''_2CR''_2$, $R''_2CSiR''_2$, $R''_2SiSiR''_2$, $R''_2CSiR''_2CR''_2$, $R''_2SiCR''_2SiR''_2$, $R''_2SiCR''_2CR''_2$, $R''_2SiSiR''_2SiR''_2$, and $R''_2Si—O—SiR''_2$, where R'' is, independently, hydrogen, hydrocarbyl, substituted hydrocarbyl, halocarbyl, substituted halocarbyl, silylcarbyl, or germylcarbyl, preferably G is $CH_2$, $CH_2CH_2$, $CH_2CH_2CH_2$, $CMe_2$, $SiMe_2$, $SiPh_2$, $SiMePh$, $Me_2SiSiMe_2$, $Me_2SiOSiMe_2$, $PhMeSiSiMePh$, $PhMeSiOSiMePh$, $Si(CH_2)_3$, or $Si(CH_2)_4$.

17. The compound of any of paragraphs 1 to 16, wherein L is selected from the group consisting of ethylene, propylene, butene, diethylether, tetrahydrofuran, furan, dimethylaniline, aniline, trimethylphosphine, trimethylamine, butylamine, and lithium chloride.

18. The compound of any of paragraphs 1 to 17, wherein each $R^1$, $R^2$, $R^3$, $R^4$, $R^5$, or $R^6$ is selected from, the group consisting of hydrogen, fluoro, methyl, ethyl, n-propyl, iso-propyl, n-butyl, sec-butyl, iso-butyl, tert-butyl, pentyl, hexyl, cyclohexyl, phenyl, and trifluoromethyl.

19. A catalyst system comprising an activator and the compound of any of paragraphs 1 to 18.

20. The catalyst system of paragraph 19, wherein the activator is an alumoxane and/or a non-coordinating anion.

21. A process to polymerize olefins comprising contacting one or more monomers with the catalyst system of paragraph 19 or 20.

22. The process of paragraph 21, wherein the monomers are contacted with the metallocene compound and the activator in a reactor and the reactor is a batch reactor.

23. The process of paragraph 21 or 22, wherein the monomers are contacted with the metallocene compound and the activator in the solution phase, slurry phase, or gas phase.

24. The process of paragraph 21, 22, or 23, wherein the monomers are contacted with the transition metal compound and the activator in a reactor and the reactor is a continuous stirred tank reactor or a continuous tubular reactor.

25. The process of paragraph 21, 22, 23, or 24, wherein the monomers comprise ethylene.

26. A process to make a metallocene precursor ligand comprising contacting:
magnesium and $X^*—Y^*—X^*$, where $X^*$ is halogen and $Y^*$ is a bridging group, with a compound represented by the formula:

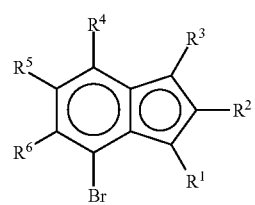

where $R^1$, $R^2$, $R^3$, $R^4$, $R^5$, and $R^6$ are independently selected from a hydrogen, fluoro, or hydrocarbyl, substituted hydrocarbyl, halocarbyl, substituted halocarbyl, silylcarbyl, substituted silylcarbyl, germylcarbyl, or substituted germylcarbyl radical, and two or more adjacent of $R^1$, $R^2$, $R^3$, $R^4$, $R^5$, and $R^6$ can join together to form a cyclic group fused to the indenyl ring;
and thereafter contacting the reaction product with R'EHLi or $R'EH_2$, where R' is selected from a hydrocarbyl, halohydrocarbyl, or substituted hydrocarbyl radical, and E is nitrogen or phosphorus.

27. The process of paragraph 26 wherein $Y^*$ is $R''_2Si$, $R''_2Ge$, $R''_2SiSiR''_2$, $R''_2SiCR''_2SiR''_2$, $R''_2SiSiR''_2SiR''_2$, $R''_2GeGeR''_2$, $R''_2GeCR''_2GeR''_2$, $R''_2SiGeR''_2$, $R''B$, $R''_2Si—O—SiR''_2$, and $R''_2Ge—O—GeR_{12}$, where each R'' is, independently, hydrogen, hydrocarbyl, substituted hydrocarbyl, halocarbyl, substituted halocarbyl, silylcarbyl, or germylcarbyl, and $X^*$ is chloro or bromo.

128. A process to make a metallocene precursor ligand comprising contacting:

magnesium and a substituted or unsubstituted N-(p-tosyl)aziridine, with a compound represented by the formula:

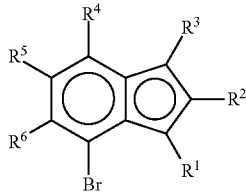

where $R^1$, $R^2$, $R^3$, $R^4$, $R^5$, and $R^6$ are independently selected from a hydrogen, fluoro, or hydrocarbyl, substituted hydrocarbyl, halocarbyl, substituted halocarbyl, silylcarbyl, substituted silylcarbyl, germylcarbyl, or substituted germylcarbyl radical, and two or more adjacent of $R^1$, $R^2$, $R^3$, $R^4$, $R^5$, and $R^6$ can join together to form a cyclic group fused to the indenyl ring;

and thereafter contacting the reaction product with 1) R'X*, where X* is a halide and R' is selected from a hydrocarbyl, halohydrocarbyl, or substituted hydrocarbyl radical, and E is nitrogen or phosphorus; and 2) $Cs_2CO_3$, and thereafter reacting the second reaction product with magnesium and $NH_4Cl$.

29 The process of paragraph 28 wherein X* is chloro or bromo and the substituted or unsubstituted N-(p-tosyl)aziridine is represented by the formula:

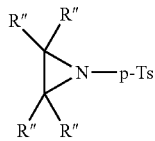

where Ts is tosyl and each R" is, independently, hydrogen, hydrocarbyl, substituted hydrocarbyl, halocarbyl, substituted halocarbyl, silylcarbyl, or germylcarbyl.

30. A process to make a metallocene precursor ligand comprising contacting:

NaBH4 and $C_1$ to $C_{12}$ alky iodide with a compound represented by the formula:

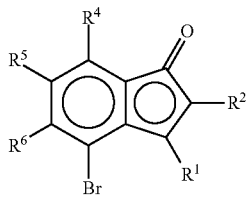

where $R^1$, $R^2$, $R^4$, $R^5$, and $R^6$ are independently selected from a hydrogen, fluoro, or hydrocarbyl, substituted hydrocarbyl, halocarbyl, substituted halocarbyl, silylcarbyl, substituted silylcarbyl, germylcarbyl, or substituted germylcarbyl radical, and two or more adjacent of $R^1$, $R^2$, $R^3$, $R^4$, $R^5$, and $R^6$ can join together to form a cyclic group fused to the indenyl ring;

thereafter contacting the reaction product with alkyl lithium and a compound represented by the formula:

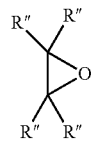

where each R" is, independently, hydrogen, hydrocarbyl, substituted hydrocarbyl, halocarbyl, substituted halocarbyl, silylcarbyl, or germylcarbyl, and thereafter reacting the second reaction product with dimethylformamide and PPh3, where Ph is phenyl, and thereafter reacting the third reaction product with TsOH, where Ts is tosyl, and hereafter reacting the fourth reaction product with $R'NH_2$, $K_2CO_3$ and dimethylformamide, where R' is selected from a hydrocarbyl, halohydrocarbyl, or substituted hydrocarbyl radical.

31. A process to make a metallocene precursor ligand comprising contacting:

NaBH4 and $C_1$ to $C_{12}$ alky iodide with a compound represented by the formula:

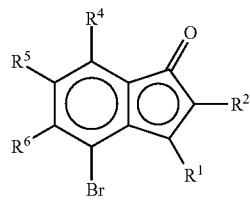

where $R^1$, $R^2$, $R^4$, $R^5$, and $R^6$ are independently selected from a hydrogen, fluoro, or hydrocarbyl, substituted hydrocarbyl, halocarbyl, substituted halocarbyl, silylcarbyl, substituted silylcarbyl, germylcarbyl, or substituted germylcarbyl radical, and two or more adjacent of $R^1$, $R^2$, $R^3$, $R^4$, $R^5$, and $R^6$ can join together to form a cyclic group fused to the indenyl ring; thereafter contacting the reaction product with alkyl lithium and dimethylformamide and thereafter reacting the second reaction product with $NaBH_4$, and hereafter reacting the third reaction product with N-bromosuccinimide and $PPh_3$, where Ph is phenyl, and thereafter reacting the fourth reaction product with TsOH where Ts is tosyl, thereafter reacting the fifth reaction product with $R'NH_2$ and $K_2CO_3$ and dimethylformamide; and where R' is selected from a hydrocarbyl, halohydrocarbyl, or substituted hydrocarbyl radical.

EXPERIMENTAL

Synthesis of Pre-Catalysts

All manipulations with air and moisture sensitive compounds were performed either in an atmosphere of thoroughly purified argon using standard Schlenk techniques or in a controlled atmosphere glove box (Vacuum Atmospheres Co.). Tetrahydrofuran (THF, Merck=Merck KGaA, Darmstadt, Germany) and diethyl ether (Merck) were purified by distillation over $LiAlH_4$, and stored over sodium benzophenone ketyl under an inert atmosphere; prior to use, the solvents were distilled from the benzophenone ketyl. Hydrocarbon solvents such as toluene (Merck) and hexanes (Merck) (and $C_6D_6$ for NMR experiments) were typically distilled over $CaH_2$, and were stored over Na/K alloy under an inert atmosphere; prior to use, the solvents were distilled from the Na/K alloy. Dimethylformamide ("DMF", Merck) was distilled over BaO and stored over molecular shieves 3A (Merck). CD$_2$Cl$_2$ (Cambridge Isotope Laboratories, Inc.) was distilled and stored over CaH$_2$ under an inert atmosphere; prior to use, the solvent was distilled from the CaH$_2$. Sodium metal (Merck) was used as received. CDCl$_3$ (Merck) was distilled over P$_4$O$_{10}$ and stored over molecular sieves (3 Å). Dimethyldichlorosilane (Merck) and 1,1,2,2-tetramethyl-1,2-dichlorodisilane (Aldrich) were distilled before use. Cyclopentylamine (Acros Organics) and tert-butylamine were dried over CaH$_2$ and distilled before use. Methanol (Merck), anhydrous ethanol (Merck), dichloromethane (Reachim, Moscow, Russia), ZrCl$_4$(THF)$_2$ (Aldrich), TiCl$_4$ (Merck), $^n$BuLi in hexanes (Chemetall Chemical Products), anhydrous K$_2$CO$_3$ (Merck), anhydrous Na$_2$CO$_3$ (Merck), anhydrous Cs$_2$CO$_3$ (Aldrich), KOH (Merck), NH$_4$Cl (Merck), NaI (Merck), methyl iodide (Merck), isopropyl iodide (Aldrich), benzyl chloride (Merck), Mg turnings (Acros Organics), p-toluidine (Acros Organics), o-toluidine (Acros Organics), triphenylphosphine (Acros Organics), N-bromosuccinimide ("NBS," Acros Organics), 4-tert-butyltoluene (Acros Organics), p-methoxyaniline (Acros Organics), benzoyl peroxide (Aldrich), 4-bromo-2-fluorotoluene (Aldrich), 3,5-dimethylaniline (Acros Organics), 4-bromoaniline (Acros Organics), diethyl malonate (Acros Organics), diethyl methylmalonate (Acros Organics), ethyl bromide (Acros Organics), iodine (Merck), isopropyl iodide (Acros Organics), potassium iodide (Merck), benzyl chloride (Acros Organics), 1,2-dibromoethane (Acros Organics), methyl-tert-butyl ether (Acros Organics), NaBH$_4$ (Acros Organics), AlCl$_3$ (Merck), para-toluene sulfonic acid (Aldrich), bromine (Merck), Na$_2$SO$_4$ (Akzo Nobel), carbon tetrachloride (Reakhim, Moscow, Russia). Silica Gel 60, 40-63 μm (Merck), 12 M HCl (diluted as needed; Reachim, Moscow, Russia), KOH (Reachim, Moscow, Russia): iodine (Merck), oxalic acid hydrate (Acros Organics), ethylene oxide (Acros Organics), TsOH (Ts=tosyl; Acros Organics), para-toluene sulfonic acid hydrate (p-TolSO$_3$H.H$_2$O), sodium iodide (Merck), sodium ethoxide (Acros Organics) were used as obtained. Thionyl chloride (Merck) was distilled before use.

7-Bromo-2-methylindene and 4-bromo-2-methyl-1-methoxyindane were obtained from 2-bromobenzylbromide (Aldrich) and diethyl methylmalonate (Acros Organics) as described in Izmer, V. V.; Lebedev, A. Y.; Nikulin, M. V.; Ryabov, A. N.; Asachenko, A. F.; Lygin, A. V.; Sorokin, D. A.; Voskoboynikov, A. Z. *Organometallics* 2006, 25, 1217 4-Bromo-1-methoxyindane was obtained from 2-bromobenzylbromide (Aldrich) and diethyl malonate (Acros Organics) as described in. Voskoboynikov, A. Z.; Izmer, V. V.; Asachenko, A. F.; Nikulin, M. V.; Ryabov, A. N.; Lebedev, A. Y.; Coker, C. L.; Canich, J. A. M. U.S. Patent Application Publication U.S. 2007/135597 for ExxonMobil Chemical Co., 2007. 7-Bromo-4-fluoro-2-methyl-1H-indene was obtained from 4-fluoro-1-bromobenzene (Aldrich) and diethyl methylmalonate (Acros Organics) as described in Voskoboynikov, A. Z.; Ryabov, A. N.; Nikulin, M. V.; Lygin, A. V.; Coker, C. L.; Canich, J. A. M. U.S. Patent Application Publication U.S. 2007135595 for ExxonMobil Chemical Co., 2007. 4-Bromo-6-tert-butyl-2-methylindan-1-one was obtained from 4-tert-butyltoluene (Merck) and diethyl methylmalonate (Acros Organics) as described in Resconi, L.; Nifant'ev, I. E.; Ivchenko, P. V.; Bagrov, V.; Focante, F.; Moscardi, G. International Patent Application WO 2007107448 for Basell Polyolefine GmbH, 2007. N-(p-tosyl)aziridine was obtained from p-tosyl chloride (Acros Organics) and 2-aminoethanol (Merck) as described in Bieber, L. W.; de Araujo, M. C. F. *Molecules* 2002, 7, 902.

Analytical and semi-preparative liquid chromatography was performed using a Waters Delta 600 HPLC system including a 996 Photodiode Array Detector, Nova-Pack C18 or HR Silica (60A, 6 μm, 3.9 and 19×300 mm) and Symmetry C18 (5 μm, 4.6×250 mm) columns. MPLC (Medium Pressure Liquid Chromatography, pressure 5-15 bars) was performed using MPLC glass columns and fittings (Ace Glass), a PD5130 pump drive equipped with a J1 gear-well pump head (Heidolph), a 996 Photodiode Array Detector and a Fraction Collector II (Waters Corp.). $^1$H and $^{13}$C spectra were recorded with a Brucker Avance-400 spectrometer. Chemical shifts for $^1$H and $^{13}$C were measured relative to tetramethylsilane (TMS). $^1$H NMR spectral assignments were made on the basis of double resonance and Nuclear Overhauser Effect (NOE) experiments. CHN microanalyses were done using a CHN—O-Rapid analyzer (Heraecus Ltd., Banau, Germany).

ALKYL-BRIDGED EXAMPLES

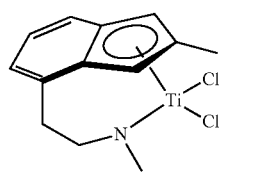

A

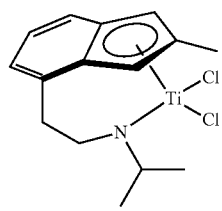

B

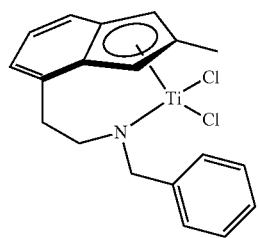

C

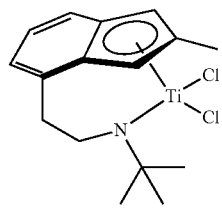

D

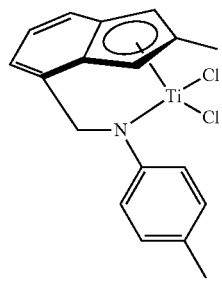

E

-continued

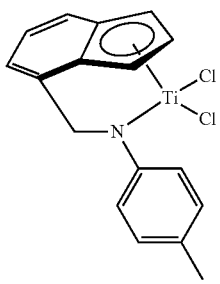

F

Example 1

Preparation of [η⁵:η¹-N-Methyl-2-(2-methylinden-4-yl)ethanamido]titanium dichloride (Compound A)

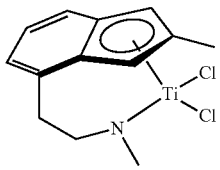

1a): 4-Methyl-N-[2-(2-methyl-1H-inden-7-yl)ethyl]benzenesulfonamide

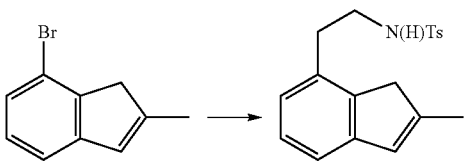

To 2.43 g (100 mmol) of magnesium turnings (preliminary activated by I₂ in THF) in 200 mL of THF at reflux, a solution of 20.9 g (100 mmol) of 2-methyl-7-bromoindene in 50 mL of THF was added dropwise. The mixture was additionally refluxed for 30 minutes. To the resulting mixture now cooled to 10° C. while vigorously stirred, a solution 19.7 g N-(p-tosyl)aziridine in 250 mL of THF was added dropwise. This mixture was stirred overnight at room temperature. Then, 400 mL of water was added, and the product was extracted with 3×200 mL of dichloromethane. The combined extract was evaporated to dryness. The product was isolated by flash chromatography on silica gel 60 (40-63 um, eluent—dichloromethane). Yield, 30.5 g (93%) of white solid. $^1$H NMR (CDCl₃): δ 7.65 (d, J=8.1 Hz, 2H, 2,6-H in p-tosyl), 7.25 (d, J=8.1 Hz, 2H, 3,5-H in p-tosyl), 7.12 (m, 2H, 5,6-H in indenyl), 6.77 (dd, J=6.6 Hz, J=2.0 Hz, 1H, 4-H in indenyl), 6.45 (m, 1H, 3-H in indenyl), 4.45 (m, 1H, NH), 3.23 (m, 2H, CH₂CH₂N), 3.09 (s, 2H, 1,1'-H of indenyl), 2.81 (t, J=7.1 Hz, 2H, CH₂CH₂N), 2.40 (s, 3H, Me in p-tosyl), 2.12 (s, 3H, Me in indenyl). $^{13}$C{$^1$H} NMR (CDCl₃): δ 146.3, 145.9, 143.3, 142.0, 136.7, 132.1, 129.6, 127.3, 127.1, 127.0, 123.8, 118.5, 42.9, 41.2, 33.2, 21.5, 16.7. Anal. Calc. for C₁₉H₂₁NO₂S: C, 69.69; H, 6.46; N, 4.28%. Found: C, 69.40; H, 6.61; N, 4.05%.

1b): N,4-Dimethyl-N-[2-(2-methyl-1H-inden-7-yl)ethyl]benzenesulfonamide

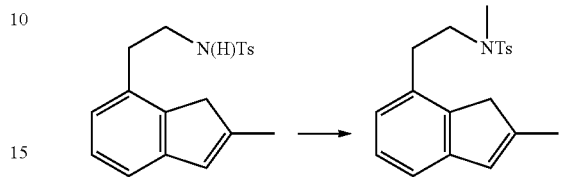

To a solution of 15.0 g (45.8 mmol) of 4-methyl-N-[2-(2-methyl-1H-inden-7-yl)ethyl]-benzenesulfonamide in 100 mL of dry DMF at room temperature, 22.4 g (68.7 mmol) of Cs₂CO₃ was added, followed by the dropwise addition of 10.0 g (70.4 mmol) of MeI over a 10 minute period. This mixture was stirred for 24 hours at 50° C. and then evaporated under vacuum. To the residue, 200 mL of water and 200 mL of dichloromethane were added. The organic layer was separated, and the aqueous layer was washed with 200 mL of dichloromethane. The combined organic extract was evaporated to dryness. The product was isolated by flash chromatography on silica gel 60 (40-63 um, eluent—dichloromethane). Yield, 14.1 g (90%) of white solid. This product was further used without an additional purification. $^1$H NMR (CDCl₃): δ 7.50-7.55 (m, 2H, 2,6-H in p-tolyl), 7.15-7.20 (m, 2H, 3,5-H in p-tolyl), 7.04 (m, 1H, 5-H in indenyl), 7.01 (m, 1H, 6-H in indenyl), 6.78 (m, 1H, 4-H in indenyl), 6.36 (m, 1H, 3-H in indenyl), 3.08-3.18 (m, 6H, 1,1'-H in indenyl and CH₂CH₂), 2.69 (s, 3H, NMe), 2.67 (s, 3H, 4-Me in p-tolyl), 2.05 (s, 3H, 2-Me in indenyl). Anal. Calc. for C₂₀H₂₃NO₂S: C, 70.35; H, 6.79; N, 4.10%. Found: C, 70.95; H, 7.13; N, 3.78%.

1c): N-Methyl-2-(2-methyl-1/3H-inden-7/4-yl)ethanamine

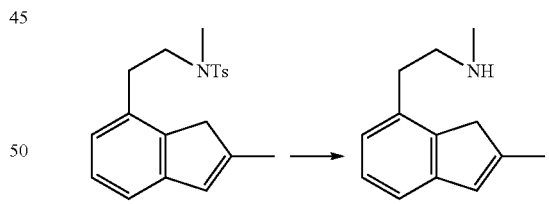

In 250 mL round-bottom flask equipped with reflux condenser and placed in ultrasound bath containing a solution of 8.33 g (24.4 mmol) of N,4-dimethyl-N-[2-(2-methyl-1H-inden-7-yl)ethyl]benzenesulfonamide in 110 mL of methanol heated to 50° C., 1.78 g (73.2 mmol) of magnesium turnings were added in small portions at such a speed that the mixture continued to boil. After all the magnesium reacted, the resulting mixture was evaporated to dryness, and to the residue, 300 mL of saturated aqueous NH₄Cl and 200 mL of dichloromethane were added. The organic layer was separated, and the aqueous layer was washed with 2×200 mL of dichloromethane. The combined organic extract was evaporated to dryness. The residue was dissolved in 20 mL of methanol, and a saturated solution of 8.57 g (68.0 mmol) of oxalic acid hydrate in methanol was added. The formed suspension was refluxed for 5 minutes and then slowly cooled to room temperature. The formed precipitate was filtered off (G3), dried in vacuum, and then treated with 20% aqueous KOH. Further on, the product was extracted with 3×200 mL of dichloromethane. The combined organic extract was evaporated to dryness to give 4.16 g (91%) of a colorless oil as a mixture of the isomers. $^1$H NMR (CDCl$_3$) of N-methyl-2-(2-methyl-1H-inden-7-yl)ethanamine (major isomer): δ 7.17 (t, J=7.3 Hz, 1H, 5-H), 7.11 (d, J=7.3 Hz, 1H, 4-H), 6.94 (d, J=7.3 Hz, 1H, 6-H), 6.48 (m, 1H, 3-H), 3.26 (s, 2H, 1,1'-H in indenyl), 2.88 (m, 4H, CH$_2$CH$_2$), 2.45 (s, 3H, NMe), 2.15 (s, 3H, 2-Me in indenyl); 1.89 (br.s, 1H, NH); N-methyl-2-(2-methyl-3H-inden-4-yl)ethanamine (minor isomer): 7.23 (m, 1H, 5-H), 7.04 (m, 2H, 6,7-H), 6.62 (m, 1H, 3-H), 3.29 (s, 2H, 1,1'-H in indenyl), 2.91 (m, 4H, CH$_2$CH$_2$), 2.45 (s, 3H, NMe), 2.15 (s, 3H, 2-Me in indenyl), 1.89 (br.s, 1H, NH). Anal. Calc. for C$_{13}$H$_{17}$N: C, 83.37; H, 9.15; N, 7.48%. Found: C, 83.68; H, 9.31; N, 7.25%.

1d): [η$^5$:η$^1$-N-Methyl-2-(2-methylinden-4-yl) ethanamido]titaniumdichloride (Compound A)

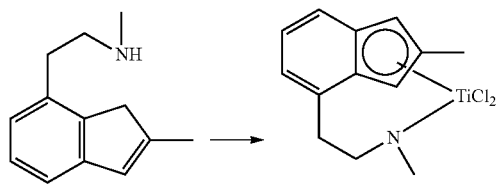

To a solution of 1.53 g (8.17 mmol) of N-methyl-2-(2-methyl-1/3H-inden-7/4-yl)ethanamine in 150 mL of dry ether, 6.54 mL (16.3 mmol) of 2.5 M $^n$BuLi in hexanes was added at room temperature. This mixture was additionally stirred for 12 hours at this temperature, and then a solution of 1.55 g (8.17 mmol) of TiCl$_4$ in 20 mL of hexanes was added at 0° C. The resulting mixture was stirred for additional 12 hours at room temperature and then evaporated to dryness. The residue was dried in vacuum, and then 50 mL of toluene was added. The obtained suspension was stirred for 2 hours at 50° C., filtered through glass frit (G3), and the precipitate was additionally washed with 10 mL of toluene. The combined filtrate was dried in vacuum. To the obtained solid, 20 mL of hexanes was added, and the formed suspension was stirred for 30 minutes at room temperature. Further on, this suspension was filtered through glass frit (G3), the precipitate was washed with 2×10 mL of hexanes, and then dried in vacuum. Yield, 0.79 g (32%) of the title titanium complex. $^1$H NMR (CD$_2$Cl$_2$): δ 7.31 (d, J=8.3 Hz, 1H, 5-H), 7.13 (dd, J=8.3 Hz, J=6.6 Hz, 1H, 6-H), 7.06 (d, J=6.6 Hz, 1H, 7-H), 6.87 (d, J=2.0 Hz, 1H, 1-H in indenyl), 6.77 (d, J=2.0 Hz, 1H, 3-H in indenyl), 4.03 (br.ddd, J=12.8 Hz, J=10.4 Hz, J=7.4 Hz, 1H, NCHH'CH$_2$), 3.84 (ddt, J=16.0 Hz, J=7.4 Hz, J=1.2 Hz, 1H, NCHH'CH$_2$), 3.53 (t, J=1.2 Hz, 3H, NMe), 3.30 (br.dd, J=12.8 Hz, J=7.1 Hz, 1H, NCH$_2$CHH'), 3.12 (dddq, J=16.0 Hz, J=10.4 Hz, J=7.1 Hz, J=1.2 Hz, 1H, NCH$_2$CHH'), 2.88 (s, 3H, 2-Me in indenyl). $^{13}$C{$^1$H} NMR (CD$_2$Cl$_2$): δ 140.2, 138.2, 132.4, 129.9, 123.3 (two resonances), 121.7, 115.8, 110.3, 70.7, 44.9, 33.6, 19.3. Anal. Calc. for C$_{13}$H$_{15}$Cl$_2$NTi: C, 51.36; H, 4.97; N, 4.61%. Found: C, 51.22; H, 5.11; N, 4.49%.

Example 2

Preparation of [η$^5$:η$^1$-N-Isopropyl-2-(2-methylinden-4-yl)ethanamido]titanium dichloride (Compound B)

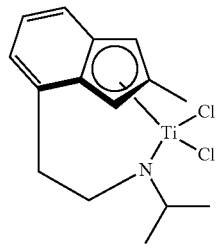

2a): N-Isopropyl-4-methyl-N-[2-(2-methyl-4H-inden-7-yl)ethyl]benzenesulfonamide

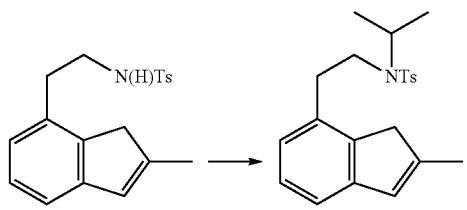

At room temperature, to a solution of 11.4 g (34.8 mmol) of 4-methyl-N-[2-(2-methyl-1H-inden-7-yl)ethyl]-benzenesulfonamide in 75 mL of dry DMF, 17.0 g (52.3 mmol) of Cs$_2$CO$_3$ was added, and then 11.9 g (69.8 mmol) of $^i$PrI was added dropwise over a period of 10 minutes. This mixture was then stirred for 3 days at 50° C., and then evaporated via vacuum. To the residue, 200 mL of water and 200 mL of dichloromethane were added. The organic layer was separated, and the aqueous layer was washed with 200 mL of dichloromethane. The combined organic extract was evaporated to dryness. The product was isolated by flash chromatography on silica gel 60 (40-63 um, eluent—dichloromethane). Yield, 10.9 g (85%) of white solid. This product was further used without additional purification. $^1$H NMR (CDCl$_3$): δ 7.20 (m, 1H, 5-H in indenyl), 7.15 (m, 1H, 6-H in indenyl), 6.95 (m, 1H, 4-H in indenyl), 6.52 (m, 1H, 3-H in indenyl), 4.06 (set, J=6.8 Hz, 1H, CHMe$_2$), 3.13-3.27 (m, 4H, 1,1'-H in indenyl and CH$_2$CH$_2$N), 2.96-3.07 (m, 2H, CH$_2$CH$_2$N), 2.34 (s, 3H, 2-Me in indenyl), 0.99 (d, J=6.8 Hz, 6H, CHMe$_2$). Anal. Calc. for C$_{22}$H$_{27}$NO$_2$S: C, 71.51; H, 7.36; N, 3.79%. Found: C, 72.01; H, 7.49; N, 3.33%.

2b): N-Isopropyl-2-(2-methyl-1/3H-inden-7/4-yl) ethanamine

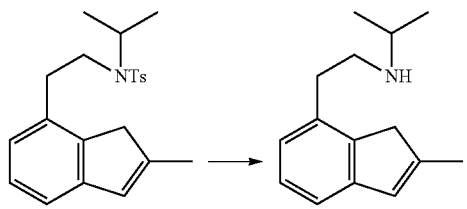

In 250 mL round-bottom flask equipped with reflux condenser and placed in ultrasound bath, to a heated (50° C.)

solution of 9.02 g (24.4 mmol) of N-isopropyl-4-methyl-N-[2-(2-methyl-1H-inden-7-yl)ethyl]benzenesulfonamide in 110 mL of methanol, 1.78 g (73.2 mmol) of magnesium turnings were added in small portions at such a speed that the mixture continued to boil. After all the magnesium reacted, the resulting mixture was evaporated to dryness, and to the residue 300 mL of saturated aqueous NH$_4$Cl and 200 mL of dichloromethane were added. The organic layer was separated, and the aqueous layer was washed with 2×200 mL of dichloromethane. The combined organic extract was evaporated to dryness. The residue was dissolved in 20 mL of methanol, and saturated solution of 8.57 g (68.0 mmol) of oxalic acid hydrate in methanol was added. The formed suspension was refluxed for 5 minutes and then slowly cooled to room temperature. The formed precipitate was filtered off (G3), dried in vacuum, and then treated with 20% aqueous KOH. Further on, the product was extracted with 3×200 mL of dichloromethane. The combined organic extract was evaporated to dryness to give 4.73 g (90%) of colorless oil as a mixture of the isomers. $^1$H NMR (CDCl$_3$) of N-isopropyl-2-(2-methyl-1H-inden-7-yl)ethanamine (major isomer): δ 7.17 (t, J=7.5 Hz, 1H, 5-H), 7.11 (dd, J=7.5 Hz, J=1.0 Hz, 1H, 4-H), 6.94 (dd, J=7.5 Hz, J=1.0 Hz, 1H, 6-H), 6.48 (m, 1H, 3-H), 3.26 (s, 2H, 1,1'-H in indenyl), 2.77-2.93 (m, 5H, CH$_2$CH$_2$ and Me$_2$CH), 2.15 (m, 3H, 2-Me in indenyl); 1.26 (br.s, 1H, NH), 1.05 (d, J=6.3 Hz, 6H, Me$_2$CH); N-isopropyl-2-(2-methyl-3H-inden-4-yl)ethanamine (minor isomer): 7.23 (m, 1H, 5-H), 7.01-7.05 (m, 2H, 6,7-H), 6.62 (m, 1H, 3-H), 3.29 (s, 2H, 1,1'-H in indenyl), 2.77-2.93 (m, 5H, CH$_2$CH$_2$ and Me$_2$CH), 2.16 (s, 3H, 2-Me in indenyl), 1.26 (br.s, 1H, NH), 1.04 (d, J=6.3 Hz, 6H, Me$_2$CH). Anal. Calc. for C$_{15}$H$_{21}$N: C, 83.67; H, 9.83; N, 6.50%. Found: C, 83.90; H, 10.09; N, 6.32%.

2c): [η$^5$:η$^1$-N-Isopropyl-2-(2-methylinden-4-yl)ethanamido]titaniumdichloride (Compound B)

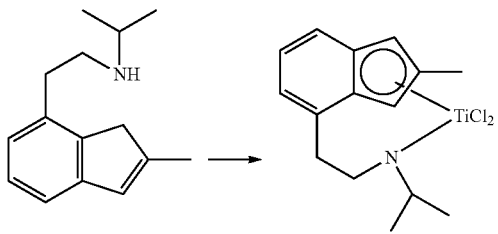

To a solution of 2.86 g (13.3 mmol) of N-isopropyl-2-(2-methyl-1/3H-inden-7/4-yl)ethanamine in 180 mL of dry ether, 10.6 mL (26.6 mmol) of 2.5 M $^n$BuLi in hexanes was added at room temperature. This mixture was additionally stirred for 12 hours at this temperature, and then a solution of 2.52 g (13.3 mmol) of TiCl$_4$ in 30 mL of hexanes was added at 0° C. The resulting mixture was stirred for additional 12 hours at room temperature and then evaporated to dryness. The residue was dried via vacuum, and then 60 mL of toluene was added. The obtained suspension was stirred for 2 hours at 50° C., filtered through glass frit (G3), and the precipitate was additionally washed with 15 mL of toluene. The combined filtrate was dried in vacuum. To the obtained solid 40 mL of hexanes was added, and the formed suspension was stirred for 30 minutes at room temperature. Further on, this suspension was filtered through glass fit (G3), the precipitate was washed with 2×15 mL of hexanes, and then dried in vacuum. Yield, 1.72 g (39%) of the title titanium complex. $^1$H NMR (CD$_2$Cl$_2$): δ 7.32 (dq, J=8.5 Hz, J=0.6 Hz, 1H, 5-H), 7.08 (dd, J=8.5 Hz, J=6.7 Hz, 1H, 6-H), 6.94 (dm, J=6.7 Hz, 1H, 7-H), 6.75 (m, 1H, 3-H in indenyl), 6.73 (m, 1H, 1-H in indenyl), 5.48 (sept, J=6.1 Hz, 1H, CHMeMe'), 3.99-4.11 (m, 1H, NCH$_2$CH$_2$), 3.84 (m, 1H, NCH$_2$CH$_2$), 2.37 (s, 3H, 2-Me in indenyl), 1.19 (d, J=6.1 Hz, 3H, CHMeMe'), 0.82 (d, J=6.1 Hz, 3H, CHMeMe'). $^{13}$C{$^1$H} NMR (CD$_2$Cl$_2$): δ 150.0, 138.0, 137.0, 130.9, 127.9, 122.5, 121.6, 113.8, 109.6, 55.4, 48.6, 32.3, 18.3, 17.6, 17.3. Anal. Calc. for C$_{15}$H$_{19}$Cl$_2$NTi: C, 54.25; H, 5.77; N, 4.22%. Found: C, 54.45; H, 5.91; N, 4.00%.

Example 3

Preparation of [η$^5$:η$^1$-N-Benzyl-2-(2-methylinden-4-yl)ethanamido]titanium dichloride (Compound C)

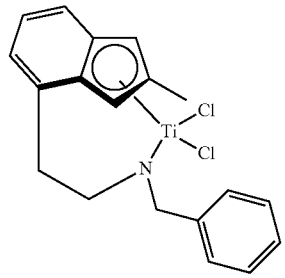

3a): N-Benzyl-4-methyl-N-[2-(2-methyl-1/3H-inden-7/4-yl)ethyl]benzenesulfonamide

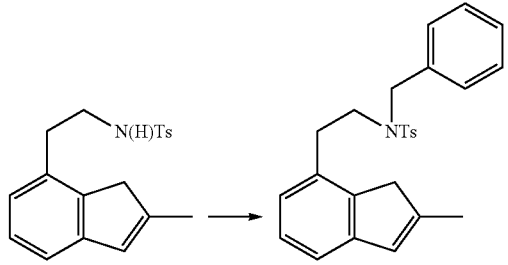

To a solution of 17.1 g (52.2 mmol) of 4-methyl-N-[2-(2-methyl-1H-inden-7-yl)ethyl]-benzenesulfonamide in 115 mL of dry DMF 25.5 g (78.4 mmol) of Cs$_2$CO$_3$ and 1 g of KI were added, and then 9.92 g (78.4 mmol) of benzyl chloride was added dropwise for 10 minutes at room temperature. This mixture was stirred for 24 hours at 80° C. and then evaporated in vacuum. To the residue 200 mL of water and 300 mL of dichloromethane were added. The organic layer was separated, and the aqueous layer was washed with 150 mL of dichloromethane. The combined organic extract was evaporated to dryness. The product was isolated by flash chromatography on silica gel 60 (40-63 um, eluent—dichloromethane). Yield 20.1 g (92%) of white solid of a ca. 3 to 1 mixture of N-benzyl-4-methyl-N-[2-(2-methyl-1H-inden-7-yl)ethyl]benzenesulfonamide and N-benzyl-4-methyl-N-[2-(2-methyl-3H-inden-4-yl)ethyl]benzenesulfonamide. This product was further used without an additional purification. $^1$H NMR (CDCl$_3$) of N-benzyl-4-methyl-N-[2-(2-methyl-1H-inden-7-yl)ethyl]benzene-sulfonamide: δ 7.27-7.34 (m, 5H, Ph), 7.03-7.08 (m, 2H, 4,5-H in indenyl), 6.67 (dd, J=6.5 Hz, J=2.0 Hz, 1H, 6-H in indenyl), 6.41 (m, 1H, 3-H in indenyl), 4.35 (s, 3H, CH$_2$Ph), 3.27 (m, 2H, CH$_2$CH$_2$N), 2.89 (s, 2H, 1,1'-H in indenyl), 2.68 (m, 2H, CH$_2$CH$_2$N), 2.09 (s, 3H, 2-Me in indenyl); N-benzyl-4-methyl-N-[2-(2-methyl-3H-inden-4-yl)ethyl]benzenesulfonamide, δ 7.27-7.34 (m, 5H, Ph), 7.16 (m, 1H, 5-H in indenyl), 6.94 (m, 1H, 6-H in indenyl), 6.78 (m, 1H, 7-H in indenyl), 6.14 (m, 1H, 3-H in indenyl), 4.36 (s, 3H, CH$_2$Ph), 3.25 (m, 2H, CH$_2$CH$_2$N), 3.21

(s, 2H, 1,1'-H in indenyl), 2.73 (m, 2H, CH$_2$CH$_2$N), 2.09 (s, 3H, 2-Me in indenyl). Anal. Calc. for C$_{26}$H$_{27}$NO$_2$S: C, 74.79; H, 6.52; N, 3.35%. Found: C, 75.18; H, 6.87; N, 2.98%.

3b): N-Benzyl-2-(2-methyl-1/3H-inden-7/4-yl)ethanamine

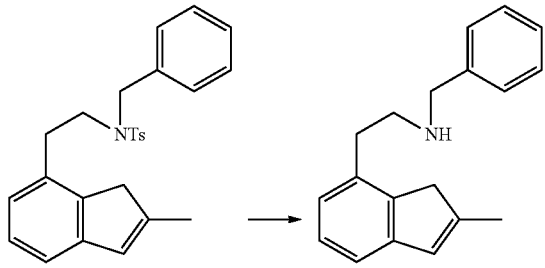

In 250 mL round-bottom flask equipped with reflux condenser and placed in ultrasound bath, to a heated (50° C.) solution of 10.0 g (24.0 mmol) of N-benzyl-4-methyl-N-[2-(2-methyl-1/3H-inden-7/4-yl)ethyl]benzenesulfonamide in 100 mL of methanol 1.75 g (72.0 mmol) of magnesium turnings were added in small portions at such a speed that the mixture continued to boil. After all the magnesium reacted, the resulting mixture was evaporated to dryness, and to the residue 300 mL of saturated aqueous NH$_4$Cl and 200 mL of dichloromethane were added. The organic layer was separated, and the aqueous layer was washed with 2×200 mL of dichloromethane. The combined organic extract was evaporated to dryness. The residue was dissolved in 20 mL of methanol, and saturated solution of 8.57 g (68.0 mmol) of oxalic acid hydrate in methanol was added. The formed suspension was refluxed for 5 minutes and then slowly cooled to room temperature. The formed precipitate was filtered off (G3), dried in vacuum, and then treated with 20% aqueous KOH. Further on, the product was extracted with 3×200 mL of dichloromethane. The combined organic extract was evaporated to dryness to give 5.94 g (94%) of colorless oil as a mixture of the isomers. $^1$H NMR (CDCl$_3$) of N-benzyl-2-(2-methyl-1H-inden-7-yl)ethanamine (major isomer): δ 6.92-7.35 (m, 8H, CH$_2$Ph and 4,5,6-H in indenyl), 6.49 (m, 1H, 3-H in indenyl), 3.83 (s, 2H, CH$_2$Ph), 3.24 (s, 2H, 1,1'-H in indenyl), 2.87-2.99 (m, 4H, CH$_2$CH$_2$), 2.16 (s, 3H, 2-Me in indenyl), 1.74 (br.s, 1H, NH); N-benzyl-2-(2-methyl-3H-inden-4-yl)ethanamine (minor isomer): 6.92-7.35 (m, 8H, CH$_2$Ph and 5,6,7-H in indenyl), 6.61 (m, 1H, 3-H in indenyl), 3.83 (s, 2H, CH$_2$Ph), 3.30 (s, 2H, 1,1'-H in indenyl), 2.87-2.99 (m, 4H, CH$_2$CH$_2$), 2.17 (s, 3H, 2-Me in indenyl), 1.74 (br.s, 1H, NH). Anal. Calc. for C$_{19}$H$_{21}$N: C, 86.65; H, 8.04; N, 5.32%. Found: C, 86.93; H, 8.38; N, 5.14%.

3c): [η$^5$:η$^1$-N-Benzyl-2-(2-methylinden-4-yl)bethanamido]titanium dichloride (Compound C)

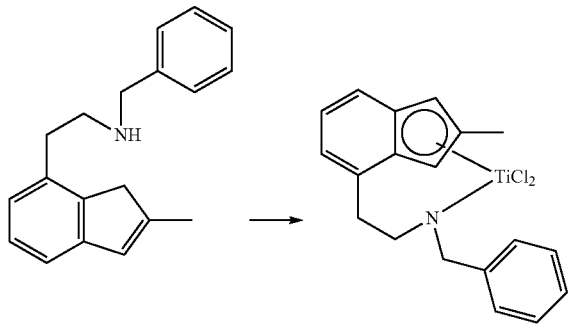

To a solution of 2.47 g (9.38 mmol) of N-benzyl-2-(2-methyl-1/3H-inden-7/4-yl)ethanamine in 150 mL of dry ether 7.50 mL (18.8 mmol) of 2.5 M $^n$BuLi in hexanes was added at room temperature. This mixture was additionally stirred for 12 hours at this temperature, and then a solution of 1.78 g (9.38 mmol) of TiCl$_4$ in 20 mL of hexanes was added at 0° C. The resulting mixture was stirred for additional 12 hours at room temperature and then evaporated to dryness. The residue was dried in vacuum, and then 50 mL of toluene was added. The obtained suspension was stirred for 2 hours at 50° C., filtered through glass frit (G3), and the precipitate was additionally washed with 15 mL of toluene. The combined filtrate was dried in vacuum. To the obtained solid 40 mL of hexanes was added, and the formed suspension was stirred for 30 minutes at room temperature. Further on, this suspension was filtered through glass frit (G3), the precipitate was washed with 2×15 mL of hexanes and then dried in vacuum. Yield 1.53 g (43%) of the title titanium complex. $^1$H NMR (CD$_2$Cl$_2$): δ 7.40 (d, J=8.6 Hz, 1H, 5-H in indenyl), 7.23-7.28 (m, 3H, 2,4,6-H in Ph), 7.19 (dd, J=8.5 Hz, J=6.7 Hz, 1H, 6-H in indenyl), 7.04 (d, J=6.7 Hz, 1H, 7-H in indenyl), 7.00-7.04 (m, 2H, 3,5-H in Ph), 6.92 (m, 1H, 1-H in indenyl), 6.85 (m, 1H, 3-H in indenyl), 5.49 (d, J=16.7 Hz, 1H, CHH'Ph), 4.90 (d, J=16.7 Hz, 1H, CHH'Ph), 3.97 (ddd, J=13.1 Hz, J=9.4 Hz, J=7.6 Hz, 1H, NCHH'CHH'), 3.80 (dd, J=15.7 Hz, J=7.6 Hz, 1H, NCHH'CHH'), 3.19 (ddd, J=13.1 Hz, J=7.6 Hz, J=1.5 Hz, 1H, NCHH'CHH'), 2.97 (m, 1H, NCHH'CHH), 2.45 (s, 3H, 2-Me in indenyl). $^{13}$C{$^1$H} NMR (CD$_2$Cl$_2$): δ 139.9, 138.8, 138.5, 132.7, 130.5, 129.9 (two resonances), 129.6, 129.0, 123.8, 123.4, 116.3, 111.1, 65.7, 58.1, 33.6, 19.3. Anal. Calc. for C$_{19}$H$_{19}$Cl$_2$NTi: C, 60.03; H, 5.04; N, 3.68%. Found: C, 59.92; H, 5.01; N, 3.79%.

Example 4

Preparation of [η$^5$:η$^1$-N-tert-Butyl-2-(2-methylinden-4-yl)ethanamido]titanium dichloride (Compound D)

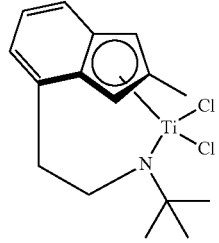

4a) 2-(1-Methoxy-2-methyl-2,3-dihydro-1H-inden-4-yl)ethanol

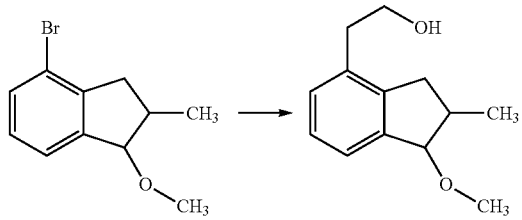

To a solution of 22.2 g (92.0 mmol) of 4-bromo-2-methyl-methoxyindane in 200 ml of THF 36.9 ml of 2.5 M (92.1 mmol) $^n$BuLi in hexanes was added for 20 minutes at −80° C. This mixture was stirred for 30 minutes at this temperature, cooled to −110° C., and 4.86 g (110 mmol) of ethylene oxide was added by one portion at vigorous stirring. The resulting mixture was stirred for 12 hours at room temperature, and then 10 ml of water was added. The organic layer was separated and evaporated to dryness. To the residue 150 ml of water was added, and the crude product was extracted with 3×100 ml of dichloromethane. The combined organic extract was dried over $Na_2SO_4$ and evaporated to dryness. The product was isolated by flash chromatography on silica gel 60 (40-63 μm, eluent: hexanes-ether=20:1, vol.). Yield 14.7 g (77%) of a ca. 1 to 1.1 mixture of two diastereomers. Anal. calc. for $C_{13}H_{18}O_2$: C, 75.69; H, 8.80. Found: C, 75.80; H, 8.94. $^1H$ NMR ($CDCl_3$): δ 7.29 (m, 2H, 6-H of both isomers), 7.23 (m, 2H, 7-H of both isomers), 7.15 (m, 2H, 5-H of both isomers), 4.58 (d, J=5.5 Hz, 1H, CHOMe of minor isomer), 4.48 (d, J=4.0 Hz, 1H, CHOMe of major isomer), 3.53 (s, 3H, OMe of major isomer), 3.48 (s, 3H, OMe of minor isomer), 3.74 (m, 4H, $CH_2Br$ of both isomers), 3.27 (dd, J=15.9 Hz, J=7.7 Hz, 1H, 3-CHH' of major isomer), 2.97 (dd, J=15.0 Hz, J=6.8 Hz, 1H, 3-CHH' of minor isomer), 2.82 (m, 4H, $CH_2CH_2Br$ of both isomers), 2.73 (dd, J=15.0 Hz, J=7.0 Hz, 1H, 3-CHH' of minor isomer), 2.54-2.71 (m, 4H, CHMe and OH of both isomers), 2.46 (dd, J=15.9 Hz, J=5.0 Hz, 3-CHH' of major isomer), 1.18 (d, J=7.0 Hz, 3H, 2-Me of major isomer), 1.15 (d, J=7.9 Hz, 3H, 2-Me of minor isomer). $^{13}C\{^1H\}$ NMR ($CDCl_3$): δ 142.6, 142.4, 141.9 (2C), 134.8, 134.6, 128.9, 128.7, 126.6, 126.2, 123.4, 123.2, 91.4, 86.1, 62.3, 62.2, 56.6, 56.2, 39.1, 38.3, 36.8, 36.5, 36.4, 36.2, 19.3, 13.5.

4b) 4-(2-Bromoethyl)-1-methoxy-2-methylindane

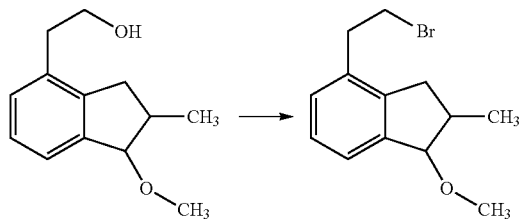

To a mixture of 12.9 g (62.5 mmol) of 2-(1-methoxy-2-methyl-2,3-dihydro-1H-inden-4-yl)ethanol and 16.4 g (62.5 mmol) of $PPh_3$ in 300 ml of THF 11.1 g (62.5 mmol) of N-bromosuccinimide was added at vigorous stirring for 5 minutes at 0° C. This mixture was stirred for 2 hours at room temperature and then evaporated to dryness. A solution of the residue in 200 ml of hexanes was filtered through glass frit (G3), and the precipitate was additionally washed by 3×100 ml of hexanes. The combined organic extract was evaporated to dryness. The product was isolated from the residue using flash chromatography on silica gel 60 (40-63 μm, eluent: hexanes-ether=20:1, vol.). Yield 12.1 g (72%) of ca. 1 to 1 mixture of the diastereomers A and B. Anal. calc. for $C_{13}H_{17}BrO$: C, 58.01; H, 6.37. Found: C, 58.24; H, 6.22. $^1H$ NMR ($CDCl_3$): δ 7.30 (m, 2H, 6-H in indenyl of A and B), 7.20 (m, 2H, 7-H in indenyl of A and B), 7.12 (m, 2H, 5-H in indenyl of A and B), 4.52 (m, 1H, 1-H in indenyl of A), 4.41 (m, 1H, 1-H in indenyl of B), 3.53 (m, 4H, $CH_2CH_2Br$ of A and B), 3.47 (s, 3H, OMe of B), 3.42 (s, 3H, OMe of A), 3.22 (dd, J=15.8 Hz, J=7.6 Hz, 1H, 3-H in indenyl of B), 3.15 (m, 4H, $CH_2CH_2Br$ of A and B), 2.92 (dd, J=14.9 Hz, J=6.7 Hz, 1H, 3-H in indenyl of A), 2.48-2.71 (m, 3H, 2,3-H in indenyl of A and 2-H in indenyl of B), 2.42 (dd, J=15.8 Hz, J=4.8 Hz, 1H, 3-H in indenyl of B), 1.18 (d, J=7.1 Hz, 3H, 2-Me in indenyl of B), 1.13 (d, J=6.6 Hz, 3H, 2-Me in indenyl of A). $^{13}C\{^1H\}$ NMR ($CDCl_3$): δ 143.1, 142.6, 142.2, 141.7, 135.1, 135.0, 128.5, 128.4, 126.8, 126.5, 124.1, 123.8, 91.3, 85.9, 56.7, 56.5, 39.4, 38.5, 36.80, 36.78, 36.7, 36.5, 31.7, 31.6, 19.4, 13.6.

4c) 4/7-(2-Bromoethyl)-2-methyl-1H-indene

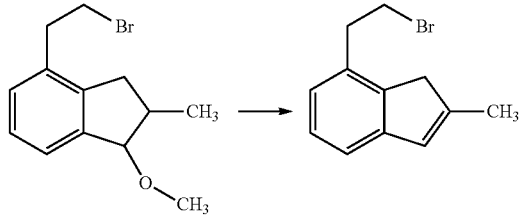

To a hot (110° C.) solution of 12.0 g (44.6 mmol) of 4-(2-bromoethyl)-1-methoxy-2-methylindane in 200 ml of toluene 1.0 g of TsOH was added. This mixture was refluxed with Dean-Stark trap for 10 minutes and then passed through 5 cm layer of silica gel 60 (40-63 μm). The silica gel layer was additionally washed by 500 ml of toluene. The combined organic extract was evaporated to dryness. The product was isolated by flash chromatography on silica gel 60 (40-63 μm, eluent: hexanes). Yield 10.2 g (97%) of a ca. 1 to 1.5 mixture of 4- and 7-(2-bromoethyl)-2-methyl-1H-indenes. Anal. calc. for $C_{12}H_{13}Br$: C, 60.78; H, 5.53. Found: C, 60.66; H, 5.46. $^1H$ NMR ($CDCl_3$): δ 6.92-7.31 (m, 6H, 5,6,7-H and 4,5,6-H of minor and major isomers, respectively), 6.60 (m, 1H, 3-H in indenyl of minor isomer), 6.51 (m, 1H, 3-H in indenyl of major isomer), 3.62 (m, 2H, $CH_2Br$ of major isomer), 3.57 (m, 2H, $CH_2Br$ of minor isomer), 3.32 (br.s, 2H, 1,1'-H in indenyl of minor isomer), 3.28 (br.s, 2H, 1,1'-H in indenyl of major isomer), 3.27 (m, 2H, $CH_2CH_2Br$ of minor isomer), 3.23 (m, 2H, $CH_2CH_2Br$ of major isomer), 2.19 (m, 3H, 2-Me in indenyl of minor isomer), 2.18 (m, 3H, 2-Me in indenyl of major isomer).

4d): N-tert-Butyl-2-(2-methyl-1/3H-inden-7/4-yl)ethanamine

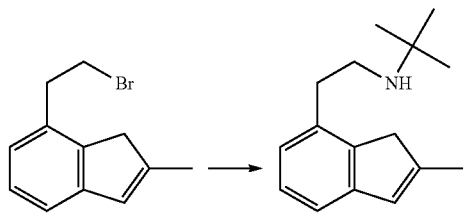

To a mixture of 5.40 g (22.7 mmol) of 7-(2-bromoethyl)-2-methyl-1H-indene, 2.42 g (22.7 mmol) of anhydrous $Na_2CO_3$, and 0.15 g of NaI in 50 mL of dry DMF a solution of 2.50 g (34.2 mmol) of tert-butylamine in 10 mL of DMF was added dropwise by vigorous stirring at room temperature. This mixture was additionally stirred for 12 hours at this temperature and then for 4 hours at 65° C. The resulting mixture was evaporated to dryness in vacuum, and to the residue 40 mL of water and 50 mL of dichloromethane were added. The organic layer was separated, and the aqueous layer was washed with 2×50 mL of dichloromethane. The combined organic extract was evaporated to dryness, and the product was isolated by flash chromatography on silica gel 60 (40-63 um, eluent—dichloromethane and then ether). Yield 3.64 g (70%) of the title product as colorless oil. $^1H$ NMR ($CDCl_3$) of N-tert-butyl-2-(2-methyl-1H-inden-7-yl)ethanamine (major isomer): δ 6.93-7.26 (m, 3H, 4,5,6-H), 6.48 (m, 1H, 3-H), 3.25 (s, 2H, 1,1'-H in indenyl), 2.94 (br.s, 1H, NH), 2.79-2.90 (m, 4H, $CH_2CH_2$), 2.15 (s, 3H, 2-Me in indenyl); 1.08 (s, 9H, $^tBu$); N-tert-butyl-2-(2-methyl-3H-inden-4-yl)ethanamine (minor isomer): 6.93-7.26 (m, 3H, 4,5, 6-H), 6.61 (m, 1H, 3-H), 3.29 (s, 2H, 1,1'-H in indenyl), 2.79-2.90 (m, 5H, CH$_2$CH$_2$ and NH), 2.15 (s, 3H, 2-Me in indenyl), 1.07 (s, 9H, $^t$Bu). Anal. Calc. for C$_{16}$H$_{23}$N: C, 83.79; H, 10.11; N, 6.11%. Found: C, 83.90; H, 10.31; N, 6.04%.

4e): [η$^5$:η$^1$-N-tert-Butyl-2-(2-methylinden-4-yl)ethanamido]titaniumdichloride (Compound D)

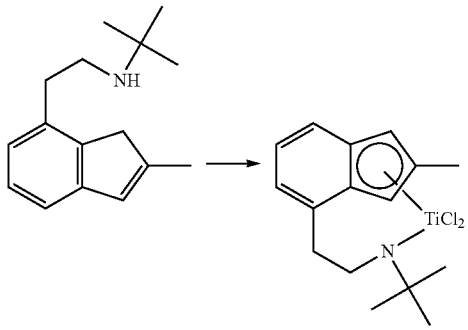

To a solution of 2.29 g (10.0 mmol) of N-tert-butyl-2-(2-methyl-1/3H-inden-7/4-yl)ethanamine in 120 mL of dry ether 8.00 mL (20.0 mmol) of 2.5 M $^n$BuLi in hexanes was added at room temperature. This mixture was additionally stirred for 12 hours at this temperature, and then a solution of 1.90 g (10.0 mmol) of TiCl$_4$ in 20 mL of hexanes was added at 0° C. The resulting mixture was stirred for additional 12 hours at room temperature and then evaporated to dryness. The residue was dried in vacuum, and then 40 mL of toluene was added. The obtained suspension was stirred for 2 hours at 50° C., filtered through glass frit (G3), and the precipitate was additionally washed with 10 mL of toluene. The combined filtrate was dried in vacuum. To the obtained solid 10 mL of hexanes was added, and the formed suspension was stirred for 30 minutes at room temperature. Further on, this suspension was filtered through glass frit (G3), the precipitate was washed with 2×7 mL of hexanes and then dried in vacuum. Yield 1.21 g (35%) of the title titanium complex. $^1$H NMR (CD$_2$Cl$_2$): δ 7.38 (m, 1H, 7-H in indenyl), 7.08 (dd, J=8.5 Hz, J=6.7 Hz, 1H, 6-H in indenyl), 6.85 (m, 1H, 5-H in indenyl), 6.66 (m, 1H, 3-H in indenyl), 6.62 (m, 1H, 1-H in indenyl), 5.44 (ddd, J=14.9 Hz, J=10.8 Hz, J=7.9 Hz, 1H, NCHH'CHH'), 4.02 (dd, J=14.9 Hz, J=7.9 Hz, 1H, NCHH'CHH'), 3.52 (dd, J=14.9 Hz, J=9.0 Hz, 1H, NCHH'CHH'), 3.02 (ddd, J=14.9 Hz, J=10.8 Hz, J=9.0 Hz, 1H, NCHH'CHH'), 2.43 (s, 3H, 2-Me in indenyl), 1.33 (s, 9H, $^t$Bu). Anal. Calc. for C$_{16}$H$_{21}$Cl$_2$NTi: C, 55.52; H, 6.12; N, 4.05%. Found: C, 55.77; H, 6.32; N, 3.80%.

Example 5

Preparation of {η$^5$:η$^1$-[(2-Methylinden-4-yl)methyl](4-methylphenyl)amido}-titaniumdichloride (Compound E)

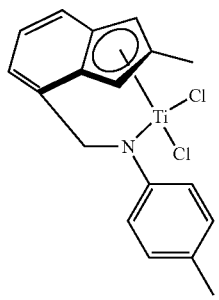

5a) 4-(Bromomethyl)-1-methoxy-2-methylindane

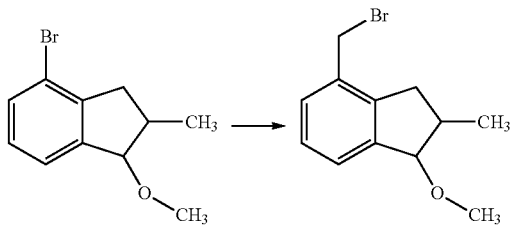

To a solution of 36.2 g (0.15 mol) of 4-bromo-2-methyl-methoxyindane in 600 ml of THF 60.0 ml 2.5 M (0.15 mol) $^n$BuLi in hexanes was added for 15 minutes at −78° C. The resulting mixture was stirred for 2 hours at this temperature, then cooled to −110° C., and 14.1 ml (13.2 g, 0.18 mol) of DMF was added at vigorous stirring. This mixture was warmed to room temperature, 10 ml of water was added, and then the resulting mixture was evaporated in vacuum. To a solution of the residue in a mixture of 500 ml of THF and 250 ml of methanol, 11.4 g (0.30 mol) of NaBH$_4$ was added in small portions at vigorous stirring for 5 minutes. This mixture was stirred for 10 minutes at room temperature and then evaporated to dryness. To the residue 400 ml of warm water was added, and the crude alcohol was extracted with 3×150 ml of dichloromethane. The combined organic extract was dried over Na$_2$SO$_4$ and then evaporated to dryness. To a mixture of the residue, 39.5 g (0.15 mol) of PPh$_3$, and 600 ml of THF 26.8 g (0.15 mol) of N-bromosuccinimide was added for ca. 5 minutes at room temperature. The resulting mixture was stirred for 5 minutes and evaporated to dryness. A mixture of the residue with 400 ml of hexanes was filtered through glass frit (G3). The precipitate was additionally washed by 3×200 ml of hexanes. The combined organic extract was evaporated to dryness. The product was isolated by flash chromatography on silica gel 60 (40-63 μm, eluent hexanes-ether=20:1, vol.). Yield 27.3 r (71%) of a ca. 1 to 1.5 mixture of two diastereomers. Anal. calc. for C$_{12}$H$_{15}$BrO: C, 56.49; H, 5.93. Found: C, 56.55; H, 6.10. $^1$H NMR (C$_6$D$_6$): δ 7.11-7.32 (m, 6H, 5,6,7-H in indenyl of both isomers), 4.47 (d, J=5.6 Hz, 1H, MeOCH of minor isomer), 4.41 (s, 2H, CH$_2$Br of major isomer), 4.40 (s, 2H, CH$_2$Br of minor isomer), 4.37 (d, J=4.1 Hz, 1H, MeOCH of major isomer), 3.42 (s, 3H, OMe of major isomer), 3.36 (s, 3H, OMe of minor isomer), 3.22 (dd, J=15.7 Hz, J=7.3 Hz, 1H, 3-CHH' of major isomer), 2.95 (dd, J=15.7 Hz, J=7.1 Hz, 1H, 3-CHH' of minor isomer), 2.41-2.71 (m, 4H, 3-CHH' and CHMe of both isomers), 1.16 (d, J=7.0 Hz, 3H, 2-Me of major isomer), 1.10 (d, J=6.9 Hz, 3H, 2-Me of minor isomer). $^{13}$C{$^1$H} NMR (C$_6$D$_6$), major isomer: δ 137.9, 137.43, 137.40, 123.4, 121.3, 120.0, 85.4, 50.8, 33.9, 30.7, 25.7, 13.7.

5b) 7-(Bromomethyl)-2-methyl-1H-indene

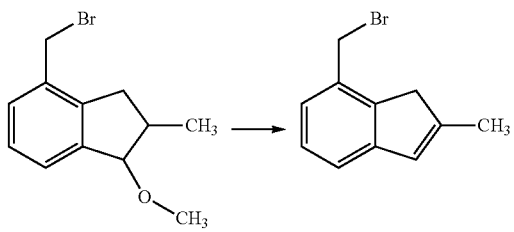

To a solution of 17.9 g (70 mmol) of 4-(bromomethyl)-1-methoxy-2-methylindane in 300 ml of toluene 2.0 g of TsOH was added at 110° C. This mixture was refluxed with Dean-Stark trap within 15 minutes and then passed through short column with silica gel 60 (40-63 μm). The silica gel layer was additionally washed by 200 ml of toluene. The combined elute was evaporated to dryness. The product was isolated by flash chromatography on silica gel 60 (40-63 μm, eluent:

hexanes). Yield 15.6 g (96%). Anal. calc. for $C_{11}H_{11}Br$: C, 59.22; H, 4.97. Found: C, 59.33; H, 5.08. $^1H$ NMR ($CDCl_3$): δ 7.19-7.23 (m, 2H, 4,6-H), 7.10 (m, 1H, 5-H), 6.50 (m, 1H, 3-H), 4.56 (s, 2H, $CH_2Br$), 3.36 (br.s, 2H, 1,1'-H), 2.19 (m, 3H, 2-Me). $^{13}C\{^1H\}$ NMR ($CDCl_3$): δ 146.6, 146.2, 142.4, 132.0, 127.17, 127.14, 124.4, 120.2, 40.9, 31.7, 16.7.

5c): [(2-Methyl-1H-inden-7/4-yl)methyl](4-methylphenyl)amine

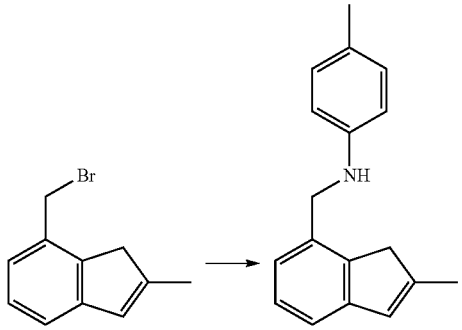

A mixture of 4.46 g (20.0 mmol) of 7-(bromomethyl)-2-methyl-1H-indene, 13.8 g (100 mmol) of anhydrous $K_2CO_3$, 3.21 g (30.0 mmol) p-toluidine, and 50 mL of dry DMF was stirred at reflux for 5 hours. Further on, an excess of DMF was distilled off in vacuum (15 mm Hg), and to the residue 40 mL of water and 50 mL of dichloromethane were added. The organic layer was separated, the aqueous layer was washed by 2×50 mL of dichloromethane. The combined organic extract was evaporated to dryness. The product was isolated by flash chromatography on silica gel 60 (40-63 um, eluent—dichloromethane). Yield 3.99 g (80%) of yellowish solid. $^1H$ NMR ($CDCl_3$) of [(2-methyl-1H-inden-7-yl)methyl](4-methylphenyl)amine (major isomer): δ 7.18-7.25 (m, 2H, 5,6-H in indenyl), 7.13 (dd, J=6.6 Hz, J=2.0 Hz, 1H, 4-H in indenyl), 6.99-7.02 (m, 2H, 3,5-H in p-tolyl), 6.56-6.60 (m, 2H, 2,6-H in p-tolyl), 6.52 (m, 1H, 3-H in indenyl), 4.33 (s, 2H, $CH_2N$), 3.83 (br.s, 1H, NH), 3.31 (s, 2H, 1,1'-H in indenyl), 2.25 (s, 3H, 2-Me in indenyl), 2.16 (s, 3H, Me in p-tolyl); [(2-methyl-1H-inden-4-yl)methyl](4-methylphenyl)amine (minor isomer): 7.32 (d, J=7.4 Hz, 1H, 7-H in indenyl), 7.18-7.25 (m, 1H, 5-H in indenyl), 7.08 (t, J=7.6 Hz, 1H, 6-H in indenyl), 7.00-7.03 (m, 2H, 3,5-H in p-tolyl), 6.66 (m, 1H, 3-H in indenyl), 6.58-6.62 (m, 2H, 2,6-H in p-tolyl), 4.36 (s, 2H, $CH_2N$), 3.83 (br s, 1H, NH), 3.33 (s, 2H, 1,1'-H in indenyl), 2.26 (s, 3H, 2-Me in indenyl), 2.17 (s, 3H, Me in p-tolyl). Anal. Calc. for $C_{18}H_{19}N$: C, 86.70; H, 7.68; N, 5.62%. Found: C, 86.57; H, 7.60; N, 5.50%.

5d): $\{\eta^5:\eta^1$-[(2-Methylinden-4-yl)methyl](4-methylphenyl)amido$\}$titaniumdichloride (Compound E)

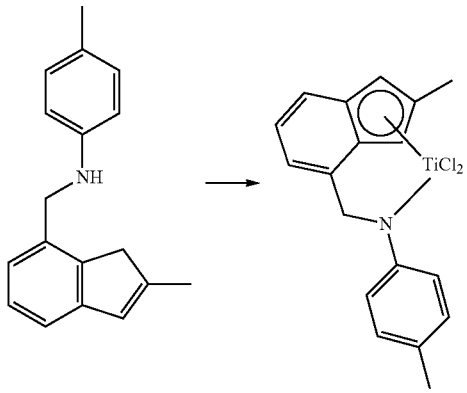

To a solution of 2.49 g (10.0 mmol) of [(2-methyl-1H-inden-7/4-yl)methyl](4-methylphenyl)amine in 100 mL of dry ether 8.00 mL (20.0 mmol) of 2.5 M $^nBuLi$ in hexanes was added at room temperature. This mixture was additionally stirred for 12 hours at this temperature, and then a solution of 1.90 g (10.0 mmol) of $TiCl_4$ in 20 mL of hexanes was added at 0° C. The resulting mixture was stirred for additional 12 hours at room temperature and then evaporated to dryness. The residue was dried in vacuum, and then 40 mL of toluene was added. The obtained suspension was stirred for 2 hours at 50° C., filtered through glass frit (G3), and the precipitate was additionally washed with 10 mL of toluene. The combined filtrate was dried in vacuum. To the obtained solid 20 mL of hexanes was added, and the formed suspension was stirred for 30 minutes at room temperature. Further on, this suspension was filtered through glass frit (G3), the precipitate was washed with 2×10 mL of hexanes and then dried in vacuum. Yield 1.21 g (33%) of the title titanium complex. $^1H$ NMR ($CD_2Cl_2$): δ 7.69 (m, 5-H in indenyl), 7.41-7.48 (m, 2H, 6,7-H in indenyl), 7.16 (m, 1H, 1-H in indenyl), 7.13 (m, 1H, 3-H in indenyl), 6.98 (m, 2H, 3,5-H in p-tolyl), 6.60 (m, 2H, 2,6-H in p-tolyl), 4.62 (s, 2H, $CH_2N$), 2.63 (s, 3H, 2-Me in indenyl), 2.22 (s, 3H, Me in p-tolyl). Anal. Calc. for $C_{18}H_{17}Cl_2NTi$: C, 59.05; H, 4.68; N, 3.83%. Found: C, 59.29; H, 4.90; N, 3.56%.

Example 6

Preparation of $\{\eta^5:\eta^1$-[(Inden-4-yl)methyl](4-methylphenyl)amido$\}$titanium dichloride (Compound F)

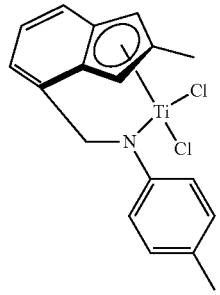

6a) 4-(Bromomethyl)-1-methoxyindane

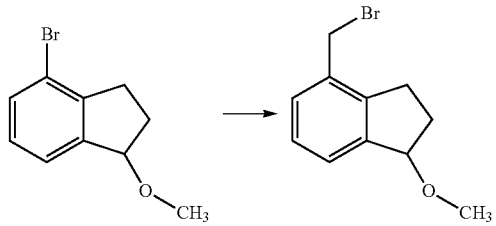

To a solution of 90.0 g (0.40 mol) of 4-bromo-1-methoxyindane in 200 ml of anhydrous THF 166 ml (0.42 mol) 2.5 M solution of $^nBuLi$ in hexanes was added dropwise by vigorous stirring at −78° C. This solution was stirred at this temperature for 1 hour, cooled to −100° C., and then 57.9 g (0.80 mol) of DMF was added dropwise to maintain temperature of the reaction mixture below −70° C. Further on, this mixture was stirred at room temperature for 3 hours, and then 15 ml of water was added. The resulting mixture was evaporated to dryness. The residue dried in vacuum was dissolved in a mixture of 600 ml of THF and 300 ml of methanol. To this solution 48.2 g (1.27 mol) of $NaBH_4$ was added in small portions by vigorous stirring at 0° C. This mixture was stirred for 12 hours at room temperature and then evaporated to dryness. The formed alcohol was extracted from a mixture of the residue with 800 ml of water by 2×400 ml of dichloromethane. The combined organic extract was dried over $Na_2SO_4$ and then evaporated to dryness. The residue was dissolved in 1 liter of THF, and 104 g (0.40 mol) of triphenylphosphine was added. This mixture was stirred for 10 minutes, and then 70.5 g (0.40 mol) of N-bromosuccinimide was added. The resulting mixture was stirred for 30 minutes at room temperature. The product was isolated by flash chromatography on silica gel 60 (40-63 μm, eluent: hexanes and then hexanes-ether=10:1, vol.). Yield 74.7 g (78%) of the title material. Anal. calc. for $C_{11}H_{13}BrO$: C, 54.79; H, 5.43. Found: C, 54.55; H, 5.54. $^1$H NMR (CDCl$_3$): δ 7.43 (m, 1H, 7-H), 7.31 (m, 1H, 5-H), 7.27 (m, 1H, 6H), 4.88 (dd, J=6.3 Hz, J=4.0 Hz, 1H, CHOMe), 4.52 (m, 2H, CH$_2$Br), 3.47 (s, 3H, OMe), 3.15 (m, 1H, 3-H), 2.93 (m, 1H, 3'-H), 2.42 (m, 1H, 2-H), 2.19 (m, 1H, 2'-H).

6b) 7-(Bromomethyl)-1H-indene

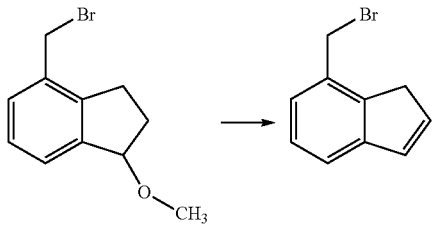

To a hot (110° C.) solution of 2.41 g (10.0 mmol) of 4-(bromomethyl)-1-methoxyindane in 40 ml of toluene 0.20 g of TsOH was added. This mixture was refluxed for 2 hours using a Dean-Stark head. The resulting mixture was passed through short column (4 cm) with silica gel 60 (40-63 μm), the silica gel layer was additionally washed by 20 ml of toluene. The combined elute was evaporated to dryness, the product was isolated by flash chromatography on silica gel 60 (40-63 μm, eluent: hexanes). Yield 1.98 g (95%) of the title material. Anal. calc. for $C_{10}H_9Br$: C, 57.44; H, 4.34. Found: C, 57.32; H, 4.41. $^1$H NMR (CDCl$_3$): δ 7.40 (m, 1H, 4-H), 7.29 (m, 1H, 5-H), 7.22 (m, 1H, 6-H), 6.92 (m, 1H, 3-H), 6.63 (m, 1H, 2-H), 4.62 (s, 2H, CH$_2$Br), 3.48 (m, 2H, 1,1'-H).

6c):
[(1H-Inden-7/4-yl)methyl](4-methylphenyl)amine

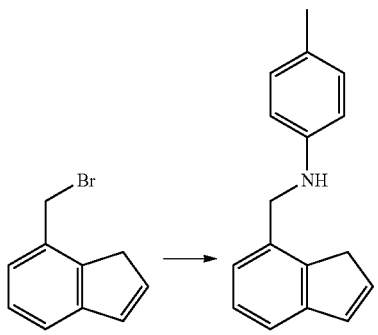

A mixture of 4.18 g (20.0 mmol) of 7-(bromomethyl)-1H-indene, 13.8 g (100 mmol) of anhydrous $K_2CO_3$, 3.21 g (30.0 mmol) p-toluidine, and 50 mL of dry DMF was stirred at reflux for 5 hours. Further on, an excess of DMF was distilled off in vacuum (15 mm Hg), and to the residue 40 mL of water and 50 mL of dichloromethane were added. The organic layer was separated, the aqueous layer was washed by 2×50 mL of dichloromethane. The combined organic extract was evaporated to dryness. The product was isolated by flash chromatography on silica gel 60 (40-63 um, eluent—dichloromethane). Yield 4.19 g (89%) of yellowish solid. $^1$H NMR (CDCl$_3$) of [(1H-inden-7-yl)methyl](4-methylphenyl)amine (major isomer): δ 7.33 (m, 1H, 6-H in indenyl), 7.23 (m, 1H, 5-H in indenyl), 7.21 (m, 1H, 4-H in indenyl), 6.88 (m, 2H, 3,5-H in p-tolyl), 6.57 (m, 2H, 2,6-H in p-tolyl), 5.94 (m, 1H, 3-H in indenyl), 4.36 (s, 2H, CH$_2$N), 3.45 (m, 2H, 1,1'-H in indenyl), 2.17 (br.s, 1H, NH), 2.15 (s, 3H, Me); [(1H-inden-4-yl)methyl](4-methylphenyl)amine (minor isomer): 7.38 (m, 1H, 5-H in indenyl), 7.27 (m, 1H, 7-H in indenyl), 7.14 (m, 1H, 6-H in indenyl), 6.96 (m, 2H, 3,5-H in p-tolyl), 6.64 (m, 2H, 2,6-H in p-tolyl), 5.96 (m, 1H, 3-H in indenyl), 4.41 (s, 2H, CH$_2$N), 3.40 (m, 2H, 1,1'-H in indenyl), 2.17 (br.s, 1H, NH), 2.15 (s, 3H, Me). Anal. Calc. for $C_{17}H_{17}N$: C, 86.77; H, 7.28; N, 5.95%. Found: C, 86.65; H, 7.13; N, 5.80%.

6d): {η$^5$:η$^1$-[(Inden-4-yl)methyl](4-methylphenyl)amido}titaniumdichloride (Compound F)

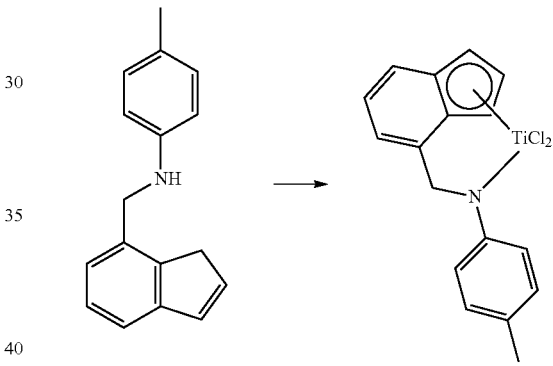

To a solution of 2.90 g (12.3 mmol) of [(1H-inden-7/4-yl)methyl](4-methyl-phenyl)-amine in 120 mL of dry ether 9.86 mL (24.6 mmol) of 2.5 M $^n$BuLi in hexanes was added at room temperature. This mixture was additionally stirred for 12 hours at this temperature, and then a solution of 2.34 g (12.3 mmol) of TiCl$_4$ in 20 mL of hexanes was added at 0° C. The resulting mixture was stirred for additional 12 hours at room temperature and then evaporated to dryness. The residue was dried in vacuum, and then 70 mL of toluene was added. The obtained suspension was stirred for 2 hours at 50° C., filtered through glass frit (G3), and the precipitate was additionally washed with 15 mL of toluene. The combined filtrate was dried in vacuum. To the obtained solid 30 mL of hexanes was added, and the formed suspension was stirred for 30 minutes at room temperature. Further on, this suspension was filtered through glass frit (G3), the precipitate was washed with 2×20 mL of hexanes and then dried in vacuum. Yield 0.65 g (15%) of the title titanium complex. $^1$H NMR (CD$_2$Cl$_2$): δ 7.76 (d, J=8.0 Hz, 5-H in indenyl), 7.47-7.55 (m, 2H, 6,7-H in indenyl), 7.33 (d, J=3.4 Hz, 2H, 1,3-H in indenyl), 7.18 (t, J=3.4 Hz, 1H, 2-H in indenyl), 6.99 (m, 2H, 3,5-H in p-tolyl), 6.60 (m, 2H, 2,6-H in p-tolyl), 4.68 (s, 2H, CH$_2$N), 2.22 (s, 3H, Me in p-tolyl). Anal. Calc. for $C_{17}H_{15}Cl_2NTi$: C, 57.99; H, 4.29; N, 3.98%. Found: C, 58.18; H, 4.43; N, 3.79%.

SILYL-BRIDGED EXAMPLES
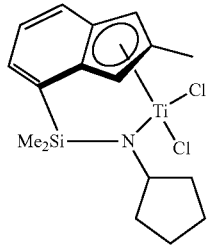
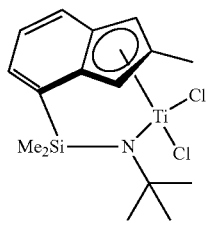
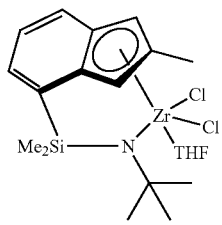
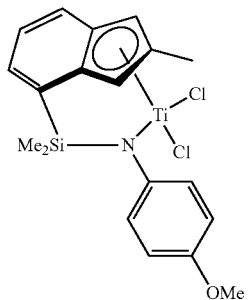
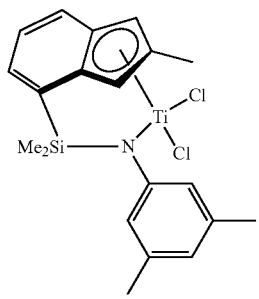
G
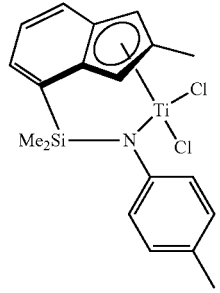
H
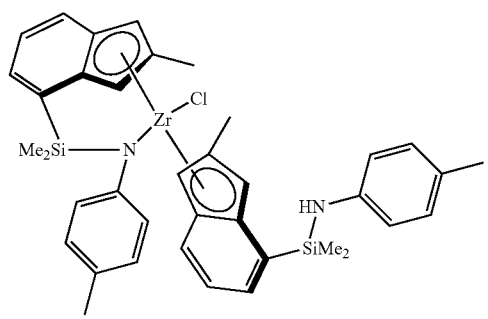
I
J
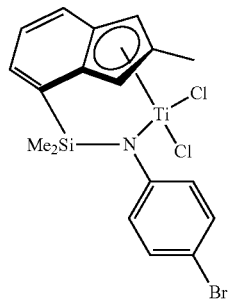
K
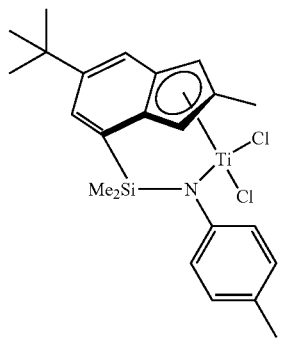
L
M
N
O

Example 7

Preparation of {η⁵:η¹-N-Cyclopentyl-1,1-dimethyl-1-(2-methylinden-4-yl)-silanamido}titanium dichloride (Compound G)

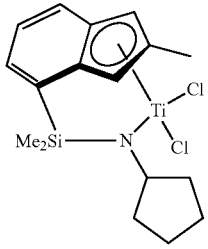

7a): Chloro(dimethyl)(2-methyl-1H-inden-7-yl)silane

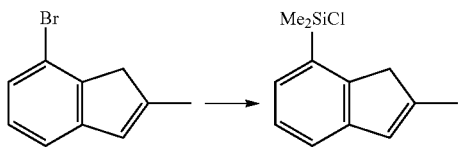

To 11.9 g (0.496 mol) of magnesium turnings in 80 mL of dry THF a solution of 50.0 g (0.239 mol) of 2-methyl-7-bromo-1H-indene and 45.0 g (0.239 mol) of 1,2-dibromoethane in 620 mL of THF was added dropwise by vigorous stirring in such rate that the mixture is refluxed. Then, this mixture was additionally refluxed for 30 minutes. Further on, to a solution of 110 g (0.853 mol) of dichlorodimethylsilane in 100 mL of THF the above-obtained solution of the Grignard reagent was added dropwise with vigorous stirring at room temperature using water bath to cool the reaction mixture. The resulting mixture was additionally stirred for 12 hours at ambient temperature, evaporated to dryness, and then 200 mL of dry ether was added. The obtained suspension was stirred for 20 minutes at room temperature and then filtered through glass frit (G3). The precipitate was additionally washed with 2×200 mL of ether. The combined filtrate was evaporated to dryness, and the residue was rectificated in vacuum, b.p. 105° C.-110° C./1 mm Hg. Yield 42.5 g (80%) of the title product. ¹H NMR (CD₂Cl₂): δ 7.37-7.41 (m, 2H, 4,6-H), 7.30 (m, 1H, 5-H), 6.57 (m, 1H, 3-H), 3.51 (m, 2H, 1,1'-H), 2.23 (m, 3H, 2-Me), 0.81 (s, 6H, SiMe₂). Anal. Calc. for C₁₂H₁₅ClSi: C, 64.69; H, 6.79%. Found: C, 64.56; H, 6.85%.

7b): N-Cyclopentyl-1,1-dimethyl-1-(2-methyl-1/3H-inden-7/4-yl)silanamine

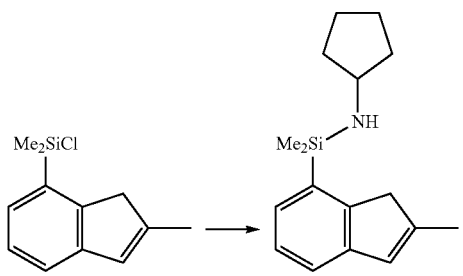

To a solution of 5.10 g (60.0 mmol) of cyclopentylamine in 120 mL of THF 24.0 mL (60.0 mmol) of 2.5 M "BuLi in hexanes was added at −80° C. This mixture was additionally stirred for 4 hours at room temperature, then cooled to −40° C., and a solution of 13.4 g (60.0 mmol) of chloro(dimethyl)(2-methyl-1H-inden-7-yl)silane in 50 mL of THF was added in one portion. The resulting mixture was stirred for 12 hours at room temperature and then evaporated to dryness. To the residue 100 mL of ether was added, and the obtained suspension was stirred for 20 minutes, and then filtered through glass frit (G3). The precipitate was additionally washed with 2×100 mL of ether. The combined filtrate was evaporated to dryness, and the residue was rectificated in vacuum, b.p. 127° C.-135° C./0.1 mm. Yield 6.83 g (42%) of colorless oil as a ca. 7 to 4 mixture of N-cyclopentyl-1,1-dimethyl-1-(2-methyl-1H-inden-7-yl)silanamine and N-cyclopentyl-1,1-dimethyl-1-(2-methyl-3H-inden-4-yl)silanamine. ¹H NMR (CD₂Cl₂), N-cyclopentyl-1,1-dimethyl-1-(2-methyl-1H-inden-7-yl)silanamine: δ 7.42 (m, 1H, 6-H in indenyl), 7.38 (m, 1H, 4-H in indenyl), 7.07 (m, 1H, 5-H in indenyl), 6.50 (m, 1H, 3-H), 3.43 (s, 2H, 1,1'-H in indenyl), 3.21 (br.s, 1H, 1-H in cyclopentyl), 2.19 (s, 3H, 2-Me in indenyl), 1.80 (br.s, 2H, 2,2'-H in cyclopentyl), 1.65 (br.s, 2H, 3/4,3'/4'-H in cyclopentyl), 1.48 (br.s, 2H, 4/3,4'/3'-H in cyclopentyl), 1.22 (br.s, 2H, 5,5'-H in cyclopentyl), 0.76 (br.s, 1H, NH), 0.37 (m, 6H, SiMe₂); N-cyclopentyl-1,1-dimethyl-1-(2-methyl-3H-inden-4-yl)silanamine, δ 7.32 (m, 1H, 6-H in indenyl), 7.26 (m, 1H, 4-H in indenyl), 7.20 (m, 1H, 5-H in indenyl), 6.85 (m, 1H, 3-H), 3.27 (s, 2H, 1,1'-H in indenyl), 3.21 (br.s, 1H, 1-H in cyclopentyl), 2.19 (s, 3H, 2-Me in indenyl), 1.80 (br.s, 2H, 2,2'-H in cyclopentyl), 1.65 (br.s, 2H, 3/4,3'/4'-H in cyclopentyl), 1.48 (br.s, 2H, 4/3,4'/3'-H in cyclopentyl), 1.22 (br.s, 2H, 5,5'-H in cyclopentyl), 0.76 (br.s, 1H, NH), 0.35 (m, 6H, SiMe₂). Anal. Calc. for C₁₇H₂₅NSi: C, 75.21; H, 9.28; N, 5.16%. Found: C, 75.42; H, 9.30; N, 5.02%.

7c): {η⁵:η¹-N-Cyclopentyl-1,1-dimethyl-1-(2-methylinden-4-yl)silanamido}titanium dichloride (Compound G)

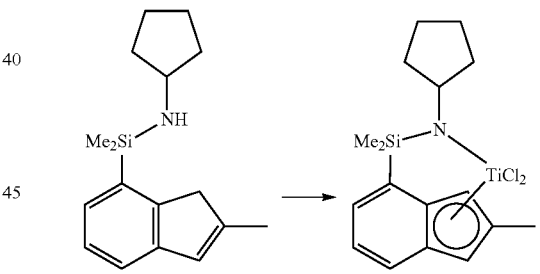

To a solution of 3.96 g (14.6 mmol) of N-cyclopentyl-1,1-dimethyl-1-(2-methyl-1/3H-inden-7/4-yl)silanamine in 300 mL of dry ether 11.7 mL (29.2 mmol) of 2.5 M "BuLi in hexanes was added at room temperature. This mixture was stirred for 12 hours at room temperature, and then a solution of 2.77 g (14.6 mmol) of TiCl₄ in 20 mL of hexanes was added at −80° C. The resulting mixture was stirred for 12 hour at room temperature and then evaporated to dryness. A mixture of the residue with 50 mL of toluene was stirred for 2 hours at 50° C. and then filtered through glass frit (G3). The precipitate was additionally washed with 10 mL of toluene. The combined filtrate was evaporated to dryness, and the residue was recrystallized from 15 mL of hexanes. Crystals precipitated at room temperature were collected, washed with 5 mL of cold hexanes, and dried in vacuum. Yield 2.38 g (42%) of black crystalline solid. ¹H NMR (CD₂Cl₂): δ 7.46 (d, J=8.3 Hz, 1H, 5-H in indenyl), 7.26 (dd, J=8.3 Hz, J=6.4 Hz, 1H, 6-H in indenyl), 7.22 (m, 1H, 7-H in indenyl), 6.93 (m, 1H, 3-H in indenyl), 6.62 (m, 1H, 1-H in indenyl), 5.35 (pent, J=8.2 Hz, 1H, 1-H in cyclopentyl), 2.42 (s, 3H, 2-Me in indenyl), 2.12 (m, 1H, cyclopentyl), 1.96 (m, 1H, cyclopentyl), 1.76 (m, 1H, cyclopentyl), 1.62 (m, 3H, cyclopentyl), 1.25 (m, 1H, cyclopentyl), 0.94 (m, 1H, cyclopentyl), 0.89 (s, 3H, SiMe), 0.49 (s, 3H, SiMe'). Anal. Calc. for $C_{17}H_{23}Cl_2NSiTi$: C, 52.59; H, 5.97; N, 3.61%. Found: C, 52.74; H, 6.12; N, 3.50%.

Example 8

{$\eta^5$:$\eta^1$-N-tert-Butyl-1,1-dimethyl-1-(2-methylinden-4-yl)silanamido}titanium dichloride and {$\eta^5$:$\eta^1$-N-tert-Butyl-1,1-dimethyl-1-(2-methylinden-4-yl)silanamido}-(tetra-hydrofurano)zirconiumdichloride (Compounds H and I)

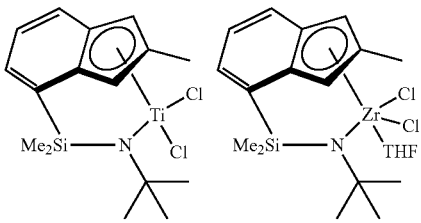

8a): N-tert-Butyl-1,1-dimethyl-1-(2-methyl-1/3H-inden-7/4-yl)silanamine

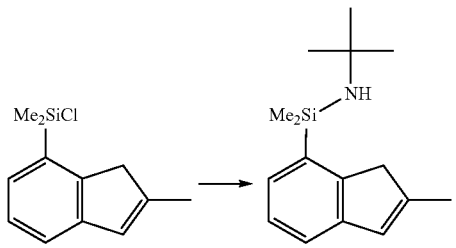

To a solution of 4.38 g (60.0 mmol) of tert-butylamine in 120 mL of THF 24.0 mL (60.0 mmol) of 2.5 M ″BuLi in hexanes was added at –80° C. This mixture was additionally stirred for 4 hours at room temperature, then cooled to –40° C., and a solution of 13.4 g (60.0 mmol) of chloro(dimethyl)(2-methyl-1H-inden-7-yOsilane in 50 mL of THF was added in one portion. The resulting mixture was stirred for 12 hours at room temperature and then evaporated to dryness. To the residue 100 mL of ether was added, and the obtained suspension was stirred for 20 minutes, and then filtered through glass frit (G3). The precipitate was additionally washed with 2×100 mL of ether. The combined filtrate was evaporated to dryness, and the residue was rectificated in vacuum, b.p. 127° C.-135° C./0.1 mm. Yield 5.76 g (37%) of colorless oil as a ca. 5 to 1 mixture of N-tert-butyl-1,1-dimethyl-1-(2-methyl-1H-inden-7-yl)silanamine and N-tert-butyl-1,1-dimethyl-1-(2-methyl-3H-inden-4-yOsilanamine $^1$H NMR ($CD_2Cl_2$), N-tert-butyl-1,1-dimethyl-1-(2-methyl-1H-inden-7-yOsilanamine: δ 7.86 (dd, J=7.3 Hz, J=1.3 Hz, 1H, 6-H in indenyl), 7.28 (dd, J=7.3 Hz, J=1.3 Hz, 1H, 4-H in indenyl), 7.22 (t, J=7.3 Hz, 1H, 5-H in indenyl), 6.63 (m, 1H, 3-H), 3.60 (br.s, 2H, 1,1'-H in indenyl), 2.21 (s, 3H, 2-Me in indenyl), 0.87 (br.s, 1H, NH), 1.16 (s, 9H, ′Bu), 0.45 (s, 6H, $SiMe_2$); N-tert-butyl-1,1-dimethyl-1-(2-methyl-3H-inden-4-yl)silanamine, δ 7.44 (m, 1H, 5-H in indenyl), 7.40 (m, 1H, 7-H in indenyl), 7.09 (t, J=7.6 Hz, 1H, 6-H in indenyl), 6.96 (m, 1H, 3-H), 3.29 (m, 2H, 1,1'-H in indenyl), 2.22 (s, 3H, 2-Me in indenyl), 0.87 (br.s, 1H, NH), 1.17 (s, 9H, ′Bu), 0.43 (s, 6H, $SiMe_2$). Anal. Calc. for $C_{16}H_{25}NSi$: C, 74.07; H, 9.71; N, 5.40%. Found: C, 73.85; H, 9.58; N, 5.19%.

8b): {$\eta^5$:$\eta^1$-N-tert-Butyl-1,1-dimethyl-1-(2-methyl-inden-4-vl)silanamido}titanium dichloride (Compound H)

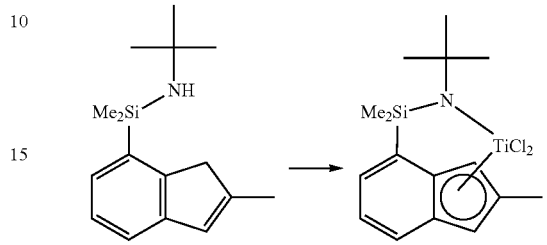

To a solution of 2.59 g (10.0 mmol) of N-tert-butyl-1,1-dimethyl-1-(2-methyl-1/3H-inden-7/4-yl)silanamine in 200 mL of dry ether 8.00 mL (20.0 mmol) of 2.5 M ″BuLi in hexanes was added at room temperature. This mixture was stirred for 12 hours at room temperature, and then a solution of 1.90 g (10.0 mmol) of $TiCl_4$ in 20 mL of hexanes was added at –80° C. The resulting mixture was stirred for 12 hours at room temperature and then evaporated to dryness. A mixture of the residue with 50 mL of toluene was stirred for 2 hours at 50° C. and then filtered through glass frit (G3). The precipitate was additionally washed with 10 mL of toluene. The combined filtrate was evaporated to dryness, and the residue was recrystallized from 20 mL of hexanes. Crystals precipitated at room temperature were collected, washed with 5 mL of cold hexanes, and dried in vacuum. Yield 2.18 g (58%) of black crystalline solid. $^1$H NMR ($CD_2Cl_2$): δ 7.51-7.55 (m, 2H, 5,7-H in indenyl), 7.33 (dd, J=7.8 Hz, J=7.3 Hz, 1H, 6-H in indenyl), 6.37 (m, 1H, 3-H in indenyl), 6.32 (pent, J=1.0 Hz, 1H, 1-H in indenyl), 2.26 (d, J=1.0 Hz, 3H, 2-Me in indenyl), 1.55 (s, 9H, ′Bu), 0.86 (s, 3H, SiMe), 0.79 (s, 3H, SiMe'). Anal. Calc. for $C_{16}H_{23}Cl_2NSiTi$: C, 51.08; H, 6.16; N, 3.72%. Found: C, 51.22; H, 6.10; N, 3.59%.

8c): {$\eta^5$:$\eta^1$-N-tert-Butyl-1,1-dimethyl-1-(2-methyl-inden-4-yl)silanamido}-(tetrahydrofurano)-zirconium dichloride (Compound I)

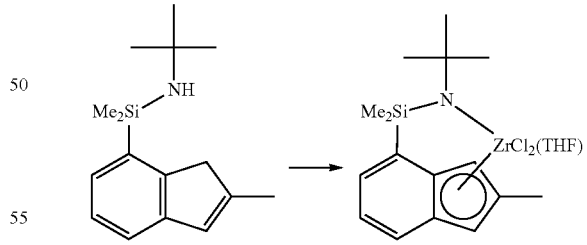

To a solution of 5.18 g (20.0 mmol) of N-tert-butyl-1,1-dimethyl-1-(2-methyl-1/3H-inden-7/4-yl)silanamine in 400 mL of dry ether 16.0 mL (40.0 mmol) of 2.5 M ″BuLi in hexanes was added at room temperature. This mixture was stirred for 12 hours at room temperature, and then a solution of 7.55 g (20.0 mmol) of $ZrCl_4(THF)_2$ was added at –50° C. The resulting mixture was stirred for 40 hours at room temperature and then evaporated to dryness. A mixture of the residue with 150 mL of toluene was stirred for 4 hours at 90° C. and then filtered through glass frit (G3). The precipitate was additionally washed with 10 mL of toluene. The combined filtrate was evaporated to dryness, and the residue was recrystallized from 100 mL of hexanes. Crystals precipitated at room temperature were collected, washed with 10 mL of cold hexanes, and dried in vacuum. Yield 6.40 g (65%) of white crystalline material. $^1$H NMR (CD$_2$Cl$_2$): δ 8.37 (dd, J=6.7 Hz, J=1.1 Hz, 1H, 5-H in indenyl), 8.01 (dt, J=8.5 Hz, J=1.1 Hz, 1H, 7-H in indenyl), 7.40 (dd, J=8.5 Hz, J=6.7 Hz, 1H, 6-H in indenyl), 6.92 (m, 1H, 1-H in indenyl), 6.44 (m, 1H, 3-H in indenyl), 4.28 (m, 4H, 2,2',5,5'-H in THF), 2.62 (s, 3H, 2-Me in indenyl), 1.86 (m, 4H, 3,3',4,4'-H in THF), 1.66 (s, 9H, $^t$Bu), 0.90 (s, 3H, SiMeMe'), 0.58 (s, 3H, SiMeMe'). Anal. Calc. for C$_{20}$H$_{31}$Cl$_2$NOSiZr: C, 48.86; H, 6.35; N, 2.85%. Found: C, 48.73; H, 6.39; N, 2.74%.

Example 9

{η$^5$:η$^1$-N-(4-Methoxyphenyl)-1,1-dimethyl-1-(2-methylinden-4-yl)silanamido}-titanium dichloride (Compound J)

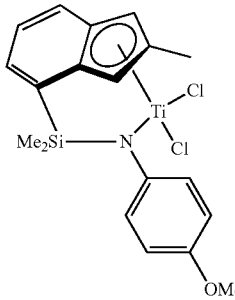

9a): N-(4-Methoxyphenyl)-1,1-dimethyl-1-(2-methyl-1/3H-inden-7/4-yl)silanamine

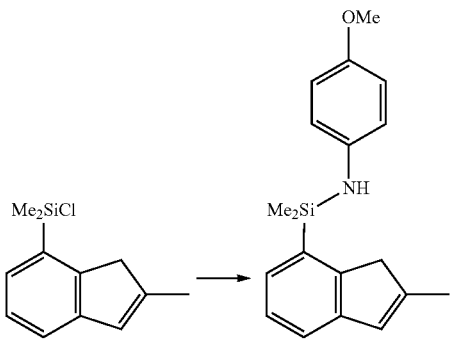

To a solution of 4.61 g (37.5 mmol) of p-methoxyaniline in 110 mL of THF 15.0 mL (37.5 mmol) of 2.5 M $^n$BuLi in hexanes was added at 0° C. This mixture was additionally stirred for 4 hours at room temperature, then cooled to −40° C., and a solution of 8.35 g (37.5 mmol) of chloro(dimethyl)(2-methyl-1H-inden-7-yl)silane in 70 mL of THF was added in one portion. The resulting mixture was stirred for 12 hours at room temperature and then evaporated to dryness. To the residue 100 mL of ether was added, and the obtained suspension was stirred for 20 minutes, and then filtered through glass fit (G3). The precipitate was additionally washed with 2×100 mL of ether. The combined filtrate was evaporated to dryness, and the residue was rectificated in vacuum, b.p. 160° C.-175° C./0.1 mm. Yield 8.00 g (69%) of colorless oil as a ca. 7 to 2 mixture of N-(4-methoxyphenyl)-1,1-dimethyl-1-(2-methyl-1H-inden-7-yl)silanamine and N-(4-methoxyphenyl)-1,1-dimethyl-1-(2-methyl-3H-inden-4-yOsilanamine. $^1$H NMR (CD$_2$Cl$_2$), N-(4-methoxyphenyl)-1,1-dimethyl-1-(2-methyl-1H-inden-7-yl)-silanamine: δ 7.39 (d, J=7.3 Hz, 1H, 6-H in indenyl), 7.32 (d, J=7.3 Hz, 1H, 4-H in indenyl), 7.26 (t, J=7.3 Hz, 1H, 5-H in indenyl), 6.55-6.70 (m, 4H, C$_6$H$_4$OMe), 6.51 (m, 1H, 3-H in indenyl), 3.69 (s, 3H, OMe), 3.40 (s, 2H, 1,1'-H in indenyl), 2.16 (s, 3H, 2-Me in indenyl), 6.56 (s, 6H, SiMe$_2$); N-(4-methoxyphenyl)-1,1-dimethyl-1-(2-methyl-3H-inden-4-yl)silanamine, δ 7.50 (d, J=7.5 Hz, 1H, 5-H in indenyl), 7.44 (d, J=7.5 Hz, 1H, 7-H in indenyl), 7.13 (t, J=7.5 Hz, 1H, 6-H in indenyl), 6.82 (m, 1H, 3-H in indenyl), 6.55-6.70 (m, 4H, C$_6$H$_4$OMe), 3.70 (s, 3H, OMe), 3.58 (br.s, 1H, NH), 3.30 (s, 2H, 1,1'-H in indenyl), 2.19 (s, 3H, 2-Me in indenyl),), 6.56 (s, 6H, SiMe$_2$). Anal. Calc. for C$_{19}$H$_{23}$NOSi: C, 73.74; H, 7.49; N, 4.53%. Found: C, 73.99; H, 7.62; N, 4.51%.

9b): {η$^5$:η$^1$-N-(4-Methoxyphenyl)-1,1-dimethyl-1-(2-methylinden-4-yl)silanamido}titanium dichloride (Compound J)

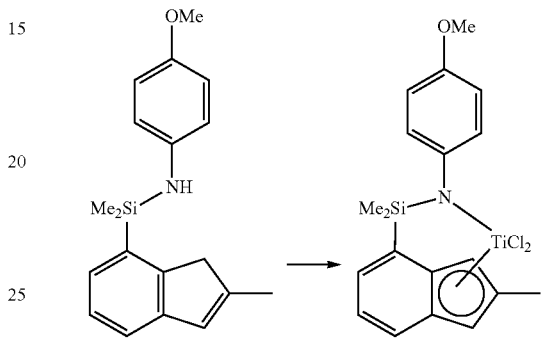

To a solution of 2.40 g (7.75 mmol) of N-(4-methoxyphenyl)-1,1-dimethyl-1-(2-methyl-1/3H-inden-7/4-yOsilanamine in 220 mL of dry ether 6.20 mL (15.5 mmol) of 2.5 M $^n$BuLi in hexanes was added at room temperature. This mixture was stirred for 12 hours at room temperature, and then a solution of 1.47 g (7.75 mmol) of TiCl$_4$ in 20 mL of hexanes was added at 0° C. The resulting mixture was stirred for 12 hours at room temperature and then evaporated to dryness. A mixture of the residue with 50 mL of toluene was stirred for 2 hours at 50° C. and then filtered through glass frit (G3). The precipitate was additionally washed with 10 mL of toluene. The combined filtrate was evaporated to dryness. A suspension of the residue in 20 mL of hexanes was stirred for 30 minutes and then filtered through glass frit (G3). The precipitate was washed by 2×10 mL of hexanes and then dried in vacuum. Yield 1.68 g (51%) of red solid. $^1$H NMR (CD$_2$Cl$_2$): δ 7.58 (d, J=8.3 Hz, 1H, 5-H in indenyl), 7.41 (m, 1H, 1-H in indenyl), 7.33 (dd, J=8.3 Hz, J=6.3 Hz, 1H, 6-H in indenyl), 7.27 (m, 1H, 7-H in indenyl), 6.84-6.88 (m, 2H, 2,6-H in C$_6$H$_4$OMe), 6.71-6.76 (m, 2H, 3,5-H in C$_6$H$_4$OMe), 6.65 (m, 1H, 3-H in indenyl), 3.77 (s, 3H, OMe), 2.46 (s, 3H, 2-Me in indenyl), 0.96 (s, 3H, SiMeMe'), −0.01 (s, 3H, SiMeMe'). Anal. Calc. for C$_{19}$H$_{21}$Cl$_2$NOSiTi: C, 53.54; H, 4.97; N, 3.29%. Found: C, 53.49; H, 5.08; N, 3.16%.

Example 10

{η$^5$:η$^1$-N-(3,5-Dimethylphenyl)-1,1-dimethyl-1-(2-methylinden-4-yl)silanamido}-titanium dichloride (Compound K)

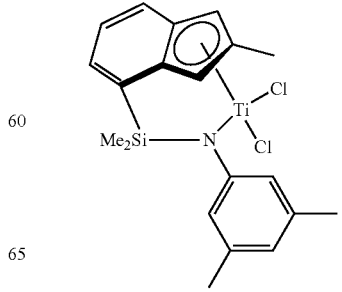

10a): N-(3,5-Dimethylphenyl)-1,1-dimethyl-1-(2-methyl-4H-inden-7-yl)silanamine

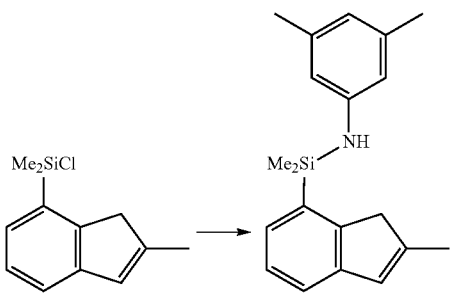

To a solution of 4.54 g (37.5 mmol) of 3,5-dimethylaniline in 110 mL of THF 15.0 mL (37.5 mmol) of 2.5 M "BuLi in hexanes was added at 0° C. This mixture was additionally stirred for 4 hours at room temperature, then cooled to −40° C., and a solution of 8.35 g (37.5 mmol) of chloro(dimethyl) (2-methyl-1H-inden-7-yl)silane in 70 mL of THF was added in one portion. The resulting mixture was stirred for 12 hours at room temperature and then evaporated to dryness. To the residue 100 mL of ether was added, and the obtained suspension was stirred for 20 minutes, and then filtered through glass frit (G3). The precipitate was additionally washed with 2×100 mL of ether. The combined filtrate was evaporated to dryness, and the residue was washed with 3×7 mL of cold hexanes and then dried in vacuum. Yield 7.26 g (63%) of white solid. $^1$H NMR (C$_6$D$_6$): δ 7.50 (dd, J=6.5 Hz, J=2.1 Hz, 1H, 6-H in indenyl), 7.24-7.30 (m, 2H, 4,5-H in indenyl), 6.35 (m, 2H, 3-H in indenyl and 4-H in 3,5-Me$_2$C$_6$H$_3$), 6.27 (s, 2H, 2,6-H in 3,5-Me$_2$C$_6$H$_3$), 3.27 (s, 2H, 1,1'-H in indenyl), 3.24 (s, 1H, NH), 2.08 (s, 6H, 3,5-Me in 3,5-Me$_2$C$_6$H$_3$), 1.83 (s, 3H, 2-Me in indenyl), 0.45 (s, 6H, SiMe$_2$). Anal. Calc. for C$_{20}$H$_{25}$NSi: C, 78.12; H, 8.19; N, 4.55%. Found: C, 78.41; H, 8.00; N, 4.38%.

10b): {η$^5$:η$^1$-N-(3,5-Dimethylphenyl)-1,1-dimethyl-1-(2-methylinden-4-yl)silanamido}-titanium dichloride (Compound K)

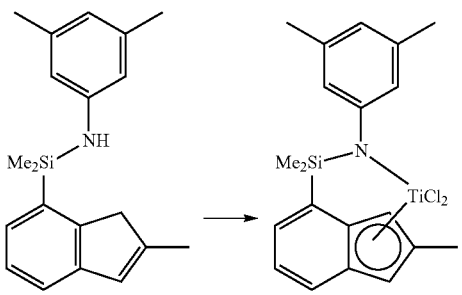

To a solution of 1.60 g (5.21 mmol) of N-(3,5-dimethylphenyl)-1,1-dimethyl-1-(2-methyl-1H-inden-7-yl)silanamine in 150 mL of dry ether 4.17 mL (10.4 mmol) of 2.5 M "BuLi in hexanes was added at room temperature. This mixture was stirred for 12 hours at room temperature, and then a solution of 0.99 g (5.21 mmol) of TiCl$_4$ in 20 mL of hexanes was added at 0° C. The resulting mixture was stirred for 12 hours at room temperature and then evaporated to dryness. A mixture of the residue with 50 mL of toluene was stirred for 2 hours at 50° C. and then filtered through glass frit (G3). The precipitate was additionally washed with 10 mL of toluene. The combined filtrate was evaporated to dryness. The residue was recrystallized from 15 mL of hexanes. Crystals precipitated at room temperature were collected, washed with 5 mL of cold hexanes, and dried in vacuum. Yield 1.30 g (59%) of dark red crystalline solid. $^1$H NMR (CD$_2$Cl$_2$): δ 7.58 (d, J=8.4 Hz, 1H, 7-H in indenyl), 7.45 (m, 1H, 1-H in indenyl), 7.33 (dd, J=8.4 Hz, J=6.4 Hz, 1H, 6-H in indenyl), 7.26 (d, J=6.4 Hz, 1H, 5-H in indenyl), 6.75 (s, 1H, 4-H in 3,5-Me$_2$C$_6$H$_4$), 6.65 (d, J=2.0 Hz, 1H, 3-H in indenyl), 6.46 (s, 2H, 2,6-H in 3,5-Me$_2$C$_6$H$_4$), 2.47 (s, 3H, 2-Me in indenyl), 2.25 (s, 6H, 3,5-Me in 3,5-Me$_2$C$_6$H$_4$), 1.00 (s, 3H, SiMeMe'), −0.01 (s, 3H, SiMeMe'). Anal. Calc. for C$_{20}$H$_{23}$Cl$_2$NSiTi: C, 56.62; H, 5.46; N, 3.30%. Found: C, 56.73; H, 5.61; N, 3.39%.

Example 11

{η$^5$:η$^1$-N-(4-Methylphenyl)-1,1-dimethyl-1-(2-methylinden-4-yl)silanamido}-titaniumdichloride and {η$^5$:η$^1$-N-(4-Methylphenyl)-1,1-dimethyl-1-(2-methylinden-4-yl)silanamido}{η$^5$-N-(4-methylphenyl)-1,1-dimethyl-1-(2-methylinden-4-yl)silanamine}-(chlorido)zirconium (Compounds L and M)

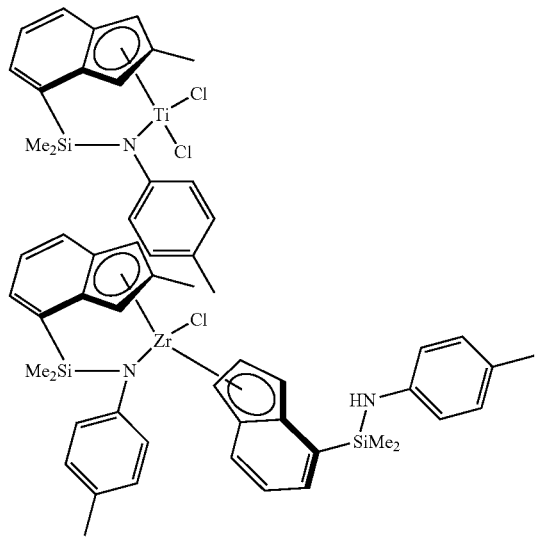

11a): N-(4-Methylphenyl)-1,1-dimethyl-1-(2-methyl-1H-inden-7-yl)silanamine

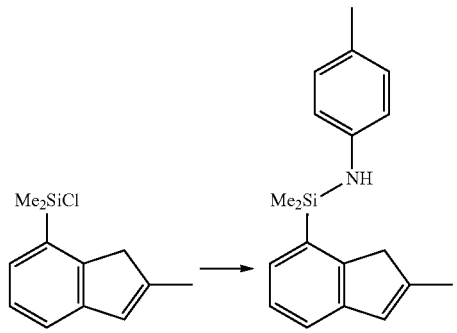

To a solution of 6.44 g (60.0 mmol) of p-toluidine in 180 mL of THF 24.0 mL (60.0 mmol) of 2.5 M "BuLi in hexanes was added at 0° C. This mixture was additionally stirred for 4 hours at room temperature, then cooled to −40° C., and a solution of 13.4 g (60.0 mmol) of chloro(dimethyl)(2-methyl-1H-inden-7-yl)silane in 50 mL of THF was added in one portion. The resulting mixture was stirred for 12 hours at room temperature and then evaporated to dryness. To the residue 100 mL of ether was added, and the obtained suspension was stirred for 20 minutes, and then filtered through glass frit (G3). The precipitate was additionally washed with 2×100 mL of ether. The combined filtrate was evaporated to dryness, and the residue was washed with 2×15 mL of cold hexanes and then dried in vacuum. Yield 11.3 g (64%) of white solid. $^1$H NMR (CD$_2$Cl$_2$): δ 7.40 (dd, J=7.3 Hz, J=1.3 Hz, 1H, 6-H in indenyl), 7.32 (dd, J=7.3 Hz, J=1.3 Hz, 1H, 4-H in indenyl), 7.26 (t, J=7.3 Hz, 1H, 5-H in indenyl), 6.88-6.91 (m, 2H, 2,6-H in p-tolyl), 6.53-6.57 (m, 2H, 3,5-H in p-tolyl), 6.52 (m, 1H, 3-H in indenyl), 3.68 (br.s, 1H, NH), 3.40 (s, 2H, 1,1'-H in indenyl), 2.20 (s, 3H, 4-Me in p-tolyl), 2.16 (m, 3H, 2-Me in indenyl), 0.57 (s, 6H, SiMe$_2$). Anal. Calc. for C$_{19}$H$_{23}$NSi: C, 77.76; H, 7.90; N, 4.77%. Found: C, 77.94; H, 8.05; N, 4.94%.

11b): {η$^5$:η$^1$-N-(4-Methylphenyl)-1,1-dimethyl-1-(2-methylinden-4-yl)silanamido}titanium dichloride (Compound L)

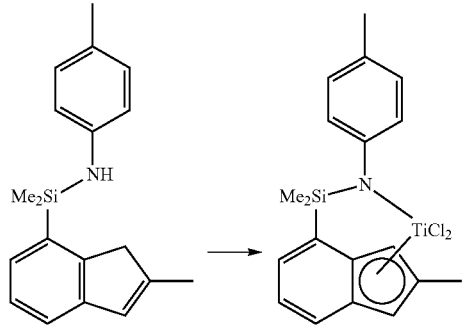

To a solution of 2.94 g (5.21 mmol) of N-(4-methylphenyl)-1,1-dimethyl-1-(2-methyl-1H-inden-7-yl)silanamine in 200 mL of dry ether 8.00 mL (20.0 mmol) of 2.5 M "BuLi in hexanes was added at room temperature. This mixture was stirred for 12 hours at room temperature, and then a solution of 1.90 g (10.0 mmol) of TiCl$_4$ in 20 mL of hexanes was added at −80° C. The resulting mixture was stirred for 12 hours at room temperature and then evaporated to dryness. A mixture of the residue with 50 mL of toluene was stirred for 2 hours at 50° C. and then filtered through glass frit (G3). The precipitate was additionally washed with 10 mL of toluene. The combined filtrate was evaporated to dryness. The residue was recrystallized from 20 mL of hexanes. Crystals precipitated at room temperature were collected, washed with 5 mL of cold hexanes, and dried in vacuum. Yield 3.49 g (85%) of red crystalline solid. $^1$H NMR (CD$_2$Cl$_2$): δ 7.58 (dt, J=8.4 Hz, J=1.0 Hz, 1H, 7-H in indenyl), 7.44 (m, 1H, 1-H in indenyl), 7.33 (dd, J=8.4 Hz, J=6.3 Hz, 1H, 6-H in indenyl), 7.27 (dd, J=6.4 Hz, J=1.0 Hz, 1H, 5-H in indenyl), 7.11-7.16 (m, 2H, 2,6-H in p-tolyl), 7.69-7.40 (m, 2H, 3,5-H in p-tolyl), 6.65 (m, 1H, 3-H in indenyl), 2.47 (s, 3H, 4-Me in p-tolyl), 2.32 (s, 3H, 2-Me in indenyl), 0.99 (s, 3H, SiMeMe'), 0.00 (s, 3H, SiMeMe'). Anal. Calc. for C$_{19}$H$_{21}$Cl$_2$NSiTi: C, 55.63; H, 5.16; N, 3.41%. Found: C, 55.82; H, 5.11; N, 3.27%.

11c): {η$^5$:η$^1$-N-(4-Methylphenyl)-1,1-dimethyl-1-(2-methylinden-4-yl)silanamido}{η$^5$-N-(4-methylphenyl)-1,1-dimethyl-1-(2-methylinden-4-yl)silanamine}(chlorido)zirconium (Compound M)

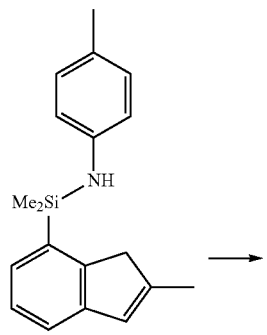

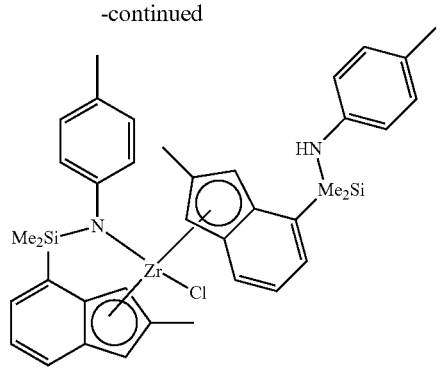

To a solution of 2.94 g (10.0 mmol) of N-(4-methylphenyl)-1,1-dimethyl-1-(2-methyl-1H-inden-7-yl)silanamine in 200 mL of dry ether 8.00 mL (20.0 mmol) of 2.5 M "BuLi in hexanes was added at room temperature. This mixture was stirred for 12 hours at room temperature, and then a solution of 3.77 g (10.0 mmol) of ZrCl$_4$(THF)$_2$ was added at −50° C. The resulting mixture was stirred for 40 hours at room temperature and then evaporated to dryness. A mixture of the residue with 150 mL of toluene was stirred for 4 hours at 90° C. and then filtered through glass frit (G3). The precipitate was additionally washed with 10 mL of toluene. The combined filtrate was evaporated to dryness. The crude product was washed with 150 mL of hot hexanes, then 40 mL of cold hexanes and, finally, dried in vacuum. Crystals precipitated at room temperature were collected, washed with 10 mL of cold hexanes, and dried in vacuum. Yield 1.13 g (32%) of white crystalline material. $^1$H NMR (CD$_2$Cl$_2$): δ 7.86 (dt, J=8.4 Hz, J=0.9 Hz, 1H), 7.48 (dd, J=6.7 Hz, J=1.0 Hz, 1H), 7.43 (dd, J=8.4 Hz, J=6.3 Hz, 1H), 7.40 (dt, J=8.4 Hz, J=1.0 Hz, 1H), 7.25 (dd, J=6.3 Hz, J=0.9 Hz, 1H), 6.97 (dd, J=8.4 Hz, J=6.7 Hz, 1H), 6.91-6.96 (m, 2H), 6.81-6.86 (m, 2H), 6.68-6.73 (m, 2H), 6.67 (m, 1H), 6.41-6.45 (m, 2H), 6.14 (m, 1H), 5.80 (d, J=2.2 Hz, 1H), 5.63 (m, 1H), 3.56 (br.s, 1H), 2.21 (s, 3H), 2.17 (s, 3H), 1.94 (s, 3H), 1.65 (s, 3H), 0.52 (s, 3H), 0.17 (s, 3H), 0.15 (s, 3H), 0.11 (s, 3H). Anal. Calc. for C$_{38}$H$_{43}$ClN$_2$Si$_2$Zr: C, 64.23; H, 6.10; N, 3.94%. Found: C, 64.41; H, 6.24; N, 4.09%.

Example 12

{η$^5$: η$^1$-N-(4-Bromophenyl)-1,1-dimethyl-1-(2-methylinden-4-yl)silanamido}-titanium dichloride (Compound N)

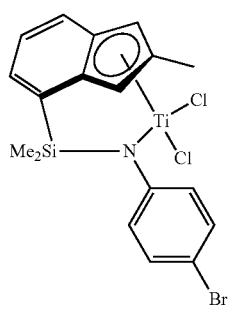

12a): N-(4-Bromophenyl)-1,1-dimethyl-1-(2-methyl-1/3H-inden-7/4-yl)silanamine

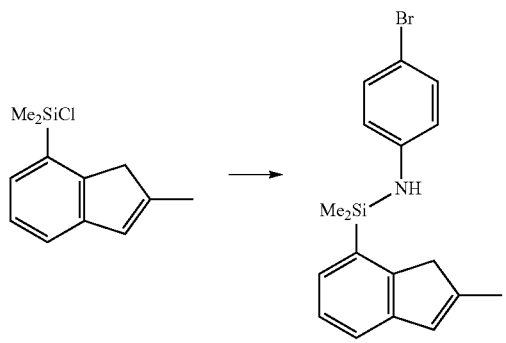

To a solution of 8.60 g (50.0 mmol) of 4-bromoaniline in 150 mL of THF 20.0 mL (50.0 mmol) of 2.5 M "BuLi in hexanes was added at 0° C. This mixture was additionally stirred for 4 hours at room temperature, then cooled to −40° C., and a solution of 11.1 g (50.0 mmol) of chloro(dimethyl) (2-methyl-1H-inden-7-yl)silane in 50 mL of THF was added in one portion. The resulting mixture was stirred for 12 hours at room temperature and then evaporated to dryness. To the residue 100 mL of ether was added, and the obtained suspension was stirred for 20 minutes, and then filtered through glass frit (G3). The precipitate was additionally washed with 2×100 mL of ether. The combined filtrate was evaporated to dryness, and the residue was washed with 2×20 mL of cold hexanes and then dried in vacuum. Yield 9.67 g (54%) of white solid as a ca. 7 to 2 mixture of N-(4-bromophenyl)-1,1-dimethyl-1-(2-methyl-1/3H-inden-7/4-yl)silanamine and N-(4-bromophenyl)-1,1-dimethyl-1-(2-methyl-1/3H-inden-7/4-yl)silanamine. $^1$H NMR (CD$_2$Cl$_2$), N-(4-methoxyphenyl)-1,1-dimethyl-1-(2-methyl-1H-inden-7-yl)-silanamine: δ 7.47 (m, 1H, 6-H in indenyl), 7.43 (m, 1H, 4-H in indenyl), 7.12-7.17 (m, 2H, 3,5-H in 4-BrC$_6$H$_4$), 7.11 (t, J=7.4 Hz, 1H, 5-H in indenyl), 6.75 (m, 1H, 3-H in indenyl), 6.52-6.57 (m, 2H, 2,6-H in 4-BrC$_6$H$_4$), 3.83 (br.s, 1H, NH), 3.28 (m, 2H, 1,1'-H in indenyl), 2.17 (m, 3H, 2-Me in indenyl), 0.55 (s, 6H, SiMe$_2$); N-(4-methoxyphenyl)-1,1-dimethyl-1-(2-methyl-3H-inden-4-yl)silanamine, δ 7.36 (dd, J=7.4 Hz, J=1.3 Hz, 1H, 5-H in indenyl), 7.31 (dd, J=7.4 Hz, J=1.3 Hz, 1H, 7-H in indenyl), 7.25 (dt, J=7.4 Hz, J=1.3 Hz, 1H, 6-H in indenyl), 7.12-7.17 (m, 2H, 3,5-H in 4-BrC$_6$H$_4$), 6.52-6.57 (m, 2H, 2,6-H in 4-BrC$_6$H$_4$), 3.83 (br.s, 1H, NH), 3.36 (m, 2H, 1,1'-H in indenyl), 2.16 2.17 (m, 3H, 2-Me in indenyl), 0.56 (s, 6H, SiMe$_2$). Anal. Calc. for C$_{18}$H$_{20}$BrNSi: C, 60.33; H, 5.63; N, 3.91%. Found: C, 60.61; H, 5.84; N, 3.67%.

12b): {η$^5$:η$^1$-N-(4-Bromophenyl)-1,1-dimethyl-1-(2-methylinden-4-yl)silanamido}titanium dichloride (Compound N)

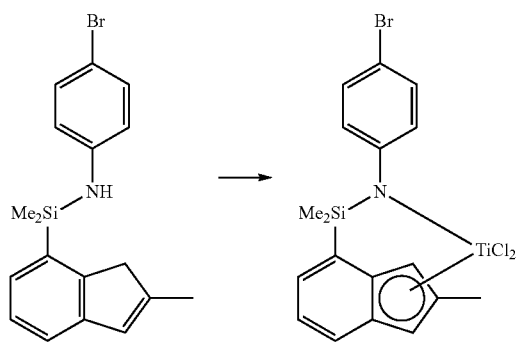

To a solution of 1.95 g (5.46 mmol) of N-(4-bromophenyl)-1,1-dimethyl-1-(2-methyl-1/3H-inden-7/4-yl)silanamine in 110 mL of dry ether 4.36 mL (10.9 mmol) of 2.5 M "BuLi in hexanes was added at room temperature. This mixture was stirred for 12 hours at room temperature, and then a solution of 1.04 g (5.46 mmol) of TiCl$_4$ in 10 mL of hexanes was added at −80° C. The resulting mixture was stirred for 12 hours at room temperature and then evaporated to dryness. A mixture of the residue with 50 mL of toluene was stirred for 2 hours at 50° C. and then filtered through glass frit (G3). The precipitate was additionally washed with 10 mL of toluene. The combined filtrate was evaporated to dryness. The residue was washed with 3×20 mL of hexanes and then recrystallized from 15 mL of hexanes. Crystals precipitated at room temperature were collected, washed with 5 mL of cold hexanes, and dried in vacuum. Yield 0.96 g (37%) of dark red crystalline solid. $^1$H NMR (CD$_2$Cl$_2$): δ 7.60 (m, 1H, 7-H in indenyl), 7.46 (m, 1H, 1-H in indenyl), 7.40-7.45 (m, 2H, 3,5-H in p-tolyl), 7.34 (dd, J=8.5 Hz, J=6.5 Hz, 1H, 6-H in indenyl), 7.28 (dd, J=6.5 Hz, J=1.0 Hz, 1H, 5-H in indenyl), 6.70-6.74 (m, 2H, 2,6-H in p-tolyl), 6.67 (d, J=2.1 Hz, 1H, 3-H in indenyl), 2.48 (s, 3H, 2-Me in indenyl), 0.99 (s, 3H, SiMeMe'), 0.01 (s, 3H, SiMeMe'). Anal. Calc. for C$_{18}$H$_{18}$BrCl$_2$NSiTi: C, 45.50; H, 3.82; N, 2.95%. Found: C, 45.44; H, 3.89; N, 2.86%.

Example 13

{η$^5$:η$^1$-1-(5-tert-Butyl-2-methylinden-7-yl)-1,1-dimethyl-N-(4-methylphenyl)-silanamido}titaniumdichloride (Compound O)

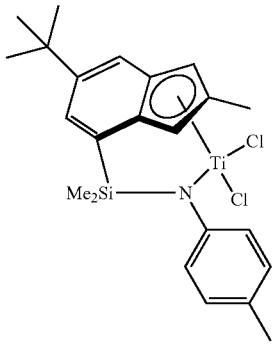

13a) 4/7-Bromo-6/5-tert-butyl-2-methyl-1H-indene

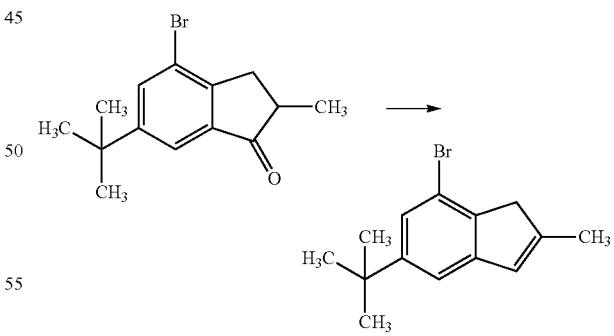

To a solution of 146 g (0.52 mol) of 4-bromo-6-tert-butyl-2-methylindan-1-one in 950 ml of THF-methanol (2:1, vol.) 38.3 g (1.02 mol) of NaBH$_4$ was added in small portions over 2 hours at 0° C. The mixture was stirred overnight at ambient temperature. The resulting mixture was poured onto 1000 cm$^3$ of ice and acidified with 10% HCl to pH 4. The organic layer was separated; the aqueous layer was extracted with 3×300 ml of methyl-tert-butyl ether. This combined extract was dried over K$_2$CO$_3$ and evaporated to dryness, and 1500 ml of toluene were added to the residue. This toluene solution was treated with a catalytic amount of $^pTolSO_3H*H_2O$ (ca. 2 g) for 2 hours at reflux. Then this mixture was cooled to room temperature and passed through a short column with Silica Gel 60 (40-63 μm). This column was additionally eluted with 250 ml of toluene. The combined extract was evaporated to dryness. Fractional distillation gave a mixture of the title indene, b.p. 124° C.-128° C./5 mm Hg. Yield 83 g (83%) of colorless solid. Anal. calc. for $C_{14}H_{17}Br$: C, 63.41; H, 6.46. Found: C, 63.61; H, 6.61. $^1H$ NMR ($CDCl_3$) of 7-bromo-2-methyl-5-tert-buthyl-1H-indene: δ 7.31 (m, J=1H, 6-H), 7.28 (m, 1H, 4-H), 6.53 (m, 1H, 3-H), 3.30 (m, 2H, 1,1'-H), 2.21 (s, 3H, 2-Me), 1.39 (s, 9H, 5-C(CH$_3$)$_3$). $^{13}C\{^1H\}$ NMR ($CDCl_3$) of 7-bromo-2-methyl-5-tert-buthyl-1H-indene: δ 152.2, 147.2, 146.8, 140.4, 127.4, 123.9, 118.1, 116.1, 43.9, 34.8, 31.6, 16.8.

13b): (5-tert-Butyl-2-methyl-1H-inden-7-yl)(chloro)dimethylsilane

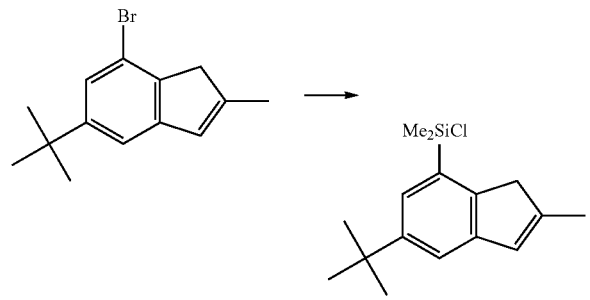

To 6.68 g (0.278 mol) of magnesium turnings in 200 mL of dry THF 5.26 g (0.028 mol) of 1,2-dibromoethane was added dropwise for 30 minutes. This mixture was stirred for additional 30 minutes, and then a solution of 66.3 g (0.250 mol) of 5-tert-butyl-2-methyl-7-bromo-1H-indene in 900 mL of THF was added dropwise by vigorous stirring in such rate that the mixture is refluxed. Then, this mixture was additionally refluxed for 30 minutes. Further on, to a solution of 113 g (0.875 mol) of dichlorodimethylsilane in 100 mL of THF the above-obtained solution of the Grignard reagent was added dropwise by vigorous stirring at room temperature using a water bath to cool the reaction mixture. The resulting mixture was additionally stirred for 12 hours at ambient temperature, evaporated to dryness, and then 200 mL of dry ether was added. The obtained suspension was stirred for 20 minutes at room temperature and then filtered through glass frit (G3). The precipitate was additionally washed by 2×100 mL of ether. The combined filtrate was evaporated to dryness, and the residue was rectificated in vacuum, b.p. 147° C.-155° C./1 mm Hg. Yield 50.1 g (72%) of the title product. $^1H$ NMR ($CD_2Cl_2$): δ 7.46 (s, 1H, 6-H), 7.43 (s, 1H, 4-H), 6.55 (s, 1H, 3-H), 3.47 (s, 2H, 1,1'-H), 2.22 (s, 3H, 2-Me), 1.41 (s, 9H, $^tBu$), 0.82 (s, 6H, SiMe$_2$). Anal. Calc. for $C_{16}H_{23}ClSi$: C, 68.91; H, 8.31%. Found: C, 69.13; H, 8.58%.

13c): 1-(5-tert-Butyl-2-methyl-1/3H-inden-7/4-yl)-1,1-dimethyl-N-(4-methylphenyl)-silanamine

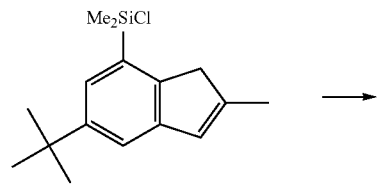

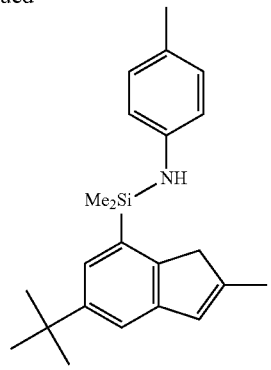

To a solution of 3.07 g (28.7 mmol) of p-toluidine in 180 mL of THF 11.5 mL (28.7 mmol) of 2.5 M $^nBuLi$ in hexanes was added at 0° C. This mixture was additionally stirred for 4 hours at room temperature, then cooled to −40° C., and a solution of 8.00 g (28.7 mmol) of (5-tert-butyl-2-methyl-1H-inden-7-yl)(chloro)dimethylsilane in 50 mL of THF was added in one portion. The resulting mixture was stirred for 12 hours at room temperature and then evaporated to dryness. To the residue 100 mL of ether was added, and the obtained suspension was stirred for 20 minutes, and then filtered through glass frit (G3). The precipitate was additionally washed with 2×100 mL of ether. The combined filtrate was evaporated to dryness, and the residue rectificated in vacuum, b.p. 178° C.-186° C./0.1 mm. Yield 7.12 g (71%) of a ca. 1 to 1 mixture of the title isomers. $^1H$ NMR ($CD_2Cl_2$): δ 7.55 (m, 1H), 7.52 (m, 1H), 7.45 (m, 1H), 7.39 (m, 1H), 6.89-6.94 (m, 4H), 6.76 (m, 1H), 6.56-6.63 (m, 1H), 6.51 (m, 1H), 3.69 (br.s, 2H), 3.37 (s, 4H), 3.30 (s, 4H), 2.23 (s, 3H), 2.22 (s, 3H), 2.19 (s, 3H), 2.16 (s, 3H), 1.37 (s, 9H), 1.36 (s, 9H), 0.58-0.60 (m, 12H). Anal. Calc. for $C_{23}H_{31}NSi$: C, 79.02; H, 8.94; N, 4.01%. Found: C, 79.30; H, 9.11; N, 3.86%

13 d): {η$^5$:η$^1$-1-(5-tert-Butyl-2-methylinden-7-yl)-1,1-dimethyl-N-(4-methylphenyl)-silanamido}titaniumdichloride (Compound O)

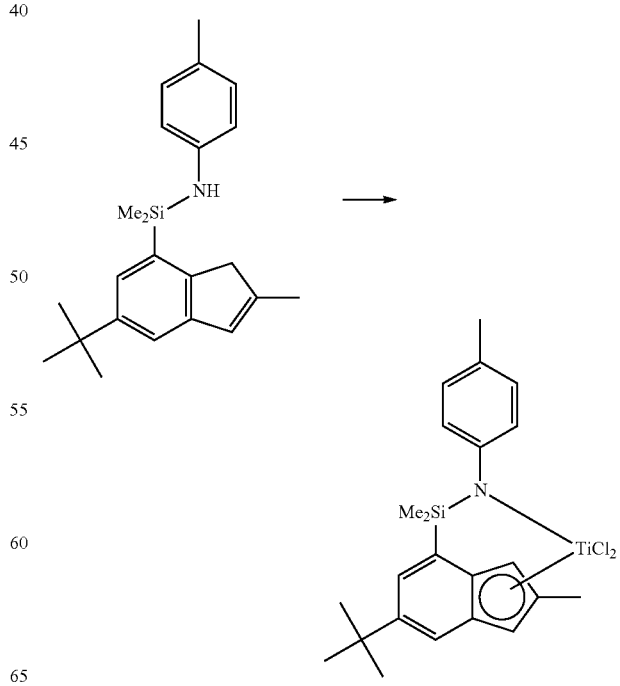

To a solution of 1.88 g (5.38 mmol) of 1-(5-tert-butyl-2-methyl-1/3H-inden-7/4-yl)-1,1-dimethyl-N-(4-methylphenyl)silanamine in 150 mL of dry ether 4.30 mL (10.8 mmol) of 2.5 M ⁿBuLi in hexanes was added at room temperature. This mixture was stirred for 12 hours at room temperature, and then a solution of 1.02 g (5.38 mmol) of TiCl₄ in 10 mL of hexanes was added at −80° C. The resulting mixture was stirred for 12 hours at room temperature and then evaporated to dryness. A mixture of the residue with 50 mL of toluene was stirred for 2 hours at 50° C. and then filtered through glass frit (G3). The precipitate was additionally washed with 10 mL of toluene. The combined filtrate was evaporated to dryness. The residue was washed with 3×15 mL of hexanes and then dried in vacuum. Yield 0.78 g (31%) of red crystalline solid. ¹H NMR (CD₂Cl₂): δ 7.49 (s, 1H, 5-H in indenyl), 7.38 (m, 1H, 1-H in indenyl), 7.34 (d, J=1.5 Hz, 1H, 7-H in indenyl), 7.10-7.15 (m, 2H, 3,5-H in p-tolyl), 6.69-6.73 (m, 2H, 2,6-H in p-tolyl), 6.58 (d, J=2.1 Hz, 1H, 3-H in indenyl), 2.44 (s, 3H, Me in p-tolyl), 2.31 (s, 3H, 2-M in indenyl), 1.34 (s, 9H, ᵗBu), 0.96 (s, 3H, SiMeMe'), −0.01 (s, 3H, SiMeMe'). Anal. Calc. for C₂₃H₂₉Cl₂NSiTi: C, 59.24; H, 6.27; N, 3.00%. Found: C, 59.21; H, 6.48; N, 3.14%.

DISLYL-BRIDGED EXAMPLES

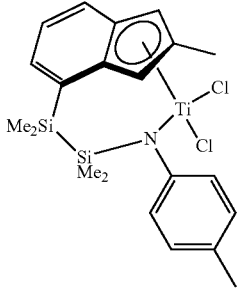

P

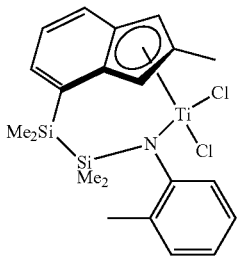

Q

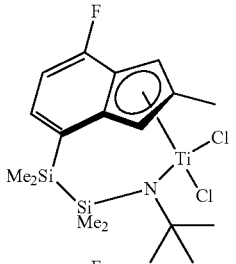

R

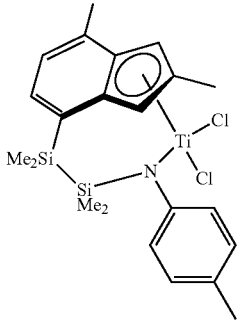

S

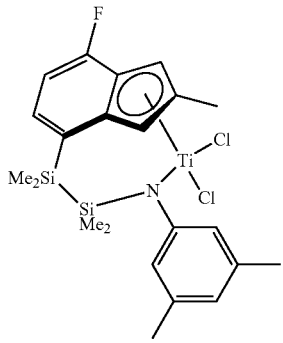

T

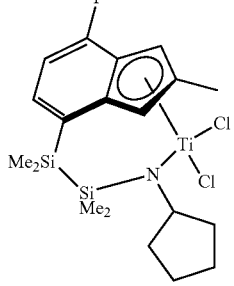

U

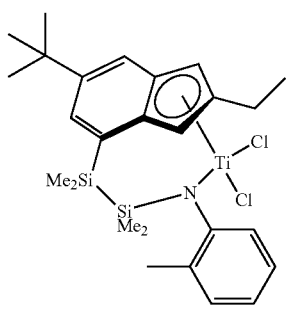

V

Example 14

{η⁵:η¹-(4-Methylphenyl)[1,1,2,2-tetramethyl-2-(2-methylinden-7-yl)disilanyl]-amido}titaniumdichloride (Compound P)

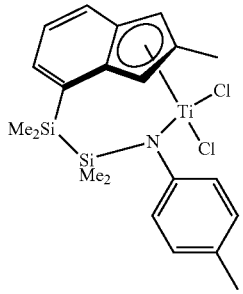

14a): 1-Chloro-1,1,2,2-tetramethyl-2-(2-methyl-1H-inden-7-yl)disilane

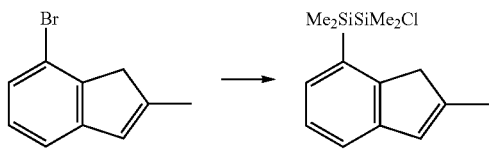

To 7.97 g (0.332 mol) of magnesium turnings in 80 mL of THF a mixture of 33.4 g (0.160 mol) of 2-methyl-7-bromo- 1H-indene, 30.0 g (0.160 mol) of 1,2-dibromoethane and 420 mL of THF was added dropwise with vigorous stirring at such rate that the mixture is refluxed. Further on, this mixture was additionally refluxed for 30 minutes. The obtained solution was added dropwise with vigorous stirring to a solution of 100 g (0.534 mol) of 1,2-dichloro-1,1,2,2-tetramethyldisilane in 100 mL of THF for 2 hours at room temperature (water bath cooling is required). The resulting mixture was stirred for 12 hours at ambient temperature and then evaporated to dryness. To the residue 100 mL of dry ether was added, and the obtained suspension was stirred for 20 minutes and then filtered through glass frit (G3). The precipitate was washed with 2×100 mL of ether. The combined filtrate was evaporated to dryness, the residue was dried and then rectificated in vacuum, b.p. 140° C.-145° C./1 mm Hg. Yield 26.3 g (58%) of the title product. $^1$H NMR (CD$_2$Cl$_2$): δ 7.22-7.32 (m, 3H, 4,5,6-H), 6.54 (m, 1H, 3-H), 3.39 (s, 2H, 1,1'-H), 2.21 (s, 3H, 2-Me), 0.66 (m, 3H, SiMe), 0.61 (m, 3H, SiMe), 0.59 (m, 3H, SiMe), 0.50 (m, 3H, SiMe). Anal. Calc. for C$_{14}$H$_{21}$ClSi$_2$: C, 59.85; H, 7.53%. Found: C, 59.65; H, 7.72%.

14b): (4-Methylphenyl)[1,1,2,2-tetramethyl-2-(2-methyl-1/3H-inden-7/4-yl)disilanyl]amine

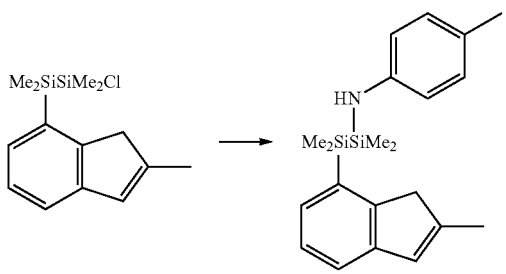

To a solution of 1.93 g (18.0 mmol) of p-toluidine in 50 mL of THF 7.20 mL (18.0 mmol) of 2.5 M "BuLi in hexanes was added at room temperature. This mixture was additionally stirred for 3 hours at ambient temperature, then cooled to −40° C., and a solution of 5.05 g (18.0 mmol) of 1-chloro-1,1,2,2-tetramethyl-2-(2-methyl-1H-inden-7-yOdisilane in 30 mL of THF was added in one portion. The resulting mixture was stirred for 12 hours at room temperature, then evaporated to dryness, and the residue was dried in vacuum. Further on, 50 mL of ether was added, the obtained suspension was stirred for 20 minutes at room temperature and then filtered through glass frit (G3). The precipitate was additionally washed with 2×50 mL of ether. The combined filtrate was evaporated to dryness, and the residue was rectificated in vacuum, b.p. 170° C.-195° C./0.1 mm Hg. Yield 4.80 g (76%) of viscous oil as a ca. 1 to 1 mixture of two isomeric compounds. $^1$H NMR (CD$_2$Cl$_2$): δ 7.37 (d, J=7.3 Hz, 1H), 7.31 (d, J=7.3 Hz, 1H), 7.18-7.26 (m, 3H), 7.07 (t, J=7.3 Hz, 1H), 6.82-6.90 (m, 4H), 6.57 (s, 1H), 6.42-6.50 (m, 5H), 3.80 (s, 1H), 3.27 (s, 2H), 3.25 (s, 1H), 3.19 (s, 2H), 2.21 (s, 3H), 2.20 (s, 3H), 2.14 (s, 3H), 2.10 (s, 3H), 0.49 (s, 6H), 0.46 (s, 6H), 0.32 (s, 12H). Anal. Calc. for C$_{21}$H$_{29}$NSi$_2$: C, 71.73; H, 8.31; N, 3.98%. Found: C, 71.93; H, 8.13; N, 4.10%.

14c): {η$^5$:η$^1$-(4-Methylphenyl)[1,1,2,2-tetramethyl-2-(2-methylinden-7-yl)disilanyl]amido}-titanium-dichloride (Compound P)

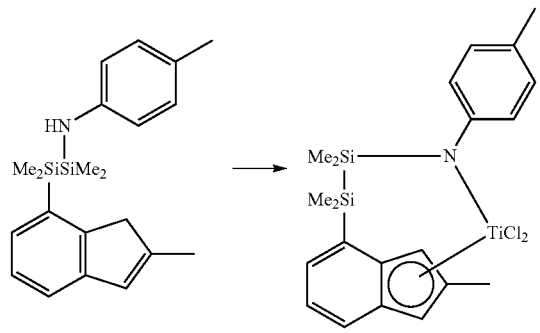

To a solution of 3.35 g (9.53 mmol) of (4-methylphenyl)[1,1,2,2-tetramethyl-2-(2-methyl-1/3H-inden-7/4-yl)disilanyl]amine in 150 mL of dry ether 7.62 mL (19.1 mmol) of 2.5 M "BuLi in hexanes was added at room temperature. This mixture was stirred for 12 hours at room temperature, and then a solution of 1.81 g (9.53 mmol) of TiCl$_4$ in 20 mL of hexanes was added at 0° C. The resulting mixture was stirred for 12 hours at room temperature, then evaporated to dryness, and the residue was dried in vacuum. Further on, 50 mL of toluene was added, the obtained suspension was stirred for 2 hours at 50° C., and, finally, filtered through glass frit (G3). The precipitate was additionally washed with 10 mL of toluene. The combined filtrate was evaporated to dryness, and to the residue 20 mL of hexanes was added. The obtained suspension was stirred for 30 minutes at ambient temperature and then filtered through glass frit (G3). The precipitate was additionally washed with 2×10 mL of hexanes. Yield 2.68 g (60%) of red solid. $^1$H NMR (C$_6$D$_6$): δ 7.49 (d, J=8.6 Hz, 1H, 5-H in indenyl), 7.18 (dd, J=6.6 Hz, J=2.2 Hz, 1H, 7-H in indenyl), 7.15 (d, J=1.9 Hz, 1H, 3-H in p-tolyl), 7.03 (dd, J=8.6 Hz, J=6.6 Hz, 1H, 6-H in indenyl), 6.96 (br.d, J=2.2 Hz, 1H, 5-H in p-tolyl), 6.95 (br.d, J=2.2 Hz, 1H, 4-H in p-tolyl), 6.81 (m, 1H, 3-H in indenyl), 6.68 (dd, J=8.1 Hz, J=2.2 Hz, 1H, 1-H in indenyl), 6.27 (d, J=1.9 Hz, 1H, 3-H in p-tolyl), 2.29 (s, 3H, Me in p-tolyl), 1.97 (s, 3H, 2-Me in indenyl), 0.51 (s, 3H, SiMe), 0.48 (s, 3H, SiMe), 0.30 (s, 3H, SiMe), −0.41 (s, 3H, SiMe). Anal. Calc. for C$_{21}$H$_{27}$Cl$_2$NSi$_2$Ti: C, 53.85; H, 5.81; N, 2.99%. Found: C, 54.09; H, 6.07; N, 3.16%.

Example 15

{η$^5$:η$^1$-(2-Methylphenyl)[1,1,2,2-tetramethyl-2-(2-methylinden-7-yl)disilanyl]-amido}-titaniumdichloride (Compound Q)

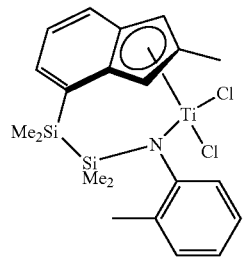

15a): (2-Methylphenyl)[1,1,2,2-tetramethyl-2-(2-methyl-1/3H-inden-7/4-yl)disilanyl]amine

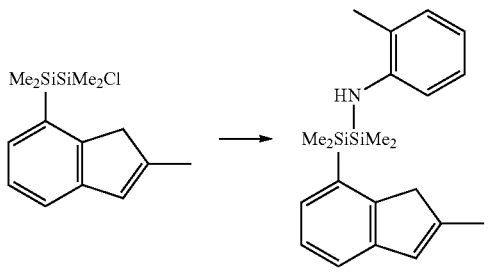

To a solution of 1.93 g (18.0 mmol) of o-toluidine in 50 mL of THF 7.20 mL (18.0 mmol) of 2.5 M "BuLi in hexanes was added at room temperature. This mixture was additionally stirred for 3 hours at ambient temperature, then cooled to −40° C., and a solution of 5.05 g (18.0 mmol) of 1-chloro-1,1,2,2-tetramethyl-2-(2-methyl-1H-inden-7-yl)disilane in 30 mL of THF was added in one portion. The resulting mixture was stirred for 12 hours at room temperature, then evaporated to dryness, and the residue was dried in vacuum. Further on, 50 mL of ether was added, the obtained suspension was stirred for 20 minutes at room temperature and then filtered through glass frit (G3). The precipitate was additionally washed with 2×50 mL of ether. The combined filtrate was evaporated to dryness, and the residue was rectificated in vacuum, b.p. 170° C.-190° C./0.1 mm. Yield 4.56 g (72%) of viscous oil as a ca. 1 to 1 mixture of two isomeric compounds. $^1$H NMR (CD$_2$Cl$_2$): δ 7.36 (d, J=7.3 Hz, 1H), 7.30 (d, J=7.3 Hz, 1H), 7.17-7.26 (m, 3H), 7.07 (t, J=7.3 Hz, 1H), 6.88-6.97 (m, 4H), 6.66 (d, J=8.1 Hz, 1H), 6.64 (d, J=8.1 Hz, 1H), 6.53-6.60 (m, 3H), 6.47 (s, 1H), 3.26 (s, 2H), 3.22 (s, 2H), 3.16 (s, 1H), 3.10 (s, 1H), 2.12 (s, 3H), 2.10 (s, 3H), 1.83 (s, 3H), 1.79 (s, 3H), 0.50 (s, 6H), 0.47 (s, 6H), 0.37 (m, 12H). Anal. Calc. for C$_{21}$H$_{29}$NSi$_2$: C, 71.73; H, 8.31; N, 3.98%. Found: C, 71.61; H, 8.20; N, 4.16%.

15b): {η$^5$:η$^1$-(2-Methylphenyl)[1,1,2,2-tetramethyl-2-(2-methylinden-7-yl)disilanyl]amido}-titanium-dichloride (Compound Q)

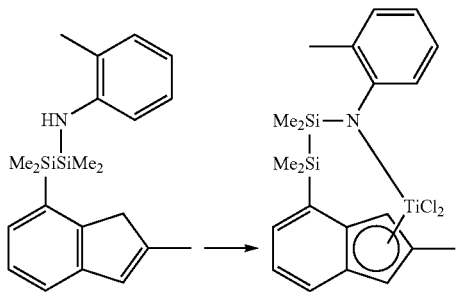

To a solution of 2.67 g (7.59 mmol) of (2-methylphenyl)[1,1,2,2-tetramethyl-2-(2-methyl-1/3H-inden-7/4-yl)disilanyl]amine in 150 mL of dry ether 6.07 mL (15.2 mmol) of 2.5 M "BuLi in hexanes was added at room temperature. This mixture was stirred for 12 hours at room temperature, and then a solution of 1.44 g (7.59 mmol) of TiCl$_4$ in 20 mL of hexanes was added at 0° C. The resulting mixture was stirred for 12 hours at room temperature, then evaporated to dryness, and the residue was dried in vacuum. Further on, 50 mL of toluene was added, the obtained suspension was stirred for 2 hours at 50° C., and, finally, filtered through glass frit (G3). The precipitate was additionally washed with 10 mL of toluene. The combined filtrate was evaporated to dryness, and to the residue 20 mL of hexanes was added. The obtained suspension was stirred for 30 minutes at ambient temperature and then filtered through glass frit (G3). The precipitate was additionally washed with 2×10 mL of hexanes. Yield 1.49 g (42%) of red solid. $^1$H NMR (C$_6$D$_6$): δ 7.61 (d, J=8.7 Hz, 1H, 5-H in indenyl), 7.44 (dd, J=6.6 Hz, J=0.9 Hz, 1H, 7-H in indenyl), 7.26 (m, 1H, H in o-tolyl), 7.22 (dd, J=8.7 Hz, J=6.6 Hz, 1H, 6-H in indenyl), 7.16 (m, 1H, H in o-tolyl), 7.03 (m, 2H, 2H in o-tolyl), 6.93 (m, 1H, 3-H in indenyl), 6.71 (m, 1H, 1-H in indenyl), 2.51 (s, 3H, Me in p-tolyl), 1.15 (s, 3H, 2-Me in indenyl), 0.74 (s, 3H, SiMe), 0.60 (s, 3H, SiMe), 0.56 (s, 3H, SiMe), −0.51 (s, 3H, SiMe). Anal. Calc. for C$_{21}$H$_{27}$Cl$_2$NSi$_2$Ti: C, 53.85; H, 5.81; N, 2.99%. Found: C, 54.02; H, 5.94; N, 2.78%.

Example 16

{η$^5$:η$^1$-N-(tert-Butyl)-2-(7-fluoro-2-methylinden-4-yl)-1,1,2,2-tetramethyl-disilamido}titaniumdichloride (Compound R)

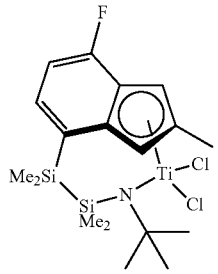

16a): 1-Chloro-1,1,2,2-tetramethyl-2-(4-fluoro-2-methyl-1/3H-inden-7/4-yl)disilane

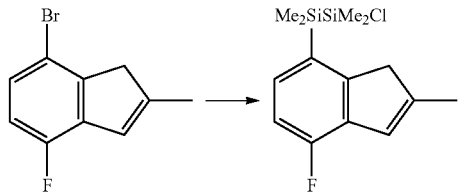

To 4.70 g (0.196 mol) of magnesium turnings in 60 mL of THF 4.70 g (0.025 mol) of 1,2-dibromoethane was added. This mixture was stirred for 1 hour and then a solution of 40.0 g (0.176 mol) of 7-bromo-4-fluoro-2-methyl-1H-indene in 550 mL of THF was added dropwise with vigorous stirring at such rate that the mixture is refluxed. Further on, the obtained solution was added dropwise at vigorous stirring to a solution of 115 g (0.616 mol) of 1,2-dichloro-1,1,2,2-tetramethyldisilane in 100 mL of THF for 2 hours at room temperature (water bath cooling is required). The resulting mixture was stirred for 12 hours at ambient temperature and then evaporated to dryness. To the residue 200 mL of dry ether was added, and the obtained suspension was stirred for 20 minutes and then filtered through glass frit (G3). The precipitate was washed with 2×100 mL of ether. The combined filtrate was evaporated to dryness, the residue was dried and then rectificated in vacuum, b.p. 124° C.-130° C./1 mm. Yield 38.4 g (73%) of a ca. 4 to 1 mixture of 1-chloro-1,1,2,2-tetramethyl-2-(4-fluoro-2-methyl-1H-inden-7-yl)disilane and 1-chloro-1,1,2,2-tetramethyl-2-(4-fluoro-2-methyl-3H-inden-4-yl)disilane. $^1$H NMR (C$_6$D$_6$), 1-chloro-1,1,2,2-tetramethyl-2-(4-fluoro- 2-methyl-1H-inden-7-yl)disilane: δ 7.22 (dd, J=8.3 Hz, J=5.6 Hz, 1H, 6-H in indenyl), 6.78 (dd, J=9.1 Hz, J=8.3 Hz, 1H, 5-H in indenyl), 6.66 (m, 1H, 3-H in indenyl), 2.91 (s, 2H, 1,1'-H in indenyl), 1.76 (s, 3H, 2-Me in indenyl), 0.45 (s, 6H, SiMe$_2$SiMe$_2$Cl), 0.36 (s, 6H, SiMe$_2$SiMe$_2$Cl); 1-chloro-1,1,2,2-tetramethyl-2-(4-fluoro-2-methyl-3H-inden-4-yl)disilane: δ 7.05 (dd, J=8.3 Hz, J=5.6 Hz, 1H, 5-H in indenyl), 6.89 (dd, J=9.6 Hz, J=8.3 Hz, 1H, 6-H in indenyl), 6.59 (m, 1H, 3-H in indenyl), 3.18 (s, 2H, 1,1'-H in indenyl), 1.78 (s, 3H, 2-Me in indenyl), 0.38 (s, 6H, SiMe$_2$SiMe$_2$Cl), 0.29 (s, 6H, SiMe$_2$SiMe$_2$Cl). Anal. Calc. for C$_{14}$H$_{20}$ClFSi$_2$: C, 56.25; H, 6.74%. Found: C, 56.49; H, 6.88%.

16b): N-(tert-Butyl)-2-(4-fluoro-2-methyl-1/3H-inden-7/4-yl)-1,1,2,2-tetramethyldisilanamine

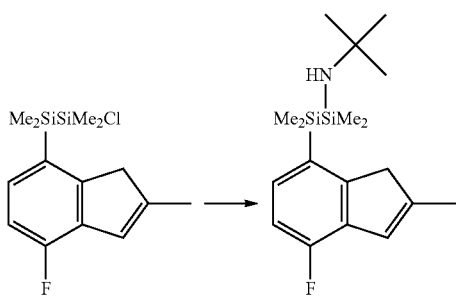

To a solution of 2.48 g (34.0 mmol) of tert-butylamine in 100 mL of THF 13.6 mL (34.0 mmol) of 2.5 M "BuLi in hexanes was added at room temperature. This mixture was additionally stirred for 3 hours at ambient temperature, then cooled to −40° C., and a solution of 10.2 g (34.0 mmol) of 1-chloro-1,1,2,2-tetramethyl-2-(4-fluoro-2-methyl-1/3H-inden-7/4-yl)disilane in 30 mL of THF was added in one portion. The resulting mixture was stirred for 12 hours at room temperature, then evaporated to dryness, and the residue was dried in vacuum. Further on, 50 mL of ether was added, the obtained suspension was stirred for 20 minutes at room temperature and then filtered through glass fit (G3). The precipitate was additionally washed with 2×50 mL of ether. The combined filtrate was evaporated to dryness, and the residue was rectificated in vacuum, b.p. 127° C.-145° C./0.1 mm. Yield 7.29 g (64%) of viscous oil as a ca. 2 to 1 mixture of N-(tert-butyl)-2-(4-fluoro-2-methyl-1H-inden-7-yl)-1,1,2,2-tetramethyldisilanamine and N-(tert-butyl)-2-(4-fluoro-2-methyl-3H-inden-4-yl)-1,1,2,2-tetramethyldisilanamine. $^1$H NMR (CD$_2$Cl$_2$), N-(tert-butyl)-2-(4-fluoro-2-methyl-1H-inden-7-yl)-1,1,2,2-tetramethyldisilanamine: δ 7.34 (dd, J=8.2 Hz, J=5.8 Hz, 1H, 6-H in indenyl), 6.78 (dd, J=9.4 Hz, J=8.2 Hz, 1H, 5-H in indenyl), 6.69 (m, 1H, 3-H in indenyl), 3.33 (s, 2H, 1.1'-H in indenyl), 2.20 (s, 3H, 2-Me in indenyl), 1.09 (s, 9H, $^t$Bu), 0.57 (br.s, 1H, NH), 0.40 (s, 6H, SiMe$_2$SiMe$_2$Cl), 0.20 (s, 6H, SiMe$_2$SiMe$_2$Cl); N-(tert-butyl)-2-(4-fluoro-2-methyl-3H-inden-4-yl)-1,1,2,2-tetramethyldisilanamine: δ 7.21 (dd, J=8.2 Hz, J=5.7 Hz, 1H, 5-H in indenyl), 6.90 (dd, J=8.2 Hz, J=9.7 Hz, 1H, 6-H in indenyl), 6.62 (m, 1H, 3-H in indenyl), 3.45 (s, 2H, 1.1'-H in indenyl), 2.18 (s, 3H, 2-Me in indenyl), 1.06 (s, 9H, $^t$Bu), 0.50 (br.s, 1H, NH), 0.42 (s, 6H, SiMe$_2$SiMe$_2$Cl), 0.20 (s, 6H, SiMe$_2$SiMe$_2$Cl). Anal. Calc. for C$_{18}$H$_{30}$FNSi$_2$: C, 64.42; H, 9.01; N, 4.17%. Found: C, 64.27; H, 9.15; N, 4.01%.

16c): {η$^5$:η$^1$-N-(tert-Butyl)-2-(7-fluoro-2-methylinden-4-yl)-1,1,2,2-tetramethyldisilamido}-titaniumdichloride (Compound R)

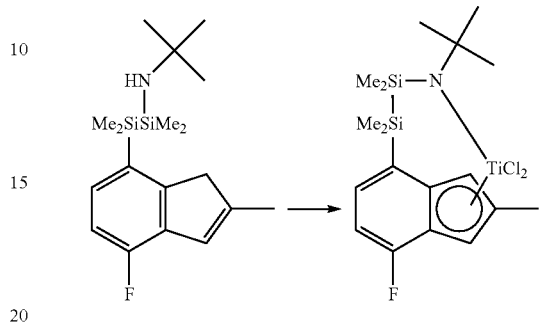

To a solution of 4.00 g (11.9 mmol) of N-(tert-butyl)-2-(4-fluoro-2-methyl-1/3H-inden-7/4-yl)-1,1,2,2-tetramethyldisilanamine in 150 mL of dry ether 9.55 mL (23.9 mmol) of 2.5 M "BuLi in hexanes was added at room temperature. This mixture was stirred for 12 hours at room temperature, and then a solution of 2.27 g (11.9 mmol) of TiCl$_4$ in 20 mL of hexanes was added at 0° C. The resulting mixture was stirred for 12 hours at room temperature, then evaporated to dryness, and the residue was dried in vacuum. Further on, 50 mL of toluene was added, the obtained suspension was stirred for 2 hours at 50° C., and, finally, filtered through glass frit (G3). The precipitate was additionally washed with 10 mL of toluene. The combined filtrate was evaporated to dryness, and the obtained residue was recrystallized from 20 mL of hexanes. Crystals precipitated at −30° C. were collected, washed by 5 mL of cold hexanes, and dried in vacuum. Yield 0.38 g (7%) of red crystalline solid. $^1$H NMR (C$_6$D$_6$): δ 6.89 (dd, J=7.2 Hz, J=5.4 Hz, 1H, 5-H in indenyl), 6.71 (dd, J=10.3 Hz, J=7.2 Hz, 1H, 6-H in indenyl), 6.64 (dd, J=3.0 Hz, J=1.7 Hz, 1H, 1-H in indenyl), 6.56 (d, J=1.7 Hz, 1H, 3-H in indenyl), 2.12 (s, 3H, 2-Me in indenyl), 1.50 (s, 9H, $^t$Bu), 0.56 (s, 3H, SiMe), 0.37 (s, 3H, SiMe), 0.36 (s, 3H, SiMe), 0.27 (s, 3H, SiMe). Anal. Calc. for C$_{18}$H$_{28}$Cl$_2$FNSi$_2$Ti: C, 47.79; H, 6.24; N, 3.10%. Found: C, 47.88; H, 6.29; N, 3.03%.

Example 17

{η$^5$:η$^1$-2-(7-fluoro-2-methylinden-4-yl)-1,1,2,2-tetramethyl-N-(4-methylphenyl)-disilanamido}titanium dichloride (Compound S)

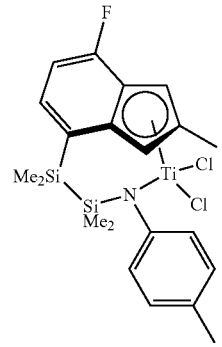

17a): 2-(4-Fluoro-2-methyl-1/3H-inden-7/4-yl)-1,1,2,2-tetramethyl-N-(4-methylphenyl)-disilanamine

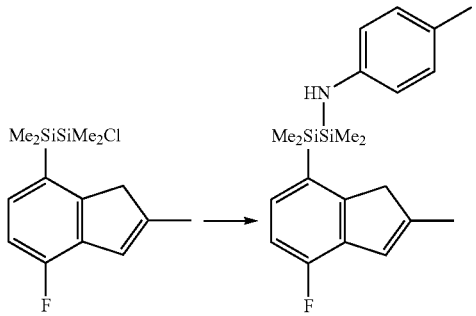

To a solution of 3.64 g (34.0 mmol) of p-toluidine in 100 mL of THF 13.6 mL (34.0 mmol) of 2.5 M "BuLi in hexanes was added at room temperature. This mixture was additionally stirred for 3 hours at ambient temperature, then cooled to −40° C., and a solution of 10.2 g (34.0 mmol) of 1-chloro-1,1,2,2-tetramethyl-2-(4-fluoro-2-methyl-1/3H-inden-7/4-yl) disilane in 30 mL of THF was added in one portion. The resulting mixture was stirred for 12 hours at room temperature, then evaporated to dryness, and the residue was dried in vacuum. Further on, 50 mL of ether was added, the obtained suspension was stirred for 20 minutes at room temperature and then filtered through glass frit (G3). The precipitate was additionally washed with 2×50 mL of ether. The combined filtrate was evaporated to dryness, and the residue was rectificated in vacuum, b.p. 170° C.-176° C./0.1 mm. Yield 7.92 g (63%) of viscous oil as a ca. 2 to 1 mixture of 2-(4-fluoro-2-methyl-1H-inden-7-yl)-1,1,2,2-tetramethyl-N-(4-methylphenyl)disilanamine and 2-(4-fluoro-2-methyl-3H-inden-4-yl)-1,1,2,2-tetramethyl-N-(4-methylphenyl)disilanamine. $^1$H NMR (CD$_2$Cl$_2$), 2-(4-fluoro-2-methyl-1H-inden-7-yl)-1,1,2,2-tetramethyl-N-(4-methylphenyl)-disilanamine: δ 7.28 (dd, J=8.2 Hz, J=5.8 Hz, 1H, 6-H in indenyl), 6.83-6.89 (m, 2H, 2,6-H in p-tolyl), 6.78 (dd, J=9.5 Hz, J=8.2 Hz, 1H, 5-H in indenyl), 6.53 (m, 1H, 3-H in indenyl), 6.44-6.80 (m, 2H, 3,5-H in p-tolyl), 3.30 (s, 2H, 1.1'-H in indenyl), 3.20 (s, 1H, NH), 2.20 (s, 3H, 2-Me in indenyl), 2.14 (s, 3H, 4-Me in p-tolyl), 0.44 (s, 6H, SiMe$_2$SiMe$_2$Cl), 0.31 (s, 6H, SiMe$_2$SiMe$_2$Cl); 2-(4-fluoro-2-methyl-3H-inden-4-yl)-1,1,2,2-tetramethyl-N-(4-methylphenyl)-disilanamine: δ 7.15 (dd, J=8.1 Hz, J=5.6 Hz, 1H, 5-H in indenyl), 6.90-6.94 (m, 2H, 2,6-H in p-tolyl), 6.81-6.85 (m, 1H, 6-H in indenyl), 6.68 (m, 1H, 3-H in indenyl), 6.40-6.43 (m, 2H, 3,5-H in p-tolyl), 3.27 (s, 2H, 1.1'-H in indenyl), 3.23 (s, 1H, NH), 2.19 (s, 3H, 2-Me in indenyl), 2.09 (s, 3H, 4-Me in p-tolyl), 0.47 (s, 6H, SiMe$_2$SiMe$_2$Cl), 0.31 (s, 6H, SiMe$_2$SiMe$_2$Cl). Anal. Calc. for C$_{21}$H$_{28}$FNSi$_2$: C, 68.24; H, 7.64; N, 3.79%. Found: C, 68.11; H, 7.80; N, 3.91%.

17b): {η$^5$:η$^1$-2-(7-fluoro-2-methylinden-4-yl)-1,1,2,2-tetramethyl-N-(4-methylphenyl)-disilanamido}titanium dichloride (Compound S)

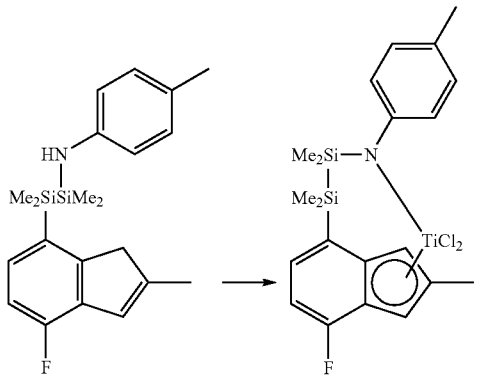

To a solution of 3.11 g (8.41 mmol) of 2-(4-fluoro-2-methyl-1/3H-inden-7/4-yl)-1,1,2,2-tetramethyl-N-(4-methylphenyl)disilanamine in 150 mL of dry ether 6.73 mL (16.8 mmol) of 2.5 M "BuLi in hexanes was added at room temperature. This mixture was stirred for 12 hours at room temperature, and then a solution of 1.60 g (8.41 mmol) of TiCl$_4$ in 20 mL of hexanes was added at 0° C. The resulting mixture was stirred for 12 hours at room temperature, then evaporated to dryness, and the residue was dried in vacuum. Further on, 50 mL of toluene was added, the obtained suspension was stirred for 2 hours at 50° C., and, finally, filtered through glass frit (G3). The precipitate was additionally washed with 10 mL of toluene. The combined filtrate was evaporated to dryness, and to the obtained residue 20 mL of hexanes was added. This suspension was stirred for 30 minutes at room temperature and then filtered through glass frit (G3). The precipitate was washed with 2×10 mL of cold hexanes and then dried in vacuum. Yield 1.02 g (25%) of red solid. $^1$H NMR (CD$_2$Cl$_2$): δ 7.29 (dd, J=7.3 Hz, J=5.3 Hz, 1H, 5-H in indenyl), 7.17 (dd, J=3.5 Hz, J=2.1 Hz, 1H, 1-H in indenyl), 7.15 (dd, J=8.2 Hz, J=1.8 Hz, 1H, 2-H in p-tolyl), 7.03 (dd, J=8.2 Hz, J=1.8 Hz, 1H, 6-H in p-tolyl), 6.94 (dd, J=8.2 Hz, J=2.3 Hz, 1H, 3/5-H in p-tolyl), 6.88 (dd, J=10.4 Hz, J=7.3 Hz, 1H, 4-H in indenyl), 6.71 (d, J=2.1 Hz, 3-H in indenyl), 6.51 (dd, J=8.2 Hz, J=2.3 Hz, 1H, 5/3-H in p-tolyl), 2.48 (s, 3H, 4-Me in p-tolyl), 2.30 (s, 3H, 2-Me in indenyl), 0.71 (s, 3H, SiMe), 0.61 (s, 3H, SiMe), 0.51 (s, 3H, SiMe), −0.44 (s, 3H, SiMe). Anal. Calc. for C$_{21}$H$_{26}$Cl$_2$FNSi$_2$Ti: C, 51.86; H, 5.39; N, 2.88%. Found: C, 52.00; H, 5.51; N, 2.94%.

Example 18

{η$^5$:η$^1$-2-(7-fluoro-2-methylinden-4-yl)-1,1,2,2-tetramethyl-N-(3,5-dimethyl-phenyl)disilanamido}titaniumdichloride (Compound T)

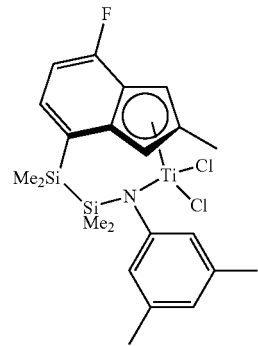

18a): 2-(4-Fluoro-2-methyl-1/3H-inden-7/4-yl)-1,1,2,2-tetramethyl-N-(3,5-dimethylphenyl)-disilanamine

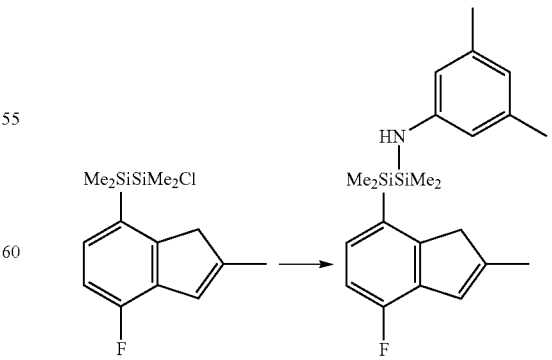

To a solution of 2.88 g (23.8 mmol) of 3,5-dimethylaniline in 70 mL of THF 9.52 mL (23.8 mmol) of 2.5 M "BuLi in hexanes was added at room temperature. This mixture was additionally stirred for 3 hours at ambient temperature, then cooled to −40° C., and a solution of 7.11 g (23.8 mmol) of 1-chloro-1,1,2,2-tetramethyl-2-(4-fluoro-2-methyl-1/3H-inden-7/4-yl)disilane in 30 mL of THF was added in one portion. The resulting mixture was stirred for 12 hours at room temperature, then evaporated to dryness, and the residue was dried in vacuum. Further on, 50 mL of ether was added, the obtained suspension was stirred for 20 minutes at room temperature and then filtered through glass frit (G3). The precipitate was additionally washed with 2×50 mL of ether. The combined filtrate was evaporated to dryness, and the residue was rectificated in vacuum, b.p. 176° C.-192° C./0.1 mm. Yield 5.48 g (60%) of viscous oil as a ca. 2 to 1 mixture of 2-(4-fluoro-2-methyl-1H-inden-7-yl)-1,1,2,2-tetramethyl-N-(3,5-dimethylphenyl)disilanamine and 2-(4-fluoro-2-methyl-3H-inden-4-yl)-1,1,2,2-tetramethyl-N-(3,5-dimethylphenyl)disilanamine. $^1$H NMR (C$_6$D$_6$), 2-(4-fluoro-2-methyl-1H-inden-7-yl)-1,1,2,2-tetramethyl-N-(3,5-dimethylphenyl)-disilanamine: δ 7.27 (dd, J=8.2 Hz, J=5.7 Hz, 1H, 6-H in indenyl), 6.82 (dd, J=9.3 Hz, J=8.2 Hz, 1H, 5-H in indenyl), 6.59 (m, 1H, 3-H in indenyl), 6.39 (m, 1H, 4-H in 3,5-Me$_2$C$_6$H$_4$), 6.06 (s, 2H, 2,6-H in 3,5-Me$_2$C$_6$H$_4$), 3.05 (s, 1H, NH), 2.96 (s, 2H, 1,1'-H in indenyl), 2.15 (m, 6H, 3,5-Me in 3,5-Me$_2$C$_6$H$_4$), 1.75 (m, 3H, 2-Me in indenyl), 0.46 (s, 6H, SiMe$_2$SiMe$_2$Cl), 0.30 (s, 6H, SiMe$_2$SiMe$_2$Cl); 2-(4-fluoro-2-methyl-3H-inden-4-yl)-1,1,2,2-tetramethyl-N-(3,5-dimethylphenyl)disilanamine: δ 7.11 (dd, J=8.2 Hz, J=5.5 Hz, 1H, 5-H in indenyl), 6.93 (dd, J=9.6 Hz, J=8.2 Hz, 1H, 6-H in indenyl), 6.60 (m, 1H, 3-H in indenyl), 6.39 (m, 1H, 4-H in 3,5-Me$_2$C$_6$H$_4$), 6.22 (s, 2H, 2,6-H in 3,5-Me$_2$C$_6$H$_4$), 3.04 (s, 2H, 1,1'-H in indenyl), 2.93 (s, 1H, NH), 2.14 (m, 6H, 3,5-Me in 3,5-Me$_2$C$_6$H$_4$), 2.09 (m, 3H, 2-Me in indenyl), 0.40 (s, 6H, SiMe$_2$SiMe$_2$Cl), 0.25 (s, 6H, SiMe$_2$SiMe$_2$Cl). Anal. Calc. for C$_{22}$H$_{30}$FNSi$_2$: C, 68.87; H, 7.88; N, 3.65%. Found: C, 69.06; H, 7.99; N, 3.50%.

18b): {η$^5$:η$^1$-2-(7-fluoro-2-methylinden-4-O-1,1,2,2-tetramethyl-N-(3,5-dimethylphenyl)-disilanamido}titaniumdichloride (Compound T)

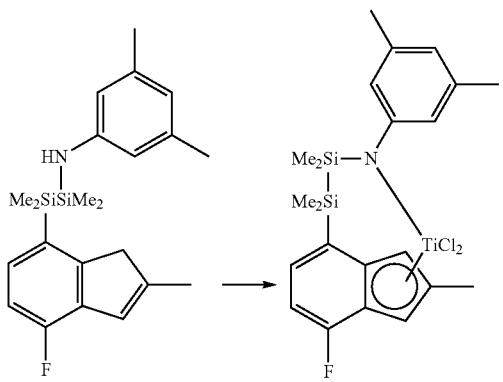

To a solution of 2.76 g (7.09 mmol) of 2-(4-fluoro-2-methyl-1/3H-inden-7/4-yl)-1,1,2,2-tetramethyl-N-(3,5-dimethylphenyl)disilanamine in 50 mL of dry ether 5.06 mL (14.2 mmol) of 2.5 M $^n$BuLi in hexanes was added at room temperature. This mixture was stirred for 12 hours at room temperature, and then a solution of 1.35 g (7.09 mmol) of TiCl$_4$ in 20 mL of hexanes was added at 0° C. The resulting mixture was stirred for 12 hours at room temperature, then evaporated to dryness, and the residue was dried in vacuum. Further on, 50 mL of toluene was added, the obtained suspension was stirred for 2 hours at 50° C., and, finally, filtered through glass frit (G3). The precipitate was additionally washed with 10 mL of toluene. The combined filtrate was evaporated to dryness, and to the obtained residue 10 mL of hexanes was added. This suspension was stirred for 30 minutes at room temperature and then filtered through glass fit (G3). The precipitate was washed with 2×5 mL of cold hexanes and then dried in vacuum. Yield 0.60 g (17%) of red solid. $^1$H NMR (C$_6$D$_6$): δ 7.95 (m, 3H, 3,5,6-H in indenyl), 6.67 (m, 1H, 1-H in indenyl), 6.62 (m, 1H, 4-H in 3,5-Me$_2$C$_6$H$_4$), 6.54 (m, 1H, 2/6-H in 3,5-Me$_2$C$_6$H$_4$), 6.42 (m, 1H, 6/2-H in 3,5-Me$_2$C$_6$H$_4$), 2.18 (s, 3H, 3/5-Me in 3,5-Me$_2$C$_6$H$_4$), 2.11 (s, 3H, 5/3-Me in 3,5-Me$_2$C$_6$H$_4$), 1.96 (s, 3H, 2-Me in indenyl), 0.52 (s, 3H, SiMe), 0.46 (s, 3H, SiMe), 0.27 (s, 3H, SiMe), −0.39 (s, 3H, SiMe). Anal. Calc. for C$_{22}$H$_{28}$Cl$_2$FNSi$_2$Ti: C, 52.80; H, 5.64; N, 2.80%. Found: C, 52.92; H, 5.61; N, 2.68%.

Example 19

{η$^5$:η$^1$-N-cyclopentyl-2-(7-fluoro-2-methylinden-4-yl)-1,1,2,2-tetramethyl-disilanamido}titanium dichloride (Compound U)

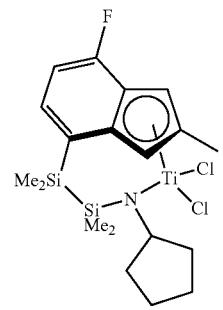

19a): N-Cyclopentyl-2-(4-fluoro-2-methyl-1/3H-inden-7/4-O-1,1,2,2-tetramethyldisilanamine

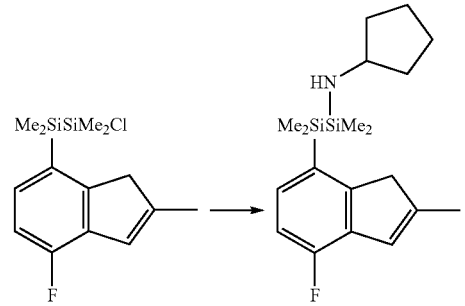

To a solution of 2.41 g (23.8 mmol) of cyclopentylamine in 70 mL of THF 9.52 mL (23.8 mmol) of 2.5 M $^n$BuLi in hexanes was added at room temperature. This mixture was additionally stirred for 3 hours at ambient temperature, then cooled to −40° C., and a solution of 7.11 g (23.8 mmol) of 1-chloro-1,1,2,2-tetramethyl-2-(4-fluoro-2-methyl-1/3H-inden-7/4-yl)disilane in 30 mL of THF was added in one portion. The resulting mixture was stirred for 12 hours at room temperature, then evaporated to dryness, and the residue was dried in vacuum. Further on, 50 mL of ether was added, the obtained suspension was stirred for 20 minutes at room temperature and then filtered through glass frit (G3). The precipitate was additionally washed with 2×50 mL of ether. The combined filtrate was evaporated to dryness, and the residue was rectificated in vacuum, b.p. 137° C.-160° C./0.1 mm.

Yield 5.04 g (61%) of viscous oil as a ca. 2 to 1 mixture of N-cyclopentyl-2-(4-fluoro-2-methyl-1H-inden-7-yl)-1,1,2,2-tetramethyldisilanamine and N-cyclopentyl-2-(4-fluoro-2-methyl-3H-inden-4-yl)-1,1,2,2-tetramethyldisilanamine. $^1$H NMR ($C_6D_6$), N-cyclopentyl-2-(4-fluoro-2-methyl-1H-inden-7-yl)-1,1,2,2-tetramethyldisilanamine: δ 7.37 (dd, J=8.2 Hz, J=5.7 Hz, 1H, 6-H in indenyl), 6.84 (dd, J=9.3 Hz, J=8.2 Hz, 1H, 5-H in indenyl), 6.78 (m, 1H, 3-H in indenyl), 3.15 (m, 1H, 1-H in cyclopentyl), 2.98 (s, 2H, 1.1'-H in indenyl), 1.81 (s, 3H, 2-Me in indenyl), 1.65-1.75 (m, 2H, 2-CH$_2$ in cyclopentyl), 1.46-1.58 (m, 2H, 3/4-CH$_2$ in cyclopentyl), 1.30-1.41 (m, 2H, 4/3-CH$_2$ in cyclopentyl), 1.02-1.12 (m, 2H, 5-CH$_2$ in cyclopentyl), 0.47 (s, 6H, SiMe$_2$SiMe$_2$Cl), 0.25 (s, 6H, SiMe$_2$SiMe$_2$Cl) (no NH resonance was found); N-cyclopentyl-2-(4-fluoro-2-methyl-3H-inden-4-yl)-1,1,2,2-tetramethyl-disilanamine: δ 7.21 (dd, J=8.1 Hz, J=5.7 Hz, 1H, 5-H in indenyl), 6.95 (dd, J=9.7 Hz, J=8.2 Hz, 1H, 6-H in indenyl), 6.65 (m, 1H, 3-H in indenyl), 3.31 (s, 2H, 1.1'-H in indenyl), 3.06 (m, 1H, 1-H in cyclopentyl), 1.84 (s, 3H, 2-Me in indenyl), 1.61-1.69 (m, 2H, 2-CH$_2$ in cyclopentyl), 1.46-1.58 (m, 2H, 3/4-CH$_2$ in cyclopentyl), 1.30-1.41 (m, 2H, 4/3-CH$_2$ in cyclopentyl), 0.96-1.06 (m, 2H, 5-CH$_2$ in cyclopentyl), 0.41 (s, 6H, SiMe$_2$SiMe$_2$Cl), 0.19 (s, 6H, SiMe$_2$SiMe$_2$Cl) (no NH resonance was found). Anal. Calc. for $C_{19}H_{30}FNSi_2$: C, 65.65; H, 8.70; N, 4.03%. Found: C, 65.84; H, 8.88; N, 3.87%.

19b): {η$^5$:η$^1$-N-cyclopentyl-2-(7-fluoro-2-methylinden-4-yl)-1,1,2,2-tetramethyldisilanamido}titanium dichloride (Compound U)

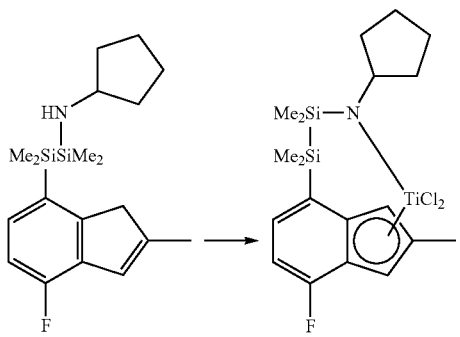

To a solution of 5.86 g (16.9 mmol) of N-cyclopentyl-2-(4-fluoro-2-methyl-1/3H-inden-7/4-yl)-1,1,2,2-tetramethyldisilanamine in 150 mL of dry ether 13.5 mL (33.7 mmol) of 2.5 M $^n$BuLi in hexanes was added at room temperature. This mixture was stirred for 12 hours at room temperature, and then a solution of 3.20 g (16.9 mmol) of TiCl$_4$ in 30 mL of hexanes was added at 0° C. The resulting mixture was stirred for 12 hours at room temperature, then evaporated to dryness, and the residue was dried in vacuum. Further on, 50 mL of toluene was added, the obtained suspension was stirred for 2 hours at 50° C., and, finally, filtered through glass frit (G3). The precipitate was additionally washed with 10 mL of toluene. The combined filtrate was evaporated to dryness, and to the obtained residue 25 mL of hexanes was added. This suspension was stirred for 30 minutes at room temperature and then filtered through glass frit (G3). The precipitate was washed with 2×15 mL of cold hexanes and then dried in vacuum. Yield 4.62 g (59%) of red solid. $^1$H NMR ($C_6D_6$): δ 6.79 (dd, J=7.2 Hz, J=5.3 Hz, 1H, 5-H in indenyl), 6.77 (m, 1H, 1-H in indenyl), 6.55 (dd, J=10.2 Hz, J=7.3 Hz, 1H, 4-H in indenyl), 6.25 (m, 3-H in indenyl), 6.32 (pent, J=7.9 Hz, 1H, 1-H in cyclopentyl), 2.50-2.58 (m, 1H, CH in cyclopentyl), 2.30-2.40 (m, 1H, CH in cyclopentyl), 2.14 (s, 3H, 2-Me in indenyl), 1.47-1.56 (m, 1H, CH in cyclopentyl), 1.36-1.46 (m, 3H, CH in cyclopentyl), 1.17-1.27 (m, 1H, CH in cyclopentyl), 0.81-0.90 (m, 1H, CH in cyclopentyl), 0.42 (s, 3H, SiMe), 0.39 (s, 3H, SiMe), 0.23 (s, 3H, SiMe), 0.08 (s, 3H, SiMe). Anal. Calc. for $C_{19}H_{28}Cl_2FNSi_2Ti$: C, 49.14; H, 6.08; N, 3.02%. Found: C, 49.30; H, 6.22; N, 2.89%.

Example 20

{η$^5$:η$^1$-2-(5-tert-Butyl-2-ethylinden-7-yl)-1,1,2,2-tetramethyl-N-(2-methylphenyl)disilanamido}titanium dichloride (Compound V)

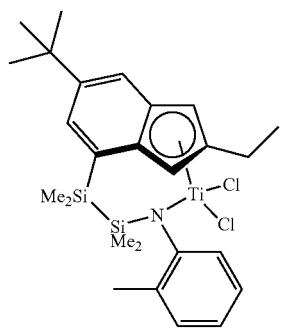

20a) 2-Bromo-4-tert-butyl-1-methylbenzene

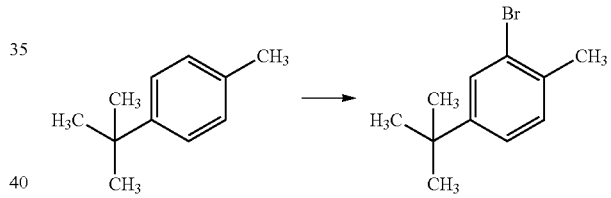

To a mixture of 416 g (2.81 mol) of 4-tert-butyltoluene and 1.0 g of iodine 468 g (2.93 mol) of bromine was added dropwise by vigorous stirring for 2 hours at 5° C. This mixture was stirred for 12 hours at room temperature, then washed by 2×300 ml of water, 300 ml of aqueous K$_2$CO$_3$, 300 ml of aqueous Na$_2$SO$_4$, and then dried over K$_2$CO$_3$. Fractional rectification of the crude product gave 548 g (86%) of colorless liquid, b.p. 105° C.-110° C./12 mm Hg. Anal. calc. for $C_{11}H_{15}Br$: C, 58.17; H, 6.66. Found: C, 58.08; H, 5.75. $^1$H NMR (CDCl$_3$): δ 7.57 (d, J=2.0 Hz, 1H, 3-H), 7.25 (dd, J=8.0 Hz, J=2.0 Hz, 1H, 5-H), 7.18 (d, J=8.0 Hz, 1H, 6-H), 2.39 (s, 3H, Me), 1.32 (s, 9H, $^t$Bu). $^{13}$C{$^1$H} NMR (CDCl$_3$): δ 134.7, 130.4, 129.3, 124.8, 124.3 (two resonances), 34.4, 31.4, 22.3.

20b) 2-Bromo-1-(bromomethyl)-4-tert-butylbenzene

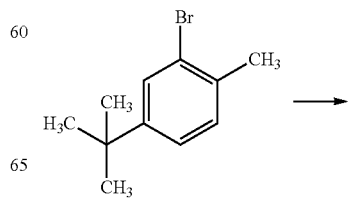

-continued

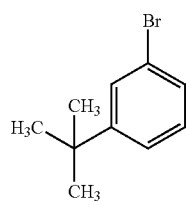

To a mixture of 227 g (1.00 mol) of 2-bromo-4-tert-butyl-1-methylbenzene, 160 g (1.00 mol) of bromine and 1.4 liter of $CCl_4$ 1.0 g of benzoyl peroxide was added. This mixture was refluxed until evolution of hydrogen bomide was stopped, and red color of bromine disappeared. The resulting mixture was evaporated using rotary evaporated. Fractional rectification of the residue gave 273 g (89%) of the title product, b.p. 138° C.-141° C./4 mm Hg. Anal. calc. for $C_{11}H_{14}Br_2$: C, 43.17; H, 4.61. Found: C, 43.30; H, 6.72. $^1H$ NMR ($CDCl_3$): δ 7.56 (d, J=1.8 Hz, 3-H), 7.37 (d, J=8.1 Hz, 1H, 5-H), 7.30 (dd, J=8.1 Hz, J=1.8 Hz, 1H, 6-H), 4.59 (s, 2H, $CH_2Br$), 1.29 (s, 9H, $^tBu$). $^{13}C\{^1H\}$ NMR ($CDCl_3$): δ 153.9, 133.9, 130.9, 130.4, 125.1, 124.4, 34.7, 33.4, 31.06.

20c) Diethyl (2-bromo-4-tert-butylbenzyl)malonate

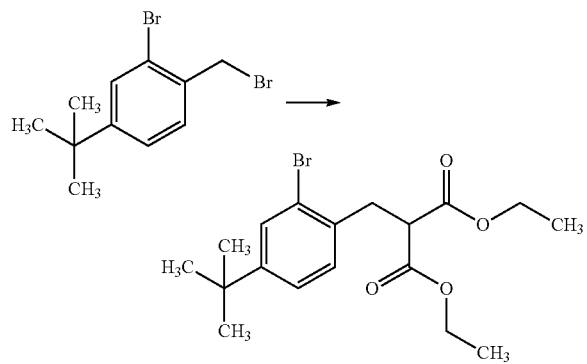

To a solution of sodium ethoxide obtained from 20.5 g (0.89 mmol) of sodium metal and 270 ml of dry ethanol 286 g (1.79 mol) of diethyl malonate was added at room temperature. To this mixture 273 g (0.89 mol) of 2-bromo-1-(bromomethyl)-4-tert-butylbenzene was added dropwise by vigorous stirring for 2 hours at room temperature. The resulting mixture was refluxed for 3 hours, and then was distilled of at atmospheric pressure. To the residue 1 liter of cold water was added. The product was extracted by 300 ml of ether. The organic layer was separated, dried over $Na_2SO_4$, and ether was evaporated using rotary evaporator. Fractional rectification of the residue gave 258 g of the title product, b.p. 185° C.-205° C./4 mm Hg. Anal. calc. for $C_{18}H_{25}BrO_4$: C, 56.11; H, 6.54. Found: C, 55.98; H, 6.00. $^1H$ NMR ($CDCl_3$): δ 7.53 (d, J=1.8 Hz, 1H, 3-H in $C_6H_3$), 7.22 (dd, J=8.0 Hz, J=1.8 Hz, 1H, 5-H in $C_6H_3$), 7.16 (d, J=8.0 Hz, 1H, 6-H in $C_6H_3$), 4.16 (q, J=7.1 Hz, 4H, $CH_2Me$), 3.83 (t, J=7.8 Hz, 1H, $CH_2CH$), 3.30 (d, J=7.8 Hz, 2H, $CH_2CH$), 1.28 (s, 9H, $^tBu$), 1.20 (t, J=7.1 Hz, 6H, $CH_2Me$). $^{13}C\{^1H\}$ NMR ($CDCl_3$): δ 168.7, 152.0, 133.8, 130.9, 129.8, 124.4, 124.3, 61.3, 51.4, 34.5, 34.4, 31.1, 13.9.

20d) 2-(2-Bromo-4-tert-butylbenzyl)butanoyl chloride

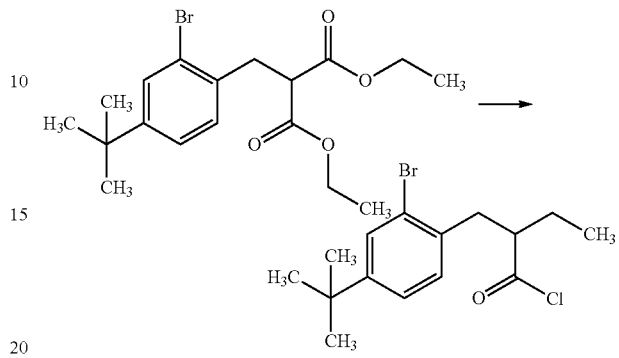

To a mixture of sodium ethoxide obtained from 13.7 g (0.60 mol) of sodium metal and 375 ml of dry ethanol and 193 g (0.50 mol) of diethyl (2-bromo-4-tert-butylbenzyl)malonate 65.5 g (0.60 mol) of ethyl bromide was added dropwise by vigorous stirring. This mixture was refluxed for 4 hours, then cooled, and a solution of 100 g of KOH in 270 ml of water was added. The obtained mixture was refluxed for 5 hours, then ethanol was distilled off. A mixture of the obtained solution and 1.5 liters of cold water was acidified by 1 M HCl to pH 1. The precipitate was decanted and then dissolved in 500 ml of ether. This solution was evaporated to dryness, and the residue was decarboxilated for ca. 2 hours at 180° C. To the obtained 2-(2-bromo-4-tert-butylbenzyl)butanoic acid 128 ml (209 g, 1.76 mol) of thionyl chloride was added. The resulting mixture was stirred for 12 hours at room temperature. An excess of thionyl chloride was distilled off. Fractional rectification of the residue gave 116 g (70%) of yellowish liquid, b.p. 137° C.-142° C./1 mm Hg. Anal. calc. for $C_{15}H_{20}BrClO$: C, 54.32; H, 6.08. Found: C, 54.43; H, 6.20. $^1H$ NMR ($CDCl_3$): δ 7.54 (d, J=1.9 Hz, 1H, 3-H in $C_6H_3$), 7.25 (dd, J=8.0 Hz, J=1.9 Hz, 1H, 5-H in $C_6H_3$), 7.16 (d, J=8.0 Hz, 1H, 6-H in $C_6H_3$), 3.24-3.06 (m, 2H, $CH_2CHCH_2Me$), 2.93 (dd, J=13.6 Hz, J=6.1 Hz, 1H, $CHCH_2Me$), 1.89-1.69 (m, 2H, $CH_2Me$), 1.28 (s, 9H, $^tBu$), 1.02 (t, J=7.5 Hz, $CH_2Me$). $^{13}C\{^1H\}$ NMR ($CDCl_3$): δ 176.4, 152.1, 133.9, 130.9, 130.1, 124.7, 124.4, 58.3, 37.1, 34.5, 31.1, 24.9, 11.0.

20e) 4-Bromo-6-tert-butyl-2-ethylindan-1-one

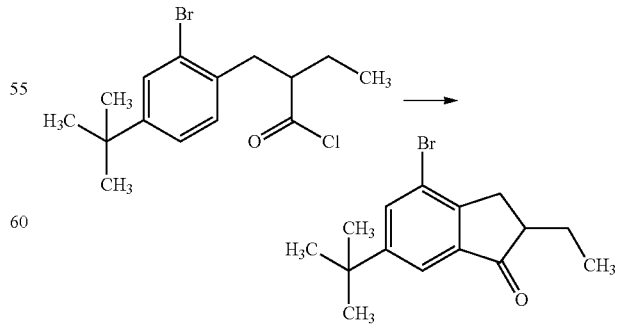

A solution of 116 g (0.35 mol) of 2-(2-bromo-4-tert-butylbenzyl)butanoyl chloride in 150 ml of dry dichloromethane was added dropwise to a suspension of 56.2 g (0.42 mol) of powdered AlCl$_3$ in 500 ml of dry dichloromethane for 1.5 hours at 0° C. The resulting mixture was stirred overnight at room temperature and then poured on 500 cm$^3$ of ice. The organic layer was separated, and the aqueous layer was extracted by 3×100 ml of dichloromethane. The combined organic extract was washed by saturated aqueous NaHCO$_3$, dried over K$_2$CO$_3$, and evaporated to dryness. Fractional rectification of the residue gave 92.2 g (89%) of the title product, b.p. 142° C.-147° C./1 mm Hg. Anal. calc. for C$_{15}$H$_{19}$BrO: C, 61.03; H, 6.49. Found: C, 59.88; H, 6.37. $^1$H NMR (CDCl$_3$): δ 7.80 (d, J=1.5 Hz, 1H, 5-H), 7.71 (d, J=1.5 Hz, 1H, 7-H), 3.22 (dd, J=17.4 Hz, J=7.6 Hz, 1H, 3-H), 2.75-2.62 (m, 2H, 3'-H and 2-H), 1.98 (m, 1H, CHH'Me), 1.55 (m, 1H, CHH'Me), 1.34 (s, 9H, $^t$Bu), 1.03 (t, J=1.4 Hz, CH$_2$Me). $^{13}$C{$^1$H} NMR (CDCl$_3$): δ 208.4, 153.3, 150.7, 138.7, 135.1, 121.8, 119.3, 49.2, 35.0, 32.9, 31.2, 24.4, 11.5.

20f) 7-Bromo-6-tert-butyl-2-ethyl-1H-indene

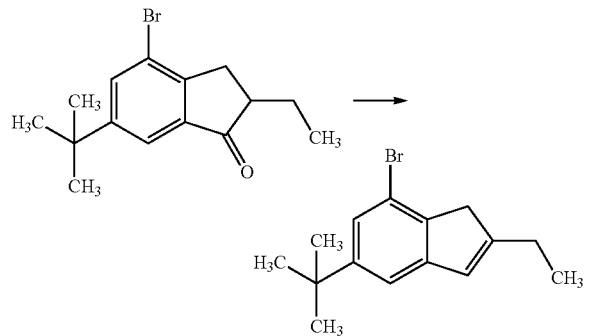

To a solution of 92.2 g (0.31 mol) of 4-bromo-6-tert-butyl-2-ethylindan-1-one in 320 ml of THF cooled to 5° C. 17.7 g (0.47 mol) of NaBH$_4$ was added, and then 160 ml of methanol was added dropwise by vigorous stirring for ca. 5 hours at this temperature. The reaction mixture was added to 1 liter of cold water, acidified by 4 M HCl to pH 5. The product was extracted by 3×200 ml of dichloromethane. The combined organic extract was evaporated to dryness, 150 ml of toluene was added, and the resulting solution was evaporated to dryness again. To a solution of the residue in 650 ml of toluene 1.0 g of TsOH was added. The resulting mixture was refluxed using Dean-Stark head for 1 hour, cooled to room temperature, washed by saturated aqueous NaHCO$_3$, and dried over K$_2$CO$_3$. The obtained solution was passed through short column with silica gel 60 (40-63 um) to remove TsOH traces. The silica gel layer was additionally washed by 100 ml of toluene. The combined elute was evaporated to dryness in vacuum. Fractional rectification of the residue gave 80.7 g (0.29 mmol) of the title product, 153° C.-159° C./5 mm Hg. Anal. calc. for C$_{15}$H$_{19}$Br: C, 64.52; H, 6.86. Found: C, 64.45; H, 6.82. $^1$H NMR (CDCl$_3$): δ 7.24 (m, 2H, 4,6-H), 6.49 (m, 1H, 3-H), 3.25 (m, 2H, 1,1'-H), 2.48 (q, J=7.4 Hz, 2H, CH$_2$Me), 1.31 (s, 9H, $^t$Bu), 1.20 (t, J=7.4 Hz, 3H, CH$_2$Me). $^{13}$C{$^1$H} NMR (CDCl$_3$): δ 153.2, 152.1, 147.0, 140.2, 125.4, 123.8, 118.2, 116.2, 42.1, 34.8, 31.5, 24.3, 13.3.

20g): 1-(5-tert-Butyl-2-ethyl-1/3H-inden-7/4-yl)-2-chloro-1,1,2,2-tetramethyldisilane

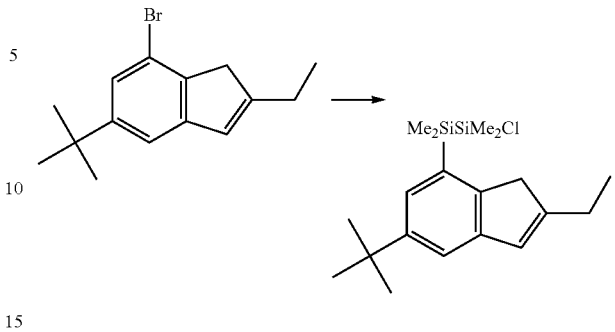

To 6.10 g (0.251 mol) of magnesium turnings in 80 mL of THF a mixture of 34.1 g (0.122 mol) of 7-bromo-6-tert-butyl-2-ethyl-1H-indene, 22.9 g (0.122 mol) of 1,2-dibromoethane and 420 mL of dry THF was added dropwise with vigorous stirring at such a rate that the mixture is refluxed. Further on, the obtained solution was added dropwise at vigorous stirring to a solution of 80.0 g (0.427 mol) of 1,2-dichloro-1,1,2,2-tetramethyldisilane in 100 mL of THF for 2 hours at room temperature (water bath cooling is required). The resulting mixture was stirred for 12 hours at ambient temperature and then evaporated to dryness. To the residue 100 mL of dry ether was added, and the obtained suspension was stirred for 20 minutes and then filtered through glass frit (G3). The precipitate was washed by 2×100 mL of ether. The combined filtrate was evaporated to dryness, the residue was dried and then rectificated in vacuum, b.p. 137° C.-148° C./0.1 mm. Yield 33.4 g (78%) of a ca. 1 to 1 mixture of the title isomers. $^1$H NMR (CD$_2$Cl$_2$): δ 7.48 (m, 1H, C$_6$H$_2$ in indenyl), 7.38 (m, 1H, C$_6$H$_2$ in indenyl), 7.35 (m, 1H, C$_6$H$_2$ in indenyl), 7.28 (m, 1H, C$_6$H$_2$ in indenyl), 6.62 (m, 1H, 3-H in indenyl), 6.51 (m, 1H, 3-H in indenyl), 3.34 (m, 2H, 1,1'-H in indenyl), 3.31 (m, 2H, 1,1'-H in indenyl), 2.53 (m, 4H, 2×CH$_2$Me), 1.35 (s, 18H, 2×$^t$Bu), 1.24 (t, J=7.6 Hz, 6H, 2×CH$_2$Me), 0.56 (s, 6H, SiMe$_2$SiMe$_2$Cl), 0.54 (s, 6H, SiMe$_2$SiMe$_2$Cl), 0.50 (s, 6H, SiMe$_2$SiMe$_2$Cl), 0.49 (s, 6H, SiMe$_2$SiMe$_2$Cl). Anal. Calc. for C$_{19}$H$_{31}$ClSi$_2$: C, 65.00; H, 8.90%. Found: C, 65.32; H, 9.17%.

20h): 2-(5-tert-Butyl-2-ethyl-1/3H-inden-7/4-O-1,1,2,2-tetramethyl-N-(2-methylphenyl)-disilanamine

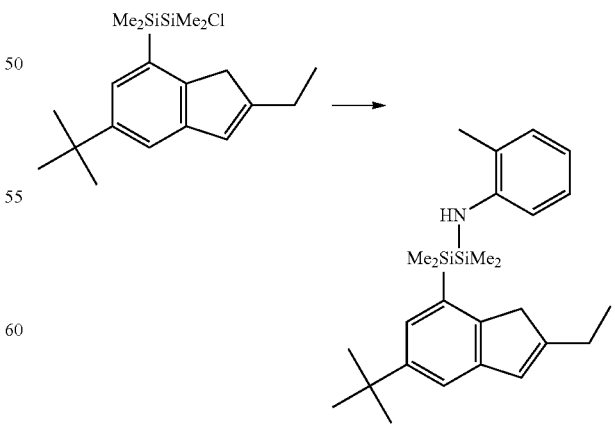

To a solution of 3.25 g (30.0 mmol) of o-toluidine in 100 mL of THF 12.0 mL (30.0 mmol) of 2.5 M $^n$BuLi in hexanes was added at room temperature. This mixture was additionally stirred for 3 hours at ambient temperature, then cooled to −40° C., and a solution of 10.5 g (30.0 mmol) of 1-(5-tert-butyl-2-ethyl-1/3H-inden-7/4-yl)-2-chloro-1,1,2,2-tetramethyldisilane in 30 mL of THF was added in one portion. The resulting mixture was stirred for 12 hours at room temperature, then evaporated to dryness, and the residue was dried in vacuum. Further on, 50 mL of ether was added, the obtained suspension was stirred for 20 minutes at room temperature and then filtered through glass frit (G3). The precipitate was additionally washed with 2×50 mL of ether. The combined filtrate was evaporated to dryness, and the residue was rectificated in vacuum, b.p. 195° C.-210° C./0.1 mm. Yield 9.23 g (73%) of viscous oil as a ca. 1 to 1 mixture of the title isomeric compounds. $^1$H NMR (C$_6$D$_6$): δ 7.35 (m, 1H, C$_6$H$_2$ in indenyl), 7.29 (m, 1H, C$_6$H$_2$ in indenyl), 7.25 (m, 1H, C$_6$H$_2$ in indenyl), 7.19 (m, 1H, C$_6$H$_2$ in indenyl), 6.85-6.91 (m, 4H, 2,5-H in o-tolyl), 6.60 (m, 2H, 3/4-H in o-tolyl), 6.52 (m, 2H, 4/3-H in o-tolyl), 6.47 (s, 1H, 3-H in indenyl), 6.40 (s, 1H, 3-H in indenyl), 3.18 (s, 2H, 1,1'-H in indenyl), 3.13 (s, 2H, 1,1'-H in indenyl), 3.06 (s, 1H, NH), 3.01 (s, 1H, NH), 2.38 (m, 4H, CH$_2$Me), 2.09 (s, 6H, 2-Me in o-tolyl), 1.71 (s, 3H, 2-Me in indenyl), 1.68 (s, 3H, 2-Me in indenyl), 1.26 (s, 18H, $^t$Bu), 1.10 (t, J=7.4 Hz, 6H, CH$_2$Me), 0.43 (s, 6H, SiMe), 0.42 (s, 6H, SiMe), 0.33 (s, 6H, SiMe), 0.32 (s, 6H, SiMe). Anal. Calc. for C$_{26}$H$_{39}$NSi$_2$: C, 74.04; H, 9.32; N, 3.32%. Found: C, 74.38; H, 9.46; N, 3.18%.

20i): {η$^5$:η$^1$-2-(5-tert-Butyl-2-ethylinden-7-yl)-1,1,2,2-tetramethyl-N-(2-methylphenyl)-disilanamido}titanium dichloride (Compound V)

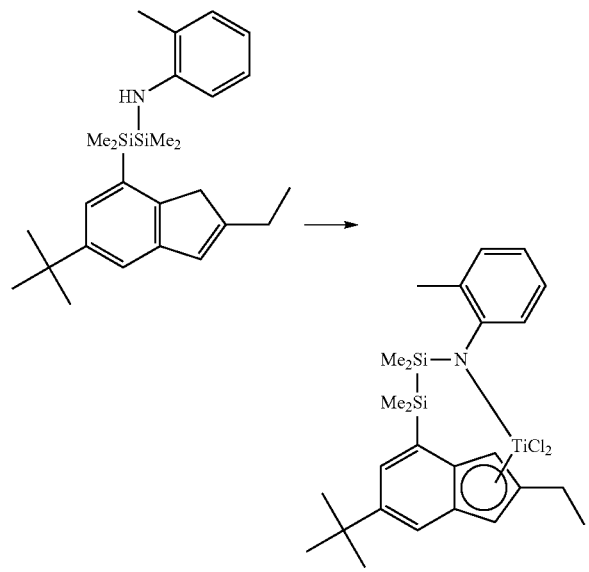

To a solution of 2.91 g (6.90 mmol) of 2-(5-tert-butyl-2-ethyl-1/3H-inden-7/4-yl)-1,1,2,2-tetramethyl-N-(2-methylphenyl)disilanamine in 50 mL of dry ether 5.52 mL (13.8 mmol) of 2.5 M $^n$BuLi in hexanes was added at room temperature. This mixture was stirred for 12 hours at room temperature, and then a solution of 1.31 g (6.90 mmol) of TiCl$_4$ in 20 mL of hexanes was added at 0° C. The resulting mixture was stirred for 12 hours at room temperature, then evaporated to dryness, and the residue was dried in vacuum. Further on, 50 mL of toluene was added, the obtained suspension was stirred for 2 hours at 50° C., and, finally, filtered through glass frit (G3). The precipitate was additionally washed with 10 mL of toluene. The combined filtrate was evaporated to dryness, and to the obtained residue 10 mL of hexanes was added. This suspension was stirred for 30 minutes at room temperature and then filtered through glass frit (G3). The filtrate was evaporated to ca. 2 mL. Crystals precipitated at room temperature were separated, washed with 2×1 mL of cold (−30° C.) hexanes, and then dried in vacuum. Yield 0.45 g (12%) of red crystalline solid. $^1$H NMR (CD$_2$Cl$_2$): δ 7.64 (dd, J=1.8 Hz, J=1.0 Hz, 1H, 7-H in indenyl), 7.41 (d, J=1.8 Hz, 1H, 5-H in indenyl), 7.06-7.17 (m, 3H, 2,3/4,5-H in o-tolyl), 6.93-6.98 (m, 1H, 4/3-H in o-tolyl), 6.73 (dt, J=2.2 Hz, J=0.5 Hz, 1H, 3-H in indenyl), 6.57 (m, 1H, 1-H in indenyl), 3.00 (m, 1H, CHH'Me), 2.89 (m, 1H, CHH'Me), 2.33 (s, 3-H, 2-Me in o-tolyl), 1.35 (s, 9H, $^t$Bu), 1.29 (t, J=7.5 Hz, 3H, CH$_2$Me), 0.72 (s, 3H, SiMe), 0.55 (s, 3H, SiMe), 0.52 (s, 3H, SiMe), 0.11 (s, 3H, SiMe). Anal. Calc. for C$_{26}$H$_{37}$Cl$_2$NSi$_2$Ti: C, 57.99; H, 6.93; N, 2.60%. Found: C, 60.21; H, 7.18; N, 2.75%.

Polymerizations

In the following experiments pressure is reported in atmospheres (atm) and pounds per square inch (psi). The conversion factors to S. I. Units are: 1 psi equals 6.894757 kPa and 1 atm equals 101.325 kPa. Micromole is often abbreviated as "umol". Microliters are often abbreviated as "ul".

The transition metal compounds (pre-catalysts) used in the polymerizations are identified by the letters A through V which correspond to the compound letters in the above experimental section.

Transition metal compound (TMC) solutions were typically prepared using toluene (ExxonMobil Chemical—anhydrous, stored under N$_2$) (98%). TMC solutions were typically 0.2 mmol/L in toluene. In some ethylene-octene copolymerizations, the TMC was diluted in toluene and pre-activated with 10 or 20 equivalents of MAO. In these instances, TMC solutions were typically 0.2 mmol TMC/L and 2 or 4 mmol MAO/L in toluene. Table 2 distinguishes those experiments by the "MAO Pre-activator (umol)" column. When preactivation was used the total Al/M molar ratio used in the experiment, remained at 500.

MAO (methylalumoxane, 10 wt % in toluene) was purchased from Albemarle Corporation and was used as a 0.5 wt %, 1 wt % or 2 wt % in toluene solution. Micromoles of MAO reported in the experimental section are based on the micromoles of aluminum in MAO. The formula weight of MAO is 58.0 grams/mole.

Solvents, polymerization grade toluene and isohexanes were supplied by ExxonMobil Chemical Co. and thoroughly dried and degassed prior to use.

Polymerization grade ethylene was used and further purified by passing it through a series of columns: 500 cc Oxyclear cylinder from Labelear (Oakland, Calif.) followed by a 500 cc column packed with dried 3A mole sieves purchased from Aldrich Chemical Company, and a 500 cc column packed with dried 5A mole sieves purchased from Aldrich Chemical Company.

Reactor Description and Preparation:

Polymerizations were conducted in an inert atmosphere (N2) drybox using autoclaves equipped with an external heater for temperature control, glass inserts (internal volume of reactor=23.5 mL or 22.5 mL), septum inlets, regulated supply of nitrogen, ethylene and propylene, and equipped with disposable PEEK mechanical stirrers (800 RPM). The autoclaves were typically prepared by purging with dry nitrogen at 110° C. or 115° C. for 5 hours and then at 25° C. for 5 hours.

Ethylene Polymerization or Ethylene/1-octene Copolymerization:

The reactor was prepared as described above, and then purged with ethylene. Toluene, 1-octene (100 µL when used), and activator (MAO) were added via syringe at room temperature and atmospheric pressure. The reactor was then brought to process temperature (80° C.) and charged with ethylene to the process pressure indicated in Tables 1 and 2 (75 psig=618.5 kPa, 150 psig=1135.6 kPa, 200 psig=1480.3 kPa) while stirring at 800 RPM. The transition metal compound (TMC) solution was added via syringe with the reactor at process conditions. In cases where some MAO was also precontacted with the TMC, the MAO was added to the TMC first and then the resulting solution was added to the reactor at process conditions. Amounts of reagents not specified above are given in Tables 1 and 2. Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 50 psi of ultra high purity air to the autoclaves for approximately 30 seconds. The polymerizations were quenched based on a predetermined ethylene uptake pressure as indicated by "Quench Value" in psi, or if the quench value was not reached, by a maximum time as indicated by "Maximum Reaction Time" or "Max Rxn time" in minutes. Both values, in addition to the actual quench time measured in seconds, are reported in Table 2 for each run, or as a footnote in Table 1. After quenching, the reactors were cooled and vented. The polymer was isolated after the solvent was removed in-vacuo. Yields (grams) reported include total weight of polymer and residual catalyst. Catalyst activity is reported as grams of polymer per mmol transition metal compound per atmosphere ethylene per hour of reaction time (g/mmol·hr·atm).

For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 165° C. in a shaker oven for approximately 3 hours. The typical concentration of polymer in solution is between 0.1 to 0.9 mg/mL with a BHT concentration of 1.25 mg BHT/mL of TCB. Samples are cooled to 135° C. for testing.

High temperature size exclusion chromatography was performed using an automated "Rapid GPC" system as described in U.S. Pat. Nos. 6,491,816; 6,491,823; 6,475,391; 6,461,515; 6,436,292; 6,406,632; 6,175,409; 6,454,947; 6,260,407; and 6,294,388; each of which is incorporated herein by reference. Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector and calibrated using polystyrene standards (Polymer Laboratories: Polystyrene Calibration Kit S-M-10: Mp (peak Mw) between 5000 and 3,390,000). Samples (250 uL of a polymer solution in TCB were injected into the system) were run at an eluent flow rate of 2.0 mL/minute (135° C. sample temperatures, 165° C. oven/columns) using three Polymer Laboratories: PLgel 10 µm Mixed-B 300×7.5 mm columns in series. No column spreading corrections were employed. Numerical analyses were performed using Epoch® software available from Symyx Technologies. The molecular weights obtained are relative to linear polystyrene standards.

Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minute and then cooled at a rate of 50° C./minute. Melting points were collected during the heating period. The results are reported in the tables as $T_m$ (° C.).

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pikes' MappIR specular reflectance sample accessory. Spectra, covering a spectral range of 5000 $cm^{-1}$ to 500 $cm^{-1}$, were collected at a 2 $cm^{-1}$ resolution with 32 scans.

For ethylene-1-octene copolymers, the wt % copolymer is determined via measurement of the methyl deformation band at ~1375 $cm^{-1}$. The peak height of this band is normalized by the combination and overtone band at ~4321 $cm^{-1}$, which corrects for path length differences. The normalized peak height is correlated to individual calibration curves from $^1$H NMR data to predict the wt % copolymer content within a concentration range of ~2 to 35 wt % for octene. Typically, $R^2$ correlations of 0.98 or greater are achieved. These numbers are reported in Table 2 under the heading C8 wt %).

Polymerization results are collected in Tables 1 and 2 below.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

TABLE 1

Ethylene homopolymerizations

| Ex # | TMC | TMC (umol) | MAO (umol) | time (s) | yield (g) | Activity | Mn | Mw | PDI | Tm (° C.) |
|---|---|---|---|---|---|---|---|---|---|---|
| PE-1 | A | 0.040 | 20 | 1800 | 0.0299 | 245 | 1,097,930 | 2,546,493 | 2.3 | |
| PE-2 | A | 0.040 | 20 | 1801 | 0.0162 | 133 | 763,440 | 2,012,924 | 2.6 | |
| PE-3 | A | 0.040 | 20 | 1801 | 0.0184 | 151 | 754,121 | 1,935,688 | 2.6 | |
| PE-4 | B | 0.040 | 20 | 1801 | 0.0311 | 255 | 995,073 | 2,159,317 | 2.2 | |
| PE-5 | B | 0.040 | 20 | 1801 | 0.0315 | 258 | 1,019,735 | 2,250,004 | 2.2 | |
| PE-6 | B | 0.040 | 20 | 1800 | 0.0327 | 268 | 1,095,661 | 2,374,537 | 2.2 | |
| PE-7 | C | 0.040 | 20 | 1802 | 0.0174 | 142 | 902,124 | 2,014,229 | 2.2 | |
| PE-8 | C | 0.040 | 20 | 1801 | 0.0213 | 174 | 891,058 | 1,947,989 | 2.2 | |

TABLE 1-continued

Ethylene homopolymerizations

| Ex # | TMC | TMC (umol) | MAO (umol) | time (s) | yield (g) | Activity | Mn | Mw | PDI | Tm (° C.) |
|---|---|---|---|---|---|---|---|---|---|---|
| PE-9 | C | 0.040 | 20 | 1802 | 0.0191 | 156 | 837,401 | 1,899,459 | 2.3 | |
| PE-10 | D | 0.040 | 20 | 1801 | 0.0216 | 177 | 893,497 | 1,958,655 | 2.2 | |
| PE-11 | D | 0.040 | 20 | 1801 | 0.0194 | 159 | 853,786 | 1,905,395 | 2.2 | |
| PE-12 | D | 0.040 | 20 | 1802 | 0.0245 | 201 | 858,402 | 1,943,103 | 2.3 | |
| PE-13 | E | 0.025 | 12.5 | 1802 | 0.0153 | 200 | 414,298 | 1,970,758 | 4.8 | |
| PE-14 | E | 0.025 | 12.5 | 1801 | 0.0154 | 202 | 1,142,421 | 3,769,184 | 3.3 | |
| PE-15 | E | 0.025 | 12.5 | 1802 | 0.0174 | 228 | 859,715 | 4,032,106 | 4.7 | 136.8 |
| PE-16* | E | 0.040 | 20 | 1804 | 0.0247 | 202 | 1,569,930 | 2,684,159 | 1.7 | 136.4 |
| PE-17* | E | 0.040 | 20 | 1801 | 0.0121 | 99 | 1,328,080 | 2,621,990 | 2 | 136.0 |
| PE-18* | E | 0.040 | 20 | 1801 | 0.0159 | 130 | 1,253,963 | 2,973,828 | 2.4 | 136.5 |
| PE-19 | E | 0.040 | 20 | 1801 | 0.0266 | 218 | | | | |
| PE-20 | E | 0.040 | 20 | 1802 | 0.0219 | 179 | | | | |
| PE-21 | E | 0.040 | 20 | 1806 | 0.0261 | 213 | | | | |
| PE-22 | F | 0.025 | 12.5 | 1801 | 0.0106 | 139 | 1,712,203 | 3,166,460 | 1.9 | |
| PE-23 | F | 0.025 | 12.5 | 1801 | 0.0147 | 193 | 885,656 | 2,912,961 | 3.3 | 135.3 |
| PE-24 | F | 0.025 | 12.5 | 1800 | 0.0123 | 161 | 1,582,545 | 3,245,386 | 2.1 | 129.8 |
| PE-25* | F | 0.040 | 20 | 1802 | 0.0049 | 40 | | | | |
| PE-26* | F | 0.040 | 20 | 1800 | 0.0042 | 34 | | | | |
| PE-27* | F | 0.040 | 20 | 1800 | 0.0041 | 34 | | | | |
| PE-28 | F | 0.040 | 20 | 1804 | 0.0289 | 236 | 688,855 | 1,906,479 | 2.8 | 134.4 |
| PE-29 | F | 0.040 | 20 | 1802 | 0.0223 | 183 | 1,128,666 | 1,994,982 | 1.8 | 137.2 |
| PE-30 | F | 0.040 | 20 | 1800 | 0.0210 | 172 | 923,786 | 1,996,161 | 2.2 | 134.4 |
| PE-31 | G | 0.040 | 20 | 1804 | 0.0100 | 82 | | | | |
| PE-32 | G | 0.040 | 20 | 1805 | 0.0108 | 88 | 178,048 | 1,365,512 | 7.7 | 150.2 |
| PE-33 | G | 0.040 | 20 | 1800 | 0.0096 | 79 | | | | |
| PE-34 | H | 0.040 | 20 | 600 | 0.0385 | 946 | 421,700 | 1,145,738 | 2.7 | 133.8 |
| PE-35 | H | 0.040 | 20 | 889 | 0.0378 | 627 | 372,596 | 1,179,889 | 3.2 | 136.9 |
| PE-36 | H | 0.040 | 20 | 1250 | 0.0341 | 403 | 365,012 | 1,200,082 | 3.3 | 137.7 |
| PE-37 | I | 0.040 | 20 | 1800 | 0.0239 | 196 | 212,253 | 1,193,991 | 5.6 | 137.4 |
| PE-38 | I | 0.040 | 20 | 1801 | 0.0239 | 196 | 224,994 | 1,169,159 | 5.2 | 136.5 |
| PE-39 | I | 0.040 | 20 | 1801 | 0.0227 | 186 | 110,632 | 1,240,800 | 11 | 137.0 |
| PE-40 | J | 0.040 | 20 | 1803 | 0.0170 | 139 | 881,896 | 3,055,349 | 3.5 | 134.5 |
| PE-41 | J | 0.040 | 20 | 1802 | 0.0162 | 133 | 1,012,476 | 3,308,256 | 3.3 | 135.6 |
| PE-42 | J | 0.040 | 20 | 1800 | 0.0178 | 146 | 2,283,564 | 3,780,906 | 1.7 | 134.7 |
| PE-43 | K | 0.040 | 20 | 1801 | 0.0191 | 156 | | | | 133.3 |
| PE-44 | K | 0.040 | 20 | 1802 | 0.0179 | 146 | 863,379 | 2,213,807 | 2.6 | 134.4 |
| PE-45 | K | 0.040 | 20 | 1801 | 0.0184 | 151 | 841,442 | 2,353,219 | 2.8 | 135.9 |
| PE-46 | L | 0.040 | 20 | 1802 | 0.0200 | 164 | 170,462 | 539,841 | 3.2 | 132.4 |
| PE-47 | L | 0.040 | 20 | 1805 | 0.0610 | 498 | | | | |
| PE-48 | L | 0.040 | 20 | 1805 | 0.0235 | 192 | | | | 136.1 |
| PE-49 | N | 0.040 | 20 | 684 | 0.0400 | 863 | | | | |
| PE-50 | N | 0.040 | 20 | 786 | 0.0394 | 740 | | | | |
| PE-51 | N | 0.040 | 20 | 1279 | 0.0488 | 563 | | | | |
| PE-52 | O | 0.040 | 20 | 1802 | 0.0270 | 221 | 1,755,531 | 3,304,312 | 1.9 | 136.1 |
| PE-53 | O | 0.040 | 20 | 1801 | 0.0251 | 206 | 1,038,724 | 2,710,217 | 2.6 | 134.4 |
| PE-54 | O | 0.040 | 20 | 1800 | 0.0260 | 213 | 609,381 | 1,675,929 | 2.8 | 133.6 |
| PE-55 | P | 0.040 | 20 | 259 | 0.0719 | 4096 | 758,556 | 1,477,602 | 2 | 137.7 |
| PE-56 | P | 0.040 | 20 | 450 | 0.0611 | 2002 | 871,608 | 1,510,411 | 1.7 | 134.3 |
| PE-57 | P | 0.040 | 20 | 313 | 0.0752 | 3544 | 1,178,544 | 2,176,690 | 1.9 | 136.6 |
| PE-58* | Q | 0.040 | 20 | 783 | 0.0371 | 698 | 567,105 | 971,702 | 1.7 | 135.9 |
| PE-59* | Q | 0.040 | 20 | 795 | 0.0406 | 753 | 632,906 | 1,033,069 | 1.6 | 136.1 |
| PE-60* | Q | 0.040 | 20 | 1611 | 0.0375 | 343 | 682,050 | 1,127,800 | 1.7 | 135.9 |
| PE-61 | Q | 0.040 | 20 | 1802 | 0.0209 | 171 | 162,621 | 1,780,200 | 11 | 136.0 |
| PE-62 | Q | 0.040 | 20 | 1802 | 0.0211 | 173 | 277,736 | 2,260,042 | 8.1 | 124.6 |
| PE-63 | Q | 0.040 | 20 | 1802 | 0.0203 | 166 | 194,002 | 1,555,856 | 8 | |
| PE-64 | Q | 0.040 | 20 | 1670 | 0.0330 | 291 | 749,417 | 1,351,013 | 1.8 | 137.4 |
| PE-65 | Q | 0.040 | 20 | 976 | 0.0332 | 502 | 802,249 | 1,521,679 | 1.9 | 138.7 |
| PE-66 | Q | 0.040 | 20 | 1206 | 0.0328 | 401 | 812,047 | 1,771,562 | 2.2 | 138.6 |
| PE-67 | Q | 0.040 | 20 | 1148 | 0.0387 | 497 | 1,092,591 | 1,704,497 | 1.6 | 136.0 |
| PE-68 | Q | 0.040 | 20 | 831 | 0.0344 | 610 | 979,308 | 1,501,201 | 1.5 | 135.4 |
| PE-69 | Q | 0.040 | 20 | 1342 | 0.0362 | 398 | 1,333,702 | 1,924,579 | 1.4 | 137.2 |
| PE-70 | R | 0.040 | 20 | 1800 | 0.0270 | 221 | 1,416,536 | 2,324,650 | 1.6 | |
| PE-71 | R | 0.040 | 20 | 1802 | 0.0277 | 227 | 1,047,535 | 1,958,110 | 1.9 | |
| PE-72 | R | 0.040 | 20 | 1802 | 0.0239 | 196 | 995,798 | 1,681,094 | 1.7 | |
| PE-73 | S | 0.040 | 20 | 95 | 0.0746 | 11558 | 247,126 | 391,066 | 1.6 | 106.8 |
| PE-74 | S | 0.040 | 20 | 79 | 0.0759 | 14261 | 257,060 | 424,385 | 1.7 | |
| PE-75 | S | 0.040 | 20 | 87 | 0.0768 | 13095 | 252,297 | 390,305 | 1.6 | 100.9 |
| PE-76 | T | 0.040 | 20 | 119 | 0.0657 | 8143 | 309,553 | 460,071 | 1.5 | |
| PE-77 | T | 0.040 | 20 | 195 | 0.0776 | 5872 | 365,208 | 585,618 | 1.6 | 107.0 |
| PE-78 | T | 0.040 | 20 | 124 | 0.0657 | 7808 | 311,401 | 461,369 | 1.5 | 101.0 |
| PE-79 | U | 0.040 | 20 | 1802 | 0.0168 | 138 | 570,142 | 1,272,890 | 2.2 | |
| PE-80 | U | 0.040 | 20 | 1801 | 0.0139 | 114 | 565,826 | 1,254,322 | 2.2 | 106.9 |
| PE-81 | U | 0.040 | 20 | 1801 | 0.0166 | 136 | 519,314 | 1,139,034 | 2.2 | 110.4 |
| PE-82* | V | 0.040 | 20 | 96 | 0.0578 | 8843 | 699,159 | 1,073,877 | 1.5 | 136.0 |
| PE-83* | V | 0.040 | 20 | 68 | 0.0568 | 12356 | 753,486 | 1,142,752 | 1.5 | 136.4 |

TABLE 1-continued

Ethylene homopolymerizations

| Ex # | TMC | TMC (umol) | MAO (umol) | time (s) | yield (g) | Activity | Mn | Mw | PDI | Tm (° C.) |
|---|---|---|---|---|---|---|---|---|---|---|
| PE-84* | V | 0.040 | 20 | 72  | 0.0541 | 11098 | 728,666   | 1,100,249 | 1.5 | 136.4 |
| PE-85  | V | 0.040 | 20 | 323 | 0.0755 | 3450  | 748,091   | 1,426,218 | 1.9 | 137.1 |
| PE-86  | V | 0.040 | 20 | 433 | 0.0703 | 2396  | 644,639   | 1,197,824 | 1.9 | 134.1 |
| PE-87  | V | 0.040 | 20 | 169 | 0.0825 | 7200  | 764,983   | 1,541,696 | 2   | 137.3 |
| PE-88  | V | 0.040 | 20 | 265 | 0.0784 | 4359  | 766,618   | 1,468,906 | 1.9 | 134.6 |
| PE-89  | V | 0.040 | 20 | 298 | 0.0777 | 3846  | 1,014,490 | 1,801,727 | 1.8 | 137.2 |
| PE-90  | V | 0.040 | 20 | 359 | 0.0758 | 3113  | 792,522   | 1,339,127 | 1.7 | 135.1 |
| PE-91  | V | 0.040 | 20 | 452 | 0.0732 | 2387  | 644,977   | 1,073,377 | 1.7 | 131.6 |
| PE-92  | V | 0.040 | 20 | 363 | 0.0754 | 3065  | 766,923   | 1,428,076 | 1.9 | 134.5 |
| PE-93  | V | 0.040 | 20 | 414 | 0.0740 | 2635  |           |           |     |        |

General conditions used: 5 mL total solvent; solvent toluene unless otherwise noted; total molar MAO/TMC = 500; reaction temperature = 80° C.; stirrer speed 800 rpm; reactor maintained with 75 psig ethylene; quench value set to 20 psi ethylene uptake or 30 minutes maximum reaction time.
*347 ul toluene used for delivering TMC and MAO; remaining solvent isohexane.

TABLE 2

Ethylene 1-octene copolymerizations

| Ex. # | TMC | TMC (umol) | MAO (umol) | MAO Pre-activator (umol) | C2 (psig) | Quench Value (psi) | Max Rxn time (min) | time (s) | yield (g) | Activity | Mn | Mw | PDI | C8 (wt %) | $T_m$ (° C.) |
|---|---|---|---|---|---|---|---|---|---|---|---|---|---|---|---|
| EO-1  | A | 0.040 | 20   | 0   | 75  | 20 | 30 | 1801 | 0.0096 | 79   |           |           |      |      |       |
| EO-2  | A | 0.040 | 20   | 0   | 75  | 20 | 30 | 1800 | 0.0393 | 322  | 1,159,674 | 2,176,451 | 1.88 |      |       |
| EO-3  | A | 0.040 | 20   | 0   | 200 | 15 | 30 | 79   | 0.0679 | 5276 | 2,102,274 | 3,637,446 | 1.73 | 5.2  |       |
| EO-4  | A | 0.040 | 20   | 0   | 200 | 15 | 30 | 65   | 0.0692 | 6580 | 1,669,417 | 3,063,355 | 1.83 | 4.4  |       |
| EO-5  | A | 0.040 | 20   | 0   | 200 | 15 | 30 | 85   | 0.0629 | 4560 | 2,019,378 | 3,533,547 | 1.75 | 5.2  |       |
| EO-6  | B | 0.040 | 20   | 0   | 75  | 20 | 30 | 1802 | 0.0295 | 241  | 739,365   | 1,669,399 | 2.26 | 12   |       |
| EO-7  | B | 0.040 | 20   | 0   | 75  | 20 | 30 | 1802 | 0.0284 | 233  | 912,012   | 1,764,452 | 1.93 | 8.7  |       |
| EO-8  | B | 0.040 | 20   | 0   | 75  | 20 | 30 | 1802 | 0.0302 | 247  | 816,259   | 1,758,543 | 2.15 | 7.6  |       |
| EO-9  | B | 0.040 | 20   | 0   | 200 | 15 | 30 | 138  | 0.0717 | 3213 | 1,496,888 | 2,783,474 | 1.86 | 4.7  |       |
| EO-10 | B | 0.040 | 20   | 0   | 200 | 15 | 30 | 117  | 0.0602 | 3160 | 1,339,796 | 2,603,968 | 1.94 | 4.1  |       |
| EO-11 | B | 0.040 | 20   | 0   | 200 | 15 | 30 | 227  | 0.0721 | 1961 | 1,358,170 | 2,628,864 | 1.94 | 4.4  |       |
| EO-12 | C | 0.040 | 20   | 0   | 75  | 20 | 30 | 1802 | 0.0077 | 63   |           |           |      |      |       |
| EO-13 | C | 0.040 | 20   | 0   | 75  | 20 | 30 | 1803 | 0.0135 | 110  | 571,984   | 1,466,121 | 2.56 | 6.5  |       |
| EO-14 | C | 0.040 | 20   | 0   | 75  | 20 | 30 | 1802 | 0.0098 | 80   |           |           |      |      |       |
| EO-15 | C | 0.040 | 20   | 0   | 200 | 15 | 30 | 1801 | 0.0355 | 121  | 922,660   | 2,087,412 | 2.26 |      |       |
| EO-16 | C | 0.040 | 20   | 0   | 200 | 15 | 30 | 1021 | 0.0262 | 158  | 847,975   | 2,066,966 | 2.44 | 5    |       |
| EO-17 | C | 0.040 | 20   | 0   | 200 | 15 | 30 | 1802 | 0.0420 | 144  | 1,014,624 | 2,148,445 | 2.12 | 4.1  |       |
| EO-18 | D | 0.040 | 20   | 0   | 75  | 20 | 30 | 1801 | 0.0125 | 102  | 856,070   | 1,559,179 | 1.82 | 5.9  |       |
| EO-19 | D | 0.040 | 20   | 0   | 75  | 20 | 30 | 1801 | 0.0120 | 98   | 801,557   | 1,549,610 | 1.93 | 6.9  |       |
| EO-20 | D | 0.040 | 20   | 0   | 75  | 20 | 30 | 1802 | 0.0175 | 143  | 893,984   | 1,701,537 | 1.9  | 6.2  |       |
| EO-21 | D | 0.040 | 20   | 0   | 200 | 15 | 30 | 1602 | 0.0371 | 143  | 1,006,189 | 1,896,512 | 1.88 | 3.4  |       |
| EO-22 | D | 0.040 | 20   | 0   | 200 | 15 | 30 | 989  | 0.0640 | 399  | 1,191,235 | 2,260,592 | 1.9  | 4.2  |       |
| EO-23 | D | 0.040 | 20   | 0   | 200 | 15 | 30 | 931  | 0.0490 | 324  | 1,233,568 | 2,461,528 | 2    | 3.6  |       |
| EO-24 | E | 0.040 | 20   | 0   | 75  | 20 | 30 | 1801 | 0.0170 | 139  | 535,235   | 2,441,071 | 4.56 |      | 127.7 |
| EO-25 | E | 0.040 | 20   | 0   | 75  | 20 | 30 | 1802 | 0.0192 | 157  | 452,310   | 2,324,212 | 5.14 |      | 127.6 |
| EO-26 | E | 0.040 | 20   | 0   | 75  | 20 | 30 | 1801 | 0.0173 | 142  | 627,966   | 2,866,035 | 4.56 |      |       |
| EO-27 | E | 0.040 | 19.6 | 0.4 | 75  | 20 | 30 | 1801 | 0.0154 | 126  | 480,022   | 2,549,299 | 5.31 | 5.2  | 129.3 |
| EO-28 | E | 0.040 | 19.6 | 0.4 | 75  | 20 | 30 | 1802 | 0.0158 | 129  | 488,093   | 2,608,417 | 5.34 |      | 129.2 |
| EO-29 | E | 0.040 | 19.6 | 0.4 | 75  | 20 | 30 | 1802 | 0.0154 | 126  | 581,756   | 2,541,737 | 4.37 | 5.7  | 128.5 |
| EO-30 | E | 0.025 | 12.5 | 0   | 75  | 20 | 30 | 1801 | 0.0103 | 135  | 1,520,423 | 2,489,473 | 1.64 |      | 124.4 |
| EO-31 | E | 0.025 | 12.5 | 0   | 75  | 20 | 30 | 1802 | 0.0176 | 230  | 701,302   | 3,806,968 | 5.43 |      |       |
| EO-32 | E | 0.025 | 12.5 | 0   | 75  | 20 | 30 | 1801 | 0.0098 | 128  |           |           |      |      |       |
| EO-33*| E | 0.040 | 20   | 0   | 75  | 20 | 30 | 1802 | 0.0089 | 73   |           |           |      |      |       |
| EO-34*| E | 0.040 | 20   | 0   | 75  | 20 | 30 | 1802 | 0.0076 | 62   |           |           |      |      | 125.4 |
| EO-35*| E | 0.040 | 20   | 0   | 75  | 20 | 30 | 1801 | 0.0075 | 61   |           |           |      |      | 125.2 |
| EO-36 | E | 0.040 | 20   | 0   | 75  | 20 | 30 | 1800 | 0.0164 | 134  |           |           |      |      |       |
| EO-37 | E | 0.040 | 20   | 0   | 75  | 20 | 30 | 1804 | 0.0198 | 162  |           |           |      |      |       |
| EO-38 | E | 0.040 | 20   | 0   | 75  | 20 | 30 | 1802 | 0.0171 | 140  |           |           |      |      |       |
| EO-39 | E | 0.040 | 20   | 0   | 200 | 20 | 30 | 1079 | 0.0387 | 221  | 592,233   | 2,623,049 | 4.43 |      | 130.1 |
| EO-40 | E | 0.040 | 20   | 0   | 200 | 20 | 30 | 1027 | 0.0400 | 240  | 566,939   | 2,555,546 | 4.51 | 3.6  | 129.7 |
| EO-41 | E | 0.040 | 19.6 | 0.4 | 200 | 20 | 30 | 1014 | 0.0352 | 214  | 2,060,891 | 3,271,910 | 1.59 | 3.9  |       |
| EO-42 | E | 0.040 | 19.6 | 0.4 | 200 | 20 | 30 | 1010 | 0.0310 | 189  | 398,231   | 2,663,217 | 6.69 |      | 129.5 |
| EO-43 | E | 0.040 | 19.6 | 0.4 | 200 | 20 | 30 | 1008 | 0.0299 | 183  | 536,140   | 2,570,438 | 4.79 |      | 130.2 |
| EO-44 | E | 0.025 | 12.5 | 0   | 200 | 15 | 30 | 1017 | 0.0180 | 174  | 1,127,724 | 3,686,498 | 3.27 | 65.7 |       |
| EO-45 | E | 0.025 | 12.5 | 0   | 200 | 15 | 30 | 1334 | 0.0184 | 136  | 680,256   | 2,430,098 | 3.57 |      |       |
| EO-46 | E | 0.025 | 12.5 | 0   | 200 | 15 | 30 | 1252 | 0.0200 | 157  | 758,828   | 2,452,308 | 3.23 |      |       |
| EO-47*| E | 0.040 | 20   | 0   | 200 | 15 | 30 | 1220 | 0.0269 | 136  | 1,827,955 | 3,038,167 | 1.66 | 3.6  | 127.8 |
| EO-48*| E | 0.040 | 20   | 0   | 200 | 15 | 30 | 1511 | 0.0299 | 122  | 1,776,696 | 2,942,608 | 1.66 | 3.1  | 128.9 |
| EO-49*| E | 0.040 | 20   | 0   | 200 | 15 | 30 | 1802 | 0.0288 | 98   | 1,727,800 | 3,002,433 | 1.74 | 2.9  | 127.7 |

TABLE 2-continued

Ethylene 1-octene copolymerizations

| Ex. # | TMC | TMC (umol) | MAO (umol) | MAO Pre-activator (umol) | C2 (psig) | Quench Value (psi) | Max Rxn time (min) | time (s) | yield (g) | Activity | Mn | Mw | PDI | C8 (wt %) | $T_m$ (° C.) |
|---|---|---|---|---|---|---|---|---|---|---|---|---|---|---|---|
| EO-50 | E | 0.040 | 20 | 0 | 200 | 15 | 30 | 937 | 0.0277 | 182 | | | | | |
| EO-51 | E | 0.040 | 20 | 0 | 200 | 15 | 30 | 1806 | 0.0369 | 126 | | | | | |
| EO-52 | E | 0.040 | 20 | 0 | 200 | 15 | 30 | 1152 | 0.0261 | 140 | | | | | |
| EO-53 | F | 0.040 | 19.6 | 0.4 | 75 | 20 | 30 | 1802 | 0.0200 | 164 | 318,030 | 1,321,537 | 4.16 | 3.9 | 124.9 |
| EO-54 | F | 0.040 | 19.6 | 0.4 | 75 | 20 | 30 | 1801 | 0.0194 | 159 | 407,349 | 1,577,500 | 3.87 | 3.9 | 126.5 |
| EO-55 | F | 0.040 | 19.6 | 0.4 | 75 | 20 | 30 | 1801 | 0.0138 | 113 | 71,729 | 1,305,825 | 18.2 | 4.1 | 126.3 |
| EO-56 | F | 0.040 | 19.6 | 0.4 | 75 | 20 | 30 | 1802 | 0.0138 | 113 | 102,817 | 1,252,670 | 12.2 | 3.8 | 127.0 |
| EO-57 | F | 0.040 | 19.6 | 0.4 | 75 | 20 | 30 | 1802 | 0.0118 | 97 | 62,109 | 1,166,762 | 18.8 | 4.4 | 126.7 |
| EO-58 | F | 0.025 | 12.5 | 0 | 75 | 20 | 30 | 1801 | 0.0103 | 135 | 372,308 | 1,481,639 | 3.98 | | 123.0 |
| EO-59 | F | 0.025 | 12.5 | 0 | 75 | 20 | 30 | 1801 | 0.0066 | 86 | | | | | |
| EO-60 | F | 0.025 | 12.5 | 0 | 75 | 20 | 30 | 1801 | 0.0081 | 106 | | | | | |
| EO-61* | F | 0.040 | 20 | 0 | 75 | 20 | 30 | 1802 | 0.0033 | 27 | | | | | |
| EO-62* | F | 0.040 | 20 | 0 | 75 | 20 | 30 | 1802 | 0.0072 | 59 | | | | | |
| EO-63* | F | 0.040 | 20 | 0 | 75 | 20 | 30 | 1801 | 0.0035 | 29 | | | | | 129.5 |
| EO-64 | F | 0.040 | 20 | 0 | 75 | 20 | 30 | 1801 | 0.0167 | 137 | 949,033 | 1,697,495 | 1.79 | 4.2 | 125.1 |
| EO-65 | F | 0.040 | 20 | 0 | 75 | 20 | 30 | 1804 | 0.0087 | 71 | | | | | |
| EO-66 | F | 0.040 | 20 | 0 | 75 | 20 | 30 | 1801 | 0.0072 | 59 | | | | | |
| EO-67 | F | 0.040 | 19.6 | 0.4 | 200 | 20 | 30 | 929 | 0.0477 | 316 | 676,730 | 1,841,033 | 2.72 | 2.1 | 129.2 |
| EO-68 | F | 0.040 | 19.6 | 0.4 | 200 | 20 | 30 | 748 | 0.0381 | 314 | 378,305 | 1,897,207 | 5.02 | 1.8 | 129.1 |
| EO-69 | F | 0.040 | 19.6 | 0.4 | 200 | 20 | 30 | 1155 | 0.0375 | 200 | 203,075 | 1,797,501 | 8.85 | 2 | 129.6 |
| EO-70 | F | 0.040 | 19.6 | 0.4 | 200 | 20 | 30 | 1015 | 0.0295 | 179 | 168,733 | 1,691,692 | 10 | 2.2 | 130.2 |
| EO-71 | F | 0.040 | 19.6 | 0.4 | 200 | 20 | 30 | 1226 | 0.0304 | 153 | 156,284 | 1,790,888 | 11.5 | 2.5 | 129.8 |
| EO-72 | F | 0.025 | 12.5 | 0 | 200 | 15 | 30 | 1590 | 0.0187 | 116 | 748,182 | 2,158,313 | 2.88 | | 125.1 |
| EO-73 | F | 0.025 | 12.5 | 0 | 200 | 15 | 30 | 1242 | 0.0168 | 133 | 861,817 | 2,318,531 | 2.69 | 1.7 | 124.6 |
| EO-74 | F | 0.025 | 12.5 | 0 | 200 | 15 | 30 | 1802 | 0.0289 | 158 | 97,007 | 1,593,581 | 16.4 | 2.2 | 124.6 |
| EO-75* | F | 0.040 | 20 | 0 | 200 | 15 | 30 | 1801 | 0.0266 | 91 | 1,528,595 | 2,866,720 | 1.88 | 2.9 | 128.6 |
| EO-76* | F | 0.040 | 20 | 0 | 200 | 15 | 30 | 1802 | 0.0188 | 64 | 1,762,365 | 3,042,079 | 1.73 | 2.7 | 128.6 |
| EO-77* | F | 0.040 | 20 | 0 | 200 | 15 | 30 | 1801 | 0.0273 | 93 | 1,728,294 | 2,916,591 | 1.69 | | 129.6 |
| EO-78 | F | 0.040 | 20 | 0 | 200 | 15 | 30 | 1800 | 0.0321 | 110 | 1,305,078 | 1,968,625 | 1.51 | 3.2 | 128.4 |
| EO-79 | F | 0.040 | 20 | 0 | 200 | 15 | 30 | 1406 | 0.0209 | 92 | 6,592 | 6,611 | 1 | 3.2 | 128.4 |
| EO-80 | F | 0.040 | 20 | 0 | 200 | 15 | 30 | 1353 | 0.0210 | 96 | 726,204 | 1,701,752 | 2.34 | 3.7 | |
| EO-81 | G | 0.040 | 19.6 | 0.4 | 75 | 20 | 30 | 1801 | 0.0115 | 94 | 80,794 | 620,308 | 7.68 | 6.5 | 124.2 |
| EO-82 | G | 0.040 | 19.6 | 0.4 | 75 | 20 | 30 | 1801 | 0.0104 | 85 | 83,732 | 760,829 | 9.09 | 7.4 | 124.2 |
| EO-83 | G | 0.040 | 19.6 | 0.4 | 75 | 20 | 30 | 1800 | 0.0106 | 87 | 119,994 | 552,470 | 4.6 | 7 | 124.1 |
| EO-84 | G | 0.040 | 19.6 | 0.4 | 75 | 20 | 30 | 1801 | 0.0089 | 73 | | | | | |
| EO-85 | G | 0.040 | 19.6 | 0.4 | 75 | 20 | 30 | 1800 | 0.0071 | 58 | | | | | |
| EO-86 | G | 0.040 | 19.6 | 0.4 | 75 | 20 | 30 | 1801 | 0.0065 | 53 | | | | | |
| EO-87 | G | 0.040 | 20 | 0 | 75 | 20 | 30 | 1802 | 0.0068 | 56 | | | | | |
| EO-88 | G | 0.040 | 20 | 0 | 75 | 20 | 30 | 1801 | 0.0165 | 135 | 88,184 | 1,404,545 | 15.9 | 1.2 | 128.0 |
| EO-89 | G | 0.040 | 20 | 0 | 75 | 20 | 30 | 1802 | 0.0067 | 55 | | | | | |
| EO-90 | G | 0.040 | 19.6 | 0.4 | 200 | 20 | 30 | 1801 | 0.0286 | 98 | 138,951 | 1,204,270 | 8.67 | 3.3 | 127.4 |
| EO-91 | G | 0.040 | 19.6 | 0.4 | 200 | 20 | 30 | 1801 | 0.0327 | 112 | 134,064 | 1,250,687 | 9.33 | 3.4 | 127.2 |
| EO-92 | G | 0.040 | 19.6 | 0.4 | 200 | 20 | 30 | 1802 | 0.0234 | 80 | 151,358 | 1,599,063 | 10.6 | 2.8 | 127.3 |
| EO-93 | G | 0.040 | 19.6 | 0.4 | 200 | 20 | 30 | 1801 | 0.0211 | 72 | 173,702 | 1,540,322 | 8.87 | 3.2 | 128.1 |
| EO-94 | G | 0.040 | 19.6 | 0.4 | 200 | 20 | 30 | 1802 | 0.0188 | 64 | 142,449 | 1,796,251 | 12.6 | 2.8 | 127.8 |
| EO-95 | G | 0.040 | 20 | 0 | 200 | 15 | 30 | 1800 | 0.0149 | 51 | 70,988 | 1,426,737 | 20.1 | 6.1 | 128.6 |
| EO-96 | G | 0.040 | 20 | 0 | 200 | 15 | 30 | 1036 | 0 | 0 | | | | | |
| EO-97 | G | 0.040 | 20 | 0 | 200 | 15 | 30 | 1801 | 0.0177 | 61 | 65,656 | 1,294,284 | 19.7 | 50.2 | 127.1 |
| EO-98 | H | 0.020 | 9.6 | 0.4 | 75 | 20 | 20 | 1202 | 0.0075 | 184 | | | | | |
| EO-99 | H | 0.020 | 9.6 | 0.4 | 75 | 20 | 20 | 1202 | 0.0076 | 187 | | | | | |
| EO-100 | H | 0.020 | 9.6 | 0.4 | 75 | 20 | 20 | 1200 | 0.0065 | 160 | | | | | |
| EO-101 | H | 0.020 | 9.6 | 0.4 | 75 | 20 | 20 | 1201 | 0.0081 | 199 | | | | | |
| EO-102 | H | 0.020 | 9.6 | 0.4 | 75 | 20 | 20 | 1200 | 0.0078 | 192 | | | | | |
| EO-103 | H | 0.020 | 9.6 | 0.4 | 75 | 20 | 20 | 1200 | 0.0071 | 174 | | | | | |
| EO-104 | H | 0.040 | 20 | 0 | 75 | 20 | 30 | 1802 | 0.0206 | 169 | 93,117 | 794,702 | 8.53 | 14.6 | 124.2 |
| EO-105 | H | 0.040 | 20 | 0 | 75 | 20 | 30 | 1801 | 0.0182 | 149 | 142,505 | 1,592,495 | 11.2 | 15.2 | 124.3 |
| EO-106 | H | 0.040 | 20 | 0 | 75 | 20 | 30 | 1800 | 0.0188 | 154 | 172,703 | 2,246,001 | 13 | 14.8 | 122.8 |
| EO-107 | H | 0.040 | 19.6 | 0.4 | 75 | 20 | 30 | 1802 | 0.0204 | 167 | 2,278,359 | 3,460,993 | 1.52 | 16.5 | 125.2 |
| EO-108 | H | 0.040 | 19.6 | 0.4 | 75 | 20 | 30 | 1801 | 0.0190 | 156 | 68,833 | 903,698 | 13.1 | 14.5 | 126.4 |
| EO-109 | H | 0.040 | 19.6 | 0.4 | 75 | 20 | 30 | 1801 | 0.0182 | 149 | 173,692 | 2,218,534 | 12.8 | 20.9 | 124.6 |
| EO-110 | H | 0.040 | 19.6 | 0.4 | 75 | 20 | 30 | 1801 | 0.0213 | 174 | 89,552 | 703,970 | 7.86 | 11.3 | 123.2 |
| EO-111 | H | 0.040 | 19.6 | 0.4 | 75 | 20 | 30 | 1802 | 0.0228 | 187 | 48,269 | 897,777 | 18.6 | 11.8 | 124.5 |
| EO-112 | H | 0.040 | 19.6 | 0.4 | 75 | 20 | 30 | 1802 | 0.0233 | 191 | 93,041 | 1,055,502 | 11.3 | 11.7 | 122.8 |
| EO-113 | H | 0.040 | 20 | 0 | 75 | 20 | 30 | 1802 | 0.0301 | 246 | 153,347 | 1,397,764 | 9.12 | 6.5 | 111.3 |
| EO-114 | H | 0.040 | 20 | 0 | 75 | 20 | 30 | 1801 | 0.0279 | 228 | 220,187 | 1,036,905 | 4.71 | 5.7 | 126.9 |
| EO-115 | H | 0.040 | 20 | 0 | 75 | 20 | 30 | 1802 | 0.0284 | 232 | 67,538 | 1,191,756 | 17.7 | 8.9 | 153.0 |
| EO-116 | H | 0.020 | 9.6 | 0.4 | 150 | 20 | 20 | 1202 | 0.0195 | 261 | 73,486 | 1,646,825 | 22.4 | 4.4 | 125.8 |
| EO-117 | H | 0.020 | 9.6 | 0.4 | 150 | 20 | 20 | 1202 | 0.0178 | 238 | 297,232 | 1,951,542 | 6.57 | 3.3 | 126.6 |
| EO-118 | H | 0.020 | 9.6 | 0.4 | 150 | 20 | 20 | 1200 | 0.0217 | 290 | 345,747 | 1,946,478 | 5.63 | 3.5 | 125.5 |
| EO-119 | H | 0.020 | 9.6 | 0.4 | 150 | 20 | 20 | 1202 | 0.0194 | 259 | 138,889 | 1,430,068 | 10.3 | 5.9 | 125.4 |
| EO-120 | H | 0.020 | 9.6 | 0.4 | 150 | 20 | 20 | 1202 | 0.0179 | 239 | 221,153 | 1,187,542 | 5.37 | 3.8 | |
| EO-121 | H | 0.040 | 20 | 0 | 200 | 20 | 30 | 1802 | 0.0567 | 194 | 373,405 | 1,924,996 | 5.16 | 6.2 | 124.5 |
| EO-122 | H | 0.040 | 20 | 0 | 200 | 20 | 30 | 1197 | 0.0479 | 247 | 363,705 | 2,068,405 | 5.69 | | 124.3 |

TABLE 2-continued

Ethylene 1-octene copolymerizations

| Ex. # | TMC | TMC (umol) | MAO (umol) | MAO Pre-activator (umol) | C2 (psig) | Quench Value (psi) | Max Rxn time (min) | time (s) | yield (g) | Activity | Mn | Mw | PDI | C8 (wt %) | $T_m$ (°C.) |
|---|---|---|---|---|---|---|---|---|---|---|---|---|---|---|---|
| EO-123 | H | 0.040 | 20 | 0 | 200 | 20 | 30 | 1801 | 0.0564 | 193 | 1,976,011 | 2,802,387 | 1.42 | | 121.5 |
| EO-124 | H | 0.040 | 19.6 | 0.4 | 200 | 20 | 30 | 1801 | 0.0593 | 203 | 2,014,214 | 2,950,371 | 1.46 | 5.7 | 125.4 |
| EO-125 | H | 0.040 | 19.6 | 0.4 | 200 | 20 | 30 | 1801 | 0.0630 | 216 | 415,375 | 2,513,018 | 6.05 | | 125.4 |
| EO-126 | H | 0.040 | 19.6 | 0.4 | 200 | 20 | 30 | 1801 | 0.0610 | 209 | 2,252,485 | 3,387,248 | 1.5 | | 121.6 |
| EO-127 | H | 0.040 | 19.6 | 0.4 | 200 | 20 | 30 | 1460 | 0.0516 | 218 | 326,684 | 2,147,979 | 6.58 | 4.3 | 127.1 |
| EO-128 | H | 0.040 | 20 | 0 | 200 | 15 | 30 | 633 | 0.0181 | 176 | 204,482 | 1,089,484 | 5.33 | 5.7 | 125.2 |
| EO-129 | H | 0.040 | 20 | 0 | 200 | 15 | 30 | 1802 | 0.0187 | 64 | 131,611 | 1,433,459 | 10.9 | 5.3 | 126.6 |
| EO-130 | H | 0.040 | 20 | 0 | 200 | 15 | 30 | 1158 | 0.0148 | 79 | 126,719 | 857,447 | 6.77 | 10.9 | 124.7 |
| EO-131 | I | 0.020 | 9.6 | 0.4 | 75 | 20 | 20 | 1202 | 0.0261 | 640 | 605,951 | 1,146,279 | 1.89 | 2.4 | 125.8 |
| EO-132 | I | 0.020 | 9.6 | 0.4 | 75 | 20 | 20 | 1201 | 0.0183 | 450 | 531,660 | 1,277,678 | 2.4 | 1.7 | 128.2 |
| EO-133 | I | 0.020 | 9.6 | 0.4 | 75 | 20 | 20 | 1201 | 0.0190 | 467 | 377,271 | 1,101,200 | 2.92 | 1.2 | 127.7 |
| EO-134 | I | 0.020 | 9.6 | 0.4 | 75 | 20 | 20 | 1201 | 0.0183 | 449 | 586,225 | 1,546,689 | 2.64 | 2.5 | 128.4 |
| EO-135 | I | 0.020 | 9.6 | 0.4 | 75 | 20 | 20 | 1201 | 0.0198 | 486 | 696,936 | 1,427,563 | 2.05 | 1.5 | 126.3 |
| EO-136 | I | 0.020 | 9.6 | 0.4 | 75 | 20 | 20 | 1201 | 0.0154 | 378 | 596,557 | 1,504,100 | 2.52 | 1 | 127.8 |
| EO-137 | I | 0.040 | 20 | 0 | 75 | 20 | 30 | 1800 | 0.0276 | 226 | 744,777 | 1,521,230 | 2.04 | 3.3 | 128.8 |
| EO-138 | I | 0.040 | 20 | 0 | 75 | 20 | 30 | 1801 | 0.0306 | 251 | 628,249 | 1,483,206 | 2.36 | 3.6 | 128.5 |
| EO-139 | I | 0.040 | 20 | 0 | 75 | 20 | 30 | 1800 | 0.0336 | 275 | 873,622 | 1,662,731 | 1.9 | 4.6 | 128.7 |
| EO-140 | I | 0.040 | 20 | 0 | 75 | 20 | 30 | 1801 | 0.0344 | 282 | 78,912 | 997,842 | 12.6 | 6 | 128.6 |
| EO-141 | I | 0.040 | 20 | 0 | 75 | 20 | 30 | 1758 | 0.0303 | 254 | 75,992 | 898,284 | 11.8 | 5.3 | 124.2 |
| EO-142 | I | 0.040 | 19.6 | 0.4 | 75 | 20 | 30 | 1802 | 0.0408 | 334 | 736,170 | 1,585,979 | 2.15 | 2.7 | 128.6 |
| EO-143 | I | 0.040 | 19.6 | 0.4 | 75 | 20 | 30 | 1800 | 0.0388 | 318 | 737,392 | 1,647,474 | 2.23 | 3.4 | 128.2 |
| EO-144 | I | 0.040 | 19.6 | 0.4 | 75 | 20 | 30 | 1665 | 0.0366 | 324 | 882,665 | 1,736,843 | 1.97 | 3.8 | 129.3 |
| EO-145 | I | 0.040 | 19.6 | 0.4 | 75 | 20 | 30 | 1802 | 0.0447 | 366 | 958,650 | 1,847,627 | 1.93 | 5.3 | 130.0 |
| EO-146 | I | 0.040 | 19.6 | 0.4 | 75 | 20 | 30 | 1801 | 0.0428 | 351 | 871,639 | 1,545,109 | 1.77 | 5.7 | 129.1 |
| EO-147 | I | 0.040 | 20 | 0 | 75 | 20 | 30 | 1801 | 0.0142 | 116 | 193,570 | 1,027,927 | 5.31 | 6 | 127.0 |
| EO-148 | I | 0.040 | 20 | 0 | 75 | 20 | 30 | 1802 | 0.0128 | 105 | 27,809 | 781,005 | 28.1 | 5.7 | 129.5 |
| EO-149 | I | 0.040 | 19.6 | 0.4 | 75 | 20 | 30 | 1802 | 0.0159 | 130 | 64,434 | 1,581,593 | 24.6 | 2.6 | 130.8 |
| EO-150 | I | 0.040 | 19.6 | 0.4 | 75 | 20 | 30 | 1800 | 0.0145 | 119 | 77,093 | 1,292,542 | 16.8 | 3.1 | 130.7 |
| EO-151 | I | 0.040 | 20 | 0 | 75 | 20 | 30 | 1800 | 0.0411 | 337 | 234,213 | 1,318,267 | 5.63 | 2.3 | 131.7 |
| EO-152 | I | 0.040 | 20 | 0 | 75 | 20 | 30 | 1801 | 0.0190 | 156 | 106,983 | 1,011,024 | 9.45 | 2.8 | 131.1 |
| EO-153 | I | 0.040 | 20 | 0 | 75 | 20 | 30 | 1801 | 0.0248 | 203 | 118,938 | 1,425,908 | 12 | 2 | 133.2 |
| EO-154 | I | 0.020 | 9.6 | 0.4 | 150 | 20 | 20 | 1201 | 0.0487 | 651 | 792,687 | 1,307,601 | 1.65 | 1.3 | 129.5 |
| EO-155 | I | 0.020 | 9.6 | 0.4 | 150 | 20 | 20 | 1202 | 0.0256 | 342 | 753,508 | 1,432,017 | 1.9 | 1.1 | 128.4 |
| EO-156 | I | 0.020 | 9.6 | 0.4 | 150 | 20 | 20 | 1202 | 0.0322 | 431 | 818,180 | 1,401,586 | 1.71 | 1.4 | 130.0 |
| EO-157 | I | 0.020 | 9.6 | 0.4 | 150 | 20 | 20 | 1201 | 0.0566 | 757 | 810,217 | 1,305,891 | 1.61 | 1.6 | 129.0 |
| EO-158 | I | 0.020 | 9.6 | 0.4 | 150 | 20 | 20 | 1160 | 0.0390 | 540 | 909,224 | 1,471,523 | 1.62 | 1.3 | 129.4 |
| EO-159 | I | 0.020 | 9.6 | 0.4 | 150 | 20 | 20 | 1201 | 0.0463 | 619 | 837,896 | 1,397,871 | 1.67 | 1.1 | 129.2 |
| EO-160 | I | 0.040 | 20 | 0 | 200 | 20 | 30 | 1801 | 0.0545 | 186 | 1,694,234 | 2,933,486 | 1.73 | | 130.2 |
| EO-161 | I | 0.040 | 20 | 0 | 200 | 20 | 30 | 1800 | 0.0393 | 135 | 1,257,265 | 2,678,836 | 2.13 | 13 | 131.7 |
| EO-162 | I | 0.040 | 19.6 | 0.4 | 200 | 20 | 30 | 1801 | 0.0412 | 141 | 1,692,387 | 3,156,867 | 1.87 | 4.7 | 131.4 |
| EO-163 | I | 0.040 | 19.6 | 0.4 | 200 | 20 | 30 | 1802 | 0.0403 | 138 | 53,322 | 2,029,040 | 38.1 | 6.9 | 132.1 |
| EO-164 | I | 0.040 | 20 | 0 | 200 | 15 | 30 | 977 | 0.0128 | 81 | 93,580 | 960,568 | 10.3 | 3.3 | 130.8 |
| EO-165 | I | 0.040 | 20 | 0 | 200 | 15 | 30 | 722 | 0.0290 | 247 | 85,224 | 1,287,413 | 15.1 | 2.4 | 133.1 |
| EO-166 | I | 0.040 | 20 | 0 | 200 | 15 | 30 | 574 | 0.0160 | 172 | 77,234 | 1,038,264 | 13.4 | 2.5 | 130.2 |
| EO-167 | J | 0.040 | 20 | 0 | 75 | 20 | 30 | 1800 | 0.0082 | 67 | | | | | |
| EO-168 | J | 0.040 | 20 | 0 | 75 | 20 | 30 | 1802 | 0.0083 | 68 | | | | | |
| EO-169 | J | 0.040 | 20 | 0 | 75 | 20 | 30 | 1802 | 0.0077 | 63 | | | | | |
| EO-170 | J | 0.040 | 19.6 | 0.4 | 75 | 20 | 30 | 1802 | 0.0073 | 60 | | | | | |
| EO-171 | J | 0.040 | 19.6 | 0.4 | 75 | 20 | 30 | 1800 | 0.0077 | 63 | | | | | |
| EO-172 | J | 0.040 | 19.6 | 0.4 | 75 | 20 | 30 | 1801 | 0.0072 | 59 | | | | | |
| EO-173 | J | 0.040 | 20 | 0 | 75 | 20 | 30 | 1800 | 0.0108 | 88 | 43,797 | 824,296 | 18.8 | 12.7 | |
| EO-174 | J | 0.040 | 20 | 0 | 75 | 20 | 30 | 1800 | 0.0271 | 222 | | | | | |
| EO-175 | J | 0.040 | 20 | 0 | 75 | 20 | 30 | 1800 | 0.0100 | 82 | 152,434 | 1,459,889 | 9.58 | 8.3 | 138.6 |
| EO-176 | J | 0.040 | 20 | 0 | 200 | 20 | 30 | 1801 | 0.0346 | 118 | 178,191 | 2,598,291 | 14.6 | 4 | 122.0 |
| EO-177 | J | 0.040 | 20 | 0 | 200 | 20 | 30 | 1801 | 0.0351 | 120 | 528,935 | 3,235,710 | 6.12 | 6.5 | 124.2 |
| EO-178 | J | 0.040 | 19.6 | 0.4 | 200 | 20 | 30 | 1779 | 0.0369 | 128 | 1,982,977 | 3,875,114 | 1.95 | | 122.0 |
| EO-179 | J | 0.040 | 19.6 | 0.4 | 200 | 20 | 30 | 1802 | 0.0351 | 120 | | | | | |
| EO-180 | J | 0.040 | 19.6 | 0.4 | 200 | 20 | 30 | 1742 | 0.0347 | 123 | | | | | |
| EO-181 | J | 0.040 | 20 | 0 | 200 | 15 | 30 | 1335 | 0.0363 | 168 | 477,144 | 3,505,503 | 7.35 | | |
| EO-182 | J | 0.040 | 20 | 0 | 200 | 15 | 30 | 916 | 0.0301 | 203 | 297,051 | 1,953,862 | 6.58 | 9.2 | 124.7 |
| EO-183 | J | 0.040 | 20 | 0 | 200 | 15 | 30 | 1132 | 0.0311 | 169 | | | | | |
| EO-184 | K | 0.040 | 20 | 0 | 75 | 20 | 30 | 1801 | 0.0232 | 190 | 140,713 | 576,987 | 4.1 | 23.7 | |
| EO-185 | K | 0.040 | 20 | 0 | 75 | 20 | 30 | 1800 | 0.0241 | 197 | 106,345 | 903,166 | 8.49 | 6.1 | 119.4 |
| EO-186 | K | 0.040 | 20 | 0 | 75 | 20 | 30 | 1801 | 0.0236 | 193 | | | | 5 | |
| EO-187 | K | 0.040 | 19.6 | 0.4 | 75 | 20 | 30 | 1802 | 0.0181 | 148 | 95,098 | 1,673,700 | 17.6 | 5.8 | |
| EO-188 | K | 0.040 | 19.6 | 0.4 | 75 | 20 | 30 | 1802 | 0.0181 | 148 | 80,541 | 828,993 | 10.3 | | |
| EO-189 | K | 0.040 | 19.6 | 0.4 | 75 | 20 | 30 | 1802 | 0.0174 | 142 | 128,162 | 889,198 | 6.94 | 14.6 | 121.7 |
| EO-190 | K | 0.040 | 20 | 0 | 75 | 20 | 30 | 1802 | 0.0236 | 193 | | | | | |
| EO-191 | K | 0.040 | 20 | 0 | 75 | 20 | 30 | 1800 | 0.0106 | 87 | 274,209 | 1,447,396 | 5.28 | 9.6 | 123.5 |
| EO-192 | K | 0.040 | 20 | 0 | 75 | 20 | 30 | 1802 | 0.0199 | 163 | 697,353 | 2,215,222 | 3.18 | 6.7 | 125.2 |
| EO-193 | K | 0.040 | 20 | 0 | 200 | 20 | 30 | 1457 | 0.0747 | 316 | 120,188 | 757,789 | 6.31 | | 121.3 |
| EO-194 | K | 0.040 | 20 | 0 | 200 | 20 | 30 | 659 | 0.0685 | 641 | 221,796 | 2,101,112 | 9.47 | | |
| EO-195 | K | 0.040 | 19.6 | 0.4 | 200 | 20 | 30 | 1275 | 0.0686 | 332 | 33,014 | 2,412,768 | 73.1 | | |

TABLE 2-continued

Ethylene 1-octene copolymerizations

| Ex. # | TMC | TMC (umol) | MAO (umol) | MAO Pre-activator (umol) | C2 (psig) | Quench Value (psi) | Max Rxn time (min) | time (s) | yield (g) | Activity | Mn | Mw | PDI | C8 (wt %) | $T_m$ (°C.) |
|---|---|---|---|---|---|---|---|---|---|---|---|---|---|---|---|
| EO-196 | K | 0.040 | 19.6 | 0.4 | 200 | 20 | 30 | 871 | 0.0571 | 404 | 295,163 | 2,282,057 | 7.73 | | 120.4 |
| EO-197 | K | 0.040 | 19.6 | 0.4 | 200 | 20 | 30 | 1227 | 0.0739 | 371 | 85,131 | 921,370 | 10.8 | | 120.0 |
| EO-198 | K | 0.040 | 20 | 0 | 200 | 15 | 30 | 1020 | 0.0262 | 158 | | | | | |
| EO-199 | K | 0.040 | 20 | 0 | 200 | 15 | 30 | 801 | 0.0931 | 717 | 184,938 | 1,476,677 | 7.98 | 8.2 | 122.2 |
| EO-200 | L | 0.020 | 9.6 | 0.4 | 75 | 20 | 20 | 1201 | 0.0096 | 236 | 135,170 | 970,972 | 7.18 | 7.9 | |
| EO-201 | L | 0.020 | 9.6 | 0.4 | 75 | 20 | 20 | 1201 | 0.0102 | 251 | 99,815 | 900,020 | 9.02 | 12.5 | |
| EO-202 | L | 0.020 | 9.6 | 0.4 | 75 | 20 | 20 | 1200 | 0.0111 | 273 | 105,358 | 524,776 | 4.98 | 10.3 | |
| EO-203 | L | 0.020 | 9.6 | 0.4 | 75 | 20 | 20 | 1202 | 0.0100 | 245 | 90,270 | 315,981 | 3.5 | 11.7 | |
| EO-204 | L | 0.020 | 9.6 | 0.4 | 75 | 20 | 20 | 1202 | 0.0103 | 253 | 126,922 | 635,976 | 5.01 | 13.4 | |
| EO-205 | L | 0.020 | 9.6 | 0.4 | 75 | 20 | 20 | 1202 | 0.0098 | 241 | 51,743 | 238,326 | 4.61 | 15.3 | |
| EO-206 | L | 0.040 | 20 | 0 | 75 | 20 | 30 | 1802 | 0.0210 | 172 | 123,179 | 555,803 | 4.51 | 11.4 | 119.1 |
| EO-207 | L | 0.040 | 20 | 0 | 75 | 20 | 30 | 1802 | 0.0244 | 200 | 115,203 | 555,868 | 4.83 | 13.8 | 117.6 |
| EO-208 | L | 0.040 | 20 | 0 | 75 | 20 | 30 | 1801 | 0.0223 | 183 | 124,457 | 194,650 | 1.56 | 15.1 | |
| EO-209 | L | 0.040 | 20 | 0 | 75 | 20 | 30 | 1801 | 0.0334 | 273 | 33,302 | 373,421 | 11.2 | 12.5 | 120.4 |
| EO-210 | L | 0.040 | 20 | 0 | 75 | 20 | 30 | 1801 | 0.0260 | 213 | 31,840 | 285,501 | 8.97 | 14.2 | 121.4 |
| EO-211 | L | 0.040 | 19.6 | 0.4 | 75 | 20 | 30 | 1801 | 0.0184 | 151 | 81,178 | 560,011 | 6.9 | 14.8 | 121.7 |
| EO-212 | L | 0.040 | 19.6 | 0.4 | 75 | 20 | 30 | 1801 | 0.0196 | 161 | 135,260 | 912,731 | 6.75 | 13.7 | 120.8 |
| EO-213 | L | 0.040 | 19.6 | 0.4 | 75 | 20 | 30 | 1801 | 0.0172 | 141 | 88,057 | 568,856 | 6.46 | 15.4 | 118.7 |
| EO-214 | L | 0.040 | 19.6 | 0.4 | 75 | 20 | 30 | 1801 | 0.0282 | 231 | 33,948 | 441,265 | 13 | 10.5 | 122.4 |
| EO-215 | L | 0.040 | 19.6 | 0.4 | 75 | 20 | 30 | 1801 | 0.0255 | 209 | 31,334 | 512,992 | 16.4 | 10.2 | 122.7 |
| EO-216 | L | 0.040 | 20 | 0 | 75 | 20 | 30 | 1801 | 0.0273 | 224 | 84,009 | 502,599 | 5.98 | 18.4 | |
| EO-217 | L | 0.040 | 20 | 0 | 75 | 20 | 30 | 1347 | 0.0306 | 335 | 103,174 | 762,255 | 7.39 | 15 | |
| EO-218 | L | 0.040 | 20 | 0 | 75 | 20 | 30 | 1801 | 0.0287 | 235 | 91,125 | 452,266 | 4.96 | 20.2 | |
| EO-219 | L | 0.040 | 19.6 | 0.4 | 75 | 20 | 30 | 1802 | 0.0217 | 178 | 75,023 | 802,352 | 10.7 | 23.7 | |
| EO-220 | L | 0.040 | 19.6 | 0.4 | 75 | 20 | 30 | 1800 | 0.0219 | 179 | 92,559 | 536,153 | 5.79 | 21.2 | |
| EO-221 | L | 0.040 | 19.6 | 0.4 | 75 | 20 | 30 | 1800 | 0.0215 | 176 | 86,009 | 920,571 | 10.7 | 17.3 | |
| EO-222 | L | 0.040 | 19.6 | 0.4 | 75 | 20 | 30 | 1802 | 0.0147 | 120 | 74,599 | 1,199,180 | 16.1 | 9.8 | 124.3 |
| EO-223 | L | 0.040 | 19.6 | 0.4 | 75 | 20 | 30 | 1802 | 0.0157 | 129 | 41,444 | 309,240 | 7.46 | 11 | |
| EO-224 | L | 0.040 | 19.6 | 0.4 | 75 | 20 | 30 | 1802 | 0.0150 | 123 | 65,553 | 581,161 | 8.87 | 13.2 | |
| EO-225 | L | 0.040 | 20 | 0 | 75 | 20 | 30 | 1802 | 0.0187 | 153 | | | | | |
| EO-226 | L | 0.040 | 20 | 0 | 75 | 20 | 30 | 1802 | 0.0413 | 338 | | | | | |
| EO-227 | L | 0.040 | 20 | 0 | 75 | 20 | 30 | 1801 | 0.0170 | 139 | | | | 13.8 | 123.8 |
| EO-228 | L | 0.020 | 9.6 | 0.4 | 150 | 20 | 20 | 1201 | 0.0293 | 392 | 2,834,808 | 4,199,273 | 1.48 | 14 | 122.3 |
| EO-229 | L | 0.020 | 9.6 | 0.4 | 150 | 20 | 20 | 1201 | 0.0309 | 413 | 121,419 | 260,093 | 2.14 | 3.3 | |
| EO-230 | L | 0.020 | 9.6 | 0.4 | 150 | 20 | 20 | 1201 | 0.0377 | 504 | 341,980 | 2,744,206 | 8.02 | 6.4 | |
| EO-231 | L | 0.020 | 9.6 | 0.4 | 150 | 20 | 20 | 1202 | 0.0286 | 382 | 144,282 | 680,916 | 4.72 | 6.8 | |
| EO-232 | L | 0.020 | 9.6 | 0.4 | 150 | 20 | 20 | 1201 | 0.0265 | 354 | 217,868 | 2,526,523 | 11.6 | 7.3 | 118.4 |
| EO-233 | L | 0.040 | 20 | 0 | 200 | 20 | 30 | 509 | 0.0723 | 875 | | | | 3 | |
| EO-234 | L | 0.040 | 20 | 0 | 200 | 20 | 30 | 641 | 0.1087 | 1044 | | | | | |
| EO-235 | L | 0.040 | 20 | 0 | 200 | 20 | 30 | 608 | 0.0829 | 840 | 61,307 | 981,814 | 16 | | |
| EO-236 | L | 0.040 | 19.6 | 0.4 | 200 | 20 | 30 | 766 | 0.0617 | 496 | 871,996 | 2,381,368 | 2.73 | | |
| EO-237 | L | 0.040 | 19.6 | 0.4 | 200 | 20 | 30 | 659 | 0.0684 | 640 | 383,144 | 2,998,530 | 7.83 | 1.5 | |
| EO-238 | L | 0.040 | 19.6 | 0.4 | 200 | 20 | 30 | 876 | 0.0754 | 530 | 51,724 | 3,973,721 | 76.8 | | |
| EO-239 | L | 0.040 | 19.6 | 0.4 | 200 | 20 | 30 | 1343 | 0.0629 | 289 | 2,968,917 | 4,120,835 | 1.39 | 4.3 | 121.9 |
| EO-240 | L | 0.040 | 19.6 | 0.4 | 200 | 20 | 30 | 1254 | 0.0580 | 285 | 1,839,612 | 2,888,571 | 1.57 | 3.4 | 122.7 |
| EO-241 | L | 0.040 | 19.6 | 0.4 | 200 | 20 | 30 | 1201 | 0.0619 | 318 | 2,795,238 | 3,841,870 | 1.37 | 5 | 137.1 |
| EO-242 | L | 0.040 | 20 | 0 | 200 | 15 | 30 | 1255 | 0.0258 | 127 | 2,194,957 | 3,768,523 | 1.72 | 1.2 | 136.1 |
| EO-243 | L | 0.040 | 20 | 0 | 200 | 15 | 30 | 872 | −0.0162 | 0 | | | | | |
| EO-244 | L | 0.040 | 20 | 0 | 200 | 15 | 30 | 985 | 0.0543 | 340 | | | | | |
| EO-245 | M | 0.040 | 20 | 0 | 75 | 20 | 30 | 1801 | 0.0071 | 58 | | | | | |
| EO-246 | M | 0.040 | 20 | 0 | 75 | 20 | 30 | 1801 | 0.0068 | 56 | | | | | |
| EO-247 | M | 0.040 | 20 | 0 | 75 | 20 | 30 | 1801 | 0.0081 | 66 | | | | | |
| EO-248 | M | 0.040 | 19.6 | 0.4 | 75 | 20 | 30 | 1801 | 0.0101 | 83 | 336,888 | 730,840 | 2.17 | 3.5 | 128.8 |
| EO-249 | M | 0.040 | 19.6 | 0.4 | 75 | 20 | 30 | 1801 | 0.0088 | 72 | | | | | |
| EO-250 | M | 0.040 | 19.6 | 0.4 | 75 | 20 | 30 | 1801 | 0.0085 | 70 | | | | | |
| EO-251 | M | 0.040 | 20 | 0 | 200 | 20 | 30 | 1519 | 0.0247 | 100 | 376,758 | 1,358,193 | 3.6 | 2 | 130.9 |
| EO-252 | M | 0.040 | 20 | 0 | 200 | 20 | 30 | 1800 | 0.0281 | 96 | 335,993 | 1,316,589 | 3.92 | 1.8 | 131.8 |
| EO-253 | M | 0.040 | 20 | 0 | 200 | 20 | 30 | 1802 | 0.0272 | 93 | 377,856 | 1,073,202 | 2.84 | 2 | 131.5 |
| EO-254 | M | 0.040 | 19.6 | 0.4 | 200 | 20 | 30 | 1802 | 0.0296 | 101 | 356,732 | 1,026,139 | 2.88 | 2.9 | |
| EO-255 | M | 0.040 | 19.6 | 0.4 | 200 | 20 | 30 | 1802 | 0.0298 | 102 | 388,482 | 1,117,727 | 2.88 | 2 | 131.0 |
| EO-256 | M | 0.040 | 19.6 | 0.4 | 200 | 20 | 30 | 1802 | 0.0285 | 97 | 402,914 | 975,026 | 2.42 | 2.3 | 130.4 |
| EO-257 | N | 0.040 | 20 | 0 | 75 | 20 | 30 | 1617 | 0.0476 | 434 | 1,598,349 | 2,347,902 | 1.47 | 9.5 | 110.5 |
| EO-258 | N | 0.040 | 20 | 0 | 75 | 20 | 30 | 1802 | 0.0455 | 372 | 1,383,816 | 2,309,560 | 1.67 | 7.6 | |
| EO-259 | N | 0.040 | 19.6 | 0.4 | 75 | 20 | 30 | 1691 | 0.0473 | 413 | 1,365,257 | 2,477,334 | 1.81 | 8.6 | 111.7 |
| EO-260 | N | 0.040 | 19.6 | 0.4 | 75 | 20 | 30 | 1304 | 0.0480 | 543 | 1,670,744 | 2,610,514 | 1.56 | 9.1 | 111.5 |
| EO-261 | N | 0.040 | 20 | 0 | 75 | 20 | 30 | 1806 | 0.0539 | 440 | 1,989,256 | 3,446,898 | 1.73 | | 122.7 |
| EO-262 | N | 0.040 | 20 | 0 | 75 | 20 | 30 | 1557 | 0.0443 | 420 | 1,609,871 | 2,833,612 | 1.76 | 9 | 117.5 |
| EO-263 | N | 0.040 | 20 | 0 | 75 | 20 | 30 | 1802 | 0.0725 | 593 | | | | | |
| EO-264 | N | 0.040 | 20 | 0 | 200 | 20 | 30 | 303 | 0.0679 | 1379 | 1,803,121 | 2,965,422 | 1.64 | 8.7 | 121.4 |
| EO-265 | N | 0.040 | 20 | 0 | 200 | 20 | 30 | 201 | 0.0572 | 1754 | 2,212,301 | 3,134,426 | 1.42 | 0.4 | 120.8 |
| EO-266 | N | 0.040 | 19.6 | 0.4 | 200 | 20 | 30 | 396 | 0.0752 | 1170 | 2,331,493 | 3,286,119 | 1.41 | | 120.4 |
| EO-267 | N | 0.040 | 19.6 | 0.4 | 200 | 20 | 30 | 162 | 0.0553 | 2098 | 2,197,126 | 3,115,378 | 1.42 | 4.9 | 120.6 |
| EO-268 | N | 0.040 | 20 | 0 | 200 | 15 | 30 | 224 | 0.0188 | 518 | 1,800,429 | 3,370,417 | 1.87 | 11.2 | 115.6 |

TABLE 2-continued

Ethylene 1-octene copolymerizations

| Ex. # | TMC | TMC (umol) | MAO (umol) | MAO Pre-activator (umol) | C2 (psig) | Quench Value (psi) | Max Rxn time (min) | time (s) | yield (g) | Activity | Mn | Mw | PDI | C8 (wt %) | $T_m$ (° C.) |
|---|---|---|---|---|---|---|---|---|---|---|---|---|---|---|---|
| EO-269 | N | 0.040 | 20 | 0 | 200 | 15 | 30 | 687 | 0.0672 | 603 | 2,998,836 | 4,752,547 | 1.58 | | 122.1 |
| EO-270 | N | 0.040 | 20 | 0 | 200 | 15 | 30 | 359 | 0.0405 | 695 | 1,736,588 | 3,279,765 | 1.89 | 9.2 | 116.8 |
| EO-271 | O | 0.040 | 19.6 | 0.4 | 75 | 20 | 30 | 1324 | 0.0329 | 367 | 173,950 | 1,178,126 | 6.77 | 7 | 124.5 |
| EO-272 | O | 0.040 | 19.6 | 0.4 | 75 | 20 | 30 | 1801 | 0.0288 | 236 | 183,419 | 986,770 | 5.38 | 8 | 122.7 |
| EO-273 | O | 0.040 | 19.6 | 0.4 | 75 | 20 | 30 | 1802 | 0.0240 | 196 | 92,319 | 994,159 | 10.8 | 8.3 | 122.1 |
| EO-274 | O | 0.040 | 19.6 | 0.4 | 75 | 20 | 30 | 1801 | 0.0168 | 138 | 85,446 | 705,443 | 8.26 | 10.4 | 120.1 |
| EO-275 | O | 0.040 | 19.6 | 0.4 | 75 | 20 | 30 | 1801 | 0.0168 | 138 | 74,595 | 344,950 | 4.62 | 11.9 | 119.5 |
| EO-276 | O | 0.040 | 19.6 | 0.4 | 75 | 20 | 30 | 1800 | 0.0144 | 118 | 40,234 | 755,332 | 18.8 | 10.1 | 122.0 |
| EO-277 | O | 0.040 | 20 | 0 | 75 | 20 | 30 | 1802 | 0.0164 | 134 | 184,556 | 365,375 | 1.98 | 10.5 | 121.0 |
| EO-278 | O | 0.040 | 20 | 0 | 75 | 20 | 30 | 1801 | 0.0172 | 141 | 115,878 | 214,101 | 1.85 | 15.7 | 94.8 |
| EO-279 | O | 0.040 | 20 | 0 | 75 | 20 | 30 | 1801 | 0.0218 | 179 | 188,179 | 398,647 | 2.12 | 10 | 121.4 |
| EO-280 | O | 0.040 | 19.6 | 0.4 | 200 | 20 | 30 | 551 | 0.0658 | 736 | 230,698 | 1,375,784 | 5.96 | 3.6 | 126.0 |
| EO-281 | O | 0.040 | 19.6 | 0.4 | 200 | 20 | 30 | 587 | 0.0594 | 623 | 175,136 | 1,287,535 | 7.35 | 4.4 | 124.2 |
| EO-282 | O | 0.040 | 19.6 | 0.4 | 200 | 20 | 30 | 642 | 0.0430 | 413 | 204,047 | 1,356,900 | 6.65 | 3.7 | 123.8 |
| EO-283 | O | 0.040 | 19.6 | 0.4 | 200 | 20 | 30 | 662 | 0.0425 | 395 | 185,092 | 1,172,313 | 6.33 | 5.1 | 126.3 |
| EO-284 | O | 0.040 | 19.6 | 0.4 | 200 | 20 | 30 | 690 | 0.0391 | 349 | 200,653 | 1,108,434 | 5.52 | 5.1 | 123.3 |
| EO-285 | O | 0.040 | 20 | 0 | 200 | 15 | 30 | 280 | 0.0305 | 671 | 237,971 | 423,889 | 1.78 | 9.3 | 114.9 |
| EO-286 | O | 0.040 | 20 | 0 | 200 | 15 | 30 | 365 | 0.0329 | 556 | 238,966 | 422,658 | 1.77 | 8.1 | 118.1 |
| EO-287 | O | 0.040 | 20 | 0 | 200 | 15 | 30 | 475 | 0.0340 | 442 | 216,469 | 439,451 | 2.03 | 9.6 | 117.7 |
| EO-288 | P | 0.040 | 20 | 0 | 75 | 20 | 30 | 600 | 0.0523 | 1285 | 1,502,988 | 2,181,528 | 1.45 | 5 | 118.5 |
| EO-289 | P | 0.040 | 20 | 0 | 75 | 20 | 30 | 608 | 0.0501 | 1216 | 1,281,701 | 1,879,372 | 1.47 | 5.4 | 118.4 |
| EO-290 | P | 0.040 | 20 | 0 | 75 | 20 | 30 | 596 | 0.0398 | 985 | 1,293,829 | 1,880,060 | 1.45 | 10.1 | 118.4 |
| EO-291 | P | 0.040 | 20 | 0 | 200 | 15 | 30 | 108 | 0.0666 | 3803 | 2,304,944 | 3,311,753 | 1.44 | 5.6 | 124.6 |
| EO-292 | P | 0.040 | 20 | 0 | 200 | 15 | 30 | 98 | 0.0629 | 3967 | 2,152,091 | 3,163,073 | 1.47 | 8.1 | 124.7 |
| EO-293 | P | 0.040 | 20 | 0 | 200 | 15 | 30 | 130 | 0.0734 | 3471 | 2,045,372 | 2,997,914 | 1.47 | 4.3 | 124.1 |
| EO-294* | Q | 0.040 | 20 | 0 | 75 | 20 | 30 | 1807 | 0.0095 | 78 | | | | | 130.3 |
| EO-295* | Q | 0.040 | 20 | 0 | 75 | 20 | 30 | 1806 | 0.0179 | 146 | 413,205 | 729,602 | 1.77 | 2.7 | 124.2 |
| EO-296* | Q | 0.040 | 20 | 0 | 75 | 20 | 30 | 1804 | 0.0229 | 187 | 386,522 | 678,271 | 1.75 | 3.3 | 123.6 |
| EO-297 | Q | 0.040 | 20 | 0 | 75 | 20 | 30 | 1801 | 0.0155 | 127 | 105,934 | 941,904 | 8.89 | 3.3 | 130.3 |
| EO-298 | Q | 0.040 | 20 | 0 | 75 | 20 | 30 | 1802 | 0.0112 | 92 | 77,717 | 653,750 | 8.41 | 3.9 | 130.5 |
| EO-299 | Q | 0.040 | 20 | 0 | 75 | 20 | 30 | 1800 | 0.0151 | 124 | 88,779 | 894,952 | 10.1 | 3.6 | 131.4 |
| EO-300 | Q | 0.040 | 20 | 0 | 75 | 20 | 30 | 1802 | 0.0064 | 52 | | | | | |
| EO-301 | Q | 0.040 | 20 | 0 | 75 | 20 | 30 | 1802 | 0.0247 | 202 | 531,529 | 1,146,803 | 2.16 | 8.2 | 129.1 |
| EO-302 | Q | 0.040 | 20 | 0 | 75 | 20 | 30 | 1800 | 0.0191 | 157 | 395,599 | 1,096,667 | 2.77 | 3.6 | 129.3 |
| EO-303 | Q | 0.040 | 20 | 0 | 75 | 20 | 30 | 1801 | 0.0191 | 156 | 380,762 | 1,246,279 | 3.27 | 3.2 | 128.5 |
| EO-304 | Q | 0.040 | 20 | 0 | 75 | 20 | 30 | 1801 | 0.0268 | 219 | 547,354 | 1,155,278 | 2.11 | 2.9 | 146.4 |
| EO-305 | Q | 0.040 | 20 | 0 | 75 | 20 | 30 | 1802 | 0.0211 | 173 | 567,731 | 1,391,534 | 2.45 | 2.8 | |
| EO-306* | Q | 0.040 | 20 | 0 | 200 | 15 | 30 | 244 | 0.0491 | 1243 | 830,140 | 1,317,709 | 1.59 | 2.1 | 128.8 |
| EO-307* | Q | 0.040 | 20 | 0 | 200 | 15 | 30 | 602 | 0.0425 | 435 | 944,370 | 1,629,373 | 1.73 | 2.2 | 128.7 |
| EO-308* | Q | 0.040 | 20 | 0 | 200 | 15 | 30 | 775 | 0.0306 | 243 | 982,364 | 1,779,324 | 1.81 | 1.9 | 129.4 |
| EO-309 | Q | 0.040 | 20 | 0 | 200 | 15 | 30 | 561 | 0.0262 | 288 | 279,144 | 1,634,951 | 5.86 | 2.2 | 132.5 |
| EO-310 | Q | 0.040 | 20 | 0 | 200 | 15 | 30 | 813 | 0.0279 | 212 | 178,580 | 1,534,658 | 8.59 | 2.5 | 132.6 |
| EO-311 | Q | 0.040 | 20 | 0 | 200 | 15 | 30 | 687 | 0.0266 | 239 | 212,824 | 1,379,361 | 6.48 | 2.7 | 131.9 |
| EO-312 | Q | 0.040 | 20 | 0 | 200 | 15 | 30 | 393 | 0.0321 | 504 | 1,278,980 | 1,973,794 | 1.54 | 2.5 | 137.5 |
| EO-313 | Q | 0.040 | 20 | 0 | 200 | 15 | 30 | 664 | 0.0343 | 318 | 493,679 | 1,451,014 | 2.94 | 8.2 | 134.3 |
| EO-314 | Q | 0.040 | 20 | 0 | 200 | 15 | 30 | 546 | 0.0315 | 355 | 485,135 | 1,571,174 | 3.24 | 2.9 | 132.0 |
| EO-315 | Q | 0.040 | 20 | 0 | 200 | 15 | 30 | 350 | 0.0352 | 620 | 728,957 | 1,411,022 | 1.94 | 2.1 | 130.3 |
| EO-316 | Q | 0.040 | 20 | 0 | 200 | 15 | 30 | 426 | 0.0287 | 415 | 463,776 | 1,074,650 | 2.32 | 4.2 | 132.1 |
| EO-317 | Q | 0.040 | 20 | 0 | 200 | 15 | 30 | 486 | 0.0320 | 406 | 641,144 | 1,561,526 | 2.44 | 3.4 | 130.4 |
| EO-318 | R | 0.040 | 20 | 0 | 75 | 20 | 30 | 1801 | 0.0199 | 163 | 858,171 | 1,588,230 | 1.85 | 5 | |
| EO-319 | R | 0.040 | 20 | 0 | 75 | 20 | 30 | 1801 | 0.0193 | 158 | 959,243 | 1,605,969 | 1.67 | 6 | |
| EO-320 | R | 0.040 | 20 | 0 | 75 | 20 | 30 | 1800 | 0.0199 | 163 | 893,548 | 1,630,343 | 1.82 | 4.5 | |
| EO-321 | R | 0.040 | 20 | 0 | 200 | 15 | 30 | 1570 | 0.0322 | 126 | 994,905 | 1,965,919 | 1.98 | 3.5 | |
| EO-322 | R | 0.040 | 20 | 0 | 200 | 15 | 30 | 1801 | 0.0534 | 183 | 173,174 | 1,637,935 | 9.46 | 3.7 | |
| EO-323 | R | 0.040 | 20 | 0 | 200 | 15 | 30 | 1617 | 0.0267 | 102 | 1,002,943 | 1,834,911 | 1.83 | 3.3 | |
| EO-324 | S | 0.040 | 20 | 0 | 75 | 20 | 30 | 135 | 0.0452 | 4957 | 195,581 | 263,655 | 1.35 | 7.5 | |
| EO-325 | S | 0.040 | 20 | 0 | 75 | 20 | 30 | 132 | 0.0483 | 5393 | 194,476 | 262,828 | 1.35 | 6.9 | 82.4 |
| EO-326 | S | 0.040 | 20 | 0 | 75 | 20 | 30 | 122 | 0.0467 | 5655 | 214,309 | 271,187 | 1.27 | 7.7 | 77.1 |
| EO-327 | S | 0.040 | 20 | 0 | 200 | 15 | 30 | 161 | 0.1358 | 5211 | 336,864 | 434,169 | 1.29 | 4.8 | |
| EO-328 | S | 0.040 | 20 | 0 | 200 | 15 | 30 | 164 | 0.1362 | 5127 | 303,312 | 460,822 | 1.52 | 5 | |
| EO-329 | S | 0.040 | 20 | 0 | 200 | 15 | 30 | 143 | 0.1304 | 5627 | 289,748 | 476,943 | 1.65 | 4.8 | |
| EO-330 | T | 0.040 | 20 | 0 | 75 | 20 | 30 | 438 | 0.0373 | 1256 | 349,293 | 521,405 | 1.49 | 6.4 | |
| EO-331 | T | 0.040 | 20 | 0 | 75 | 20 | 30 | 521 | 0.0394 | 1115 | 375,396 | 525,552 | 1.4 | 6.1 | 116.1 |
| EO-332 | T | 0.040 | 20 | 0 | 75 | 20 | 30 | 447 | 0.0389 | 1284 | 389,644 | 528,166 | 1.36 | 6.3 | 82.9 |
| EO-333 | T | 0.040 | 20 | 0 | 200 | 15 | 30 | 217 | 0.0986 | 2801 | 532,747 | 775,490 | 1.46 | 3.7 | 85.8 |
| EO-334 | T | 0.040 | 20 | 0 | 200 | 15 | 30 | 205 | 0.0852 | 2556 | 546,984 | 795,923 | 1.46 | 3.9 | 86.2 |
| EO-335 | T | 0.040 | 20 | 0 | 200 | 15 | 30 | 165 | 0.0876 | 3268 | 594,100 | 874,615 | 1.47 | 4.1 | |
| EO-336 | U | 0.040 | 20 | 0 | 75 | 20 | 30 | 1802 | 0.0042 | 34 | | | | | |
| EO-337 | U | 0.040 | 20 | 0 | 75 | 20 | 30 | 1801 | 0.0061 | 50 | | | | | |
| EO-338 | U | 0.040 | 20 | 0 | 75 | 20 | 30 | 1802 | 0.0042 | 34 | | | | | |
| EO-339 | U | 0.040 | 20 | 0 | 200 | 15 | 30 | 1800 | 0.0130 | 44 | 828,494 | 1,809,958 | 2.18 | 7.3 | 126.7 |
| EO-340 | U | 0.040 | 20 | 0 | 200 | 15 | 30 | 1801 | 0.0123 | 42 | 629,579 | 1,654,744 | 2.63 | 4.5 | 114.1 |
| EO-341 | U | 0.040 | 20 | 0 | 200 | 15 | 30 | 1801 | 0.0114 | 39 | 658,964 | 1,713,334 | 2.6 | 4.4 | 118.8 |

TABLE 2-continued

Ethylene 1-octene copolymerizations

| Ex. # | TMC | TMC (umol) | MAO (umol) | MAO Pre-activator (umol) | C2 (psig) | Quench Value (psi) | Max Rxn time (min) | time (s) | yield (g) | Activity | Mn | Mw | PDI | C8 (wt %) | $T_m$ (°C.) |
|---|---|---|---|---|---|---|---|---|---|---|---|---|---|---|---|
| EO-342* | V | 0.040 | 20 | 0 | 75 | 20 | 30 | 650 | 0.0416 | 944 | 279,840 | 393,559 | 1.41 | 8.4 | 109.8 |
| EO-343* | V | 0.040 | 20 | 0 | 75 | 20 | 30 | 593 | 0.0286 | 711 | 304,598 | 445,931 | 1.46 | 7.9 | 106.4 |
| EO-344* | V | 0.040 | 20 | 0 | 75 | 20 | 30 | 525 | 0.0422 | 1187 | 336,921 | 480,039 | 1.42 | 7.6 | 109.2 |
| EO-345 | V | 0.040 | 20 | 0 | 75 | 20 | 30 | 284 | 0.0572 | 2966 | 807,369 | 1,161,490 | 1.44 | 7.3 | 114.0 |
| EO-346 | V | 0.040 | 20 | 0 | 75 | 20 | 30 | 241 | 0.0556 | 3408 | 743,289 | 1,068,272 | 1.44 | 6.6 | 114.4 |
| EO-347 | V | 0.040 | 20 | 0 | 75 | 20 | 30 | 259 | 0.0569 | 3239 | 807,744 | 1,158,919 | 1.43 | 6.8 | 113.8 |
| EO-348 | V | 0.040 | 20 | 0 | 75 | 20 | 30 | 266 | 0.0506 | 2810 | 798,704 | 1,177,717 | 1.47 | 7 | 113.1 |
| EO-349 | V | 0.040 | 20 | 0 | 75 | 20 | 30 | 572 | 0.0672 | 1734 | 893,428 | 1,278,662 | 1.43 | 6.7 | 114.0 |
| EO-350 | V | 0.040 | 20 | 0 | 75 | 20 | 30 | 340 | 0.0555 | 2410 | 947,366 | 1,376,087 | 1.45 | 8.6 | 112.6 |
| EO-351 | V | 0.040 | 20 | 0 | 75 | 20 | 30 | 316 | 0.0658 | 3068 | 746,216 | 1,151,821 | 1.54 | 7.6 | 112.3 |
| EO-352 | V | 0.040 | 20 | 0 | 75 | 20 | 30 | 225 | 0.0488 | 3202 | 779,645 | 1,128,944 | 1.45 | 7.3 | 112.5 |
| EO-353 | V | 0.040 | 20 | 0 | 75 | 20 | 30 | 287 | 0.0595 | 3058 | | | | | |
| EO-354* | V | 0.040 | 20 | 0 | 200 | 15 | 30 | 214 | 0.1128 | 3254 | 561,651 | 836,723 | 1.49 | 5.6 | 118.3 |
| EO-355* | V | 0.040 | 20 | 0 | 200 | 15 | 30 | 241 | 0.1240 | 3176 | 508,399 | 760,860 | 1.5 | 5.2 | 117.0 |
| EO-356* | V | 0.040 | 20 | 0 | 200 | 15 | 30 | 164 | 0.0983 | 3705 | 565,276 | 829,956 | 1.47 | 4.5 | 118.4 |
| EO-357 | V | 0.040 | 20 | 0 | 200 | 15 | 30 | 116 | 0.1208 | 6412 | 1,053,126 | 1,654,382 | 1.57 | 6.3 | 120.2 |
| EO-358 | V | 0.040 | 20 | 0 | 200 | 15 | 30 | 108 | 0.1135 | 6482 | 1,089,887 | 1,724,925 | 1.58 | 4.1 | 121.3 |
| EO-359 | V | 0.040 | 20 | 0 | 200 | 15 | 30 | 117 | 0.1129 | 5956 | 1,009,148 | 1,611,012 | 1.6 | 4.2 | 121.5 |
| EO-360 | V | 0.040 | 20 | 0 | 200 | 15 | 30 | 116 | 0.1286 | 6825 | 1,050,461 | 1,744,245 | 1.66 | 5 | 120.7 |
| EO-361 | V | 0.040 | 20 | 0 | 200 | 15 | 30 | 116 | 0.1103 | 5864 | 846,037 | 1,433,682 | 1.69 | 3.6 | 121.2 |
| EO-362 | V | 0.040 | 20 | 0 | 200 | 15 | 30 | 111 | 0.1165 | 6497 | 894,016 | 1,572,077 | 1.76 | 5.4 | 122.3 |
| EO-363 | V | 0.040 | 20 | 0 | 200 | 15 | 30 | 149 | 0.1465 | 6059 | 1,007,048 | 1,465,733 | 1.46 | 5.7 | 118.7 |
| EO-364 | V | 0.040 | 20 | 0 | 200 | 15 | 30 | 139 | 0.1264 | 5616 | 923,972 | 1,390,060 | 1.5 | 5.2 | 119.3 |
| EO-365 | V | 0.040 | 20 | 0 | 200 | 15 | 30 | 151 | 0.1439 | 5884 | | | | | |

General conditions used: 5 mL total solvent; solvent toluene unless otherwise noted; 100 uL 1-octene used; total molar MAO/TMC = 500; reaction temperature = 80° C.; stirrer speed 800 rpm.
*347 uL toluene used for delivering TMC and MAO; remaining solvent isohexane.

The invention claimed is:

1. A transition metal compound represented by the formula:

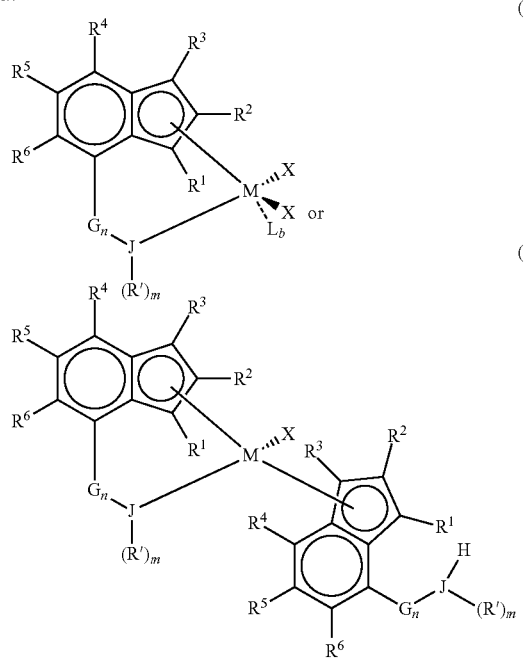

where M is a group 3, 4, 5 or 6 metal; J is a group 15 or 16 atom, and when J is a group 15 metal, m is 1, indicating the presence of R', and when J is a group 16 metal, m is zero, indicating the absence of R; G is a bridging group and n is 1, 2 or 3 indicating the number of atoms in the direct chain between the indenyl ring and the ligand J; $R^1$, $R^2$, $R^3$, $R^4$, $R^5$, and $R^6$ are independently selected from a hydrogen, fluoro, hydrocarbyl, substituted hydrocarbyl, halocarbyl, substituted halocarbyl, silylcarbyl, substituted silylcarbyl, germylcarbyl, or substituted germylcarbyl radical, and two or more adjacent $R^1$, $R^2$, $R^3$, $R^4$, $R^5$, and $R^6$ can join together to form a cyclic group fused to the indenyl ring; R' is selected from a hydrocarbyl, halohydrocarbyl, or substituted hydrocarbyl radical; X is a univalent ionic ligand, L is a Lewis base ligand and b is 0, 1 or 2 representing the presence (b=1 or 2) or absence (b=0) of L, provided that when n is 2, G is not O—$SiR_2$, or $R_4Ph$, and when n is 3, G is not $SiR_2(R_4Ph)$, where Ph is phenyl and each R is as defined for R'.

2. The compound of claim 1 wherein M is a group 4 metal.

3. The compound of claim 1 wherein J is N, P, O, or S.

4. The compound of claim 1 wherein $R^2$ is methyl and $R^1$, $R^3$, $R^4$, $R^5$, and $R^6$ are hydrogen radicals.

5. The compound of claim 1 wherein $R^2$ is methyl, $R^4$ is fluoro and $R^1$, $R^3$, $R^5$, and $R^6$ are hydrogen radicals.

6. The compound of claim 1 wherein R' is selected from tert-butyl, cyclopentyl, cyclohexyl, cyclododecyl, 2-norbornyl, 1-adamantyl, benzyl, phenyl, 2-methylphenyl, 3-methylphenyl, 4-methylphenyl, 3,5-dimethylphenyl, 3,5-diisopropylphenyl, 4-bromophenyl, and 4-methoxyphenyl, n is 1 or 2, at least one of $R^1$, $R^2$, $R^3$, $R^4$, $R^5$, and $R^6$ is fluoro and each X is, independently, Cl, Br, F, I, methyl, ethyl, propyl, butyl, phenyl, or benzyl.

7. The compound of claim 1 wherein G is $CH_2$, $CH_2CH_2$, $CH_2CH_2CH_2$, $CMe_2$, $SiMe_2$, $SiPh_2$, $SiMePh$, $Me_2SiSiMe_2$, $Me_2SiOSiMe_2$, $PhMeSiSiMePh$, $PhMeSiOSiMePh$, $Si(CH_2)_3$, or $Si(CH_2)_4$.

8. A catalyst system comprising an activator and the transition metal compound of claim 1.

9. The catalyst system of claim 8 wherein M is a group 4 metal and J is N, P, O, or S.

10. The catalyst system of claim 8 wherein $R^2$ is methyl, $R^4$ is fluoro and $R^1$, $R^3$, $R^5$, and $R^6$ are hydrogen radicals.

11. The catalyst system of claim 8 wherein R' is selected from tert-butyl, cyclopentyl, cyclohexyl, cyclododecyl, 2-norbornyl, 1-adamantyl, benzyl, phenyl, 2-methylphenyl, 3-methylphenyl, 4-methylphenyl, 3,5-dimethylphenyl, 3,5-diisopropylphenyl, 4-bromophenyl, and 4-methoxyphenyl, n is 1 or 2, at least one of $R^1$, $R^2$, $R^3$, $R^4$, $R^5$, and $R^6$ is fluoro, and each X is Cl, Br, F, I, methyl, ethyl, propyl, butyl, phenyl, or benzyl.

12. The catalyst system of claim 8, wherein G is $CH_2$, $CH_2CH_2$, $CH_2CH_2CH_2$, $CMe_2$, $SiMe_2$, $SiPh_2$, $SiMePh$, $Me_2SiSiMe_2$, $Me_2SiOSiMe_2$, $PhMeSiSiMePh$, $PhMeSiOSiMePh$, $Si(CH_2)_3$, or $Si(CH_2)_4$.

13. The catalyst system of claim 8, wherein L is selected from the group consisting of ethylene, propylene, butene, diethylether, tetrahydrofuran, furan, dimethylaniline, aniline, trimethylphosphine, trimethylamine, butylamine, and lithium chloride.

14. The catalyst system of claim 8, wherein each $R^1$, $R^2$, $R^3$, $R^4$, $R^5$, or $R^6$ is selected from, the group consisting of hydrogen, fluoro, methyl, ethyl, n-propyl, iso-propyl, n-butyl, sec-butyl, iso-butyl, tert-butyl, pentyl, hexyl, cyclohexyl, phenyl, and trifluoromethyl.

15. A process to polymerize olefins comprising contacting monomers with the catalyst system of claim 8.

16. The process of claim 15, wherein the monomers are contacted with the transition metal compound and the activator in a reactor and the reactor is a continuous stirred tank reactor or a continuous tubular reactor.

17. The process of claim 15, wherein the monomers comprise ethylene.

18. The process of claim 15, wherein the activator is a non-coordinating anion.

19. The process of claim 15, wherein R' is selected from tert-butyl, cyclopentyl, cyclohexyl, cyclododecyl, 2-norbornyl, 1-adamantyl, benzyl, phenyl, 2-methylphenyl, 3-methylphenyl, 4-methylphenyl, 3,5-dimethylphenyl, 3,5-diisopropylphenyl, 4-bromophenyl, and 4-methoxyphenyl, n is 1 or 2, at least one of $R^1$, $R^2$, $R^3$, $R^4$, $R^5$, and $R^6$ is fluoro and each X is Cl, Br, F, I, methyl, ethyl, propyl, butyl, phenyl, or benzyl.

20. The process of claim 15, wherein G is $CH_2$, $CH_2CH_2$, $CH_2CH_2CH_2$, $CMe_2$, $SiMe_2$, $SiPh_2$, $SiMePh$, $Me_2SiSiMe_2$, $Me_2SiOSiMe_2$, $PhMeSiSiMePh$, $PhMeSiOSiMePh$, $Si(CH_2)_3$, or $Si(CH_2)_4$, L is selected from the group consisting of ethylene, propylene, butene, diethylether, tetrahydrofuran, furan, dimethylaniline, aniline, trimethylphosphine, trimethylamine, butylamine, and lithium chloride, and each $R^1$, $R^2$, $R^3$, $R^4$, $R^5$, or $R^6$ is selected from the group consisting of hydrogen, fluoro, methyl, ethyl, n-propyl, iso-propyl, n-butyl, sec-butyl, iso-butyl, tert-butyl, pentyl, hexyl, cyclohexyl, phenyl, and trifluoromethyl.

\* \* \* \* \*